US010973920B2

(12) United States Patent
Helin et al.

(10) Patent No.: US 10,973,920 B2
(45) Date of Patent: Apr. 13, 2021

(54) SACCHARIDE DERIVATIVE OF A TOXIC PAYLOAD AND ANTIBODY CONJUGATES THEREOF

(71) Applicant: Glykos Finland Oy, Helsinki (FI)

(72) Inventors: Jari Helin, Rajamaki (FI); Juhani Saarinen, Helsinki (FI); Tero Satomaa, Helsinki (FI); Filip S. Ekholm, Porvoo (FI)

(73) Assignee: GLYKOS FINLAND OY, Helsinki (FI)

( * ) Notice: Subject to any disclaimer, the term of this patent is extended or adjusted under 35 U.S.C. 154(b) by 694 days.

(21) Appl. No.: 15/320,917

(22) PCT Filed: Jun. 26, 2015

(86) PCT No.: PCT/FI2015/050471
§ 371 (c)(1),
(2) Date: Dec. 21, 2016

(87) PCT Pub. No.: WO2016/001485
PCT Pub. Date: Jan. 7, 2016

(65) Prior Publication Data
US 2018/0228906 A1 Aug. 16, 2018

(30) Foreign Application Priority Data

Jun. 30, 2014 (FI) .................... 20145634
Dec. 5, 2014 (FI) .................... 20146069
Feb. 23, 2015 (FI) .................... 20155120

(51) Int. Cl.
*A61K 47/54* (2017.01)
*A61K 47/68* (2017.01)
*A61P 35/02* (2006.01)

(52) U.S. Cl.
CPC ........ *A61K 47/549* (2017.08); *A61K 47/6803* (2017.08); *A61K 47/6809* (2017.08);
(Continued)

(58) Field of Classification Search
None
See application file for complete search history.

(56) References Cited

U.S. PATENT DOCUMENTS 4,307,016 A 12/1981 Asai et al.
4,361,650 A 11/1982 Asai et al.
(Continued)

FOREIGN PATENT DOCUMENTS

DE 4415463 A1 11/1995
GB 2511137 A1 8/2014
(Continued)

OTHER PUBLICATIONS

Okeley et al. ("Okeley"Bioconjugate Chem., 2013, 24, 1650-1655) (Year: 2013).*
(Continued)

*Primary Examiner* — Karl J Puttlitz
(74) *Attorney, Agent, or Firm* — Patrick J. Halloran

(57) ABSTRACT

A molecule comprising a saccharide bound via an O-glycosidic bond to a hydroxyl group of a toxic payload molecule is disclosed. An antibody-drug conjugate comprising an antibody covalently bound to a toxic payload molecule, optionally via a linker group, and a saccharide bound via an O-glycosidic bond to a hydroxyl group of the toxic payload molecule is further disclosed.

33 Claims, 8 Drawing Sheets

Figure 1:
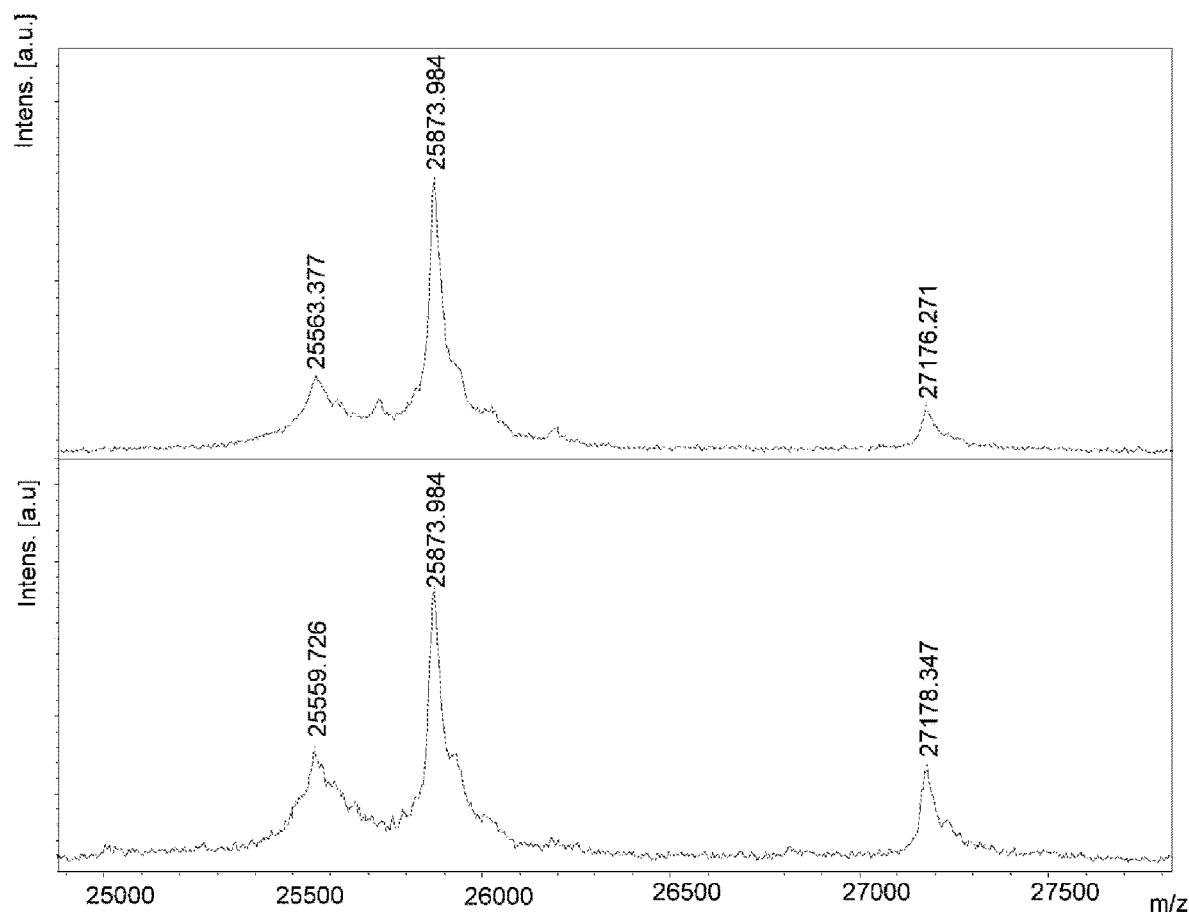

Specification includes a Sequence Listing.

(52) U.S. Cl.
CPC ...... *A61K 47/6829* (2017.08); *A61K 47/6831* (2017.08); *A61K 47/6849* (2017.08); *A61K 47/6855* (2017.08); *A61P 35/02* (2018.01)

(56) References Cited

U.S. PATENT DOCUMENTS

| | | | |
|---|---|---|---|
| 5,208,020 | A | 5/1993 | Chari et al. |
| 5,443,953 | A | 8/1995 | Hansen et al. |
| 5,635,483 | A | 3/1997 | Powell |
| 5,635,603 | A | 6/1997 | Pettit et al. |
| 5,639,783 | A | 6/1997 | Ando et al. |
| 5,843,937 | A | 12/1998 | Wang et al. |
| 6,214,345 | B1 | 4/2001 | Firestone et al. |
| 6,372,883 | B1 | 4/2002 | Attwood et al. |
| 6,441,163 | B1 | 8/2002 | Chari et al. |
| 6,476,198 | B1 | 11/2002 | Kang |
| 6,573,245 | B1 | 6/2003 | Marciani |
| 6,884,869 | B2 | 4/2005 | Senter et al. |
| 7,090,843 | B1 | 8/2006 | Francisco et al. |
| 7,091,186 | B2 | 8/2006 | Senter et al. |
| 7,098,308 | B2 | 8/2006 | Senter et al. |
| 7,214,685 | B2 | 5/2007 | Tietze et al. |
| 7,223,837 | B2 | 5/2007 | De Groot et al. |
| 7,256,257 | B2 | 8/2007 | Doronina et al. |
| 7,368,565 | B2 | 5/2008 | Chari et al. |
| 7,375,078 | B2 | 5/2008 | Feng |
| 7,423,116 | B2 | 9/2008 | Doronina et al. |
| 7,553,816 | B2 | 6/2009 | Senter et al. |
| 7,605,125 | B2 | 10/2009 | Szekely et al. |
| 7,659,241 | B2 | 2/2010 | Senter et al. |
| 7,691,962 | B2 | 4/2010 | Boyd et al. |
| 7,750,116 | B1 | 7/2010 | Doronina et al. |
| 7,754,681 | B2 | 7/2010 | Feng |
| 7,811,572 | B2 | 10/2010 | Dai et al. |
| 7,820,714 | B2 | 10/2010 | Kelm et al. |
| 7,837,980 | B2 | 11/2010 | Alley et al. |
| 7,989,434 | B2 | 8/2011 | Feng |
| 8,039,273 | B2 | 10/2011 | Jeffrey |
| 8,084,026 | B2 | 12/2011 | Glaser et al. |
| 8,163,888 | B2 | 4/2012 | Steeves et al. |
| 8,236,319 | B2 | 8/2012 | Chari et al. |
| 8,263,083 | B2 | 9/2012 | Oflazoglu et al. |
| 8,333,971 | B2 | 12/2012 | Goldenberg et al. |
| 8,357,671 | B2 | 1/2013 | Paulson et al. |
| 8,470,329 | B2 | 6/2013 | Oflazoglu et al. |
| 8,557,984 | B2 | 10/2013 | Bouillot et al. |
| 8,568,728 | B2 | 10/2013 | Jeffrey |
| 8,613,930 | B2 | 12/2013 | Chari et al. |
| 8,765,920 | B2 | 7/2014 | Barbas, III et al. |
| 8,778,914 | B2 | 7/2014 | Kratz et al. |
| 8,940,784 | B2 | 1/2015 | Beusker et al. |
| 9,011,864 | B2 | 4/2015 | Schulz et al. |
| 9,061,995 | B2 | 6/2015 | Chari et al. |
| 9,120,854 | B2 | 9/2015 | Ryan et al. |
| 9,221,914 | B2 | 12/2015 | Kraus et al. |
| 9,254,339 | B2 | 2/2016 | Yurkovetskiy et al. |
| 9,260,467 | B2 | 2/2016 | Brossmer et al. |
| 9,289,509 | B2 | 3/2016 | Osterroth et al. |
| 9,326,939 | B2 | 5/2016 | Paulson et al. |
| 9,387,261 | B2 | 7/2016 | Kraus et al. |
| 9,446,146 | B2 | 9/2016 | Daelken et al. |
| 9,498,541 | B2 | 11/2016 | Chari et al. |
| 2002/0103345 | A1 | 8/2002 | Zhu |
| 2004/0018194 | A1 | 1/2004 | Francisco et al. |
| 2004/0121940 | A1 | 6/2004 | De Groot et al. |
| 2004/0157782 | A1 | 8/2004 | Doronina et al. |
| 2005/0026971 | A1 | 2/2005 | Berger |
| 2005/0238649 | A1 | 10/2005 | Doronina et al. |
| 2006/0024317 | A1 | 2/2006 | Boyd et al. |
| 2006/0074008 | A1 | 4/2006 | Senter et al. |
| 2006/0116422 | A1 | 6/2006 | De Groot et al. |
| 2006/0166929 | A1 | 7/2006 | Kajihara et al. |
| 2007/0027068 | A1 | 2/2007 | DeFrees et al. |
| 2007/0082922 | A1 | 4/2007 | Pan |
| 2007/0258987 | A1 | 11/2007 | Francisco et al. |
| 2008/0213289 | A1 | 9/2008 | Francisco et al. |
| 2008/0241128 | A1 | 10/2008 | Jeffrey |
| 2008/0299120 | A1 | 12/2008 | Miller et al. |
| 2008/0311136 | A1 | 12/2008 | Beukser et al. |
| 2008/0317747 | A1 | 12/2008 | Francisco et al. |
| 2009/0010945 | A1 | 1/2009 | Alley et al. |
| 2009/0041758 | A1 | 2/2009 | Glaser et al. |
| 2009/0111756 | A1* | 4/2009 | Doronina ........... C07K 16/2866 514/1.1 |
| 2009/0118349 | A1 | 5/2009 | Szekely et al. |
| 2009/0274713 | A1 | 11/2009 | Chari et al. |
| 2009/0312335 | A1 | 12/2009 | Wai et al. |
| 2010/0081796 | A1 | 4/2010 | Brinkmann et al. |
| 2010/0178292 | A1 | 7/2010 | Wang et al. |
| 2010/0256338 | A1 | 7/2010 | Brinkmann et al. |
| 2010/0322934 | A1 | 12/2010 | Imhof-Jung et al. |
| 2010/0323973 | A1 | 12/2010 | Leamon et al. |
| 2011/0003969 | A1 | 1/2011 | Kellogg et al. |
| 2011/0020343 | A1 | 1/2011 | Senter et al. |
| 2011/0070248 | A1 | 3/2011 | Ichikawa et al. |
| 2011/0159018 | A1 | 6/2011 | Stoiber |
| 2011/0166319 | A1 | 7/2011 | Dai et al. |
| 2011/0177064 | A1 | 7/2011 | Whiteman et al. |
| 2011/0268751 | A1 | 11/2011 | Sievers et al. |
| 2011/0293613 | A1 | 12/2011 | Brinkmann et al. |
| 2012/0226026 | A1 | 9/2012 | Singh et al. |
| 2012/0253021 | A1 | 10/2012 | Li et al. |
| 2012/0259100 | A1 | 10/2012 | Jin |
| 2013/0084291 | A1 | 4/2013 | Seehra et al. |
| 2013/0129753 | A1 | 5/2013 | Doroski et al. |
| 2013/0144045 | A1 | 6/2013 | Papot et al. |
| 2013/0237490 | A2 | 9/2013 | Carr et al. |
| 2013/0280282 | A1 | 10/2013 | Ohtsuka et al. |
| 2014/0031535 | A1 | 1/2014 | Jeffrey |
| 2014/0161829 | A1 | 6/2014 | Kim et al. |
| 2014/0161884 | A1 | 6/2014 | Wong et al. |
| 2014/0275009 | A1 | 9/2014 | Brenchly et al. |
| 2014/0288280 | A1 | 9/2014 | Bhakta et al. |
| 2014/0308201 | A1 | 10/2014 | Batt et al. |
| 2014/0363454 | A1 | 12/2014 | Jackson et al. |
| 2015/0174262 | A1 | 6/2015 | Brossmer et al. |
| 2015/0209445 | A1 | 7/2015 | Maderna et al. |
| 2015/0322155 | A1 | 11/2015 | Zhao |
| 2016/0106860 | A1* | 4/2016 | Satomaa ........... A61K 47/6849 424/181.1 |
| 2016/0193355 | A1 | 7/2016 | Qin et al. |

FOREIGN PATENT DOCUMENTS

| | | |
|---|---|---|
| WO | 88/04323 A1 | 6/1988 |
| WO | 90/002746 A1 | 3/1990 |
| WO | 95/009917 A1 | 4/1995 |
| WO | 95/15769 A1 | 6/1995 |
| WO | 97/001580 A1 | 1/1997 |
| WO | 97/014719 A1 | 4/1997 |
| WO | 97/34632 A1 | 9/1997 |
| WO | 97/44000 A2 | 11/1997 |
| WO | 98/009966 A1 | 3/1998 |
| WO | 98/012214 A1 | 3/1998 |
| WO | 98/012218 A1 | 3/1998 |
| WO | 98/012219 A1 | 3/1998 |
| WO | 99/031052 A1 | 6/1999 |
| WO | 99/052936 A2 | 10/1999 |
| WO | 00/061746 A1 | 10/2000 |
| WO | 00/064864 A1 | 11/2000 |
| WO | 01/083448 A2 | 11/2001 |
| WO | 02/026262 A2 | 4/2002 |
| WO | 02/055485 A1 | 7/2002 |
| WO | 02/067937 A2 | 9/2002 |
| WO | 02/088172 A2 | 11/2002 |
| WO | 03/031464 A2 | 4/2003 |
| WO | 03/072058 A2 | 9/2003 |
| WO | 03/086312 A2 | 10/2003 |
| WO | 03/102583 A1 | 12/2003 |
| WO | 2004/003211 A1 | 1/2004 |
| WO | 2004/010957 A2 | 2/2004 |
| WO | 2005/012484 A2 | 2/2005 |
| WO | 2005/035003 A2 | 4/2005 |
| WO | 2005/056577 A2 | 6/2005 |

(56) References Cited

FOREIGN PATENT DOCUMENTS

| WO | 2005/081711 | A2 | 9/2005 | | |
|---|---|---|---|---|---|
| WO | 2005/085259 | A2 | 9/2005 | | |
| WO | 2005/112919 | A2 | 12/2005 | | |
| WO | 2006/043839 | A1 | 4/2006 | | |
| WO | 2007/011968 | A2 | 1/2007 | | |
| WO | 2007/018431 | A2 | 2/2007 | | |
| WO | 2007/089149 | A2 | 8/2007 | | |
| WO | 2007/109254 | A2 | 9/2007 | | |
| WO | 2007/133855 | A2 | 11/2007 | | |
| WO | 2008/074004 | A2 | 6/2008 | | |
| WO | 2008/083312 | A2 | 7/2008 | | |
| WO | 2008/090151 | A1 | 7/2008 | | |
| WO | 2008/140493 | A2 | 11/2008 | | |
| WO | 2009/006620 | A1 | 1/2009 | | |
| WO | 2009/016647 | A1 | 2/2009 | | |
| WO | 2009/017394 | A1 | 2/2009 | | |
| WO | 2009/033670 | A2 | 3/2009 | | |
| WO | 2009/052431 | A2 | 4/2009 | | |
| WO | 2009/134976 | A1 | 11/2009 | | |
| WO | 2009/134977 | A1 | 11/2009 | | |
| WO | 2010/015722 | A1 | 2/2010 | | |
| WO | 2010/062171 | A2 | 6/2010 | | |
| WO | 2010/111018 | A1 | 9/2010 | | |
| WO | 2011/031870 | A1 | 3/2011 | | |
| WO | 2011/050180 | A1 | 4/2011 | | |
| WO | 2011/051484 | A1 | 5/2011 | | |
| WO | 2011/054837 | A2 | 5/2011 | | |
| WO | 2011/064303 | A1 | 6/2011 | | |
| WO | 2011/133039 | A2 | 10/2011 | | |
| WO | 2012/025525 | A1 | 3/2012 | | |
| WO | 2012/030904 | A1 | 3/2012 | | |
| WO | 2012/041805 | A1 | 4/2012 | | |
| WO | 2012/054748 | A2 | 4/2012 | | |
| WO | 2012/059882 | A2 | 5/2012 | | |
| WO | 2012/076883 | A1 | 6/2012 | | |
| WO | 2012/122420 | A2 | 9/2012 | | |
| WO | 2012/122514 | A1 | 9/2012 | | |
| WO | 2012/153193 | A1 | 11/2012 | | |
| WO | 2012/162482 | A1 | 11/2012 | | |
| WO | 2012/166559 | A1 | 12/2012 | | |
| WO | 2012/166560 | A1 | 12/2012 | | |
| WO | 2013/012961 | A2 | 1/2013 | | |
| WO | 2013/033396 | A2 | 3/2013 | | |
| WO | 2013/037824 | A1 | 3/2013 | | |
| WO | 2013/072813 | A2 | 5/2013 | | |
| WO | 2013/087992 | A1 | 6/2013 | | |
| WO | 2013/087993 | A1 | 6/2013 | | |
| WO | 2013/093809 | A1 | 6/2013 | | |
| WO | 2013/142817 | A2 | 9/2013 | | |
| WO | 2014/009774 | A1 | 1/2014 | | |
| WO | 2014/011519 | A1 | 1/2014 | | |
| WO | 2014/047199 | A1 | 3/2014 | | |
| WO | 2014/061277 | A1 | 4/2014 | | |
| WO | 2014/065661 | A1 | 5/2014 | | |
| WO | 2014/080251 | A1 | 5/2014 | | |
| WO | 2014/096551 | A1 | 6/2014 | | |
| WO | WO-2014086952 | A1 | * | 6/2014 | ......... A61K 47/6415 |
| WO | 2014/139008 | A1 | 9/2014 | | |
| WO | 2014/159981 | A2 | 10/2014 | | |
| WO | 2014/164942 | A1 | 10/2014 | | |
| WO | 2014/174060 | A1 | 10/2014 | | |
| WO | 2014/177771 | A1 | 11/2014 | | |
| WO | 2014/197854 | A1 | 12/2014 | | |
| WO | 2014/197909 | A1 | 12/2014 | | |
| WO | 2014/210064 | A1 | 12/2014 | | |
| WO | 2015/015448 | A2 | 2/2015 | | |
| WO | 2015/023355 | A1 | 2/2015 | | |
| WO | 2015/038426 | A1 | 3/2015 | | |
| WO | 2015/057063 | A1 | 4/2015 | | |
| WO | 2015/057064 | A1 | 4/2015 | | |
| WO | 2015/057065 | A1 | 4/2015 | | |
| WO | 2015/057066 | A1 | 4/2015 | | |
| WO | 2015/075269 | A1 | 5/2015 | | |
| WO | 2015/095755 | A1 | 6/2015 | | |
| WO | 2015/110935 | A1 | 7/2015 | | |
| WO | 2015/113476 | A1 | 8/2015 | | |
| WO | 2015/128344 | A1 | 9/2015 | | |
| WO | 2015/151079 | A2 | 10/2015 | | |
| WO | 2015/151080 | A2 | 10/2015 | | |
| WO | 2015/162293 | A1 | 10/2015 | | |
| WO | 2015/162563 | A1 | 10/2015 | | |
| WO | 2015/187596 | A2 | 12/2015 | | |
| WO | 2015/197919 | A1 | 12/2015 | | |
| WO | 2016/023511 | A1 | 2/2016 | | |
| WO | 2016/073845 | A1 | 5/2016 | | |
| WO | 2016/080626 | A2 | 5/2016 | | |
| WO | 2015/081857 | A1 | 6/2016 | | |
| WO | 2016/094837 | A2 | 6/2016 | | |

OTHER PUBLICATIONS

Abdu-Allah et al. Design and synthesis of a multivalent heterobifunctional CD22 ligand as a potential immunomodulator, Synthesis. 2011; 18:2968-2974.

Afar D. et al. Preclinical validation of anti-TMEFF2-auristatin E-conjugated antibodies in the treatment of prostate cancer, Mol. Cancer Ther. 2004; 3(8): 921-932.

Allen TM. Ligand-targeted therapeutics in anticancer therapy. Nat Rev Cancer. Oct. 2002;2(10):750-63.

Alley SC et al. The pharmacologic basis for antibody-auristatin conjugate activity. J Pharmacol Exp Ther. Sep. 2009;330(3):932-8.

Alsarraf J et al. A dendritic β-galactosidase-responsive folate-monomethylauristatin E conjugate. Chem Commun (Camb). Nov. 11, 2015;51(87):15792-5.

Bai R et al. Intracellular Activation and Deactivation of Tasidotin, an Analog of Dolastatin 15: Correlation with Cytotoxicity, Mol. Pharmacol. 2009; 75(1): 218-226.

Beerli RR et al. Sortase Enzyme-Mediated Generation of Site-Specifically Conjugated Antibody Drug Conjugates with High In Vitro and In Vivo Potency. PLoS One. Jul. 1, 2015;10(7):e0131177.

Brimble MA et al. Synthesis of fluorescein-labelled O-mannosylated peptides as components for synthetic vaccines: comparison of two synthetic strategies. Org Biomol Chem. Jan. 7, 2008;6(1):112-21.

Burke PJ et al. Development of Novel Quaternary Ammonium Linkers for Antibody-Drug Conjugates. Mol Cancer Ther. May 2016;15(5):938-45.

Calarese DA et al. Dissection of the carbohydrate specificity of the broadly neutralizing anti-HIV-1 antibody 2G12. Proc Natl Acad Sci U S A. Sep. 20, 2005;102(38):13372-7.

Carlson E et al. Improved Chemical Syntheses of 1- and 5-Deazariboflavin, Jour. Org. Chem. Apr. 2, 2004; 69: 2614-2617.

Carter PJ and Senter PD. Antibody-drug conjugates for cancer therapy. Cancer J. May-Jun. 2008;14(3):154-69.

Chao Z et al. Development of an indirect competitive enzyme-linked immunosorbent assay (icELISA) using highly specific monoclonal antibody against paclitaxel. J Nat Med. Jul. 2013;67(3):512-8.

Chen WC et al. In vivo targeting of B-cell lymphoma with glycan ligands of CD22. Blood. 2010; 115(23): 4778-4786.

Chen J et al. Development of a native nanoelectrospray mass spectrometry method for determination of the drug-to-antibody ratio of antibody-drug conjugates. Anal Chem. Feb. 5, 2013;85(3):1699-1704.

Chen KC et al. Selective cancer therapy by extracellular activation of a highly potent glycosidic duocarmycin analogue. Mol Pharm. 2013; 10:1773-1782.

Chester MA. (1998) IUPAC-IUB Joint Commission on Biochemical Nomenclature (JCBN). Nomenclature of glycolipids—recommendations 1997. Eur J Biochem. Oct. 15, 1998; 257(2):293-8.

Chung NP et al. Stable 293 T and CHO cell lines expressing cleaved, stable HIV-1 envelope glycoprotein trimers for structural and vaccine studies. Retrovirology. Apr. 25, 2014;11:33.

Cohen R et al. Development of novel ADCs: conjugation of tubulysin analogues to trastuzumab monitored by dual radiolabeling. Cancer Res. Oct. 15, 2014;74(20):5700-10. Epub Aug. 21, 2014.

(56) References Cited

OTHER PUBLICATIONS

Damle NK. Antibody-drug conjugates ace the tolerability test. Nat Biotechnol. Aug. 2008;26(8):884-5.
Doronina. SO et al. Development of potent monoclonal antibody auristatin conjugates for cancer therapy. Nat Biotechnol. Jul. 2003;21(7):778-84.
Doronina SO et al. Enhanced activity of monomethylauristatin F through monoclonal antibody delivery: effects of linker technology on efficacy and toxicity. Bioconjug Chem. Jan.-Feb. 2006;17(1):114-24.
Doronina So et al. Novel peptide linkers for highly potent antibody-auristatin conjugate. Bioconj. Chem. Oct. 2008;19(10):1960-3. Epub Sep. 20, 2008.
Dosio F et al. Immunotoxins and Anticancer Drug Conjugate assemblies: The Role of the Linkage between Components. Toxins. Jul. 2011;3(7):848-83. Epub Jul. 14, 2011.
Eissler S et al. Efficient synthesis of cryptophycin-52 and novel para-alkoxymethyl unit A analogues. Chemistry. Oct. 26, 2009;15(42):11273-87.
Ekholm FS et al. Introducing Glycolinkers for the Functionalization of Cytotoxic Drugs and Applications in Antibody-Drug Conjugation Chemistry. ChemMedChem. Nov. 21, 2016;11(22):2501-2505. Epub Oct. 27, 2016.
Ekholm FS et al. Synthesis of the copper chelator TGTA and evaluation of its ability to protect biomolecules from copper induced degradation during copper catalyzed azide-alkyne bioconjugation reactions. Org Biomol Chem. Jan. 21, 2016;14(3):849-52. Epub Dec. 8, 2015.
Elgersma RC et al. Design, Synthesis, and Evaluation of Linker-Duocarmycin Payloads: Toward Selection of HER2-Targeting Antibody-Drug Conjugate SYD985. Mol Pharm. Jun. 1, 2015;12(6):1813-35.
Finnish Search Report for Finnish Patent Application No. 20135451 dated Feb. 28, 2014.
Finnish Search Report for Finnish Patent Application No. 20145616 dated Dec. 10, 2014.
Francisco JA et al. cAC10-vcMMAE, an anti-CD30-monomethyl auristatin E conjugate with potent and selective antitumor activity. Blood. Aug. 15, 2003;102(4):1458-65. Epub Apr. 24, 2003.
Friend DR et al. Drug glycosides: potential prodrugs for colon-specific drug delivery. J Med Chem. Jan. 1985;28(1):51-7.
Gao F et al. Cross-reactive monoclonal antibodies to multiple HIV-1 subtype and SIVcpz envelope glycoproteins. Virology. Nov. 10, 2009;394(1):91-8. Epub Sep. 9, 2009.
Gavrilyuk J et al. Antibody conjugation approach enhances breadth and potency of neutralization of anti-HIV-1 antibodies and CD4-IgG. J Virol. May 2013;87(9):4985-93. Epub Feb. 20, 2013.
Gerratana B. Biosynthesis, synthesis, and biological activities of pyrrolobenzodiazepines. Med Res Rev. Mar. 2012;32(2):254-93. Epub Jun. 13, 2010.
Greenaway J et al. Thrombospondin-1 inhibits VEGF levels in the ovary directly by binding and internalization via the low density lipoprotein receptor-related protein-1 (LRP-1). J Cell Physiol. Mar. 2007;210(3):807-18.
Gunther KU and Ziegler T. Synthesis of 1,2,3-Triazole-Linked Glycoconjugates of N-(2-Aminoethyl)glycine: Building Blocks for the Construction of Combinatorial Glycopeptide Libraries. Synthesis. Jun. 12, 2014; 46(17): 2362-2370.
Hara M et al. DC 102, a new glycosidic pyrrolo(1,4)benzodiazepine antibiotic produced by *Streptomyces* sp. J Antibiot (Tokyo). May 1988;41(5):702-4.
Ho PT. Synthesis of maytansinoids: synthesis of an intermediate from D-glucose for the construction of maytansine. Canadian Journal of Chemistry, 1980, 58(8): 858-860.
International Preliminary Report on Patentability for International Patent Application No. PCT/FI2013/051193 dated Jun. 23, 2015.
International Search Report for International Patent Application No. PCT/FI2013/051193 dated Apr. 17, 2014.
International Preliminary Report on Patentability for International Patent Application No. PCT/FI2014/050322 dated Nov. 3, 2015.
International Search Report for International Patent Application No. PCT/FI2014/050322 dated Aug. 21, 2014.
International Preliminary Report on Patentability for International Patent Application No. PCT/FI2015/050471 dated Jan. 3, 2017.
International Search Report for International Patent Application No. PCT/FI2015/050471 dated Oct. 16, 2015.
International Search Report for International Patent Application No. PCT/2015/050466 dated Dec. 7, 2015.
International Preliminary Report on Patentability for International Patent Application No. PCT/FI2015/050466 dated Dec. 27, 2016.
IUPAC. Nomenclature of glycolipids. Carbohydrate Res. Nov. 1998; 312(4):167-175.
Jeffrey SC et al. Development and properties of beta-glucuronide linkers for monoclonal antibody-drug conjugates. Bioconjug Chem. May-Jun. 2006;17(3):831-40.
Jeffrey SC et al. Minor groove binder antibody conjugates employing a water soluble beta-glucuronide linker. Bioorg Med Chem Lett. Apr. 15, 2007;17(8):2278-80.
Kadlcik S et al. Adaptation of an L-proline adenylation domain to use 4-propyl-L-proline in the evolution of incosamide biosynthesis. PLoS One. Dec. 27, 2013;8(12):e84902.
Khedri Z et al. Chemoenzymatic synthesis of sialosides containing C7-modified sialic acids and their application in sialidase substrate specificity studies. Carbohydr Res. May 7, 2014;389:100-11. Epub Mar. 6, 2014.
Kim BC et al. Quantitative detection of HIV-1 particles using HIV-1 neutralizing antibody-conjugated beads. Anal Chem. Mar. 15, 2009;81(6):2388-93.
Kinghorn A. et al. Editors, "The Epothilones: An Outstanding Family of Anti-Tumor Agents", Springer-Verlag/Wien, 2009.
Kirsch P. et al. Synthesis of N-acetylglucosaminyl asparagine-substituted puromycin analogues. Bioorg Med Chem. Dec. 1995;3(12):1631-6.
Klussman K et al. Secondary mAb-vcMMAE conjugates are highly sensitive reporters of antibody internalization via the lysosome pathway. Bioconjug Chem. Jul.-Aug. 2004;15(4):765-73.
Kolakowski RV et al. The Methylene Alkoxy Carbamate Self-Immolative Unit: Utilization for the Targeted Delivery of Alcohol-Containing Payloads with Antibody-Drug Conjugates. Angew Chem Int Ed Engl. Jul. 4, 2016;55(28):7948-51.
Legigan T et al. Synthesis and antitumor efficacy of a β-glucuronidase-responsive albumin-binding prodrug of doxorubicin. J Med Chem. May 10, 2012a;55(9):4516-20. Epub Apr. 30, 2012.
Legigan T et al. The first generation of β-galactosidase-responsive prodrugs designed for the selective treatment of solid tumors in prodrug monotherapy. Angew Chem Int Ed Engl. Nov. 12, 2012b;51(46):11606-100. Epub Sep. 20, 2012.
Legigan T et al. Synthesis and biological evaluations of a monomethylauristatin E glucuronide prodrug for selective cancer chemotherapy. Eur J Med Chem. Sep. 2013;67:75-80. Epub Jun. 25, 2013.
Li W et al. Biosynthesis of sibiromycin, a potent antitumor antibiotic. Appl Environ Microbiol. May 2009;75(9):2869-78. Epub Mar. 6, 2009.
Li Y et al. Dual carbamoylations on the polyketide and glycosyl moiety by asm21 result in extended ansamitocin biosynthesis. Chem Biol. Dec. 23, 2011;18(12):1571-80.
Lu C et al. A novel amide N-glycoside of ansamitocins from Actinosynnema pretiosum. J Antibiot (Tokyo). May 2004;57(5):348-50.
Mbadugha BN and Menger FM. Sugar/steroid/sugar conjugates: sensitivity of lipid binding to sugar structure. Org Lett. Oct. 30, 2003;5(22):4041-4.
Mbua NE et al. Selective exo-enzymatic labeling of N-glycans on the surface of living cells by recombinant ST6Gal I. Angew Chem Int Ed Engl. Dec. 2, 2013;52(49):13012-5.
Mcnaught AD. (1997) International Union of Pure and Applied Chemistry and International Union of Biochemistry and Molecular Biology. Joint Commission on Biochemical Nomenclature. Nomenclature of carbohydrates. Carbohydr Res. Jan. 2, 1997; 297(1):1-92.
Mesch S et al. From a library of MAG antagonists to nanomolar CD22 ligands. ChemMedChem. Jan. 2, 2012;7 (1):134-43. Epub Oct. 11, 2011.

(56) References Cited

OTHER PUBLICATIONS

Miyazaki K et al. Synthesis and antitumor activity of novel dolastatin 10 analogs. Chem Pharm Bull (Tokyo). 1995;43(10):1706-1718.

Mohammad RM et al. An orthotopic model of human pancreatic cancer in severe combined immunodeficient mice: potential application for preclinical studies. Clin Cancer Res. Apr. 1998a;4(4):887-94.

Mohammad RM et al. Successful treatment of human chronic lymphocytic leukemia xenografts with combination biological agents auristatin PE and bryostatin 1. Clin Cancer Res. May 1998b;4(5):1337-43.

Mohammad RM et al. A new tubulin polymerization inhibitor, auristatin PE, induces tumor regression in a human Waldenstrom's macroglobulinemia xenograft model. Int J Oncol. Aug. 1999;15(2):367-72.

Moldenhauer G et al. Therapeutic potential of amanitin-conjugated anti-epithelial cell adhesion molecule monoclonal antibody against pancreatic carcinoma. J Natl Cancer Inst. Apr. 18, 2012;104(8):622-34. Epub Mar. 27, 2012.

Muhizi T et al. Synthesis and evaluation of N-alkyl-beta-D-glucosylamines on the growth of two wood fungi, Coriolus versicolor and Poria placenta. Carbohydr Res. Sep. 22, 2008;343(14):2369-75. Epub Jul. 15, 2008.

Oflazoglu E et al. Potent anticarcinoma activity of the humanized anti-CD70 antibody h1F6 conjugated to the tubulin inhibitor auristatin via an uncleavable linker. Clin Cancer Res. Oct. 1, 2008a;14(19):6171-80. Epub Sep. 22, 2008.

Oflazoglu E et al. Combination of the anti-CD30-auristatin-E antibody-drug conjugate (SGN-35) with chemotherapy improves antitumour activity in Hodgkin lymphoma. Br J Haematol. Jul. 2008b;142(1):69-73. Epub May 8, 2008.

Payne G. Progress in immunoconjugate cancer therapeutics. Cancer Cell. Mar. 2003;3(3):207-12.

Perron V et al. A Method for the Selective Protection of Aromatic Amines in the Presence of Aliphatic Amines. Synthesis, 2009;(2):283-289. ePub Dec. 19, 2008.

Pettit G Antineoplastic agents. 592. Highly effective cancer cell growth inhibitory structural modifications of dolastatin 10. J Nat Prod. May 27, 2011;74(5):962-8. Epub May 2, 2011.

Pynnönen H et al. Novel Hydrophilic Glycolinkers for Improved Antibody-Drug Conjugates. Abstract. World ADC San Francisco. Oct. 15-16, 2013.

Pynnönen H et al. Novel Hydrophilic Glycolinkers for Improved Antibody-Drug Conjugates. Poster. World ADC San Francisco. Oct. 14-17, 2013.

Ribeiro SM et al. The activation sequence of thrombospondin-1 interacts with the latency-associated peptide to regulate activation of latent transforming growth factor-beta. J Biol Chem. May 7, 1999;274(19):13586-93.

Rillahan CD et al. Click and pick: identification of sialoside analogues for siglec-based cell targeting. Angew Chem Int Ed Engl. Oct. 29, 2012;51(44):11014-8. Epub Oct. 4, 2012.

Saarinen J et al. Impact of Different Site-Specific Payload Conjugation Chemistries on Efficacy, Achievable Drug-To-Antibody Ratio and Fc Receptor Affinity of Antibody-Drug Conjugates. Abstract. World ADC San Diego. Oct. 26-29, 2014.

Saarinen J et al. Impact of Different Site-Specific Payload Conjugation Chemistries on Efficacy, Achievable Drug-To-Antibody Ratio and Fc Receptor Affinity of Antibody-Drug Conjugates. Poster. World ADC San Diego. Oct. 26-29, 2014.

Saito G et al. Drug delivery strategy utilizing conjugation via reversible disulfide linkages: role and site of cellular reducing activities. Adv Drug Deliv Rev. Feb. 10, 2003;55(2):199-215.

Sammet B et al. Antibody-drug conjugates in tumor therapy. Pharm Pat Anal. Mar. 2012;1(1):65-73.

Sanderson RJ et al. In vivo drug-linker stability of an anti-CD30 dipeptide-linked auristatin immunoconjugate. Clin Cancer Res. Jan. 15, 2005;11(2 Pt 1):843-52.

Sarkar A et al. Nonsolvent application of ionic liquids: organo-catalysis by 1-alkyl-3-methylimidazolium cation based room-temperature ionic liquids for chemoselective N-tert-butyloxycarbonylation of amines and the influence of the C-2 hydrogen on catalytic efficiency. J Org Chem. Sep. 2, 2011;76(17):7132-40.

Satomaa T et al. Hydrophilic Character of Cytotoxic Payloads Affects Functional Properties of Antibody-Drug Conjugates. Abstract. World ADC Frankfurt. Feb. 23-25, 2015a.

Satomaa T et al. Hydrophilic Character of Cytotoxic Payloads Affects Functional Properties of Antibody-Drug Conjugates. Poster. World ADC Frankfurt Feb. 23-25, 2015a.

Satomaa T et al. (2015b) Hydrophilic Character of Cytotoxic Payloads Affects Functional Properties of Antibody-Drug Conjugates. Abstract. PEGS Boston. May 4-8, 2015b.

Satomaa T et al. (2015b) Hydrophilic Character of Cytotoxic Payloads Affects Functional Properties of Antibody-Drug Conjugates. PEGS Boston. Poster. May 4-8, 2015b.

Schuster HJ et al. Synthesis of the first spacer containing prodrug of a duocarmycin analogue and determination of its biological activity. Org Biomol Chem. Apr. 21, 2010;8(8):1833-42.

Schweizer A et al. Targeting of CD22-positive B-cell lymphoma cells by synthetic divalent sialic acid analogues. Eur J Immunol. Oct. 2012;42(10):2792-802. Epub Aug. 6, 2012.

Senter PD and Springer CJ. Selective activation of anticancer prodrugs by monoclonal antibody-enzyme conjugates. Adv Drug Deliv Rev. Dec. 31, 2001;53(3):247-64.

Senter PD. Industrial R&D glimpsed. Nature Biotech. Nov. 2007; 25(11):1219.

Seubert CM et al. Enhanced tumor therapy using vaccinia virus strain GLV-1h68 in combination with a β-galactosidase-activatable prodrug seco-analog of duocarmycin SA. Cancer Gene Ther. Jan. 2011;18(1):42-52. Epub Sep. 10, 2010.

Stahelin HF and Von Wartburg A. The chemical and biological route from podophyllotoxin glucoside to etoposide: ninth Cain memorial Award lecture. Cancer Res. Jan. 1, 1991;51(1):5-15.

Staudacher E et al. Alpha 1-6(alpha 1-3)-difucosylation of the asparagine-bound N-acetylglucosamine in honeybee venom phospholipase A2. Glycoconj J. Apr. 1992;9(2):82-5.

Sutherland MS et al. (2006) Lysosomal trafficking and cysteine protease metabolism confer target-specific cytotoxicity by peptide-linked anti-CD30-auristatin conjugates. J Biol Chem. 281(15):10540-7.

Swarts BM et al. Synthesis and CD structural studies of CD52 peptides and glycopeptides. Carbohydr Res. Nov. 24, 2008;343(17):2894-902.

Tashiro Y et al. Effect of lipophilicity on in vivo iontophoretic delivery. II. Beta-blockers. Biol Pharm Bull. Jun. 2001;24(6):671-7.

Tietze LF et al. Stereoselective synthesis of (1-alkoxyalkyl) alpha- and beta-D-glucopyranosiduronates (acetal-glucopyranosiduronates): a new approach to specific cytostatics for the treatment of cancer. Carbohydr Res. Sep. 15, 1988;180(2):253-62.

Tietze LF et al. Proton-mediated liberation of aldophosphamide from a nontoxic prodrug: a strategy for tumor-selective activation of cytocidal drugs. Cancer Res. Aug. 1, 1989;49(15):4179-84.

Tietze LF et al. Prodrugs of the Cytostatic CC-1065 That Can Be Activated in a Tumor-Selective Manner. Angewandte Chemie, International Edition, Dec. 1996; 35: 2674-2677.

Tietze LF et al. Highly selective glycosylated prodrugs of cytostatic CC-1065 analogues for antibody-directed enzyme tumor therapy. Chembiochem. Oct. 1, 2001a;2(10):758-65.

Tietze LF et al. A strategy for tumor-selective chemotherapy by enzymatic liberation of seco-duocarmycin SA-derivatives from nontoxic prodrugs. Bioorg Med Chem. Jul. 2001b;9(7):1929-1939.

Tietze LF et al. Synthesis and Biological Evaluation of Novel Analogues and Prodrugs of the Cytotoxic Antibiotic CC-1065 for Selective Cancer Therapy. Eur J Org Chem. Apr. 16, 2002a; 2002(10):1634-1645.

Tietze LF et al. Proof of principle in the selective treatment of cancer by antibody-directed enzyme prodrug therapy: the development of a highly potent prodrug. Angew Chem Int Ed Engl. Mar. 1, 2002b;41(5):759-61.

Tietze LF and Feuerstein T. Enzyme and proton-activated prodrugs for a selective cancer therapy. Curr Pharm Des. 2003;9(26):2155-75.

(56) References Cited

OTHER PUBLICATIONS

Tietze LF et al. Investigation of reactivity and selectivity of DNA-alkylating duocarmycin analogues by high-resolution mass spectrometry. Angew Chem Int Ed Engl. Oct. 6, 2006a;45(39):6570-6574.

Tietze LF et al. Antitumor agents: development of highly potent glycosidic duocarmycin analogues for selective cancer therapy. Angew Chem Int Ed Engl. Oct. 6, 2006b;45(39):6574-7.

Tietze LF et al. Selective treatment of cancer: synthesis, biological evaluation and structural elucidation of novel analogues of the antibiotic CC-1065 and the duocarmycins. Chemistry. 2007;13(16):4396-409.

Tietze LF et al. Asymmetric synthesis and biological evaluation of glycosidic prodrugs for a selective cancer therapy. ChemMedChem. Dec. 2008a;3(12):1946-55.

Tietze LF et al. Duocarmycin-based prodrugs for cancer prodrug monotherapy. Bioorg Med Chem. Jun. 15, 2008b;16(12):6312-8.

Tietze LF et al. Synthesis and biological evaluation of a novel pentagastrin-toxin conjugate designed for a targeted prodrug monotherapy of cancer Int J Mol Sci. May 2008c;9(5):821-37.

Tietze LF et al. Enantio- and diastereoselective synthesis of duocarmycine-based prodrugs for a selective treatment of cancer by epoxide opening. Chemistry. Jan. 18, 2008d;14(3):895-901. ePub Nov. 21, 2007.

Tietze LF et al. Investigation of the transformations of a novel anti-cancer agent combining HPLC, HPLC-MS and direct ESI-HRMS analyses. Anal Bioanal Chem. Sep. 2009a;395(2):437-48.

Tietze LF et al. Synthesis and biological studies of different duocarmycin based glycosidic prodrugs for their use in the antibody-directed enzyme prodrug therapy. J Med Chem. Jan. 22, 2009b;52(2):537-43.

Tietze LF et al. Determination of the biological activity and structure activity relationships of drugs based on the highly cytotoxic duocarmycins and CC-1065. Toxins (Basel). Dec. 2009c;1(2):134-50. Epub Dec. 2, 2009.

Tietze LF and Krewer B. Antibody-directed enzyme prodrug therapy: a promising approach for a selective treatment of cancer based on prodrugs and monoclonal antibodies. Chem Biol Drug Des. Sep. 2009d;74(3):205-11.

Tietze LF and Krewer B. Novel analogues of CC-1065 and the duocarmycins for the use in targeted tumour therapies. Anticancer Agents Med Chem. Mar. 2009e;9(3):304-25.

Tietze LF et al. Glycosidic prodrugs of highly potent bifunctional duocarmycin derivatives for selective treatment of cancer. Angew Chem Int Ed Engl. Sep. 24, 2010a;49(40):7336-9.

Tietze LF et al. Synthesis of Fluorescence-Labelled Glycosidic Prodrugs Based on the Cytotoxic Antibiotic Duocarmycin. Eur. J Org Chem. Dec. 2010b;2010(36):6909-6921. DOI: 10.1002/ejoc.201000966.

Tietze LF et al. Synthesis and biological evaluation of prodrugs based on the natural antibiotic duocarmycin for use in ADEPT and PMT. Chemistry. Feb. 7, 2011a;17(6):1922-9. Epub Jan. 7, 2011.

Tietze LF and Schmuck K. Prodrugs for targeted tumor therapies: recent developments in ADEPT, GDEPT and PMT. Curr Pharm Des. 2011b;17(32):3527-47.

Tietze LF et al. Synthesis, biological evaluation, and live cell imaging of novel fluorescent duocarmycin analogs. Chem Biodivers. Nov. 2012;9(11):2559-70.

Tietze LF et al. Photoactivatable prodrugs of highly potent duocarmycin analogues for a selective cancer therapy. Chemistry. Jan. 28, 2013;19(5):1726-31.

Trail PA et al. Monoclonal antibody drug immunoconjugates for targeted treatment of cancer. Cancer Immunol Immunother May 2003;52(5):328-37.

Tranoy-Opalinski I et al. β-Glucuronidase-responsive prodrugs for selective cancer chemotherapy: an update. Eur J Med Chem. Mar. 3, 2014;74:302-13. Epub Jan. 11, 2014.

Trouet A et al. A covalent linkage between daunorubicin and proteins that is stable in serum and reversible by lysosomal hydrolases, as required for a lysosomotropic drug-carrier conjugate: in vitro and in vivo studies. Proc Natl Acad Sci U S A. Jan. 1982;79(2):626-9.

Umemoto N et al. Preparation and in vitro cytotoxicity of a methotrexate-anti-MM46 monoclonal antibody conjugate via an oligopeptide spacer. Int J Cancer. Apr. 15, 1989;43(4):677-84.

Van Der Lee MM et al. The Preclinical Profile of the Duocarmycin-Based HER2-Targeting ADC SYD985 Predicts for Clinical Benefit in Low HER2-Expressing Breast Cancers. Mol Cancer Ther. Mar. 2015;14(3):692-703. Epub Jan. 14, 2015.

Van Geel R et al. Chemoenzymatic Conjugation of Toxic Payloads to the Globally Conserved N-Glycan of Native mAbs Provides Homogeneous and Highly Efficacious Antibody-Drug Conjugates. Bioconjug Chem. Nov. 18, 2015;26(11):2233-42. Epub Jun. 10, 2015.

Wang Y et al. Synthesis and preliminary cytotoxicity study of glucuronide derivatives of CC-1065 analogues. Bioorg Med Chem. Apr. 3, 2003;11(7):1569-75.

Wirth T et al. The two faces of potent antitumor duocarmycin-based drugs: a structural dissection reveals disparate motifs for DNA versus aldehyde dehydrogenase 1 affinity. Angew Chem Int Ed Engl. Jul. 1, 2013;52(27):6921-5. Epub May 16, 2013.

Woyke T et al. In vitro activities and postantifungal effects of the potent dolastatin 10 derivative auristatin PHE. Antimicrob Agents Chemother Dec. 2001;45(12):3580-4.

Woyke T et al. Effect of auristatin PHE on microtubule integrity and nuclear localization in Cryptococcus neoformans. Antimicrob Agents Chemother. Dec. 2002;46(12):3802-8.

Yang J et al. Studies on the substrate specificity of *Escherichia coli* galactokinase. Org Lett. Jun. 26, 2003;5(13):2223-6.

Yonemoto IT et al. Mutasynthesis of a potent anticancer sibiromycin analogue. ACS Chem Biol. Jun. 15, 2012;7(6):973-7.

Zajackowski I et al. New dimeric tetrapeptide enkephalin analogs with five or six carbon hydrophilic spacers. Z. Naturforsch. 1995;50b:1329-1334.

Zhang G et al. Syntheses and biological activities of disaccharide daunorubicins. J Med Chem. Aug. 1, 2005;48(16):5269-78.

Zhao P et al . Amide N-glycosylation by Asm25, an N-glycosyltransferase of ansamitocins. Chem Biol. Aug. 25, 2008;15(8):863-74.

Zhu Z et al. Site-specific antibody-drug conjugation through an engineered glycotransferase and a chemically reactive sugar. MAbs. 2014;6(5):1190-200.

\* cited by examiner

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Peptide cleavable by a lysosomal peptidase

<400> SEQUENCE: 1

Ala Leu Ala Leu
1
```

SACCHARIDE DERIVATIVE OF A TOXIC PAYLOAD AND ANTIBODY CONJUGATES THEREOF

This application is filed under 35 U.S.C. § 371 and claims priority to International Application No. PCT/FI2015/050471 filed on Jun. 26, 2015 and claims the benefit of FI 20145634 filed on Jun. 30, 2014, FT 20146069 filed on Dec. 5, 2014, and FI 2015512.0 filed on Feb. 23, 2015; all of which are hereby incorporated by reference in their entirety.

FIELD OF THE INVENTION

The invention relates to a molecule, an antibody-drug conjugate, methods for preparing the molecule and the antibody-drug conjugate, a pharmaceutical composition and a method of treating and/or modulating the growth of and/or prophylaxis of tumor cells.

BACKGROUND

Antibody-drug conjugates may be useful, for instance, in the therapy of cancer. A number of potential drugs are known, and the conjugates currently available utilize various chemistries to conjugate the drus; however, many of them may not be optimal in terms of e.g. activity of the drug or aqueous solubility and stability of the conjugate. Many drugs are poorly soluble in aqueous solutions, and therefore conjugating a large number of drug molecules to a single antibody molecule tends to be challenging.

A conjugate having suboptimal solubility may not be efficiently delivered to its target. A drug may not always be efficiently released from the protein and/or delivered into cells or into various parts of cells. The activity, such as toxicity, of the payload molecule may be reduced as a result of the conjugation. In some cases, the conjugate may not be stable towards chemical or biochemical degradation during manufacturing or in physiological conditions, e.g. in blood, serum, plasma or tissues.

Cytotoxic drugs used in antibody-drug conjugates may have toxicity to normal non-target cells. The hydrophobicity of the drugs may allow a drug liberated from the conjugate to enter any cell in the body. Development of hydrophilic non-cleavable linkers to join the cytotoxic drug and antibody has contributed to better safety to non-target cells. However, a bystander effect would be desirable in a drug to be used in an antibody conjugate, i.e. ability to diffuse from the first target cell to another target cell. This is especially useful when cancer cells show heterogeneous expression of the target antigen. For the bystander effect, however, hydrophilicity is not beneficial (Doronina et al. 2006, Bioconjug. Chem. 17(1):114-24).

Drugs and conjugates comprising the drugs with beneficial properties are therefore in need.

SUMMARY

The antibody-drug conjugate is characterized by what is presented in claim 1.

The molecule is disclosed herein.

The method for preparing the antibody-drug conjugate or the molecule is disclosed herein.

The method for preparing the antibody-drug conjugate is disclosed herein.

The pharmaceutical composition is characterized by what is disclosed herein.

The antibody-drug conjugate or pharmaceutical composition for use as a medicament is disclosed herein.

The antibody-drug conjugate or pharmaceutical composition for use in the treatment of cancer is disclosed herein.

The method of treating and/or modulating the growth of and/or prophylaxis of tumor cells in humans or animals is disclosed herein.

FIGURE LEGENDS

FIG. 1. MALDI analysis of Fc fragments of ADC compounds. Upper panel an anti-EGFR and lower panel an anti-HER2 antibody Fc.

Figure 2:
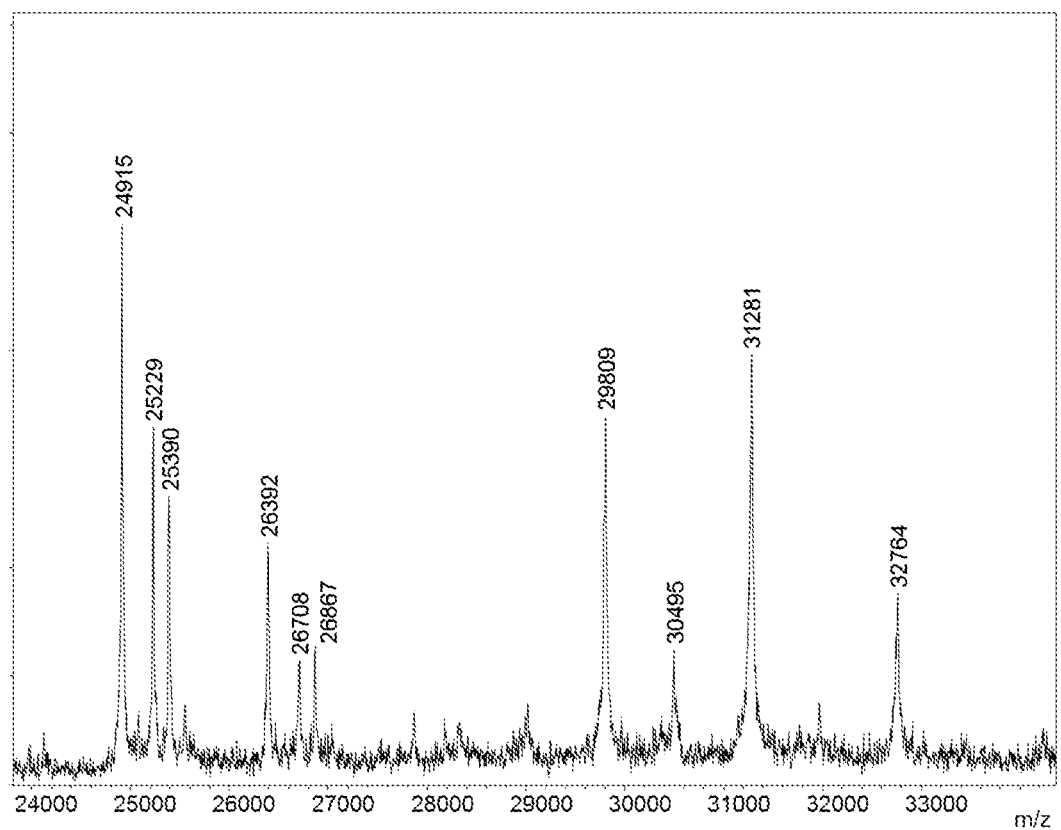

FIG. 2. MALDI-TOF analysis of FabRICATOR-digested MMAG-PAB-CV-maleimidoyl-antibody drug conjugate.

Figure 3:
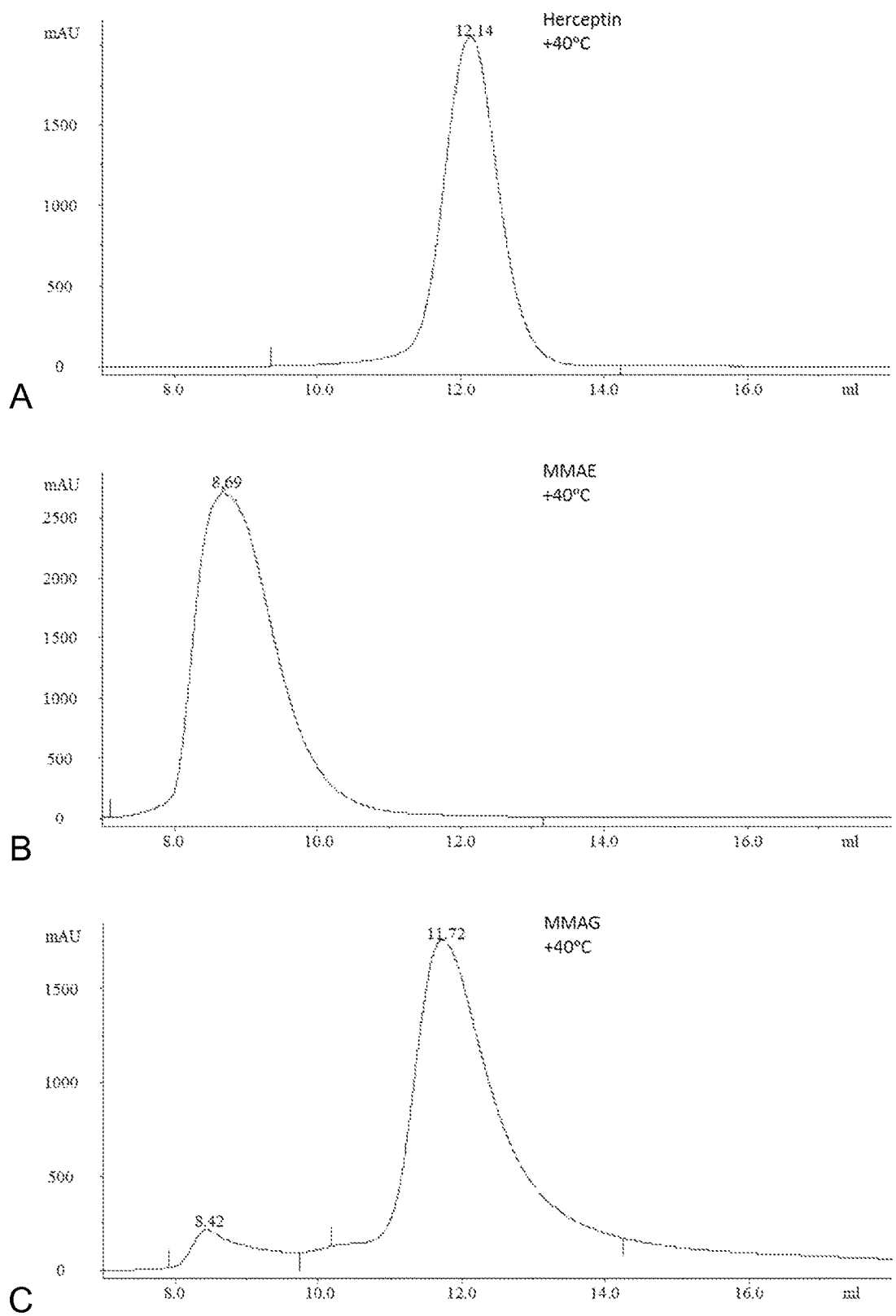

FIG. 3. Size-exclusion HPLC analysis of high-drug-to-antibody ratio antibody-drug conjugate (DAR8 ADC) aggregation under heat stress. DAR8 ADCs and control antibody were incubated at +40° C. for two days and then analyzed. Chromatograms show absorbance at 214 nm. Panel (A) Control antibody trastuzumab (Herceptin®), eluting at position of monomeric antibody at about minutes and showing no aggregation; panel (B) trastuzumab-MMAE ADC, with all ADC aggregated into high-molecular weight components eluting at about 8 minutes; and panel (C) trastuzumab-MMAG ADC, with 5% (A214 nm) of ADC aggregated into high-molecular weight components eluting at about 8 minutes, and 95% of ADC non-aggregated eluting at about 12 minutes.

Figure 4:
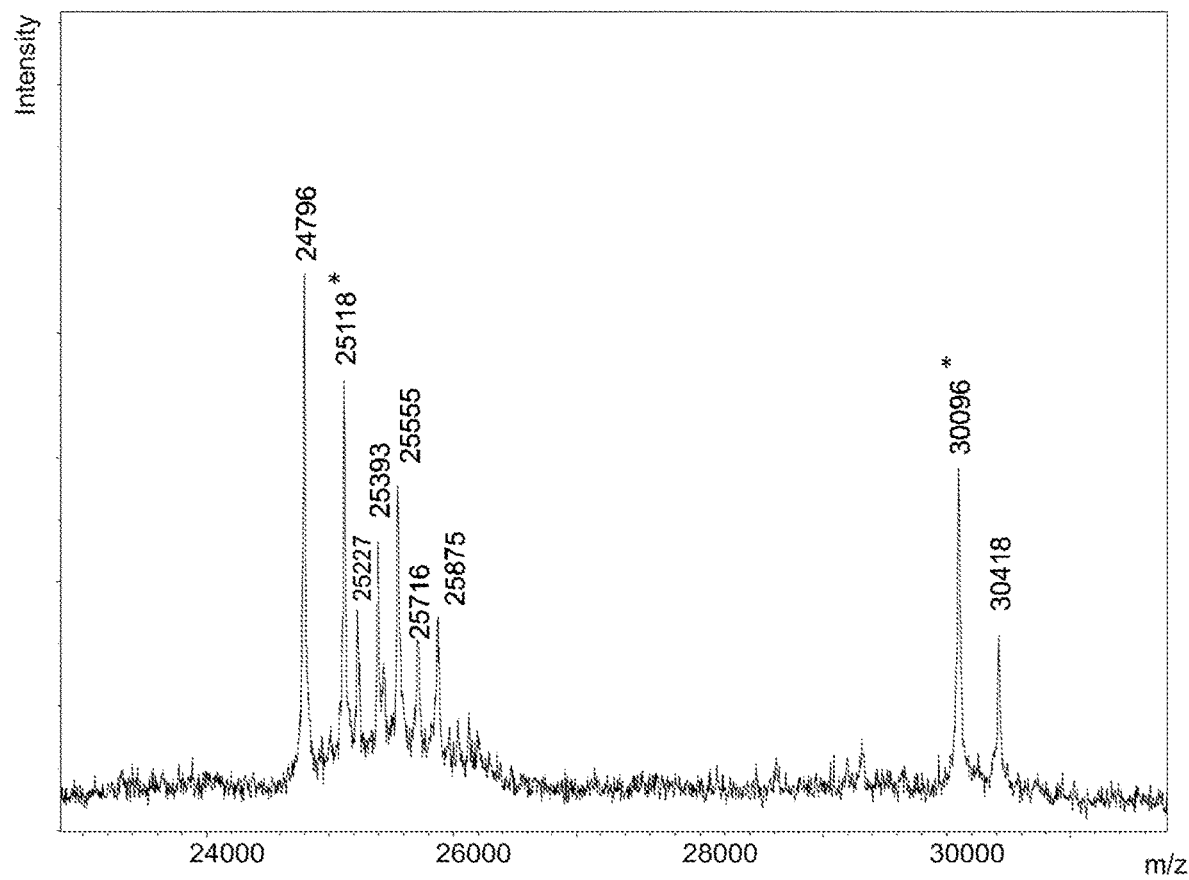

FIG. 4. MALDI-TOF-analysis of MMAG-PAB-CV-maleimidoyl-2G12-antibody drug conjugate fragments. *, unidentified signal.

Figure 5:
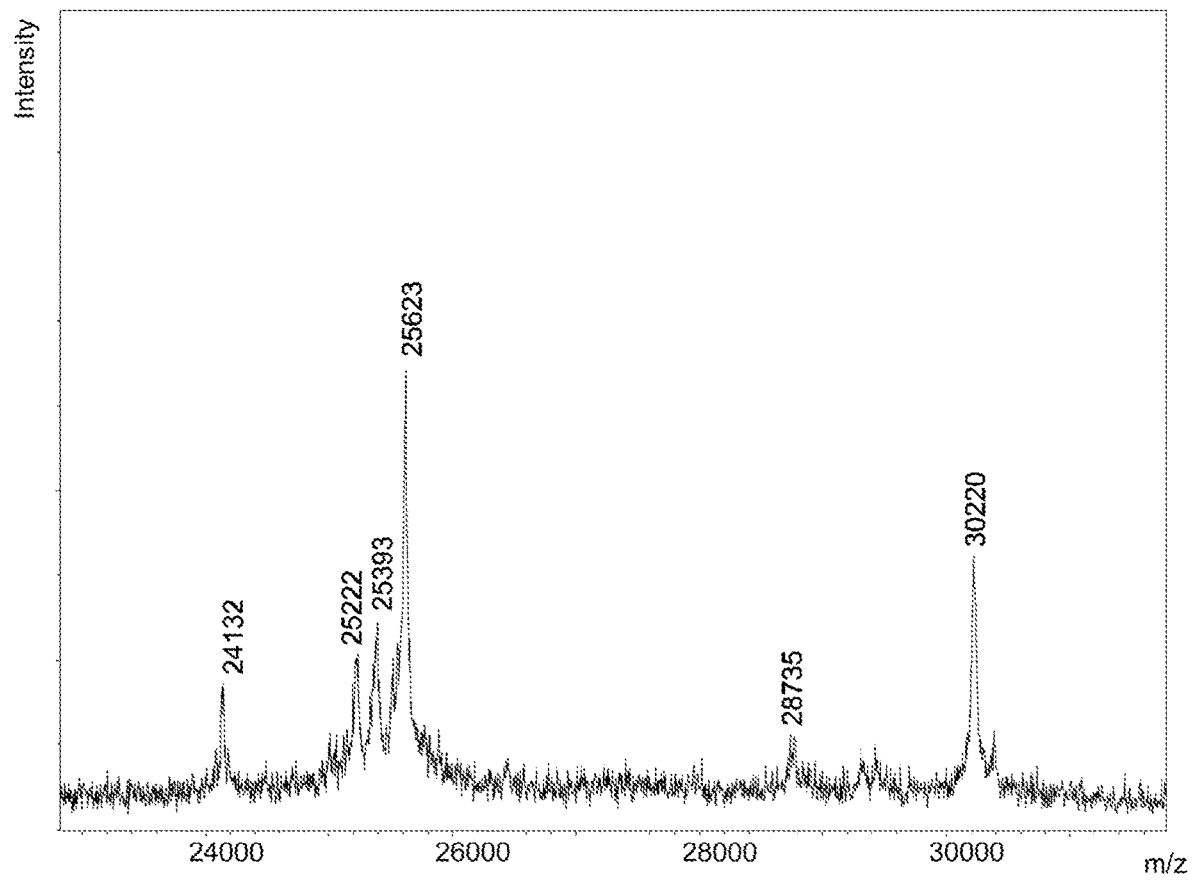

FIG. 5. MALDI-TOF-analysis of MMAG-PAB-CV-maleimidoyl-nimotuzumab-antibody drug conjugate fragments.

Figure 6:
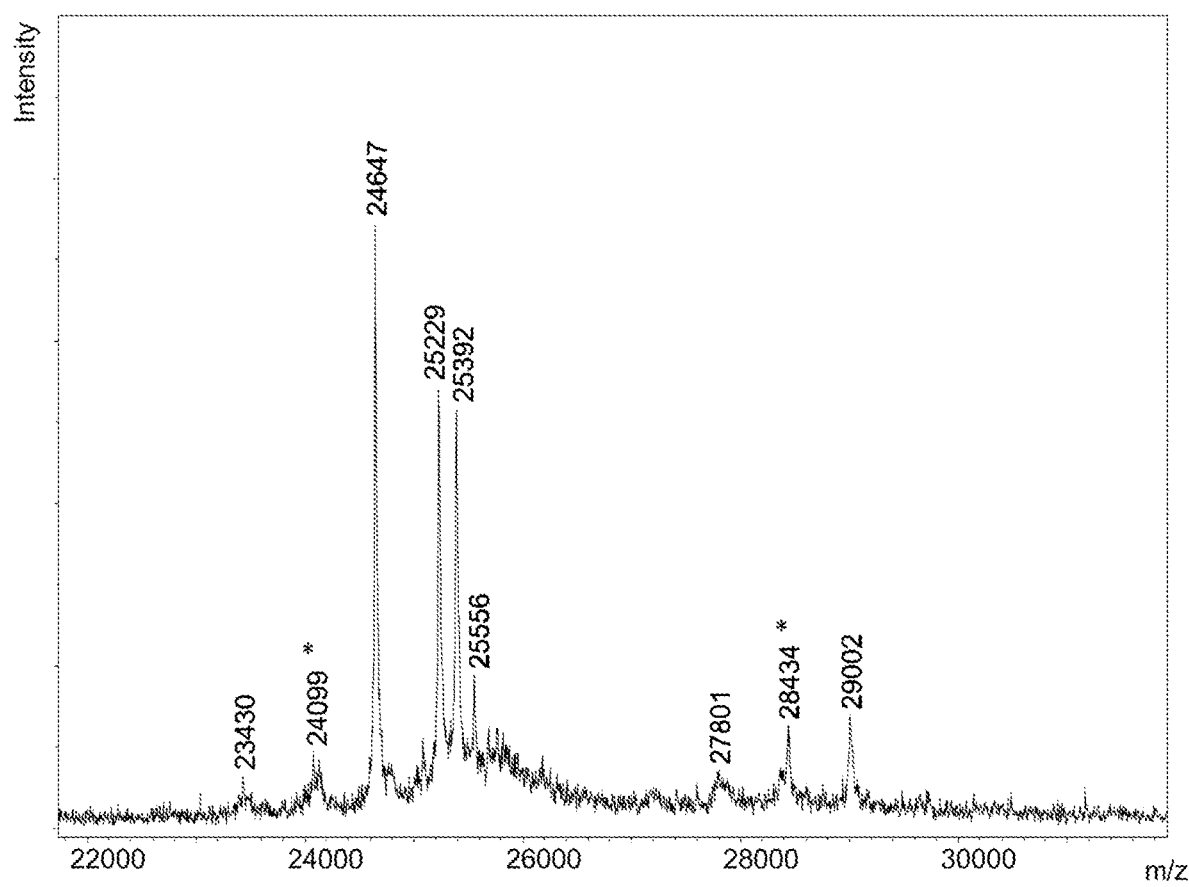

FIG. 6. MALDI-TOF-analysis of Gal-Duocarmycin-PAB-CV-maleimidoyl-antibody drug conjugate fragments. *, unidentified signal.

Figure 7:
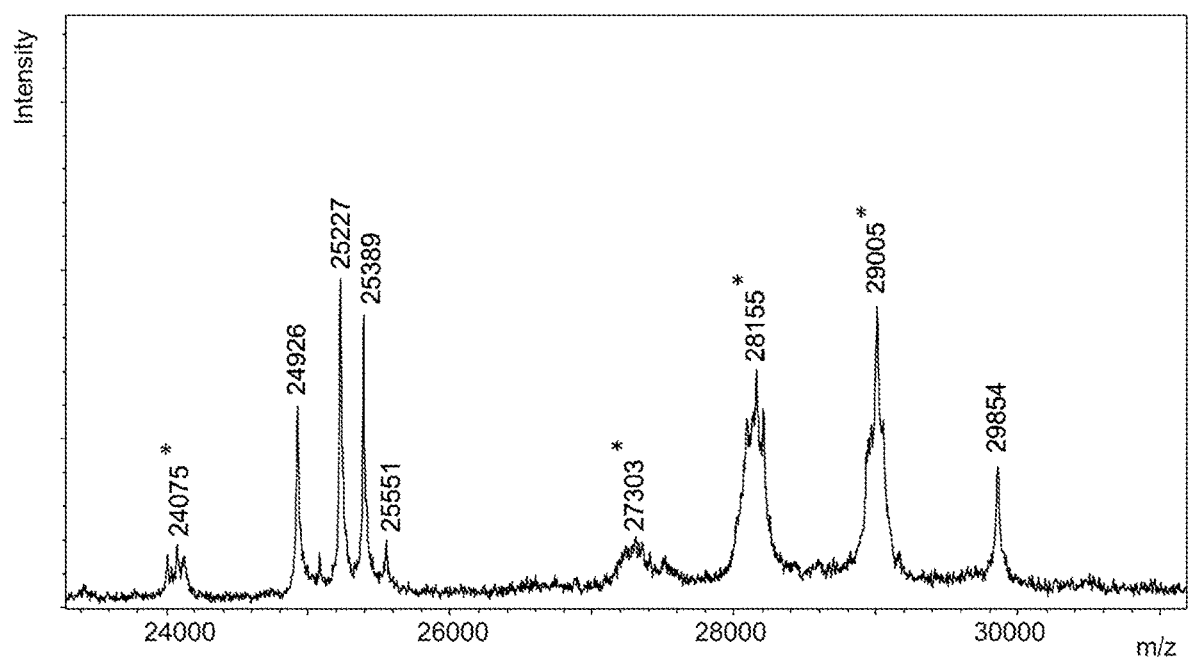

FIG. 7. MALDI-TOF-analysis of MMAU-PAB-CV-maleimidoyl-antibody drug conjugate fragments. *, unidentified signals FIG. 8. MALDI-TOF-analysis of MMAX-PAB-CV-maleimidoyl-antibody drug conjugate fragments. *, unidentified signals

DETAILED DESCRIPTION

A molecule comprising a saccharide bound via an O-glycosidic bond to a hydroxyl group of an auristatin is disclosed.

In an embodiment, the saccharide is bound via an O-glycosidic bond to an ester linker group bound via an ester bond to a hydroxyl group of the auristatin, and the ester linker group has a structure according to formula XII

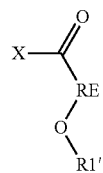

Formula XII wherein

X is the bond to the auristatin;

R1' is the saccharide bound via the O-glycosidic bond; and

RE is selected from the group consisting of —CH$_2$—, —CH$_2$CH$_2$—, —CH$_2$CH$_2$CH$_2$—, —CH$_2$CH$_2$CH$_2$CH$_2$—, C$_1$-C$_4$ alkyl, heteroalkyl, branched alkyl, branched heteroalkyl, cyclic alkyl, cyclic heteroalkyl, substituted C$_1$-C$_4$ alkyl, heteroalkyl, branched alkyl, branched heteroalkyl, cyclic alkyl, and cyclic heteroalkyl.

In the context of this specification, the term "ester linker" should be understood as referring to a group that may be bound via an O-glycosidic bond to the saccharide (e.g. R1 or R1' defined in this specification) and via an ester bond to a hydroxyl group of the toxic payload molecule. The ester bond is relatively stable in serum, but may be hydrolysable inside cells and in tumor microenvironments.

In an embodiment, the molecule is represented by formula I

Formula I wherein A is an auristatin;

R1 is a saccharide bound to a hydroxyl group of the auristatin via an O-glycosidic bond; and R2 is H or a linker group.

In an embodiment, the molecule is represented by formula I

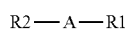

Formula I wherein A is an auristatin;

R1 is L''-R1', wherein R1' is a saccharide bound via an O-glycosidic bond to L'', and L'' is bound via an ester bond to a hydroxyl group of the auristatin and has a structure according to formula XII

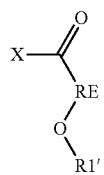

Formula XII wherein X is the bond to the toxic payload molecule; R1' is the saccharide bound via the O-glycosidic bond; and RE is selected from the group consisting of —CH$_2$—, —CH$_2$CH$_2$—, —CH$_2$CH$_2$CH$_2$—, —CH$_2$CH$_2$CH$_2$CH$_2$—, C$_1$-C$_4$ alkyl, heteroalkyl, branched alkyl, branched heteroalkyl, cyclic alkyl, cyclic heteroalkyl, substituted C$_1$-C$_4$ alkyl, heteroalkyl, branched alkyl, branched heteroalkyl, cyclic alkyl, and cyclic heteroalkyl; and R2 is H or a linker group.

In an embodiment, the saccharide is a monosaccharide, a disaccharide or an oligosaccharide.

In the context of this specification, the term "auristatin" may refer to any auristatin or auristatin derivative that comprises a hydroxyl group. It may also refer to the auristatin moiety of the molecule according to one or more embodiments; said auristatin moiety may be modified as described in this specification, e.g. by the addition of a linker group.

In an embodiment, the auristatin is monomethylauristatin E. Monomethylauristatin E comprises a free hydroxyl group, to which saccharides may be added.

In an embodiment, the auristatin is monomethylauristatin F, W or M, or an auristatin modified at the carboxy terminus with a peptide comprising a hydroxy amino acid. In an embodiment, the hydroxy amino acid is serine or threonine. These auristatins comprise a free hydroxyl group, to which saccharides may be added.

The saccharide is bound to a hydroxyl group of the auristatin via an O-glycosidic bond. In other words, the O-glycosidic bond is formed by a reaction between a hydroxyl group of the auristatin and a functional group of the saccharide. The functional group of the saccharide may be e.g. the hydroxyl group or a trichloroacetimidate group substituting the anomeric carbon. An O-glycosidic bond is a glycosidic bond formed between the hemiacetal or hemiketal group of a saccharide (or a molecule derived from a saccharide) and the hydroxyl group of the auristatin. The O-glycosidic bond binds the anomeric carbon (carbon 1, or carbon 2 in some saccharides, for instance neuraminic acids) of the saccharide to the hydroxyl group of the auristatin.

A molecule comprising a saccharide bound via a glycosidic bond to a toxic payload molecule is also disclosed. In an embodiment, the glycosidic bond is cleavable in human or animal cells so that the toxic payload molecule is liberated.

A molecule comprising a saccharide bound via an O-glycosidic bond to a hydroxyl group of a toxic payload molecule is also disclosed.

In an embodiment, the saccharide is bound via an O-glycosidic bond to an ester linker group bound via an ester bond to a hydroxyl group of the toxic payload molecule, and the ester linker group has a structure according to formula XII

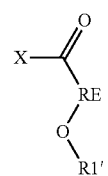

Formula XII wherein X is the bond to the toxic payload molecule; R1' is the saccharide bound via the O-glycosidic bond; and RE is selected from the group consisting of —CH$_2$—, —CH$_2$CH$_2$—, —CH$_2$CH$_2$CH$_2$—, —CH$_2$CH$_2$CH$_2$CH$_2$—, C$_1$-C$_4$ alkyl, heteroalkyl, branched alkyl, branched heteroalkyl, cyclic alkyl, cyclic heteroalkyl, substituted C$_1$-C$_4$ alkyl, heteroalkyl, branched alkyl, branched heteroalkyl, cyclic alkyl, and cyclic heteroalkyl.

In an embodiment, the molecule is represented by formula I, wherein A is a toxic payload molecule; R1 is a saccharide bound to a hydroxyl group of the toxic payload molecule via an O-glycosidic bond; and R2 is H, a linker group, or a saccharide bound to a hydroxyl group of the toxic payload molecule via an O-glycosidic bond.

In an embodiment, the molecule is represented by formula I, wherein

A is a toxic payload molecule;

R1 is L''-R1', wherein R1' is a saccharide bound via an O-glycosidic bond to L'', and L'' is bound via an ester bond to a hydroxyl group of the toxic payload molecule and has a structure according to formula XII; and R2 is H, a linker group, or a saccharide bound to a hydroxyl group of the toxic payload molecule via an O-glycosidic bond.

In the context of this specification, the term "toxic payload molecule" may refer to any toxic payload molecule or toxic payload molecule derivative that comprises a hydroxyl group. It may also refer to the toxic payload molecule moiety of the molecule according to one or more embodiments; said toxic payload molecule moiety may be modified as described in this specification, e.g. by the addition of a linker group. The term "toxic payload molecule" may also refer to a cytotoxic agent.

The toxic payload molecule may be any compound that results in the death of a cell, or induces cell death, or in some manner decreases cell viability. The toxic payload molecule can be any of many small molecule drugs, including, but not limited to, dolastatins; auristatins; epothilones; daunorubicins and doxorubicins; alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylene-phosphoramide, triethylenethiophosphaoramide and trimethylolomelamine; acetogenins (especially bullatacin and bullatacinone); camptothecins (including the synthetic analogue topotecan); bryostatin; callystatin; CC-1065 (including its adozelesin, carzelesin and bizelesin synthetic analogues); cryptophycins (particularly cryptophycin 1 and cryptophycin 8); duocarmycin (including the synthetic analogues, KW-2189 and CBI-TMI); eleutherobin; pancratistatin; sarcodictyins; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicins, especially calicheamicin γ1; dynemicin, including dynemicin A; esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, detorubicin, 6-diazo-5-oxo-L-norleucine, other doxorubicin derivatives including morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-fluorouracil; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; maytansinoids, such as maytansine and N-glucosylmaytansinoids, ansamitocins, DM-1, DM-4; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; anti-hormonal agents that act to regulate or inhibit hormone action on tumours, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA; tubulysins; amanitins, such as α-amanitin; and pharmaceutically acceptable salts, acids or derivatives of any of the above as well as analogues and derivatives thereof, some of which are described below.

In an embodiment, the toxic payload molecule is a dolastatin, auristatin, doxorubicin, DM1, epirubicin, duocarmycin or any analogue or derivative thereof.

In an embodiment, the toxic payload molecule is a dolastatin, auristatin, doxorubicin, or any analogue or derivative thereof.

In an embodiment, the toxic payload molecule is dolastatin 10 or any derivative thereof.

In an embodiment, the toxic payload molecule is dolastatin 15 or any derivative thereof.

In an embodiment, the toxic payload molecule is auristatin F or any derivative thereof.

In an embodiment, the toxic payload molecule is dolastatin 10, dolastatin 15, or auristatin F.

In an embodiment, the toxic payload molecule is dolastatin 10.

In an embodiment, the toxic payload molecule is dolastatin 15.

In an embodiment, the toxic payload molecule is auristatin F.

Dolastatins that can be used are well known in the art and can be isolated from natural sources according to known methods or prepared synthetically according to known methods.

Examples of suitable dolastatins include monomethyl and desmethyl dolastatins 10, 15, C, D and H, monomethyl and desmethyl isodolastatin H, and analogues and derivatives thereof. Dolastatins 10 and 15 are the most potent cytotoxic agents among the naturally occurring dolastatins. Monomethyl and desmethyl dolastatins 10 and 15 can be prepared by chemical synthesis according to standard peptide synthesis chemistry.

Examples of suitable auristatins that can be used include (but are not limited to) monomethyl and desmethyl auristatins E, F, EB, EFP, PY, PYE, PE, PHE, TP, 2-AQ and 6-AQ, e.g. described in U.S. Pat. No. 5,635,483; Int. J. Oncol. 15:367-72 (1999); Mol. Cancer Ther. 3:921-32 (2004); U.S. application Ser. No. 11/134,826; U.S. Patent Publication Nos. 20060074008 and 2006022925; and Pettit, G. R., et al. (2011) J. Nat. Prod. 74:962-8; and monomethyl and desmethyl auristatins W and M, described in Doronina et al. (2008) Bioconj. Chem. 19:1960-3.

In an embodiment, the toxic payload molecule is daunorubicin or doxorubicin.

In an embodiment, the toxic payload molecule is a maytansinoid. The maytansinoid may be an N-glucosylmaytansinoid. When the toxic payload molecule is an N-glucosylmaytansinoid, the saccharide may be bound via an O-glycosidic bond to a hydroxyl group of the N-glycosyl moiety.

In an embodiment, the toxic payload molecule is maytansine, an ansamitocin, DM1 or DM4 (also known as DM-4).

In an embodiment, the toxic payload molecule is DM1. DM1 is also known as DM-1 and mertansine.

In an embodiment, the toxic payload molecule is a rubicin. Suitable rubicins may be e.g. daunorubicins, doxorubicins, detorubicin, other doxorubicin derivatives including morpholino-doxorubicin, cyanomorpholino-doxorubicin, 2-pyrrolino-doxorubicin, deoxydoxorubicin, epirubicin, esorubicin, idarubicin, rodorubicin, zorubicin, and pirarubicin.

In an embodiment, the toxic payload molecule is epirubicin.

In an embodiment, the toxic payload molecule is duocarmycin. Suitable duocarmyxins may be e.g. duocarmycin A, duocarmycin B1, duocarmycin B2, duocarmycin C1, duocarmycin C2, duocarmycin D, duocarmycin SA, duocarmycin MA, and CC-1065. The term "duocarmycin" should be understood as referring also to synthetic analogs of duocarmycins, such as adozelesin, bizelesin, carzelesin, KW-2189 and CBI-TMI.

In an embodiment, the toxic payload molecule comprises a duocamycin fragment that can alkylate DNA. In an embodiment, the toxic payload molecule comprises two or more duocamycin fragments that can alkylate DNA. In an embodiment, the toxic payload molecule comprises two duocamycin fragments that can alkylate DNA.

Examples of suitable dolastatins include monomethyl and desmethyl dolastatins 10, 15, C, D and H, monomethyl and desmethyl isodolastatin H, and analogues and derivatives thereof.

In an embodiment, the toxic payload molecule is a tubulysin.

In an embodiment, the toxic payload molecule is an amanitin, such as an α-amanitin.

In an embodiment, the toxic payload molecule is a cryptophycin.

In an embodiment, the toxic payload molecule comprises a free hydroxyl group, to which saccharides may be added.

One skilled in the art of cytotoxic agents will readily understand that each of the cytotoxic agents described herein can be modified in such a manner that the resulting compound still retains the specificity and/or activity of the starting compound. In an embodiment, the cytotoxic agent is modified so that it contains a hydroxyl group whereto a saccharide is attached via an O-glycosidic bond. The skilled person will also understand that many of these compounds can be used in place of the cytotoxic agents described herein. Thus, the cytotoxic agents should be understood as including any analogues and derivatives of the compounds described herein.

In an embodiment, the saccharide is bound to a hydroxyl group of the toxic payload molecule via an O-glycosidic bond. In other words, the O-glycosidic bond is formed by a reaction between a hydroxyl group of the toxic payload molecule and a functional group of the saccharide.

In an embodiment, saccharide R1 or R1' is a monosaccharide, a disaccharide or an oligosaccharide.

The term "oligosaccharide" should be understood as referring to a saccharide comprising 2 to 8 monosaccharide units.

In the context of this specification, the term "linker group" may refer to any linker group that can be incorporated in the antibody-drug conjugate according to one or more embodiments. Linkers that may, in principle, be utilised are described e.g. in Dosio et al., Toxins 2011, 3, 848-883, and Sammet et al., Pharm. Pat. Analyst 2012, 1(1), 2046-8954. The linker group may comprise one or more linker groups or moieties. It may also comprise one or more groups formed by a reaction between two functional groups. A skilled person will realize that various different chemistries may be utilized when preparing the conjugate, and thus a variety of different functional groups and compounds containing them may be reacted to form the linker group. The linker group may also comprise a functional group that allows for conjugating the linker group to an antibody.

In an embodiment, RE is selected from the group consisting of —CH$_2$—, —CH$_2$CH$_2$—, —CH$_2$CH$_2$CH$_2$—, and —CH$_2$CH$_2$CH$_2$CH$_2$—.

In an embodiment, the molecule is represented by formula II

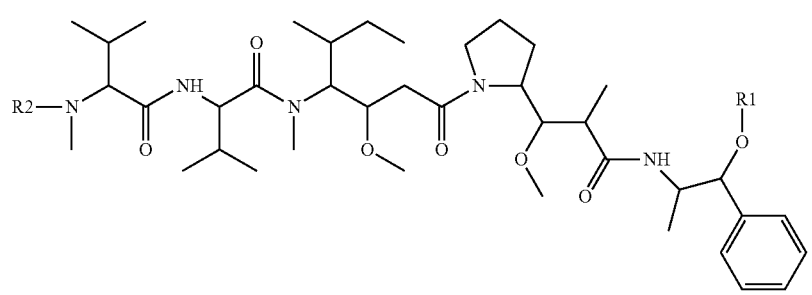

Formula II wherein R1 is a saccharide bound to the auristatin via an O-glycosidic bond, or L"-R1', wherein R1' is a saccharide bound via an O-glycosidic bond to L", and L" is bound via an ester bond to a hydroxyl group of the toxic payload molecule and has a structure according to formula XII; and R2 is H or a linker group.

In an embodiment, the molecule is represented by Formula II', Formula II", or Formula II'":

wherein R1 is a saccharide bound to the toxic payload molecule via an O-glycosidic bond, or L"-R1', wherein R1' is a saccharide bound via an O-glycosidic bond to L", and L" is bound via an ester bond to a hydroxyl group of the toxic payload molecule and has a structure according to formula XII;

AA is a peptide comprising a hydroxyl group whereto R1 is bound via the O-glycosidic bond; and R2 is H or a linker group.

In an embodiment, AA is a peptide comprising a dipeptide and a hydroxy amino acid comprising a hydroxyl group.

In an embodiment, the dipeptide is cleavable by a peptidase. In an embodiment, the dipeptide is selected from the group of $AA_1+AA_2$ dipeptides described in Doronina et al. (2008) Bioconj. Chem. 19:1961, Table 1.

In an embodiment, the hydroxy amino acid is serine or threonine.

In an embodiment, AA is Ile-Val-Ser.

In an embodiment, the saccharide comprises one or more glycosidic bonds that are cleavable by a lysosomal or an intracellular glycohydrolase.

In the context of this specification, the term glycohydrolase should be understood as referring to an enzyme capable of cleaving a glycosidic bond, regardless of the catalytic mechanism, for example a hydrolase, a lyase, an exoglycosidase, or an endoglycosidase.

In an embodiment, the saccharide comprises one or more glycosidic bonds that are cleavable by a human glycohydrolase.

In the context of this specification, the human glycohydrolase is any human glycosidase enzyme capable of removing the saccharide from the auristatin or the toxic payload.

In an embodiment, saccharide R1 or R1' is a monosaccharide, a disaccharide or an oligosaccharide.

In an embodiment, the saccharide R1 or R1' comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof.

In an embodiment, the human glycohydrolase is any human glycosidase enzyme capable of cleaving the glycosidic bond of a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof.

In an embodiment, the saccharide comprises or is a monosaccharide that can be cleaved with a human glycohydrolase.

In an embodiment, the saccharide comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D- glucose, α-D-mannose, β-D-mannose, α-L-fucose, β-D-xylose, neuraminic acid and any analogue or modification thereof, and the monosaccharide is bound via an O-glycosidic bond to a hydroxyl group of the auristatin.

In an embodiment, the saccharide R1 or R1' comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof, and the monosaccharide is bound via an O-glycosidic bond to a hydroxyl group of the toxic payload molecule.

The term "analogue" or "being analogous to" should be understood so that the analogue or the analogous monosaccharide (pyranose monosaccharide) is cleavable by the same lysosomal or intracellular glycohydrolase than the pyranose monosaccharide to which it is analogous to.

The term "modification" or "modification of a monosaccharide" should be understood so that the modification is a covalent modification of a monosaccharide resulting from substitution of a functional group or an atom of the monosaccharide.

In an embodiment, the modification is selected from the group of sulfate, phosphate, carboxyl, amino, and O-acetyl modification.

In an embodiment, the saccharide comprises a neutral monosaccharide.

In an embodiment, the saccharide comprises a charged monosaccharide.

In an embodiment, the charged monosaccharide is selected from the group of neuraminic acid, D-glucuronic acid, L-iduronic acid, and a monosaccharide modified with sulfate, phosphate, carboxyl and amino group.

In an embodiment, the monosaccharide comprises or is a β-D-galactose or a neuraminic acid.

In an embodiment, the disaccharide comprises a β-D-galactose or a neuraminic acid.

In an embodiment, the disaccharide comprises neuraminic acid α2,3- or α2,6-linked to β-D-galactose, or the disaccharide is neuraminic acid α2,3- or α2,6-linked to β-D-galactose.

In the context of this specification, the term "neuraminic acid" may refer to any sialic acid that is cleavable by a human neuraminidase, for example N-acetylneuraminic acid (Neu5Ac), N-glycolylneuraminic acid, O-acetyl-N-acetylneuraminic acid, 2-keto-3-deoxynonulosonic acid, and the like. In an embodiment, the neuraminic acid is in α-D-pyranose form.

In an embodiment, the O-glycosidic bond is the anomeric bond of a pyranose monosaccharide comprised in the saccharide that is or is analogous to β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, or neuraminic acid, respectively.

In an embodiment, the saccharide comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof, and the monosaccharide is bound to the auristatin via the O-glycosidic bond.

In an embodiment, the saccharide R1 or R1' comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof, and the monosaccharide is bound to the toxic payload molecule via the O-glycosidic bond.

In an embodiment, the saccharide R1 or R1' comprises or is a di- or trisaccharide selected from the group consisting of Neu5Acα2-6Galβ, Neu5Acα2-3Galβ, Galβ1-4Glcβ, Neu5Acα2-6Galβ1-4Glcβ, Neu5Acα2-3Galβ1-4Glcβ, Galβ1-4Glcα, Neu5Acα2-6Galβ1-4Glcα, Neu5Acα2-3Galβ1-4Glcα, Neu5Acα2-6Galβ1-4Xylβ, Neu5Acα2-3Galβ1-4Xylβ, Neu5Acα2-6Galβ1-4GlcNAcβ and Neu5Acα2-3Galβ1-4GlcNAcβ; wherein all monosaccharides are D-pyranoses.

In an embodiment, the O-glycosidic bond is hydrolysable by a lysosomal or an intracellular glycohydrolase. This embodiment has the utility that lysosomal or intracellular glycohydrolases may remove the saccharide inside a cell. A skilled person is capable of selecting an O-glycosidic bond that is hydrolysable by a lysosomal or an intracellular glycohydrolase based on biochemical literature; various such glycohydrolases having different specificities are known. For instance, currently no lysosomal or intracellular glycohydrolases capable of removing a neuraminic acid molecule bound via β-O-glycosidic bond (a β-neuraminidase) are known in humans, so in embodiments wherein the saccharide comprises a neuraminic acid the neuraminic acid may be bound via an α-O-glycosidic bond to the hydroxyl group of the auristatin or to the hydroxyl group of the toxic payload molecule.

In an embodiment, the lysosomal or intracellular glycohydrolase is capable of removing the entire saccharide inside a cell.

In an embodiment, one or more of the glycosidic bonds of the saccharide are essentially stable in neutral pH and/or in serum. In an embodiment, all glycosidic bonds of the saccharide are essentially stable in neutral pH and/or in serum.

In an embodiment, one or more of the glycosidic bonds of the saccharide are hydrolysable in tumor microenvironment outside a cell. This embodiment has the added utility that the saccharide may be removed more efficiently inside a tumor than in normal tissue and the molecule may be more efficiently taken up by cancer cells than by normal cells.

In an embodiment, the lysosomal or intracellular glycohydrolase is selected from the group consisting of β-galactosidase, β-hexosaminidase, α-N-acetylgalactosaminidase, β-N-acetylglucosaminidase, β-glucuronidase, α-L-iduronidase, α-galactosidase, α-glucosidase, β-glucosidase, α-mannosidase, β-mannosidase, α-fucosidase, β-xylosidase and neuraminidase.

In an embodiment, the human glycohydrolase is selected from the group consisting of β-galactosidase, β-hexosaminidase, α-N-acetylgalactosaminidase, β-N-acetylglucosaminidase, β-glucuronidase, α-L-iduronidase, α-galactosidase, α-glucosidase, β-glucosidase, α-mannosidase, β-mannosidase, α-fucosidase, β-xylosidase and neuraminidase.

In an embodiment, the linker group is a linker group represented by formula III

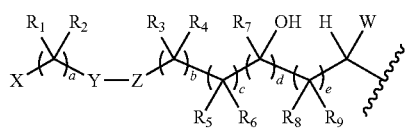

Formula III wherein

X is F-E, wherein F is a functional group that can react with an amine, thiol, azide, alkene, alkyne, aldehyde, ketone, carboxylic acid or hydroxylamine, and E is either absent or a polyethyleneoxy unit of formula $(CH_2CH_2O)_p$, wherein p is an integer from 2 to about 20;

Y is an oxygen, sulphur, amine, amide, peptide or absent, wherein the peptide is an $E_1$-P-$E_2$ unit in which $E_1$ and $E_2$ are independently either C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

$R_1$, $R_2$, $R_3$, $R_4$, $R_5$, $R_6$, $R_2$, $R_8$ and $R_9$ are each independently H, hydroxyl, amine, $C_2$-$C_6$ acylamide, carboxyl, substituted carboxyl, $C_1$-$C_6$ alkyl or substituted $C_1$-$C_6$ alkyl;

W is H, $CH_2OH$, $CH_3$, carboxyl, substituted carboxyl, $C_1$-$C_6$ alkyl or substituted $C_1$-$C_6$ alkyl;

a is an integer from 0 to 6;

b is 0 or 1;

c and e are each independently an integer from 0 to 7; and d is an integer from 1 to 7.

Various linker groups according to formula III are disclosed in WO 2014/096551 and WO 2014/177771, which is herein incorporated in its entirety.

In an embodiment, the linker group is a linker group represented by formula IV

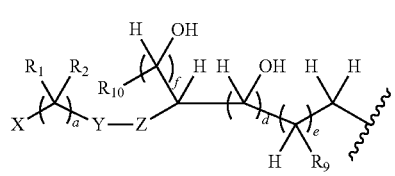

Formula IV wherein

X is F-E, wherein F is a functional group that can react with an amine, thiol, azide, alkene, alkyne, aldehyde, ketone, carboxylic acid or hydroxylamine in a cell binder, and E is either absent or a polyethyleneoxy unit of formula $(CH_2CH_2O)_p$, wherein p is an integer from 2 to about 20;

Y is an oxygen, sulphur, amine, amide, peptide or absent, wherein the peptide is an $E_1$-P-$E_2$ unit in which $E_1$ and $E_2$ are independently either C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

$R_1$, $R_2$, $R_9$ and $R_{10}$ are each independently H, hydroxyl, amine, $C_2$-$C_6$ acylamide, carboxyl, substituted carboxyl, $C_1$-$C_6$ alkyl or substituted $C_1$-$C_6$ alkyl;

a is an integer from 0 to 6;

e is an integer from 0 to 3; and d and f are integers from 0 to 4 with the proviso that their sum is from 1 to 4.

In an embodiment, the linker group is a linker group represented by formula V

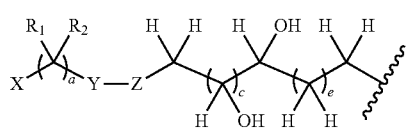

Formula V wherein

X is F-E, wherein F is a functional group that can react with an amine, thiol, azide, alkene, alkyne, aldehyde, ketone, carboxylic acid or hydroxylamine in a cell binder, and E is either absent or a polyethyleneoxy unit of formula $(CH_2CH_2O)_p$, wherein p is an integer from 2 to about 20;

Y is an oxygen, sulphur, amine, amide, peptide or absent, wherein the peptide is an $E_1$-P-$E_2$ unit in which $E_1$ and $E_2$ are independently either C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

$R_1$ and $R_2$ are each independently H, hydroxyl, amine, $C_2$-$C_6$ acylamide, carboxyl, substituted carboxyl, $C_1$-$C_6$ alkyl or substituted $C_1$-$C_6$ alkyl;

a is an integer from 0 to 6; and c and e are each independently an integer from 0 to 3.

In an embodiment, X is an amine reacting group, a thiol reactive group, an azide reactive group, an alkyne reactive group, a carbonyl reactive group or a hydroxylamine reactive group.

In an embodiment, X is an amine reacting group, such as (but not limited) to an N-hydroxysuccinimide ester, p-nitrophenyl ester, dinitrophenyl ester, or pentafluorophenyl ester.

In an embodiment, X is a thiol reactive group, such as (but not limited to) pyridyldisulfide, nitropyridyldisulfide, maleimide, haloacetate or carboxylic acid chloride.

In an embodiment, X is an azide reactive group, such as (but not limited to) alkynyl.

In an embodiment, X is an alkynyl.

In an embodiment, X is CHC.

In an embodiment, X is a cyclic alkynyl group, such as dibenzocyclooctyl (DBCO).

In an embodiment, X is an alkyne reactive group, such as (but not limited to) azide.

In an embodiment, X is azide.

In an embodiment, X is a carbonyl reactive group, such as (but not limited to) hydroxylamine.

In an embodiment, X is a hydroxylamine reactive group, such as (but not limited to) aldehyde or ketone.

In an embodiment, X is isothiocyanate, isocyanate, sulfonyl chloride, glyoxal, epoxide, oxirane, carbonate, aryl halide, imidoester, carbodiimide, or anhydride.

In an embodiment, Z is absent.

In an embodiment, Z is a saccharide.

In an embodiment, Z is an oligosaccharide with a degree of polymerization from 1 to about 20; from 1 to 10; from 1 to 8; from 1 to 6; from 1 to 5; from 1 to 4; from 1 to 3; from 1 to 2; or 1, 2, 3, 4 or 5.

In an embodiment, Z is a monosaccharide, disaccharide or trisaccharide.

In an embodiment, Z is OH.

In an embodiment, Z is H.

In an embodiment, a is 1, 2, 3, 4, 5, or 6.

In an embodiment, a is 1.

In an embodiment, b is 0.

In an embodiment, b is 1.

In an embodiment, c is 0.

In an embodiment, c is 1, 2, 3, 4, 5, 6 or 7.

In an embodiment, d is 1, 2, 3, 4, 5, 6 or 7.

In an embodiment, d is 3, 4 or 5.

In an embodiment, d is 3.

In an embodiment, d is 4.

In an embodiment, d is 5.

In an embodiment, d is 6.

In an embodiment, e is 0.

In an embodiment, e is 1, 2, 3, 4, 5, 6 or 7.

In an embodiment, d is 3; and $R_7$ is H.

In an embodiment, d is 4; and $R_7$ is H.

In an embodiment, b is 1; and $R_3$ and $R_4$ are each H.

In an embodiment, a is 1; and $R_1$ and $R_2$ are each H.

In an embodiment, e is 1; and $R_8$ and $R_9$ are each H.

In an embodiment, a, b, c, or e is 0.

In an embodiment, a, b, c, and/or e is 0.

In an embodiment, W is H.

In an embodiment, a is 2 or 3; and $R_1$ and $R_2$ are both H.

In an embodiment, Y is an oxygen.

In an embodiment, Y is a sulphur.

In an embodiment, $R_1$, $R_2$, $R_3$, $R_4$ and $R_7$ are each H; W is H; a is 1; b is 1; c and e are each 0; and d is 4.

In an embodiment, $R_3$, $R_4$, and $R_7$ are each H; W is H; b is 1; a, c and e are each 0; and d is 4.

In an embodiment, X is an alkyne; Y is an oxygen; Z is absent; $R_1$, $R_2$, $R_3$, $R_4$ and $R_7$ are each H; W is H; a is 1; b is 1; c and e are each 0; and d is 4.

In an embodiment, X is azide; Y is an oxygen; Z is absent; $R_1$, $R_2$, $R_3$, $R_4$ and $R_7$ are each H; W is H; a is 1; b is 1; c and e are each 0; and d is 4.

In an embodiment, the linker group comprises a peptide and optionally a self-immolative group linking the peptide and the auristatin.

The term "self-immolative" refers to a functional chemical moiety that is capable of covalently linking together chemical moieties (e.g. auristatin to a peptide linker group or toxic payload molecule to a peptide linker group) and that will spontaneously separate from e.g. the auristatin or toxic payload molecule if its bond to the peptide linker is cleaved.

In an embodiment, the linker group is the valine-citrulline linker.

In an embodiment, the peptide is a peptide cleavable by a lysosomal peptidase, such as cathepsin B, optionally selected from the group consisting of L-Gly-L-Gly, L-Val-L-Cit, L-Phe-L-Leu, L-Leu-L-Ala-L-Leu, L-Leu-L-Ala-L-Ala and L-Ala-L-Leu-L-Ala-L-Leu.

In an embodiment, the self-immolative group is a para-aminobenzoyl group (PAB).

In an embodiment, the linker group comprises a maleimidyl group. Said group is capable of reacting e.g. with a sulfhydryl group of an antibody; the antibody may comprise such a sulfhydryl group naturally or via chemical manipulation. In an embodiment, the linker comprises a maleimidocaproyl group.

In an embodiment, the linker is a maleimidocaproyl valine-citrulline para-aminobenzoyl linker comprising a maleimidocaproyl group joined with an amide bond to the amino group of the linker valine residue.

In an embodiment, the linker group comprises a saccharide bound to a hydroxyl group of the toxic payload molecule via an O-glycosidic bond.

An antibody-drug conjugate comprising an antibody covalently bound to an auristatin, optionally via a linker group, and a saccharide bound via an O-glycosidic bond to a hydroxyl group of the auristatin is disclosed.

An antibody-drug conjugate comprising an antibody covalently bound to a toxic payload molecule, optionally via a linker group, and a saccharide bound via an O-glycosidic bond to a hydroxyl group of the toxic payload molecule is further disclosed.

In an embodiment, the antibody-drug conjugate comprises an antibody covalently bound to a toxic payload molecule, optionally via a linker group, and a saccharide bound via an O-glycosidic bond to a hydroxyl group of the toxic payload molecule, wherein the saccharide is bound via an O-glycosidic bond to an ester linker group bound via an ester bond to a hydroxyl group of the toxic payload molecule, and wherein the ester linker group has a structure according to formula XII

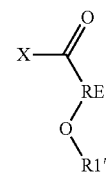

Formula XII wherein X is the bond to the toxic payload molecule; R1' is the saccharide bound via the O-glycosidic bond; and RE is selected from the group consisting of —CH$_2$—, —CH$_2$CH$_2$—, —CH$_2$CH$_2$CH$_2$—, —CH$_2$CH$_2$CH$_2$CH$_2$—, C$_1$-C$_4$ alkyl, heteroalkyl, branched alkyl, branched heteroalkyl, cyclic alkyl, cyclic heteroalkyl, and substituted C$_1$-C$_4$ alkyl, heteroalkyl, branched alkyl, branched heteroalkyl, cyclic alkyl, and cyclic heteroalkyl.

In this context, the term "drug" should be understood as referring to the auristatin moiety of the conjugate, including or not including the saccharide bound via the O-glycosidic bond. The term "drug" should also be understood as referring to the toxic payload moiety of the conjugate, including or not including the saccharide bound via the O-glycosidic bond.

In an embodiment, the antibody-drug conjugate is represented by formula VI $$\text{AB-[L-A-R1]}_n \qquad \text{Formula VI}$$

wherein
AB is an antibody;
L is absent or a linker group;
A is an auristatin;
R1 is a saccharide bound via an O-glycosidic bond to a hydroxyl group of the auristatin; and
n is at least 1.

In an embodiment, the auristatin is monomethylauristatin E.

In an embodiment, the antibody-drug conjugate is represented by formula VI wherein AB is an antibody; L is absent or a linker group; A is a toxic payload molecule; R1 is a saccharide bound via an O-glycosidic bond to a hydroxyl group of the toxic payload molecule; and n is at least 1. In the context of this embodiment, the toxic payload molecule may be any toxic payload molecule described in this specification; the antibody may be any antibody described in this specification; and the saccharide may be any saccharide described in this specification.

In an embodiment, the antibody-drug conjugate is represented by formula VI $$\text{AB-[L-A-R1]}_n \qquad \text{Formula VI}$$

wherein
AB is an antibody;
L is absent or a linker group;
A is a toxic payload molecule;
R1 is L"-R1', wherein R1' is a saccharide bound via an O-glycosidic bond to L", and L" is bound via an ester bond to a hydroxyl group of the toxic payload molecule and has a structure according to formula XII; and
n is at least 1.

In the context of this embodiment, the toxic payload molecule may be any toxic payload molecule described in this specification; the antibody may be any antibody described in this specification; and the saccharide may be any saccharide described in this specification.

In an embodiment, the antibody-drug conjugate is represented by formula VI wherein L is L'-R2, wherein R2 is a saccharide bound via an O-glycosidic bond to a hydroxyl group of the toxic payload molecule, L' is a linker group, and the saccharide R2 is bound to the linker group L' via a covalent bond.

In an embodiment, the antibody-drug conjugate is represented by formula XI:

$$\text{AB-[L'-R2-A]}_n \qquad \text{Formula XI}$$

wherein
AB is an antibody;
L' is absent or a linker group;
A is an toxic payload molecule;
R2 is a saccharide bound via an O-glycosidic bond to a hydroxyl group of the toxic payload molecule; and
n is at least 1.

In an embodiment, the antibody-drug conjugate is represented by formula XI', XI", XI'", or XI"":

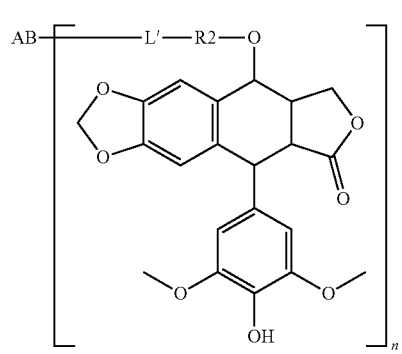

Formula XI'

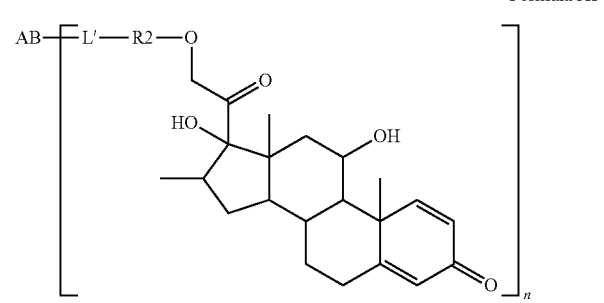

Formula XI"

Formula XI'''

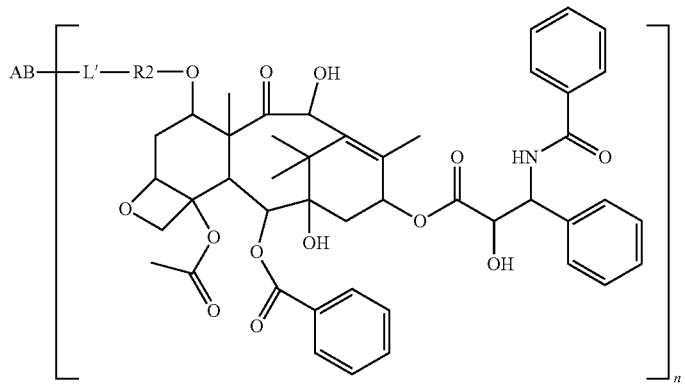

Formula XI''''

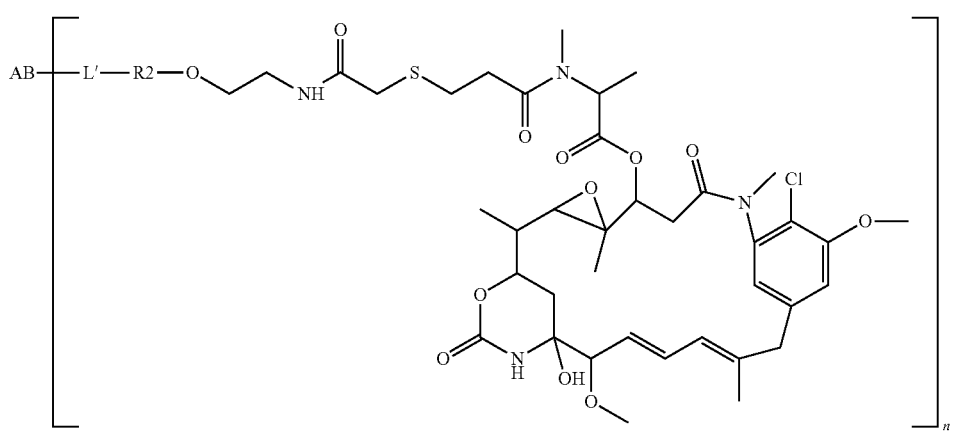

wherein
AB is an antibody;
L' is absent or a linker group;
A is an toxic payload molecule;
R2 is a saccharide bound via an O-glycosidic bond to a hydroxyl group of the toxic payload molecule; and
n is at least 1.

In an embodiment, the toxic payload molecule is a dolastatin; an auristatin; an epothilone; a daunorubicin, a doxorubicin, an alkylating agent, a thiotepa, a cyclophosphamide (CYTOXAN™); an alkyl sulfonate, a busulfan, an improsulfan, a piposulfan, an aziridine, a benzodopa, a carboquone, a meturedopa, an uredopa; an ethylenimine, a methylamelamine, an altretamine, a triethylenemelamine, a trietylene-phosphoramide, a triethylenethiophosphaoramide, a trimethylolomelamine, an acetogenin, a bullatacin, a bullatacinone, a camptothecin, a topotecan, a bryostatin; a callystatin; a CC-1065, a adozelesin, a carzelesin a bizelesin, a cryptophycin, a cryptophycin 1, a cryptophycin 8, a duocarmycin, a synthetic analogue of duocarmycin, a KW-2189, a CBI-TMI, an eleutherobin, a pancratistatin, a sarcodictyin, a spongistatin, a nitrogen mustard, a chlorambucil, a chlomaphazine, a cholophosphamide, an estramustine, an ifosfamide, a mechlorethamine, a mechlorethamine oxide hydrochloride, a melphalan, a novembichin, a phenesterine, a prednimustine, a trofosfamide, an uracil mustard, a nitrosurea, a carmustine, a chlorozotocin, a fotemustine, a lomustine, a nimustine, a ranimustine, an antibiotic, an enediyne antibiotic, a calicheamicin, a calicheamicin γ1, a dynemicin, a dynemicin A, an esperamicin, a neocarzinostatin chromophore, a chromoprotein enediyne antiobiotic chromomophore, an aclacinomysin, an actinomycin, an authramycin, an azaserine, a bleomycin, a cactinomycin, a carabicin, a caminomycin, a carzinophilin, a chromomycin, a dactinomycin, a detorubicin, a 6-diazo-5-oxo-L-norleucine, a doxorubicin derivative, a morpholino-doxorubicin, a cyanomorpholino-doxorubicin, a 2-pyrrolino-doxorubicin, a deoxydoxorubicin, an epirubicin, an esorubicin, an idarubicin, a marcellomycin, a nitomycin, a mycophenolic acid, a nogalamycin, an olivomycin, a peplomycin, a potfiromycin, a puromycin, a quelamycin, a rodorubicin, a streptonigrin, a streptozocin, a tubercidin, a ubenimex, a zinostatin, a zorubicin, an anti-metabolite, a methotrexate, a 5-fluorouracil (5-FU), a folic acid analogue, a denopterin, a pteropterin, a trimetrexate; a purine analog, a fludarabine, a 6-mercaptopurine, a thiamiprine, a thioguanine; a pyrimidine analog, an ancitabine, an azacitidine, a 6-azauridine, a carmofur, a cytarabine, a dideoxyuridine, a doxifluridine, an enocitabine, a floxuridine, a 5-fluorouracil, an androgen, a calusterone, a dromostanolone propionate, an epitiostanol, a mepitiostane, a testolactone; an anti-adrenal, an aminoglutethimide, a mitotane, a trilostane, a folic acid replenisher, a frolinic acid, an aceglatone, an aldophosphamide glycoside, an aminolevulinic acid, an amsacrine, a bestrabucil, a bisantrene, an edatraxate, a defofamine, a demecolcine, a diaziquone, an elfomithine, an elliptinium acetate, a etoglucid, a gallium nitrate, a hydroxyurea, a lentinan, a lonidamine, a maytansinoid, a maytansine, an N-glucosylmaytansinoid, an ansamitocin, a DM-1, a DM-4, a mitoguazone, a mitoxantrone, a mopidamol, a nitracrine, a pentostatin, a phenamet, a pirarubicin, a podophyllinic acid, a 2-ethylhydrazide, a procarbazine, a PSK®, a razoxane, a rhizoxin, a sizofuran, a spirogermanium, a tenuazonic acid, a triaziquone, a 2,2',2"-trichlorotriethylamine, a trichothecene, a T-2 toxin, a verracurin A, a roridin A, an anguidine, a urethane, a vindesine, a dacarbazine, a mannomustine, a mitobronitol, a mitolactol, a pipobroman, a gacytosine, an arabinoside ("Ara-C"), a cyclophosphamide, a thiotepa, a taxoid, a paclitaxel (TAXOL®, Bristol-Myers Squibb Oncology, Princeton, N.J.), a doxetaxel (TAXOTERE®, Rhone-Poulenc Rorer, Antony, France), a chlorambucil, a gemcitabine, a 6-thioguanine, a mercaptopurine, a methotrexate, a platinum analog, a cisplatin, a carboplatin, a vinblastine, a platinum, an etoposide (VP-16), an ifosfamide, a mitomycin C, a mitoxantrone, a vincristine, a vinorelbine, a navelbine, a novantrone, a teniposide, a daunomycin, an aminopterin, a xeloda, an ibandronate, a CPT-11, a topoisomerase inhibitor RFS 2000, a difluoromethylomithine (DMFO), a retinoic acid, a capecitabine, an anti-hormonal agent that acts to regulate or inhibit hormone action on tumours, an anti-estrogen, a tamoxifen, a raloxifene, an aromatase inhibiting 4(5)-imidazole, a 4-hydroxytamoxifen, a trioxifene, a keoxifene, a LY117018, a onapristone, a toremifene (Fareston), an anti-androgen, a flutamide, a nilutamide, a bicalutamide, a leuprolide, a goserelin, a siRNA, a tubulysin, an amanitin, or an α-amanitin.

In an embodiment, the toxic payload molecule is a dolastatin, auristatin, doxorubicin, DM1, epirubicin, duocarmycin or any analogue or derivative thereof.

In an embodiment, the toxic payload molecule is a dolastatin, auristatin, doxorubicin, or any analogue or derivative thereof.

In an embodiment, the toxic payload molecule is dolastatin 10 or any derivative thereof.

In an embodiment, the toxic payload molecule is dolastatin 15 or any derivative thereof.

In an embodiment, the toxic payload molecule is auristatin F or any derivative thereof.

In an embodiment, the toxic payload molecule is dolastatin 10, dolastatin 15, or auristatin F.

In an embodiment, the toxic payload molecule is dolastatin 10.

In an embodiment, the toxic payload molecule is dolastatin 15.

In an embodiment, the toxic payload molecule is auristatin F.

Dolastatins that can be used are well known in the art and can be isolated from natural sources according to known methods or prepared synthetically according to known methods.

Examples of suitable dolastatins include monomethyl and desmethyl dolastatins 10, 15, C, D and H, monomethyl and desmethyl isodolastatin H, and analogues and derivatives thereof. Dolastatins 10 and 15 are the most potent cytotoxic agents among the naturally occurring dolastatins. Monomethyl and desmethyl dolastatins 10 and 15 can be prepared by chemical synthesis according to standard peptide synthesis chemistry.

Examples of suitable auristatins that can be used include (but are not limited to) monomethyl and desmethyl auristatins E, F, EB, EFP, PY, PYE, PE, PHE, TP, 2-AQ and 6-AQ, e.g. described in U.S. Pat. No. 5,635,483; Int. J. Oncol. 15:367-72 (1999); Mol. Cancer Ther. 3:921-32 (2004); U.S. application Ser. No. 11/134,826; U.S. Patent Publication Nos. 20060074008 and 2006022925; and Pettit, G. R., et al. (2011) J. Nat. Prod. 74:962-8; and monomethyl and desmethyl auristatins W and M, described in Doronina et al. (2008) Bioconj. Chem. 19:1960-3.

In an embodiment, the toxic payload molecule is daunorubicin or doxorubicin.

In an embodiment, the toxic payload molecule is a maytansinoid.

In an embodiment, the toxic payload molecule is maytansine, an ansamitocin, DM1 or DM4 (also known as DM-4).

In an embodiment, the toxic payload molecule is DM1. DM1 is also known as DM-1 and mertansine.

In an embodiment, the toxic payload molecule is a rubicin. Suitable rubicins may be e.g. daunorubicins, doxorubicins, detorubicin, other doxorubicin derivatives including morpholino-doxorubicin, cyanomorpholino-doxorubicin, 2-pyrrolino-doxorubicin, deoxydoxorubicin, epirubicin, esorubicin, idarubicin, rodorubicin, zorubicin, and pirarubicin.

In an embodiment, the toxic payload molecule is epirubicin.

In an embodiment, the toxic payload molecule is duocarmycin. Suitable duocarmyxins may be e.g. duocarmycin A, duocarmycin B1, duocarmycin B2, duocarmycin C1, duocarmycin C2, duocarmycin D, duocarmycin SA, duocarmycin MA, and CC-1065. The term "duocarmycin" should be understood as referring also to synthetic analogs of duocarmycins, such as adozelesin, bizelesin, carzelesin, KW-2189 and CBI-TMI. In an embodiment, the toxic payload molecule comprises a duocamycin fragment that can alkylate DNA. In an embodiment, the toxic payload molecule comprises two or more duocamycin fragments that can alkylate DNA. In an embodiment, the toxic payload molecule comprises two duocamycin fragments that can alkylate DNA.

Examples of suitable dolastatins include monomethyl and desmethyl dolastatins 10, 15, C, D and H, monomethyl and desmethyl isodolastatin H, and analogues and derivatives thereof.

In an embodiment, the toxic payload molecule comprises a free hydroxyl group, to which saccharides may be added.

One skilled in the art of cytotoxic agents will readily understand that each of the cytotoxic agents described herein can be modified in such a manner that the resulting compound still retains the specificity and/or activity of the starting compound. In an embodiment, the cytotoxic agent is modified so that it contains a hydroxyl group whereto a saccharide is attached via an O-glycosidic bond. The skilled person will also understand that many of these compounds can be used in place of the cytotoxic agents described herein. Thus, the cytotoxic agents should be understood as including any analogues and derivatives of the compounds described herein.

In an embodiment, the saccharide is bound to a hydroxyl group of the toxic payload molecule via an O-glycosidic bond. In other words, the O-glycosidic bond is formed by a reaction between a hydroxyl group of the toxic payload molecule and a functional group of the saccharide.

In an embodiment, RE is selected from the group consisting of —CH$_2$—, —CH$_2$CH$_2$—, —CH$_2$CH$_2$CH$_2$—, and —CH$_2$CH$_2$CH$_2$CH$_2$—.

In an embodiment, the antibody-drug conjugate is represented by a formula selected from the group consisting of formulas VII, VII' and VII":

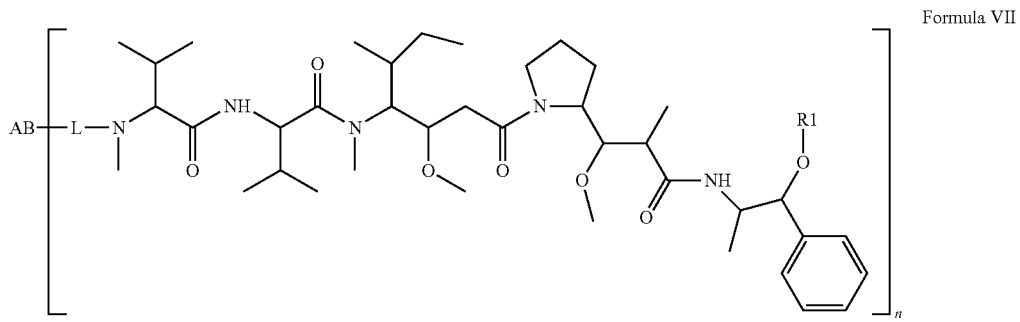

Formula VII

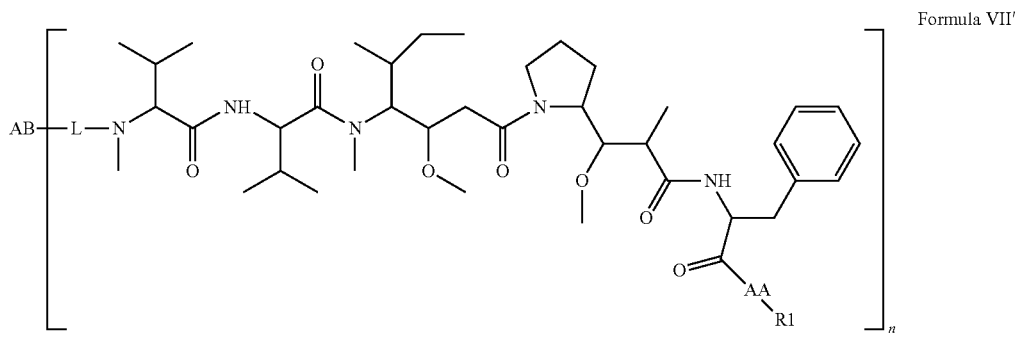

Formula VII'

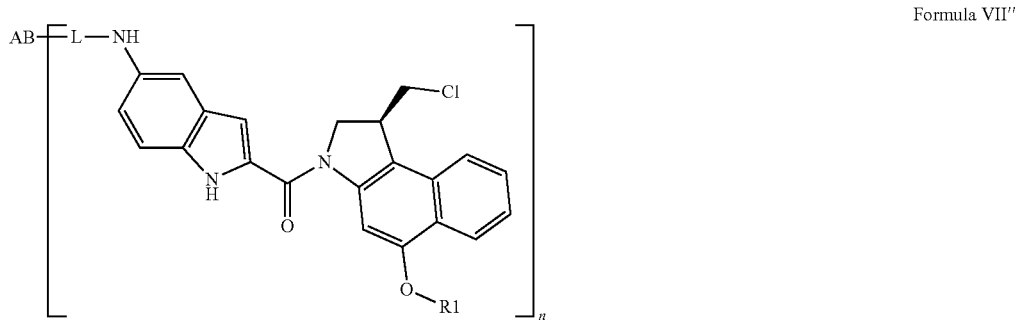

Formula VII"

wherein
AB is an antibody;
L is absent or a linker group;
R1 is a saccharide bound via an O-glycosidic bond to the auristatin or R1 is a saccharide bound via an O-glycosidic bond to the toxic payload molecule;

AA is a peptide comprising a hydroxyl group whereto R1 is bound via the O-glycosidic bond; and
n is at least 1.

In an embodiment, the antibody-drug conjugate is represented by a formula selected from the group consisting of formulas VII, VII' and VII":

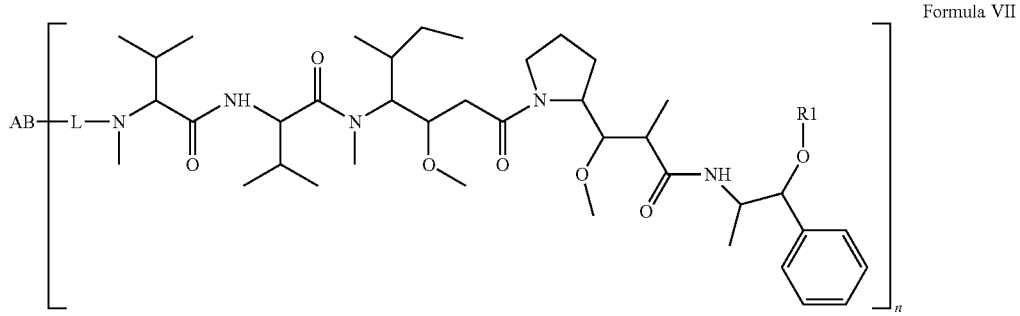

Formula VII

-continued

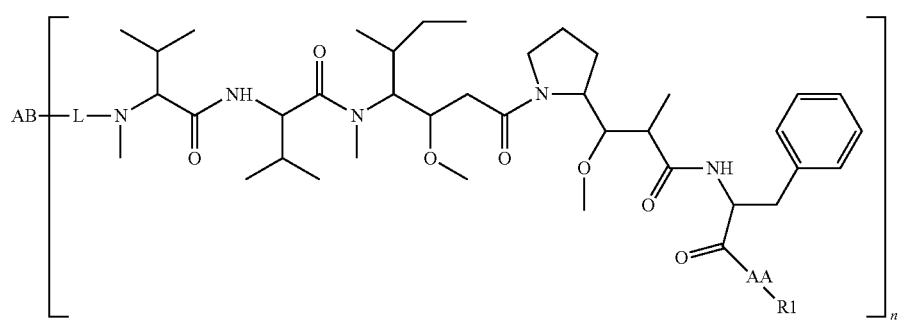

Formula VII'

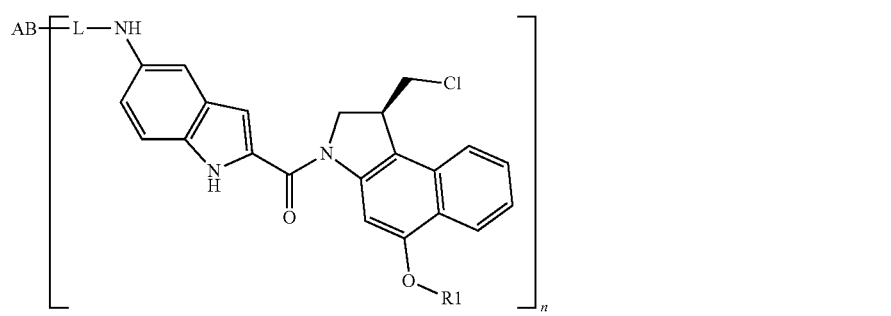

Formula VII'' wherein

AB is an antibody;

L is absent or a linker group;

R1 is L''-R1', wherein R1' is a saccharide bound via an O-glycosidic bond to L'', and L'' is bound via an ester bond to a hydroxyl group of the toxic payload molecule and has a structure according to formula XII;

AA is a peptide comprising a hydroxyl group whereto R1 is bound via the O-glycosidic bond; and n is at least 1.

In an embodiment, AA is a peptide comprising a dipeptide and a hydroxy amino acid comprising a hydroxyl group.

In an embodiment, the dipeptide is cleavable by a peptidase. In an embodiment, the dipeptide is selected from the group of $AA_1+AA_2$ dipeptides described in Doronina et al. (2008) Bioconj. Chem. 19:1961, Table 1.

In an embodiment, the hydroxy amino acid is serine or threonine.

In an embodiment, AA is Ile-Val-Ser.

In an embodiment, the saccharide is a monosaccharide, a disaccharide or an oligosaccharide.

In an embodiment, the saccharide comprises one or more glycosidic bonds that are cleavable by a lysosomal or an intracellular glycohydrolase.

In an embodiment, the saccharide R1 or R1' comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof.

In an embodiment, the saccharide comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof, and the monosaccharide is bound via an O-glycosidic bond to a hydroxyl group of the auristatin.

In an embodiment, the saccharide R1 or R1' comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof, and the monosaccharide is bound via an O-glycosidic bond to a hydroxyl group of the toxic payload molecule.

In an embodiment, the modification is selected from the group consisting of sulfate, phosphate, carboxyl, amino, and O-acetyl modification.

In an embodiment, the monosaccharide comprises a β-D-galactose or a neuraminic acid, or the monosaccharide is a β-D-galactose or a neuraminic acid.

In an embodiment, the saccharide R1 or R1' comprises a neutral monosaccharide.

In an embodiment, the saccharide R1 or R1' comprises a charged monosaccharide.

In an embodiment, the saccharide R1 or R1' comprises or is a disaccharide.

In an embodiment, the disaccharide comprises a neutral monosaccharide and a charged monosaccharide.

In an embodiment, the saccharide R2 comprises a neutral monosaccharide.

In an embodiment, the saccharide R2 comprises a charged monosaccharide.

In an embodiment, the charged monosaccharide is selected from the group of neuraminic acid, D-glucuronic acid, L-iduronic acid, and a monosaccharide modified with sulfate, phosphate, carboxyl or amino group.

In an embodiment, the O-glycosidic bond is the anomeric bond of a pyranose monosaccharide comprised in the saccharide that is or is analogous to β-D-galactose, N-acetyl- β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, or neuraminic acid, respectively. In an embodiment, the disaccharide comprises neuraminic acid α2,3- or α2,6-linked to β-D-galactose, or the saccharide is a disaccharide, wherein neuraminic acid is α2,3- or α2,6-linked to β-D-galactose. These disaccharides are very hydrophilic, and the presence of the neuraminic acid may be able to reduce the tendency of the antibody-drug conjugate to be delivered in the liver.

In an embodiment, the saccharide comprises or is a di- or trisaccharide selected from the group consisting of Neu5Acα2-6Galβ, Neu5Acα2-3Galβ, Galβ1-4Glcβ, Neu5Acα2-6Galβ1-4Glcβ, Neu5Acα2-3Galβ1-4Glcβ, Galβ1-4Glcα, Neu5Acα2-6Galβ1-4Glcα, Neu5Acα2-3Galβ1-4Glcα, Neu5Acα2-6Galβ1-4Xylβ, Neu5Acα2-3Galβ1-4Xylβ, Neu5Acα2-6Galβ1-4GlcNAcβ and Neu5Acα2-3Galβ1-4GlcNAcβ; wherein all monosaccharides are D-pyranoses.

In an embodiment, the saccharide comprises or consists of at least two monosaccharides selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid, or any modification thereof.

In an embodiment, the modification is sulfate, phosphate, carboxyl, amino, or O-acetyl modification of a monosaccharide.

In an embodiment, the saccharide comprises or is an oligosaccharide and the oligosaccharide is bound to the toxic payload molecule via the O-glycosidic bond. The oligosaccharide may also be bound via an O-glycosidic bond to L", such that L" is bound via an ester bond to a hydroxyl group of the toxic payload molecule and has a structure according to formula XII.

In an embodiment, the O-glycosidic bond is hydrolysable by a lysosomal or an intracellular glycohydrolase. This embodiment has the utility that lysosomal or intracellular glycohydrolases may remove the saccharide inside a cell, when the antibody-drug conjugate enters the cell.

In an embodiment, the lysosomal or intracellular glycohydrolase is capable of removing the entire saccharide inside a cell.

In an embodiment, one or more of the glycosidic bonds of the saccharide are essentially stable in neutral pH and/or in serum.

In an embodiment, all glycosidic bonds of the saccharide are essentially stable in neutral pH and/or in serum.

In an embodiment, one or more of the glycosidic bonds of the saccharide are hydrolysable in tumor microenvironment outside a cell. This embodiment has the added utility that the saccharide may be removed more efficiently inside a tumor than in normal tissue and the molecule may be more efficiently taken up by cancer cells than by normal cells.

In an embodiment, the lysosomal or intracellular glycohydrolase is selected from the group consisting of β-galactosidase, β-hexosaminidase, α-N-acetylgalactosaminidase, β-N-acetylglucosaminidase, β-glucuronidase, α-L-iduronidase, α-galactosidase, α-glucosidase, β-glucosidase, α-mannosidase, β-mannosidase, α-fucosidase, β-xylosidase and neuraminidase.

The antibody may, in principle, be any antibody, for instance an IgG, an scFv, a single domain antibody, an Fv, a VHH antibody, a diabody, a tandem diabody, a Fab, a Fab', a F(ab')$_2$, a Db, a dAb-Fc, a taFv, a scDb, a dAb$_2$, a DVD-Ig, a Bs(scFv)$_4$-IgG, a taFv-Fc, a scFv-Fc-scFv, a Db-Fc, a scDb-Fc, a scDb-C$_H$3, or a dAb-Fc-dAb.

In an embodiment, the antibody is a human antibody or a humanized antibody. In this context, the term "human antibody", as it is commonly used in the art, is to be understood as meaning antibodies having variable regions in which both the framework and complementary determining regions (CDRs) are derived from sequences of human origin. In this context, the term "humanized antibody", as it is commonly used in the art, is to be understood as meaning antibodies wherein residues from a CDR of an antibody of human origin are replaced by residues from a CDR of a nonhuman species (such as mouse, rat or rabbit) having the desired specificity, affinity and capacity.

In an embodiment, the antibody is capable of binding a cell surface antigen.

In an embodiment, the cell surface antigen is a tumor antigen and/or a cancer antigen.

In an embodiment, the antibody is selected from the group consisting of bevacizumab, tositumomab, etanercept, trastuzumab, adalimumab, alemtuzumab, gemtuzumab ozogamicin, efalizumab, rituximab, infliximab, abciximab, basiliximab, palivizumab, omalizumab, daclizumab, cetuximab, panitumumab, epratuzumab, 2G12, lintuzumab, nimotuzumab and ibritumomab tiuxetan.

In an embodiment, the antibody is capable of binding a target molecule selected from the group consisting of CD2, CD3, CD4, CD5, CD6, CD11, CD8, CD11a, CD19, CD20, CD22, CD25, CD26, CD30, CD33, CD34, CD37, CD38, CD40, CD44, CD46, CD52, CD56, CD79, CD105, CD138, epidermal growth factor receptor 1 (EGFR), epidermal growth factor receptor 2 (HER2/neu), HER3 or HERO receptor, LFA-1, Mac1, p150.95, VLA-4, ICAM-1, VCAM, EpCAM, alpha$_4$/beta$_7$ integrin, alpha v/beta3 integrin including either alpha or beta subunits thereof (e.g. anti-CD11a, anti-CD18 or anti-CD11b antibodies), tissue factor (TF), tumor necrosis factor alpha (INF-α), human vascular endothelial growth factor (VEGF), glycoprotein IIb/IIIa, TGF-beta, alpha interferon (alpha-IFN), IL-8, IL-2 receptor, IgE, respiratory syncytial virus (RSV), HIV-1 envelope glycoprotein gp120, cancer-associated high-mannose type N-glycans, blood group antigen Apo2, death receptor, flk2/flt3 receptor, obesity (OB) receptor, mpl receptor, CTLA-4, transferrin receptor, Lewis y, GD3 and protein C.

In an embodiment, the antibody is selected from the group consisting of abagovomab, actoxumab, adecatumumab, afutuzumab, altumomab, amatuximab, anifrolumab, apolizumab, atinumab, atlizumab, atorolimumab, bapineuzumab, basiliximab, bavituximab, belimumab, benralizumab, bertilimumab, besilesomab, bezlotoxumab, bimagrumab, bivatuzumab, blinatumomab, blosozumab, brentuximab, briakinumab, brodalumab, canakinumab, cantuzumab, caplacizumab, capromab, carlumab, catumaxomab, CC49, cedelizumab, cixutumumab, clazakizumab, clenoliximab, clivatuzumab, conatumumab, concizumab, crenezumab, CR6261, dacetuzumab, dalotuzumab, daratumumab, demcizumab, denosumab, detumomab, drozitumab, duligotumab, dupilumab, dusigitumab, ecromeximab, eculizumab, edobacomab, edrecolomab, eldelumab, elotuzumab, elsilimomab, enavatuzumab, enlimomab, enokizumab, enoticumab, ensituximab, epitumomab, epratuzumab, ertumaxomab, etaracizumab, etrolizumab, evolocumab, exbivirumab, fanolesomab, faralimomab, farletuzumab, fasinumab, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gevokizumab, girentuximab, glembatumumab, golimumab, gomiliximab, guselkumab, ibalizumab, icrucumab, imciromab, imgatuzumab, inclacumab, indatuximab, intetumumab, inolimomab, inotuzumab, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, ligelizumab, lintuzumab, lirilumab, lodelcizumab, lorvotuzumab, lucatumumab, lumiliximab, mapatumumab, margetuximab, maslimomab, mavrilimumab, matuzumab, mepolizumab, metelimumab, milatuzumab, minretumomab, mitumomab, mogamulizumab, morolimumab, motavizumab, moxetumomab, muromonab, namilumab, narnatumab, natalizumab, nebacumab, necitumumab, nerelimomab, nesvacumab, nimotuzumab, nivolumab, obinutuzumab, ocaratuzumab, ocrelizumab, odulimomab, ofatumumab, olaratumab, olokizumab, onartuzumab, oregovomab, orticumab, otelixizumab, oxelumab, ozanezumab, ozoralizumab, pagibaximab, panobacumab, parsatuzumab, pascolizumab, pateclizumab, patritumab, pemtumomab, perakizumab, pertuzumab, pi-dilizumab, pinatuzumab, pintumomab, placulumab, po-latuzumab, ponezumab, prilixumab, pritoxaximab, pritumumab, quilizumab, racotumomab, radretumab, rafivirumab, ramucirumab, raxibacumab, regavirumab, reslizumab, rilotumumab, robatumumab, roledumab, romosozumab, rontalizumab, rovelizumab, rupluzimab, samalizumab, sarilumab, satumomab, secukinumab, seribantumab, setoxaximab, sevirumab, sibrotuzumab, sifalimumab, siltuximab, simtuzumab, siplizumab, sirukumab, solanezumab, solitomab, sonepcizumab, sontuzumab, stamulumab, suvizumab, tabalumab, taca-tuzumab, talizumab, tanezumab, taplitumomab, tefiba-zumab, tenatumomab, teneliximab, teplizumab, tepro-tumumab, TGN1412, ticilimumab, tildrakizumab, tiga-tuzumab, tocilizumab, toralizumab, tovetumab, tralokinumab, TRBS07, tregalizumab, tremelimumab, tucotuzumab, tuvirumab, ublituximab, urelumab, urtoxazumab, ustekinumab, vantictumab, vapaliximab, vatelizumab, vedolizumab, veltuzumab, vepalimomab, vesencumab, visilizumab, volociximab, vorsetuzumab, votumumab, zalutumumab, zanolimumab, zatuximab, ziralimumab, 2G12 (anti-HIV-1 envelope glycoprotein gp120), and zolimomab.

In an embodiment, the antibody is selected from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the antibody is an anti-EGFR antibody.

In an embodiment, an anti-EGFR1 antibody is cetuximab, imgatuzumab, matuzumab, nimotuzumab, necitumumab, panitumumab, or zalutumumab.

In an embodiment, the antibody is an epidermal growth factor receptor 2 (HER2/neu) antibody.

In an embodiment, an anti-HER2 antibody is margetuximab, pertuzumab, trastuzumab, ertumaxomab, and 520C9XH22.

In an embodiment, the antibody is an anti-CD22 antibody.

In an embodiment, an anti-CD22 antibody is bectumomab, moxetumomab, epratuzumab, inotuzumab, or pinatuzumab.

In an embodiment, the antibody is an anti-CD30 antibody.

In an embodiment, an anti-CD30 antibody is brentuximab vedotin (or the antibody portion of the brentuximab vedotin) or iratumumab.

In an embodiment, the antibody is an anti-CD33 antibody.

In an embodiment, an anti-CD33 antibody is gemtuzumab, SGN-CD33A or lintuzumab.

In an embodiment, the antibody is genetically engineered to comprise one or more additional N-glycosylation sites. Said additional N-glycosylation sites may be in sites that are accessible to solvent and at a distance from antigen-binding or receptor-binding sites of the antibody such as a monoclonal antibody. Said sites are genetically engineered to comprise the N-glycosylation consensus sequence Asn-Xaa-Ser/Thr, wherein Xaa is any amino acid encoded in the human genetic code except that Xaa≠Pro.

In an embodiment, the antibody is an antibody genetically engineered to comprise one or more additional N-glycosylation sites in the Fc domain.

In an embodiment, the antibody is an antibody genetically engineered to comprise one or more additional N-glycosylation sites in the variable region.

In an embodiment, the antibody is an antibody genetically engineered to comprise one or more additional N-glycosylation sites in a region other than the Fc domain and the variable region.

In an embodiment, the antibody is an antibody which may be modified by the addition, deletion, or substitution of one or more amino acid residues to introduce one or more N-linked glycosylation site(s), thus resulting a "glycoform antibody". Additional N-glycosylation sites can be engineered into light and heavy chains by methods described in, for example, WO97/34632, WO95/15769, or WO2014/177771. In WO97/34632, additional N-glycosylation sites may be those of depicted in the FIG. 12 and corresponding to HCN1, HCN2, HCN3, HCN4, and/or HCN5 for heavy chain, and KCN1, KCN2, KCN3, and/or KCN4 for kappa light chain. Additional N-glycosylation sites in an antibody mean one or more non-Asn297 N-glycosylation sites. The non-Asn297 N-glycosylation sites can exist or be introduced into a heavy and/or a light chain.

In an embodiment, n is in the range of 1 to about 20, or 1 to about 15, or 1 to about 10, or 2 to 10, or 2 to 6, or 2 to 5, or 2 to 4; or n is 1, 2, 3, 4, 5, 6, 7, 8, 9, 10, 11, 12, 13, 14, 15, 16, 17, 18, 19, or 20.

In an embodiment, n is in the range of 3 to about 20, or 3 to about 15, or 3 to about 10, or 3 to about 9, or 3 to about 8, or 3 to about 7, or 3 to about 6, or 3 to 5, or 3 to 4.

In an embodiment, n is in the range of 4 to about 20, or 4 to about 15, or 4 to about 10, or 4 to about 9, or 4 to about 8, or 4 to about 7, or 4 to about 6, or 4 to 5.

In an embodiment, the antibody-drug conjugate has a high glycoside-to-antibody ratio. This embodiment has the utility that the antibody-drug conjugate is more water-soluble and biocompatible and less prone to e.g. aggregation. This embodiment has also the utility that the drug-to-antibody ratio can be higher when the glycoside-to-antibody ratio is higher, without compromising efficacy, safety or other properties of the conjugate. In the context of this specification, the glycoside-to-antibody ratio is defined as total number of monosaccharide units per antibody, wherein the monosaccharide units are joined via the O-glycosidic bonds to the toxic payload molecule.

The glycoside-to-antibody ratio is defined as the ratio of monosaccharide units conjugated (the total number of monosaccharide units in the conjugated saccharides) to the antibody (the number of antibody molecules in the conjugate). Any N- and O-glycans present in the antibody molecule(s) are not included when determining the glycoside-to-antibody ratio. Therefore the glycoside-to-antibody ratio equals n times the total number of monosaccharide units comprised in R1 and/or R2 groups of the antibody-drug conjugate. Any monosaccharide units possibly present in L' or in L (outside of R2) are also not included when determining the glycoside-to-antibody ratio.

As an example, if n is 1, R1 is a disaccharide (two monosaccharide units) and R2 is absent, the glycoside-to-antibody ratio is 1×2=2. As another example, if n is 8, R1 is a monosaccharide and R2 is absent, the glycoside-to-antibody ratio is 8×1=8. As a yet another example, if n is 2, R1 is a disaccharide (two monosaccharide units), R2 is a monosaccharide and L' comprises a monosaccharide unit somewhere in its structure (outside of R2), the glycoside-to-antibody ratio is 2×(2+1)=6; the monosaccharide comprised by L' is not included. As a yet another example, if n is 1, R1 is a disaccharide (two monosaccharide units), R2 is absent and L' comprises a monosaccharide unit somewhere in its structure (outside of R2), the glycoside-to-antibody ratio is 1×2=2; the monosaccharide comprised by L' is not included.

As n may vary in a composition comprising a number of antibody-drug conjugate molecules depending on e.g. how many toxic payload molecules are conjugated, the glycoside-to-antibody ratio of the antibody-drug conjugate or a composition comprising a mixture of the antibody-drug conjugate according to one or more embodiments may not be an integer. Experimentally, the glycoside-to-antibody ratio may be determined e.g. by MALDI-MS, for example as in Example 23, or ESI-MS.

In an embodiment, the glycoside-to-antibody ratio is in the range of 1 to about 100, or 1 to about 60, or 1 to about 20, or 1 to about 10; 2 to about 40, or 2 to about 20, or 2 to about 12, or 2 to about 10, or 2 to about 8, or 2 to about 6, or 2 to about 4; 3 to about 60, or 3 to about 40, or 3 to about 30, or 3 to about 20, or 3 to about 15, or 3 to about 10, or 3 to about 8, or 3 to about 6, or 3 to about 4; 4 to about 60, or 4 to about 40, or 4 to about 20, or 4 to about 16, or 4 to about 12, or 4 to about 10, or 4 to about 8, or 4 to about 7, or 4 to about 6, or 4 to 5; over 3, over 4, over 5, over 6, over 7, over 8, over 9, over 10, over 11, over 12, over 13, over 14, over 15, or over 16; or the glycoside-to-antibody ratio is 1, 2, 3, 4, 5, 6, 7, 8, 9, 10, 12, 14, 15, 16, 18, 20, 21, 22, 24, 25, 26, 27, 28, 30, 32, 34, 35, 36, 38, 40, 42, 44, 45, 46, 48, 50, 52, 54, 55, 56, 58, 60, 62, 63, 64, 66, 68, 70, 72, 74, 76, 78, 80, 82, 84, 86, 88, 90, 92, 94, 96, 98, 100, or more than 100.

In an embodiment, the glycoside-to-antibody ratio is at least 5, or at least 6, or at least 7, or at least 8. These glycoside-to-antibody ratios may have the added utility that they are relatively soluble and may be less prone to aggregate.

In an embodiment, the glycoside-to-antibody ratio is 5.
In an embodiment, the glycoside-to-antibody ratio is 6.
In an embodiment, the glycoside-to-antibody ratio is 7.
In an embodiment, the glycoside-to-antibody ratio is 8.
In an embodiment, the glycoside-to-antibody ratio is 9.
In an embodiment, the glycoside-to-antibody ratio is 10.
In an embodiment, the glycoside-to-antibody ratio is 11.
In an embodiment, the glycoside-to-antibody ratio is 12.
In an embodiment, the glycoside-to-antibody ratio is 13.
In an embodiment, the glycoside-to-antibody ratio is 14.
In an embodiment, the glycoside-to-antibody ratio is 15.
In an embodiment, the glycoside-to-antibody ratio is 16.
In an embodiment, the glycoside-to-antibody ratio is 17.
In an embodiment, the glycoside-to-antibody ratio is 18.
In an embodiment, the glycoside-to-antibody ratio is 19.
In an embodiment, the glycoside-to-antibody ratio is 20.

In an embodiment, n, drug-to-antibody ratio, and/or glycoside-to-antibody ratio of an antibody-drug conjugate may be determined using a MALDI-TOF MS.

In an embodiment, n, drug-to-antibody ratio, and/or glycoside-to-antibody ratio of an antibody-drug conjugate may be determined using an ESI-MS.

An exemplary method to determine n, drug-to-antibody ratio, and/or glycoside-to-antibody ratio for an antibody-drug conjugate (composition) is described in Example 23.

Exemplary methods to determine n, drug-to-antibody ratio, and/or glycoside-to-antibody ratio is described in Chen J, Yin S, Wu Y, Ouyang J. Development of a native nanoelectrospray mass spectrometry method for determination of the drug-to-antibody ratio of antibody-drug conjugates. Anal Chem. 2013 Feb. 5; 85(3):1699-1704. doi: 10.1021/ac302959p.

The auristatin and the antibody may be bound directly, via a bond, or indirectly via e.g. a linker group. The toxic payload molecule and the antibody may be bound directly, via a bond, or indirectly via e.g. a linker group. In this context, the linker group may be any linker group described in this specification.

The toxic payload molecule moiety A can be linked to the antibody through linker L. Antibody-drug conjugates can be prepared using a cross-linking reagent having a reactive functionality capable of binding to both the toxic payload molecule moiety and the antibody. For example, a cysteine, thiol or an amine, e.g. N-terminus or an amino acid side chain, such as lysine of the antibody, can form a bond with a functional group of a cross-linking reagent.

In an embodiment, L is a cleavable linker. In an embodiment, L is a non-cleavable linker. In an embodiment, the cleavable linker is an acid-labile linker, photo-labile linker, peptidase cleavable linker, esterase cleavable linker, a disulfide bond cleavable linker, a hydrophilic linker, a procharged linker, or a dicarboxylic acid based linker.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the s-amino group of lysine, are understood not to be peptidic bonds and are considered non-cleavable.

Some linkers can be cleaved by esterases, i.e. esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

Suitable cross-linking reagents that form a cleavable linker between the toxic payload molecule moiety, for example auristatin, and the antibody are well known in the art. Disulfide containing linkers are linkers cleavable through disulfide exchange, which can occur under physiological conditions. Such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)-2-sulfo-butanoate (sulfo-SPDB). These disulfide cross-linking reagents form a cleavable linker derived from disulfide-based moieties.

In an embodiment, the linker L is derived from N-succinimidyl-4-(2-pyridyldithio)butanoate (SPDB).

Suitable cross-linking reagents that form a charged linker between the drug moiety, for example auristatin, and the antibody are known as procharged cross-linking reagents. In one embodiment, the linker L is derived from the procharged cross-linking reagent 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Suitable cross-linking reagents that form a non-cleavable linker between the toxic payload molecule moiety, for example auristatin, and the antibody are well known in the art, and can form non-cleavable linkers that comprise a sulfur atom (such as SMCC) or those that are without a sulfur atom.

In an embodiment, the linker is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

In an embodiment, the linker is derived from N-succinimidyl-4-(maleimidomethyl)cyclohexane-1-carboxy-(6-amidocaproate)-, which is a "long chain" analog of SMCC (LC-SMCC), κ-maleimidoundeconoic acid N-succinimidyl ester (KMUA), γ-maleimidobutyric acid N-succinimidyl ester (GMBS), ε-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(-p-maleomidophenyl)isocyanate (PMIP) or maleimido-based cross-linking reagents containing a polyethythene glycol spacer, such as MAL-PEG-NHS. These cross-linking reagents form non-cleavable linkers derived from maleimido-based moieties.

Cross-linking reagents comprising a haloacetyle-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties.

In an embodiment, the linker L is derived from N-succinimidyl iodoacetate (SIA) or N-succinimidyl(4-iodoacetyl)aminobenzoate (SIAB).

Linker molecules and moieties include, but are not limited to, the following: amino benzoic acid spacers (see, for example and without limitation, U.S. Pat. Nos. 7,091,186 and 7,553,816, each of which is hereby incorporated by reference in its entirety); maleimidocaproyl; p-aminobenzylcarbamoyl (PAB); lysosomal enzyme-cleavable linkers (see, for example and without limitation, U.S. Pat. No. 6,214,345, hereby incorporated by reference in its entirety); maleimidocaproyl-polyethylene 20 glycol (MC(PEG)6-OH); valine-citrulline; and other linker compounds (see, for example and without limitation, U.S. Pat. No. 7,090,843 (Section 5.7 Conjugates and Fusion Proteins), U.S. Pat. No. 7,223,837 (columns 1-14 and Examples), and U.S. Pat. No. 7,659,241 (Columns 1 to 151 and Examples), and U.S. Patent Publication Nos. 2004/0018194 (paragraphs 232-309 and 329-330 and Examples), 2004/0121940 (paragraphs 1-105 and Examples), 2006/0116422 (paragraphs 39-202 and Examples), 2007/0258987 (paragraphs 222-292 and Examples), 2008/0213289 (paragraphs 225-281 and Examples), 2008/0241128 (paragraphs 11-216 and 303-306, and Examples), 2008/0311136 (paragraphs 16-365 and Examples), 2008/0317747 (paragraphs 226-282 and 299-300 and Examples), and 2009/0010945 (paragraphs 82-148 and Examples), each of which is hereby incorporated by reference in its entirety).

Various types of toxic payload molecules, linkers and methods for conjugating toxic payload molecules to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Cuff. Opin. Investig. Drugs 3:1089-1091; Senter and Springer, (2001) Adv. Drug Deliv. Rev. 53:247-264; Tranoy-Opalinski et al. (2014) β-Glucuronidase-responsive prodrugs for selective cancer chemotherapy: an update. Eur J Med Chem. 74:302-313. doi: 10.1016/j.ejmech.2013.12.045; Jeffrey et al. (2006) Development and properties of beta-glucuronide linkers for monoclonal antibody-drug conjugates. Bioconjug Chem. 17:831-840; Chen et al. (2013) Selective cancer therapy by extracellular activation of a highly potent glycosidic duocarmycin analogue. Mol Pharm. 10:1773-1782, doi: 10.1021/mp300581u; Tietze et al. (2013) Photoactivatable prodrugs of highly potent duocarmycin analogues for a selective cancer therapy. Chemistry. 19:1726-1731, doi: 10.1002/chem.201202773; Tietze and Schmuck (2011) Prodrugs for targeted tumor therapies: recent developments in ADEPT, GDEPT and PMT. Curr Pharm Des. 17:3527-3547; Tietze et al. (2011) Synthesis and biological evaluation of prodrugs based on the natural antibiotic duocarmycin for use in ADEPT and PMT. Chemistry 17:1922-1929, doi:10.1002/chem.201002798; Seubert et al. (2011) Enhanced tumor therapy using vaccinia virus strain GLV-1h68 in combination with a β-galactosidase-activatable prodrug seco-analog of duocarmycin SA. Cancer Gene Ther. 18:42-52, doi: 10.1038/cgt.2010.49; Tietze et al. (2010) Glycosidic prodrugs of highly potent bifunctional duocarmycin derivatives for selective treatment of cancer. Angew Chem Int Ed Engl. 49:7336-7339, doi:10.1002/anie.201002502; Schuster et al. (2010) Synthesis of the first spacer containing prodrug of a duocarmycin analogue and determination of its biological activity. Org Biomol Chem. 8:1833-1842, doi: 10.1039/b925070k; Tietze et al. (2009) Determination of the biological activity and structure activity relationships of drugs based on the highly cytotoxic duocarmycins and CC-1065. Toxins (Basel) 1:134-150, doi: 10.3390/toxins1020134; Tietze and Krewer (2009) Antibody-directed enzyme prodrug therapy: a promising approach for a selective treatment of cancer based on prodrugs and monoclonal antibodies. Chem Biol Drug Des.74:205-211, doi:10.1111/j.1747-0285.2009.00856.x; Tietze et al. (2008) Synthesis and biological evaluation of a novel pentagastrin-toxin conjugate designed for a targeted prodrug mono-therapy of cancer. Int J Mol Sci 9:821-837; doi: 10.3390/ijms9050821; Tietze and Krewer (2009) Novel analogues of CC-1065 and the duocarmycins for the use in targeted tumour therapies. Anticancer Agents Med Chem 9:304-325; Tietze et al. (2009) Synthesis and biological studies of different duocarmycin based glycosidic prodrugs for their use in the antibody-directed enzyme prodrug therapy. J Med Chem. 52:537-543, doi: 10.1021/jm8009102; Tietze et al. (2008) Asymmetric synthesis and biological evaluation of glycosidic prodrugs for a selective cancer therapy. Chem Med Chem. 3:1946-1955, doi: 10.1002/cmdc.200800250; Tietze et al. (2008) Duocarmycin-based prodrugs for cancer prodrug monotherapy. Bioorg Med Chem. 16:6312-6318, doi: 10.1016/j.bmc.2008.05.009; Tietze et al. (2008) Enantio- and diastereoselective synthesis of duocarmycine-based prodrugs for a selective treatment of cancer by epoxide opening. Chemistry 14:895-901; Tietze et al. (2007) Selective treatment of cancer: synthesis, biological evaluation and structural elucidation of novel analogues of the antibiotic CC-1065 and the duocarmycins. Chemistry 13:4396-4409; Tietze et al. (2006) Antitumor agents: development of highly potent glycosidic duocarmycin analogues for selective cancer therapy. Angew Chem Int Ed Engl 45:6574-6577; Tietze et al. (2006) Investigation of reactivity and selectivity of DNA-alkylating duocarmycin analogues by high-resolution mass spectrometry. Angew Chem Int Ed Engl. 45:6570-6574; Tietze and Feuerstein (2003) Enzyme and proton-activated prodrugs for a selective cancer therapy. Curr Pharm Des 9:2155-2175; Tietze et al. (2002) Proof of principle in the selective treatment of cancer by antibody-directed enzyme prodrug therapy: the development of a highly potent prodrug. Angew Chem Int Ed Engl. 41:759-761; Tietze et al. (2001) Highly selective glycosylated prodrugs of cytostatic CC-1065 analogues for antibody-directed enzyme tumor therapy. Chembiochem. 2:758-765; Tietze et al. (2001) A strategy for tumor-selective chemotherapy by enzymatic liberation of seco-duocarmycin SA-derivatives from nontoxic prodrugs. Bioorg Med Chem 9:1929-1939; Tietze et al. (1988) Stereoselective synthesis of (1-alkoxyalkyl) alpha- and beta-D-glucopyranosiduronates (acetal-glucopyranosiduronates): a new approach to specific cytostatics for the treatment of cancer. Carbohydr Res. 180:253-262; Tietze et al. (1989) Proton-mediated liberation of aldophosphamide from a nontoxic prodrug: a strategy for tumor-selective activation of cytocidal drugs. Cancer Res. 49:4179-4184; Tietze et al. (2012) Synthesis, biological evaluation, and live cell imaging of novel fluorescent duocarmycin analogs. Chem Biodivers. 9:2559-2570, doi:10.1002/cbdv.201200289; Tietze et al. (2010) Synthesis of Fluorescence-Labelled Glycosidic Prodrugs Based on the Cytotoxic Antibiotic Duocarmycin. Eur. J Org Chem 2010:6909-6921, DOI: 10.1002/ejoc.201000966; Wirth et al. (2013) The Two Faces of Potent Antitumor Duocarmycin-Based Drugs: A Structural Dissection Reveals Disparate Motifs for DNA versus Aldehyde Dehydrogenase 1 Affinity Angewandte Chemie, International Edition, 52:6921-6925. doi: 10.1002/anie.201208941; Tietze et al. (2002) Synthesis and Biological Evaluation of Novel Analogues and Prodrugs of the Cytotoxic Antibiotic CC-1065 for Selective Cancer Therapy. Eur J Org Chem 2002:1634-1645; Tietze et al. (1996) Prodrugs of the Cytostatic CC-1065 That Can Be Activated in a Tumor-Selective Manner. Angewandte Chemie, International Edition, 35:2674-2677, doi: 10.1002/anie.199626741; Zhao et al. (2008) Amide N-glycosylation by Asm25, an N-glycosyltransferase of ansamitocins. Chem Biol. 15:863-874, doi: 10.1016/j.chembiol.2008.06.007; Lu et al. 2004) A novel amide N-glycoside of ansamitocins from Actinosynnema pretiosum. J Antibiot (Tokyo) 57:348-350; WO2011/051484, WO2011/054837, WO2001/083448, WO2007/011968, WO2008/083312, WO2008/074004, WO2007/089149, and DE4415463.

The antibody-drug conjugates can be prepared by any methods known in the art, such as those described in U.S. Pat. Nos. 7,811,572, 6,411,163, 7,368,565, and 8,163,888, and US application publications 2011/0003969, 2011/0166319, 2012/0253021, 2012/0259100, and 2014/0288280. Other examples of conjugation methods are described in U.S. Pat. No. 7,837,980 (Seattle Genetics), Carter and Senter (2008) Cancer J, 14(3):154, as well as U.S. Published Application Nos. 2004/0157782 and 2005/0238649 and International Patent Application No, PCT/US04/038392. The entire teachings of these patents and patent application publications are herein incorporated by reference.

The antibody-drug conjugates can be prepared by any methods known in the art, such as those described in WO 2014/177771 (for example pages 34-51 and 59-77 and Examples).

The antibody drug conjugates can be characterized and selected for their physical/chemical properties and/or biological activities by various assays known in the art.

For example, an antibody and ADC can be tested for its antigen binding activity by known methods such as ELISA, FACS, Biacore or Western blot.

Transgenic animals and cell lines are particularly useful in screening antibody drug conjugates (ADCs) that have potential as prophylactic or therapeutic treatments of cancer of tumor-associated antigens and cell surface receptors. Screening for a useful ADC may involve administering a candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. The candidate ADC may be screened serially and individually, or in parallel under medium or high-throughput screening format.

In an embodiment, the linker group comprises a linker group represented by formula VIII Formula VIII

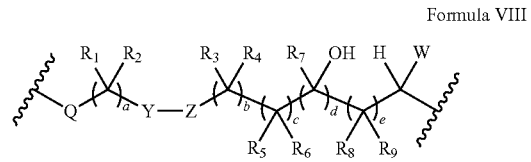

wherein

Y is an oxygen, sulphur, amine, amide, peptide or absent, wherein the peptide is an $E_1$-P-$E_2$ unit in which $E_1$ and $E_2$ are independently C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

$R_1$, $R_2$, $R_3$, $R_4$, $R_5$, $R_6$, $R_9$, $R_8$ and $R_9$ are each independently H, OH, amine, $C_2$-$C_6$ acylamide, carboxyl, substituted carboxyl, $C_1$-$C_6$ alkyl or substituted $C_1$-$C_6$ alkyl;

W is H, CH$_2$OH, CH$_3$, carboxyl, substituted carboxyl, C$_1$-C$_6$ alkyl or substituted C$_1$-C$_6$ alkyl;

a is an integer from 0 to 6;

b is 0 or 1;

c and e are each independently an integer from 0 to 7;

d is an integer in the range of 1 to 7; and

Q is E'-F'-E, wherein F' is an amine, amide, disulfide, thioether, thioester, hydrazone, Schiff base, oxime, olefin metathesis reaction product, triazole or phosphine group, or other group generated by the reaction of the functional group F-E and the functional group F', wherein F is a functional group that can react with an amine, thiol, azide, alkene, alkyne, aldehyde, ketone, carboxylic acid or hydroxylamine, and F' is an amine, thiol, azide, alkene, alkyne, aldehyde, ketone, carboxylic acid or hydroxylamine; and E is absent or a polyethyleneoxy unit of formula (CH$_2$CH$_2$O)$_p$, wherein p is an integer from 2 to about 20; and E and E' are each independently absent or a polyethyleneoxy unit of formula (CH$_2$CH$_2$O)$_p$, wherein p is an integer from 2 to about 20.

In an embodiment, Z is absent.

In an embodiment, Z is a saccharide.

In an embodiment, Z is an oligosaccharide with a degree of polymerization from 1 to about 20; from 1 to 10; from 1 to 8; from 1 to 6; from 1 to 5; from 1 to 4; from 1 to 3; from 1 to 2; or 1, 2, 3, 4 or 5.

In an embodiment, Z is a monosaccharide, disaccharide or trisaccharide.

In an embodiment, Z is OH.

In an embodiment, Z is H.

In an embodiment, a is 1, 2, 3, 4, 5, or 6.

In an embodiment, a is 1.

In an embodiment, b is 0.

In an embodiment, b is 1.

In an embodiment, c is 0.

In an embodiment, c is 1, 2, 3, 4, 5, 6 or 7.

In an embodiment, d is 1, 2, 3, 4, 5, 6 or 7.

In an embodiment, d is 3, 4 or 5.

In an embodiment, d is 3.

In an embodiment, d is 4.

In an embodiment, d is 5.

In an embodiment, d is 6.

In an embodiment, e is 0.

In an embodiment, e is 1, 2, 3, 4, 5, 6 or 7.

In an embodiment, d is 3; and R$_7$ is H.

In an embodiment, d is 4; and R$_7$ is H.

In an embodiment, b is 1; and R$_3$ and R$_4$ are each H.

In an embodiment, a is 1; and R$_1$ and R$_2$ are each H.

In an embodiment, e is 1; and R$_8$ and R$_9$ are each H.

In an embodiment, a, b, c, or e is 0.

In an embodiment, a, b, c, and/or e is 0.

In an embodiment, W is H.

In an embodiment, a is 2 or 3; and R$_1$ and R$_2$ are both H.

In an embodiment, Y is an oxygen.

In an embodiment, Y is a sulphur.

In an embodiment, R$_1$, R$_2$, R$_3$, R$_4$ and R$_7$ are each H; W is H; a is 1; b is 1; c and e are each 0; and d is 4.

In an embodiment, R$_3$, R$_4$, and R$_7$ are each H; W is H; b is 1; a, c and e are each 0; and d is 4.

In an embodiment, X is an alkyne; Y is an oxygen; Z is absent; R$_1$, R$_2$, R$_3$, R$_4$ and R$_7$ are each H; W is H; a is 1; b is 1; c and e are each 0; and d is 4.

In an embodiment, X is azide; Y is an oxygen; Z is absent; R$_1$, R$_2$, R$_3$, R$_4$ and R$_7$ are each H; W is H; a is 1; b is 1; c and e are each 0; and d is 4.

In an embodiment, the linker group comprises a peptide and optionally a self-immolative group linking the peptide and the auristatin.

In an embodiment, the linker group comprises a peptide and optionally a self-immolative group linking the peptide and the toxic payload molecule.

In an embodiment, the linker group is the valine-citrulline linker.

In an embodiment, the peptide is a peptide cleavable by a lysosomal peptidase, optionally selected from the group consisting of L-Gly-L-Gly, L-Val-L-Cit, L-Phe-L-Leu, L-Leu-L-Ala-L-Leu, L-Leu-L-Ala-L-Ala and L-Ala-L-Leu-L-Ala-L-Leu.

In an embodiment, the self-immolative group is a para-aminobenzoyl group (PAB).

In an embodiment, the linker group comprises a thioether group formed by a reaction between a maleimidyl group and a sulfhydryl group. In an embodiment, the linker comprises a thioether group formed by a reaction between a maleimidocaproyl group and a sulfhydryl group.

A method for preparing the antibody-drug conjugate or the molecule according to one or more embodiments is disclosed, comprising reacting a saccharide donor with a hydroxyl group of an auristatin so that an O-glycosidic bond is formed between the saccharide and the auristatin.

In an embodiment, the auristatin is monomethyl auristatin E.

In an embodiment, the linker group L comprises a saccharide bound to a hydroxyl group of the toxic payload molecule via an O-glycosidic bond.

In an embodiment, L is L'-R2, wherein R2 is a saccharide bound via an O-glycosidic bond to a hydroxyl group of the toxic payload molecule, L' is a linker group, and the saccharide R2 is bound to the linker group L' via a covalent bond.

In an embodiment, the saccharide R2 comprises or consists of a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof, and the monosaccharide is bound to the toxic payload molecule via the O-glycosidic bond, and the saccharide R2 is bound to the linker group L' via a covalent bond.

In an embodiment, the modification is sulfate, phosphate, carboxyl, amino, or O-acetyl modification of the monosaccharide.

In an embodiment, the saccharide R2 comprises neuraminic acid α2,3- or α2,6-linked to β-D-galactose, or the saccharide R2 is a disaccharide, wherein neuraminic acid is α2,3- or α2,6-linked to β-D-galactose.

In an embodiment, the saccharide R2 is bound to the linker group L' via a covalent bond from the 9-position of the neuraminic acid.

In an embodiment, the antibody-drug conjugate comprises the saccharide R2 and R1 is absent.

In an embodiment, the glycoside-to-antibody ratio is n times the total number of monosaccharide units comprised in R1 and R2, and wherein the glycoside-to-antibody ratio is in the range of 1 to about 100, or 1 to about 60, or 1 to about 20, or 1 to about 10; 2 to about 40, or 2 to about 20, or 2 to about 12, or 2 to about 10, or 2 to about 8, or 2 to about 6, or 2 to about 4; 3 to about 60, or 3 to about 40, or 3 to about 30, or 3 to about 20, or 3 to about 15, or 3 to about 10, or 3 to about 8, or 3 to about 6, or 3 to about 4; 4 to about 60, or 4 to about 40, or 4 to about 20, or 4 to about 16, or 4 to about 12, or 4 to about 10, or 4 to about 8, or 4 to about 7, or 4 to about 6, or 4 to 5; over 3, over 4, over 5, over 6, over 7, over 8, over 9, over 10, over 11, over 12, over 13, over 14, over 15, or over 16; or the glycoside-to-antibody ratio is 1, 2, 3, 4, 5, 6, 7, 8, 9, 10, 12, 14, 15, 16, 18, 20, 21, 22, 24, 25, 26, 27, 28, 30, 32, 34, 35, 36, 38, 40, 42, 44, 45, 46, 48, 50, 52, 54, 55, 56, 58, 60, 62, 63, 64, 66, 68, 70, 72, 74, 76, 78, 80, 82, 84, 86, 88, 90, 92, 94, 96, 98, 100, or more than 100.

A method for preparing the antibody-drug conjugate or the molecule according to one or more embodiments is disclosed, comprising reacting a saccharide donor with a hydroxyl group of a toxic payload molecule so that an O-glycosidic bond is formed between the saccharide and the toxic payload molecule.

A method for preparing the antibody-drug conjugate or the molecule according to one or more embodiments is disclosed, comprising reacting a saccharide donor with the hydroxyl group of norephedrine so that an O-glycosidic bond is formed between the saccharide and norephedrine to obtain an intermediate represented by formula IX

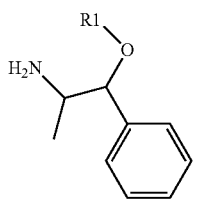

Formula IX wherein

R1 is a saccharide bound to the norephedrine via an O-glycosidic bond; and reacting the intermediate represented by formula IX with the compound represented by formula X

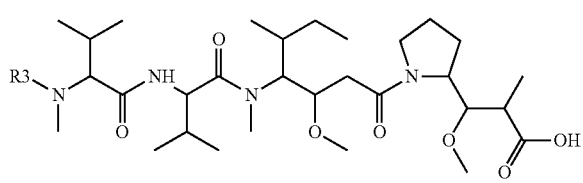

Formula X wherein R3 is H or an N-protecting group.

The intermediate represented by formula IX reacts with the compound represented by formula X by forming an amide bond.

In an embodiment, the intermediate represented by formula IX is reacted with the compound represented by formula X in the presence of an activation agent and a base catalyst in a suitable solvent. A suitable activation agent may be e.g. DMT-MM, a carbodi-imide such as EDAC or DCC, or HBTU. A suitable base catalyst may be e.g. DIPEA. A suitable solvent may be e.g. acetonitrile (ACN), dichloromethane, pyridine, dimethylformamide. They may be reacted e.g. in room temperature, or at a temperature up to about 60° C. A suitable reaction time may be e.g. in the range of from 2 hours to 3 days.

In an embodiment, the amine group of norephedrine is protected by a N-protecting group, and the N-protecting group is removed to obtain an intermediate represented by formula IX.

In an embodiment, R3 is an N-protecting group.

In an embodiment, R3 is a protecting group, and the protecting group is removed after reacting the intermediate represented by formula IX with the compound represented by formula X.

Many N-protecting groups suitable for protecting an amine group are known to a skilled person. For instance, Boc (tert-butyloxycarbonyl) or Fmoc (fluorenylmethyloxycarbonyl) are suitable N-protecting groups. Other possible N-protecting groups may be e.g. carbobenzyloxy, benzyl carbamate, methoxyphenyl, or tosyl group.

The following embodiments may be combined with either method for preparing the antibody-drug conjugate or the molecule according to one or more embodiments.

In an embodiment, the saccharide is a monosaccharide, a disaccharide or an oligosaccharide.

In an embodiment, the saccharide comprises one or more glycosidic bonds that are cleavable by a lysosomal or an intracellular glycohydrolase.

In an embodiment, the saccharide comprises or is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid and any analogue or modification thereof.

In an embodiment, the O-glycosidic bond is the anomeric bond of a pyranose monosaccharide comprised in the saccharide that is or is analogous to β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, or neuraminic acid, or modification, respectively.

In an embodiment, the O-glycosidic bond is hydrolysable by a lysosomal or an intracellular glycohydrolase.

In an embodiment, the lysosomal or intracellular glycohydrolase is capable of removing the entire saccharide inside a cell.

In an embodiment, one or more of the glycosidic bonds of the saccharide are essentially stable in neutral pH and/or in serum.

In an embodiment, all glycosidic bonds of the saccharide are essentially stable in neutral pH and/or in serum.

In an embodiment, one or more of the glycosidic bonds of the saccharide are hydrolysable in tumor microenvironment outside a cell. This embodiment has the added utility that the saccharide may be removed more efficiently inside a tumor than in normal tissue and the molecule may be more efficiently taken up by cancer cells than by normal cells.

In an embodiment, the lysosomal or intracellular glycohydrolase is selected from the group consisting of β-galactosidase, β-hexosaminidase, β-N-acetylglucosaminidase, α-N-acetylgalactosaminidase, β-glucuronidase, α-L-iduronidase, α-galactosidase, α-glucosidase, β-glucosidase, α-mannosidase, β-mannosidase, α-fucosidase, β-xylosidase and neuraminidase.

In the context of this specification, the term "saccharide donor" should be understood as referring to a molecule comprising a saccharide and a functional group capable of reacting with a hydroxyl group so that the saccharide is bound via an O-glycosidic bond to the hydroxyl group. In an embodiment, the anomeric carbon of the saccharide is substituted by the functional group. The saccharide donor may be a glycosyl donor. Non-limiting examples of the saccharide donor are e.g. 2,3,4,6-tetra-O-benzoyl-D-glucopyranosyl trichloroacetimidate or 2,3,4,6-tetra-O-acetyl-β-D-glucopyranose.

In an embodiment, the saccharide donor comprises a functional group capable of reacting with a hydroxyl group, such as a hydroxyl group or a trichloroacetimidate group.

In an embodiment, the functional group is selected from the group consisting of a hydroxyl group and a trichloroacetimidate group.

In an embodiment, the saccharide donor is a saccharide trichloroacetimidate.

In an embodiment, the saccharide donor is reacted with the hydroxyl group of norephedrine or of the auristatin in the presence of an anhydrous solvent, for instance dry $CH_2Cl_2$:ACN and trimethylsilyl trifluoromethanesulfonate.

In an embodiment, the saccharide donor is reacted with the hydroxyl group of norephedrine or of the auristatin at a temperature about or below 0° C., or below −10° C., or below −20° C.

In an embodiment, the saccharide donor is reacted with the hydroxyl group of norephedrine or of an auristatin in the presence of $BF_3$ etherate. In this reaction, the hydroxyl group of the anomeric carbon reacts with the hydroxyl group of the norephedrine or of the auristatin. Other hydroxyl groups of the saccharide donor, e.g. hydroxyl groups of carbons 2, 3, 4 and 6, may be protected by a suitable hydroxyl protecting group, such as acetyl.

The reaction in the presence of $BF_3$ etherate may be performed at a low temperature, e.g. as described in Stahelin and von Wartburg 1991, Cancer Res. 51: 5-15.

In an embodiment, free hydroxyl groups of the saccharide donor are protected by hydroxyl protecting groups prior to reacting with the hydroxyl group of norephedrine or of the auristatin. Many hydroxyl protecting groups suitable for protecting a free hydroxyl group are known to a skilled person. For instance, benzoyl is a suitable hydroxyl protecting group. Other possible hydroxyl protecting groups may be e.g. acetyl or trimethylacetyl group.

In an embodiment, the hydroxyl protecting groups are removed after reacting with the hydroxyl group of norephedrine or of the auristatin.

In an embodiment, the saccharide bound to the auristatin via the O-glycosidic bond is D-galactose; and the method further comprises sialylating the galactose. The molecule thus obtainable comprises a saccharide, wherein the saccharide comprises neuraminic acid bound to the galactose, for instance the disaccharide Neu5Acα2,6Galβ or Neu5Acα2,3Galβ, and the galactose is bound to the auristatin via the O-glycosidic bond.

In an embodiment, the saccharide bound to the auristatin via the O-glycosidic bond is D-glucose; and the method further comprises galactosylating the glucose. The molecule thus obtainable comprises a saccharide, wherein the saccharide comprises D-galactose bound to the glucose, for instance the disaccharide Galβ1,4Glcβ or Galβ1,4Glcα, and the glucose is bound to the auristatin via the O-glycosidic bond.

In an embodiment, the method further comprises sialylating the galactose or the disaccharide. The molecule thus obtainable comprises a disaccharide or a trisaccharide comprising neuraminic acid bound to galactose, and the saccharide is bound to the auristatin via the O-glycosidic bond. In an embodiment, the sialylated trisaccharide is α2,6-sialyllactose (Neu5Acα2,6Galβ1,4Glc) or α2,3-sialyllactose (Neu5Acα2,3Galβ1,4Glc), and the saccharide is bound to the auristatin via either α-O-glycosidic bond or β-O-glycosidic bond.

The sialylation and/or the galactosylation may be performed using a glycosyltransferase, such as a sialyltransferase or a galactosyltransferase.

In this context, the term "glycosyltransferase" should be understood as referring to any enzyme capable of transferring a glucosyl residue from a suitable donor molecule to the saccharide.

In an embodiment, the sialyltransferase is a α2,6-sialyltransferase, such as human ST6GAL1 or *P. damsela* α2,6-sialyltransferase, or a α2,3-sialyltransferase, such as rat α2,3-N-sialyltransferase.

A suitable donor molecule for the sialyltransferase is e.g. CMP-Neu5Ac.

In an embodiment, the galactosyltransferase is human β1,4-GalT1, human β1,4-GalT2, bovine milk β1,4-GalT or bovine β1,4-GalT1.

A suitable donor molecule for the galactosyltransferase is e.g. UDP-D-Gal.

A molecule obtainable by the method according to one or more embodiments is also disclosed.

A method for preparing the antibody-drug conjugate according to one or more embodiments is disclosed, comprising conjugating the molecule according to one or more embodiments to an antibody, optionally via a linker group.

Many ways of conjugating drugs to antibodies are known, and in principle any way that is suitable for conjugating auristatin to an antibody may be used. The molecule according to one or more embodiments may be conjugated to the antibody directly or indirectly, for instance via a linker group. In an embodiment, the amine group of auristatin is conjugated to a suitable group of the antibody, for instance a functional group capable of reacting with the amine that is introduced into the antibody prior to conjugation. Alternatively, the amine group of the auristatin may derivatized e.g. with a linker group comprising a suitable functional group that may be conjugated to another functional group of the antibody or another functional group introduced to the antibody.

In this context, the antibody may in principle be any antibody, and in particular any antibody described in this specification.

In an embodiment, the antibody is selected from the group consisting of bevacizumab, tositumomab, etanercept, trastuzumab, adalimumab, alemtuzumab, gemtuzumab ozogamicin, efalizumab, rituximab, infliximab, abciximab, basiliximab, palivizumab, omalizumab, daclizumab, cetuximab, panitumumab, epratuzumab, 2G12, lintuzumab, nimotuzumab and ibritumomab tiuxetan.

In an embodiment, the antibody is selected from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the linker group comprises a linker group represented by formula VIII Formula VIII

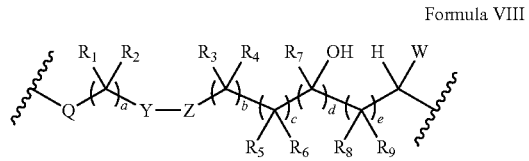

wherein

Y is an oxygen, sulphur, amine, amide, peptide or absent, wherein the peptide is an $E_1$-P-$E_2$ unit in which $E_1$ and $E_2$ are independently C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

$R_1$, $R_2$, $R_3$, $R_4$, $R_5$, $R_6$, $R_7$, $R_8$ and $R_9$ are each independently H, OH, amine, $C_2$-$C_6$ acylamide, carboxyl, substituted carboxyl, $C_1$-$C_6$ alkyl or substituted $C_1$-$C_6$ alkyl;

W is H, $CH_2OH$, $CH_3$, carboxyl, substituted carboxyl, $C_1$-$C_6$ alkyl or substituted $C_1$-$C_6$ alkyl;

a is an integer from 0 to 6;

b is 0 or 1;

c and e are each independently an integer from 0 to 7;

d is an integer in the range of 1 to 7; and

Q is E'-F'-E, wherein F' is an amine, amide, disulfide, thioester, thioester, hydrazone, Schiff base, oxime, olefin metathesis reaction product, triazole or phosphine group, or other group generated by the reaction of the functional group F-E and the functional group F', wherein F is a functional group that can react with an amine, thiol, azide, alkene, alkyne, aldehyde, ketone, carboxylic acid or hydroxylamine, and F' is an amine, thiol, azide, alkene, alkyne, aldehyde, ketone, carboxylic acid or hydroxylamine; and E is absent or a polyethyleneoxy unit of formula $(CH_2CH_2O)_p$, wherein p is an integer from 2 to about 20; and E and E' are each independently absent or a polyethyleneoxy unit of formula $(CH_2CH_2O)_p$, wherein p is an integer from 2 to about 20.

In an embodiment, $R_1$, $R_2$, $R_3$, $R_4$ and $R_7$ are each H; W is H; a is 1; b is 1; c and e are each 0; and d is 4.

In an embodiment, $R_3$, $R_4$, and $R_7$ are each H; W is H; b is 1; a, c and e are each 0; and d is 4.

In an embodiment, X is an alkyne; Y is an oxygen; Z is absent; $R_1$, $R_2$, $R_3$, $R_4$ and $R_7$ are each H; W is H; a is 1; b is 1; c and e are each 0; and d is 4.

In an embodiment, X is azide; Y is an oxygen; Z is absent; $R_1$, $R_2$, $R_3$, $R_4$ and $R_7$ are each H; W is H; a is 1; b is 1; c and e are each 0; and d is 4.

In an embodiment, the linker group comprises a peptide and optionally a self-immolative group linking the peptide and the auristatin.

In an embodiment, the linker group comprises a peptide and optionally a self-immolative group linking the peptide and the toxic-payload molecule.

In an embodiment, the linker group is the valine-citrulline linker.

In an embodiment, the peptide is a peptide cleavable by a lysosomal peptidase, optionally selected from the group consisting of L-Gly-L-Gly, L-Val-L-Cit, L-Phe-L-Leu, L-Leu-L-Ala-L-Leu, L-Leu-L-Ala-L-Ala and L-Ala-L-Leu-L-Ala-L-Leu.

In an embodiment, the self-immolative group is a para-aminobenzoyl group (PAB).

In an embodiment, the linker group comprises a thioether group formed by a reaction between a maleimidyl group and a sulfhydryl group. In an embodiment, the linker comprises a thioether group formed by a reaction between a maleimidocaproyl group and a sulfhydryl group.

In an embodiment, the linker group comprises a saccharide bound to a hydroxyl group of the toxic payload molecule via an O-glycosidic bond.

In an embodiment, the molecule comprises O-β-D-galactopyranosylmonomethylauristatin E (MMAG). In an embodiment, the molecule is MMAG. In an embodiment, the antibody-drug conjugate comprises MMAG and antibody. In an embodiment, the antibody-drug conjugate is a conjugate of MMAG and antibody. In an embodiment, the glycoside-to-antibody-ratio of the antibody-drug conjugate of MMAG and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of MMAG and an antibody is 2, 3, 4, 5, 6, 7, 8, 9, 10, 11, 12, 13, 14, 15, 16, 17, 18, 19, or 20, and the antibody is selected from the group of is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Val-Cit-PAB-MMAG. In an embodiment, the molecule is Val-Cit-PAB-MMAG. In an embodiment, the antibody-drug conjugate comprises Val-Cit-PAB-MMAG and antibody. In an embodiment, the antibody-drug conjugate is a conjugate of Val-Cit-PAB-MMAG and antibody. In an embodiment, the glycoside-to-antibody-ratio of the antibody-drug conjugate of Val-Cit-PAB-MMAG and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Val-Cit-PAB-MMAG and an antibody is 2, 3, 4, 5, 6, 7, 8, 9, 10, 11, 12, 13, 14, 15, 16, 17, 18, 19, or 20, and the antibody is selected from the group of is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises N-(6-azido-6-deoxy-D-galactosyl)-MMAG. In an embodiment, the molecule is N-(6-azido-6-deoxy-D-galactosyl)-MMAG. In an embodiment, the antibody-drug conjugate comprises N-(6-azido-6-deoxy-D-galactosyl)-MMAG and antibody. In an embodiment, the antibody-drug conjugate is a conjugate of N-(6-azido-6-deoxy-D-galactosyl)-MMAG and antibody. In an embodiment, the glycoside-to-antibody-ratio of the antibody-drug conjugate of N-(6-azido-6-deoxy-D-galactosyl)-MMAG and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of N-(6-azido-6-deoxy-D-galactosyl)-MMAG and an antibody is 2, 3, 4, 5, 6, 7, 8, 9, 10, 11, 12, 13, 14, 15, 16, 17, 18, 19, or 20, and and the antibody is selected from the group of is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody. In an embodiment, the molecule comprises O—(N-acetyl-neuraminyl-β-D-galactopyranosyl)-MMAE (MMAS). In an embodiment, the molecule is MMAS. In an embodiment, the antibody-drug conjugate comprises MMAS and antibody. In an embodiment, the antibody-drug conjugate is a conjugate of MMAS and antibody. In an embodiment, the glycoside-to-antibody-ratio of the antibody-drug conjugate of MMAS and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of MMAS and an antibody is 2, 3, 4, 5, 6, 7, 8, 9, 10, 11, 12, 13, 14, 15, 16, 17, 18, 19, or 20 and the antibody is selected from the group of is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Val-Cit-PAB-MMAS. In an embodiment, the molecule is Val-Cit-PAB-MMAS. In an embodiment, the antibody-drug conjugate comprises Val-Cit-PAB-MMAS and antibody. In an embodiment, the antibody-drug conjugate is a conjugate of Val-Cit-PAB-MMAS and antibody. In an embodiment, the glycoside-to-antibody-ratio of the antibody-drug conjugate of Val-Cit-PAB-MMAS and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Val-Cit-PAB-MMAS and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises N-(6-azido-6-deoxy-D-galactosyl)-MMAS. In an embodiment, the molecule is N-(6-azido-6-deoxy-D-galactosyl)-MMAS. In an embodiment, the antibody-drug conjugate comprises N-(6-azido-6-deoxy-D-galactosyl)-MMAS and antibody. In an embodiment, the antibody-drug conjugate is a conjugate of N-(6-azido-6-deoxy-D-galactosyl)-MMAS and antibody. In an embodiment, the glycoside-to-antibody-ratio of the conjugate of N-(6-azido-6-deoxy-D-galactosyl)-MMAS and an antibody is 2, 3, 4, 5, 6, 7, 8, 9, 10, 11, 12, 13, 14, 15, 16, 17, 18, 19, or 20. In an embodiment, the glycoside-to-antibody-ratio of the conjugate of N-(6-azido-6-deoxy-D-galactosyl)-MMAS and an antibody is 2, 3, 4, 5, 6, 7, 8, 9, 10, 11, 12, 13, 14, 15, 16, 17, 18, 19, or 20, and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the antibody-drug conjugate comprises MMAG and anti-EGFR antibody. In an embodiment, the antibody-drug conjugate comprises MMAS and anti-EGFR antibody. In an embodiment, the antibody-drug conjugate is a conjugate of MMAG and anti-EGFR antibody. In an embodiment, the antibody-drug conjugate is a conjugate of MMAS and anti-EGFR antibody. In an embodiment, the glycoside-to-antibody-ratio of the antibody-drug conjugate of MMAG and an anti-EGFR antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of MMAG and an anti-EGFR antibody is 2, 3, 4, 5, 6, 7, 8, 9, 10, 11, 12, 13, 14, 15, 16, 17, 18, 19, or 20, and the antibody is selected from the group of cetuximab, imgatuzumab, matuzumab, nimotuzumab, necitumumab, panitumumab, and zalutumumab. In an embodiment, the glycoside-to-antibody-ratio of the antibody-drug conjugate of MMAS and an anti-EGFR antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of MMAS and an anti-EGFR antibody is 2, 3, 4, 5, 6, 7, 8, 9, 10, 11, 12, 13, 14, 15, 16, 17, 18, 19, or 20, and the antibody is selected from the group of cetuximab, imgatuzumab, matuzumab, nimotuzumab, necitumumab, panitumumab, and zalutumumab or from the group consisting of an anti-EGFR1 antibody, an epidermal growth factor receptor 2 (HER2/neu) antibody, an anti- CD22 antibody, an anti-CD30 antibody, an anti-CD33 antibody, and an anti-CD20 antibody.

In an embodiment, the molecule comprises β-D-4'-demethylepipodophyllotoxin β-D-4-galactopyranosylglucopyranoside (Galβ1,4Glc-PT). In an embodiment, the molecule is Galβ1,4Glc-PT. In an embodiment, the antibody-drug conjugate comprises Galβ1,4Glc-PT and antibody. In an embodiment, the antibody-drug conjugate is a conjugate of Galβ1,4Glc-PT and antibody. In an embodiment, the glycoside-to-antibody-ratio of the antibody-drug conjugate of Galβ1,4Glc-PT and antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Galβ1,4Glc-PT and antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises α2,6-N-acetylneuraminyl-β-D-4-galactopyranosylglucopyranoside (NeuAcα2,6Galβ1,4Glc-PT). In an embodiment, the molecule is NeuAcα2,6Galβ1,4Glc-PT. In an embodiment, the antibody-drug conjugate comprises NeuAcα2,6Galβ1,4Glc-PT and antibody. In an embodiment, the antibody-drug conjugate is a conjugate of NeuAcα2,6Galβ1,4Glc-PT and antibody. In an embodiment, the glycoside-to-antibody-ratio of the antibody-drug conjugate of NeuAcα2,6Galβ1,4Glc-PT and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of NeuAcα2,6Galβ1,4Glc-PT and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises α2,6-N-acetyl-9-azidoneuraminyl-β-D-4-galactopyranos-ylglucopyranoside (9-azido-NeuAcα2,6Galβ1,4Glc-PT). In an embodiment, the molecule is 9-azido-NeuAcα2,6Galβ1,4Glc-PT. In an embodiment, the antibody-drug conjugate comprises 9-azido-NeuAcα2,6Galβ1, 4Glc-PT and antibody. In an embodiment, the antibody-drug conjugate is a conjugate of 9-azido-NeuAcα2, 6Galβ1,4Glc-PT and antibody. In an embodiment, the antibody-drug conjugate is a conjugate of 9-azido-NeuAcα2,6Galβ1,4Glc-PT and DBCO-modified antibody. In an embodiment, the glycoside-to-antibody-ratio of the antibody-drug conjugate of 9-azido-NeuAcα2,6Galβ1,4Glc-PT and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 9-azido-NeuAcα2,6Galβ1,4Glc-PT and an antibody is 2, 3, 4, 5, 6, 7, 8, 9, 10, 11, 12, 13, 14, 15, 16, 17, 18, 19, or 20 the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises galactopyranosyl-DM1. In an embodiment, the molecule is galactopyranosyl-DM1. In an embodiment, the antibody-drug conjugate comprises galactopyranosyl-DM1 and antibody. In an embodiment, the antibody-drug conjugate is a conjugate of galactopyranosyl-DM1 and antibody. In an embodiment, the glycoside-to-antibody-ratio of the antibody-drug conjugate of galactopyranosyl-DM1 and antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of galactopyranosyl-DM1 and antibody is 2, 3, 4, 5, 6, 7, 8, 9, 10, 11, 12, 13, 14, 15, 16, 17, 18, 19, or 20 the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises α2,6-NeuAc-galactopyranosyl-DM1. In an embodiment, the molecule is α2,6-NeuAc-galactopyranosyl-DM1. In an embodiment, the antibody-drug conjugate comprises α2,6-NeuAc-galactopyranosyl-DM1 and antibody. In an embodiment, the antibody-drug conjugate is a conjugate of α2,6-NeuAc-galactopyranosyl-DM1 and antibody. In an embodiment, the glycoside-to-antibody-ratio of the antibody-drug conjugate of α2,6-NeuAc-galactopyranosyl-DM1 and antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of α2,6-NeuAc-galactopyranosyl-DM1 and antibody is 2, 3, 4, 5, 6, 7, 8, 9, 10, 11, 12, 13, 14, 15, 16, 17, 18, 19, or 20 the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises 9-azido-sialyl derivative of galactopyranosyl-DM1. In an embodiment, the molecule is 9-azido-sialyl derivative of galactopyranosyl-DM1. In an embodiment, the antibody-drug conjugate comprises 9-azido-sialyl derivative of galactopyranosyl-DM1 and antibody. In an embodiment, the antibody-drug conjugate is a conjugate of 9-azido-sialyl derivative of galactopyranosyl-DM1 and antibody. In an embodiment, the antibody-drug conjugate is a conjugate of 9-azido-sialyl derivative of galactopyranosyl-DM1 and DBCO-modified antibody. In an embodiment, the glycoside-to-antibody-ratio of the antibody-drug conjugate of 9-azido-sialyl derivative of galactopyranosyl-DM1 and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 9-azido-sialyl derivative of galactopyranosyl-DM1 and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises dexamethasone 21-O-beta-D-galactopyranoside (Gal-Dexa). In an embodiment, the molecule is Gal-Dexa. In an embodiment, the antibody-drug conjugate comprises Gal-Dexa and antibody. In an embodiment, the antibody-drug conjugate is a conjugate of Gal-Dexa and antibody. In an embodiment, the glycoside-to-antibody-ratio of the antibody-drug conjugate of Gal-Dexa and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Gal-Dexa and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises NeuAcα2,6Gal-Dexa. In an embodiment, the molecule is NeuAcα2,6Gal-Dexa. In an embodiment, the antibody-drug conjugate comprises NeuAcα2,6Gal-Dexa and antibody. In an embodiment, the antibody-drug conjugate is a conjugate of NeuAcα2,6Gal-Dexa and antibody. In an embodiment, the glycoside-to-antibody-ratio of the antibody-drug conjugate of NeuAcα2,6Gal-Dexa and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of NeuAcα2,6Gal-Dexa and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises 9N3NeuAcα2,6Gal-Dexa. In an embodiment, the molecule is 9N3NeuAcα2,6Gal-Dexa. In an embodiment, the antibody-drug conjugate 9N3NeuAcα2,6Gal-Dexa and antibody. In an embodiment, the antibody-drug conjugate is a conjugate of 9N3NeuAcα2,6Gal-Dexa and antibody. In an embodiment, the antibody-drug conjugate is a conjugate of 9N3NeuAcα2,6Gal-Dexa and DBCO-modified antibody. In an embodiment, the glycoside-to-antibody-ratio of the antibody-drug conjugate of 9N3NeuAcα2,6Gal-Dexa and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 9N3NeuAcα2,6Gal-Dexa and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises β-1,4-galactosylated Xyl-taxol (Galβ1,4Xyl-Taxol). In an embodiment, the molecule is Galβ1,4Xyl-Taxol. In an embodiment, the antibody-drug conjugate comprises Galβ1,4Xyl-Taxol and antibody. In an embodiment, the antibody-drug conjugate is a conjugate of Galβ1,4Xyl-Taxol and antibody. In an embodiment, the glycoside-to-antibody-ratio of the antibody-drug conjugate of Galβ1,4Xyl-Taxol and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Galβ1,4Xyl-Taxol and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises NeuAcα2,6Galβ1,4Xyl-Taxol. In an embodiment, the molecule is NeuAcα2,6Galβ1,4Xyl-Taxol. In an embodiment, the antibody-drug conjugate comprises NeuAcα2,6Galβ1,4Xyl-Taxol and antibody. In an embodiment, the antibody-drug conjugate is a conjugate of NeuAcα2,6Galβ1,4Xyl-Taxol and antibody. In an embodiment, the glycoside-to-antibody-ratio of the antibody-drug conjugate of NeuAcα2,6Galβ1,4Xyl-Taxol and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of NeuAcα2,6Galβ1,4Xyl-Taxol and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises 9-N3-NeuAcα2,6Galβ1,4Xyl-Taxol. In an embodiment, the molecule is 9-N3-NeuAcα2,6Galβ1,4Xyl-Taxol. In an embodiment, the antibody-drug conjugate 9-N3-NeuAcα2,6Galβ1,4Xyl-Taxol and antibody. In an embodiment, the antibody-drug conjugate is a conjugate of 9-N3-NeuAcα2,6Galβ1,4Xyl-Taxol and antibody. In an embodiment, the antibody-drug conjugate is a conjugate of 9-N3-NeuAcα2,6Galβ1,4Xyl-Taxol and DBCO-modified antibody. In an embodiment, the glycoside-to-antibody-ratio of the antibody-drug conjugate of 9-N3-NeuAcα2,6Galβ1,4Xyl-Taxol and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 9-N3-NeuAcα2,6Galβ1,4Xyl-Taxol and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises N-(6-azido-6-deoxy-D-galactosyl)-MMAF-IleVal(GlcNAcβ-)Ser. In an embodiment, the molecule is N-(6-azido-6-deoxy-D-galactosyl)-MMAF-IleVal(GlcNAcβ-)Ser. In an embodiment, the antibody-drug conjugate comprises N-(6-azido-6-deoxy-D-galactosyl)-MMAF-IleVal(GlcNAcβ-)Ser and antibody. In an embodiment, the antibody-drug conjugate is a conjugate of N-(6-azido-6-deoxy-D-galactosyl)-MMAF-IleVal(GlcNAcβ-)Ser and antibody. In an embodiment, the antibody-drug conjugate is a conjugate of N-(6-azido-6-deoxy-D-galactosyl)-MMAF-IleVal(GlcNAcβ-)Ser and DBCO-modified antibody. In an embodiment, the glycoside-to-antibody-ratio of the antibody-drug conjugate of N-(6-azido-6-deoxy-D-galactosyl)-MMAF-IleVal(GlcNAcβ-)Ser and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of N-(6-azido-6-deoxy-D-galactosyl)-MMAF-IleVal(GlcNAcβ-)Ser and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti- CD22 antibody, an anti-CD30 antibody, an anti-CD33 antibody, and an anti-CD20 antibody.

In an embodiment, the molecule comprises ValCitPAB-MMAF-IleVal(GlcNAcβ)Ser. In an embodiment, the molecule is ValCitPAB-MMAF-IleVal(GlcNAcβ)Ser. In an embodiment, the antibody-drug conjugate comprises ValCitPAB-MMAF-IleVal(GlcNAcβ)Ser and antibody. In an embodiment, the antibody-drug conjugate is a conjugate of ValCitPAB-MMAF-IleVal(GlcNAcβ)Ser and antibody. In an embodiment, the glycoside-to-antibody-ratio of the antibody-drug conjugate of ValCitPAB-MMAF-IleVal(GlcNAcβ)Ser and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of ValCitPAB-MMAF-IleVal(GlcNAcβ)Ser and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises dimeric duocarmycin β-D-galactopyranoside. In an embodiment, the molecule is dimeric duocarmycin β-D-galactopyranoside. In an embodiment, the antibody-drug conjugate comprises dimeric duocarmycin β-D-galactopyranoside and antibody. In an embodiment, the antibody-drug conjugate is a conjugate of dimeric duocarmycin β-D-galactopyranoside and antibody. In an embodiment, the glycoside-to-antibody-ratio of the antibody-drug conjugate of dimeric duocarmycin β-D-galactopyranoside and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of dimeric duocarmycin β-D-galactopyranoside and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises dimeric duocarmycin sialylgalactoside. In an embodiment, the molecule is dimeric duocarmycin sialylgalactoside. In an embodiment, the antibody-drug conjugate comprises dimeric duocarmycin sialylgalactoside and antibody. In an embodiment, the antibody-drug conjugate is a conjugate of dimeric duocarmycin sialylgalactoside and antibody. In an embodiment, the antibody-drug conjugate is a conjugate of 9-azido-modified dimeric duocarmycin sialylgalactoside and antibody. In an embodiment, the antibody-drug conjugate is a conjugate of 9-azido-modified dimeric duocarmycin sialylgalactoside and DBCO-modified antibody. In an embodiment, the glycoside-to-antibody-ratio of the antibody-drug conjugate of dimeric duocarmycin sialylgalactoside or 9-azido-modified dimeric duocarmycin sialylgalactoside and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of dimeric duocarmycin sialylgalactoside or 9-azido-modified dimeric duocarmycin sialylgalactoside and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises duocarmycin β-D-galactopyranoside. In an embodiment, the molecule is duocarmycin β-D-galactopyranoside. In an embodiment, the antibody-drug conjugate is a conjugate of duocarmycin β-D-galactopyranoside and antibody. In an embodiment, the antibody-drug conjugate is a conjugate of duocarmycin β-D-galactopyranoside and antibody. In an embodiment, the glycoside-to-antibody-ratio of the antibody-drug conjugate of duocarmycin β-D-galactopyranoside and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of duocarmycin β-D-galactopyranoside and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises duocarmycin sialylgalactoside. In an embodiment, the molecule is duocarmycin sialylgalactoside. In an embodiment, the antibody-drug conjugate is a conjugate of duocarmycin sialylgalactoside and antibody. In an embodiment, the antibody-drug conjugate is a conjugate of duocarmycin sialylgalactoside and antibody. In an embodiment, the glycoside-to-antibody-ratio of the antibody-drug conjugate of duocarmycin sialylgalactoside and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of duocarmycin sialylgalactoside and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Val-Cit-Gly-duocarmycin sialylgalactoside. In an embodiment, the molecule is Val-Cit-Gly-duocarmycin sialylgalactoside. In an embodiment, the antibody-drug conjugate is a conjugate of Val-Cit-Gly-duocarmycin sialylgalactoside and antibody. In an embodiment, the antibody-drug conjugate is a conjugate of Val-Cit-Gly-duocarmycin sialylgalactoside and antibody. In an embodiment, the glycoside-to-antibody-ratio of the antibody-drug conjugate of Val-Cit-Gly-duocarmycin sialylgalactoside and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Val-Cit-Gly-duocarmycin sialylgalactoside and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Neu5Acα2,6Gal-duocarmycin. In an embodiment, the molecule is Neu5Acα2,6Gal-duocarmycin. In an embodiment, the antibody-drug conjugate is a conjugate of Neu5Acα2,6Gal-duocarmycin and antibody. In an embodiment, the antibody-drug conjugate is a conjugate of Neu5Acα2,6Gal-duocarmycin and antibody. In an embodiment, the glycoside-to-antibody-ratio of the antibody-drug conjugate of Neu5Acα2,6Gal-duocarmycin and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Neu5Acα2,6Gal-duocarmycin and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Gal-Duocarmycin-PAB-CV-DBCO. In an embodiment, the molecule is Gal-Duocarmycin-PAB-CV-DBCO. In an embodiment, the antibody-drug conjugate is a conjugate of Gal-Duocarmycin-PAB-CV-DBCO and antibody. In an embodiment, the antibody-drug conjugate is a conjugate of Gal-Duocarmycin-PAB-CV-DBCO and antibody. In an embodiment, the glycoside-to-antibody-ratio of the antibody-drug conjugate of Gal-Duocarmycin-PAB-CV-DBCO and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Gal-Duocarmycin-PAB-CV-DBCO and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Neu5Acα2,6MMAG. In an embodiment, the molecule is Neu5Acα2,6MMAG. In an embodiment, the antibody-drug conjugate is a conjugate of Neu5Acα2,6MMAG and antibody. In an embodiment, the antibody-drug conjugate is a conjugate of Neu5Acα2,6MMAG and antibody. In an embodiment, the glycoside-to-antibody-ratio of the antibody-drug conjugate of Neu5Acα2,6MMAG and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Neu5Acα2,6MMAG and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Neu5Acα2,3MMAG. In an embodiment, the molecule is Neu5Acα2,3MMAG. In an embodiment, the antibody-drug conjugate is a conjugate of Neu5Acα2,3MMAG and antibody. In an embodiment, the antibody-drug conjugate is a conjugate of Neu5Acα2,3MMAG and antibody. In an embodiment, the glycoside-to-antibody-ratio of the antibody-drug conjugate of Neu5Acα2,3MMAG and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Neu5Acα2,3MMAG and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises maleimidocaproyl-VC-PAB-MMAG. In an embodiment, the molecule is maleimidocaproyl-VC-PAB-MMAG. In an embodiment, the antibody-drug conjugate is a conjugate of maleimidocaproyl-VC-PAB-MMAG and antibody. In an embodiment, the antibody-drug conjugate is a conjugate of maleimidocaproyl-VC-PAB-MMAG and antibody. In an embodiment, the glycoside-to-antibody-ratio of the antibody-drug conjugate of maleimidocaproyl-VC-PAB-MMAG and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of maleimidocaproyl-VC-PAB-MMAG and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises beta-D-Galactopyranosyl-(glycolic acid ester)-duocarmycin. In an embodiment, the molecule is beta-D-Galactopyranosyl-(glycolic acid ester)-duocarmycin. In an embodiment, the antibody-drug conjugate is a conjugate of beta-D-Galactopyranosyl-(glycolic acid ester)-duocarmycin and antibody. In an embodiment, the antibody-drug conjugate is a conjugate of beta-D-Galactopyranosyl-(glycolic acid ester)-duocarmycin and antibody. In an embodiment, the glycoside-to-antibody-ratio of the antibody-drug conjugate of beta-D-Galactopyranosyl-(glycolic acid ester)-duocarmycin and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of beta-D-Galactopyranosyl-(glycolic acid ester)-duocarmycin and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises beta-D-Galactopyranosyl-(glycolic acid ester)-MMAE. In an embodiment, the molecule is beta-D-Galactopyranosyl-(glycolic acid ester)-MMAE. In an embodiment, the antibody-drug conjugate is a conjugate of beta-D-Galactopyranosyl-(glycolic acid ester)-MMAE and antibody. In an embodiment, the antibody-drug conjugate is a conjugate of beta-D-Galactopyranosyl-(glycolic acid ester)-MMAE and antibody. In an embodiment, the glycoside-to-antibody-ratio of the antibody-drug conjugate of beta-D-Galactopyranosyl-(glycolic acid ester)-MMAE and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of beta-D-Galactopyranosyl-(glycolic acid ester)-MMAE and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu)

antibody, an anti-CD22 antibody, an anti-CD30 antibody, an anti-CD33 antibody, and an anti-CD20 antibody.

In an embodiment, the molecule comprises sialyl-beta-D-Galactopyranosyl-(glycolic acid ester)-MMAE. In an embodiment, the molecule is sialyl-beta-D-Galactopyranosyl-(glycolic acid ester)-MMAE. In an embodiment, the antibody-drug conjugate is a conjugate of sialyl-beta-D-Galactopyranosyl-(glycolic acid ester)-MMAE and antibody. In an embodiment, the antibody-drug conjugate is a conjugate of sialyl-beta-D-Galactopyranosyl-(glycolic acid ester)-MMAE and antibody. In an embodiment, the glycoside-to-antibody-ratio of the antibody-drug conjugate of sialyl-beta-D-Galactopyranosyl-(glycolic acid ester)-MMAE and an antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of sialyl-beta-D-Galactopyranosyl-(glycolic acid ester)-MMAE and an antibody is 2, 3, 4, 5, 6, 7, 8, 9, 10, 11, 12, 13, 14, 15, 16, 17, 18, 19, or 20 and the antibody is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises 2-amino-2-deoxy-β-D-glucopyranosyl duocarmycin. In an embodiment, the molecule is 2-amino-2-deoxy-β-D-glucopyranosyl duocarmycin. In an embodiment, the antibody-drug conjugate comprises 2-amino-2-deoxy-β-D-glucopyranosyl duocarmycin and an antibody. In an embodiment, the antibody-drug conjugate is a conjugate of 2-amino-2-deoxy-β-D-glucopyranosyl duocarmycin and an antibody. In an embodiment, the glycoside-to-antibody-ratio of the antibody-drug conjugate of 2-amino-2-deoxy-β-D-glucopyranosyl duocarmycin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 2-amino-2-deoxy-β-D-glucopyranosyl duocarmycin and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises 2-acetamido-2-deoxy-β-D-glucopyranosyl duocarmycin. In an embodiment, the molecule is 2-N-acetyl-2-deoxy-β-D-glucopyranosyl duocarmycin. In an embodiment, the antibody-drug conjugate comprises 2-acetamido-2-deoxy-β-D-glucopyranosyl duocarmycin and an antibody. In an embodiment, the antibody-drug conjugate is a conjugate of 2-acetamido-2-deoxy-β-D-glucopyranosyl duocarmycin and an antibody. In an embodiment, the glycoside-to-antibody-ratio of the antibody-drug conjugate of 2-acetamido-2-deoxy-β-D-glucopyranosyl duocarmycin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 2-acetamido-2-deoxy-β-D-glucopyranosyl duocarmycin and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises 2-acylamido-2-deoxy-β-D-glucopyranosyl duocarmycin. In an embodiment, the molecule is 2-acylamido-2-deoxy-β-D-glucopyranosyl duocarmycin. In an embodiment, the antibody-drug conjugate comprises 2-acylamido-2-deoxy-β-D-glucopyranosyl duocarmycin and an antibody. In an embodiment, the antibody-drug conjugate is a conjugate of 2-acylamido-2-deoxy-β-D-glucopyranosyl duocarmycin and an antibody. In an embodiment, the glycoside-to-antibody-ratio of the antibody-drug conjugate of 2-acylamido-2-deoxy-β-D-glucopyranosyl duocarmycin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 2-acylamido-2-deoxy-β-D-glucopyranosyl duocarmycin and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises glucuronyl-duocarmycin. In an embodiment, the antibody-drug conjugate comprises glucuronyl-duocarmycin and an antibody. In an embodiment, the antibody-drug conjugate is a conjugate of glucuronyl-duocarmycin and an antibody. In an embodiment, the antibody-drug conjugate is a conjugate of glucuronyl-duocarmycin and trastuzumab. In an embodiment, the glycoside-to-antibody-ratio of the antibody-drug conjugate of glucuronyl-duocarmycin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of glucuronyl-duocarmycin and the antibody is 2, 3, 4, 5, 6, 7, 8, 9, 10, 11, 12, 13, 14, 15, 16, 17, 18, 19, or 20, and the antibody is selected from the group of is selected from the group of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises beta-glucuronyl-monomethylauristatin E (MMAU), maleimidocaproyl-VC-PAB-MMAU or MMAU-PAB-CV-maleimidoyl. In an embodiment, the molecule is MMAU, maleimidocaproyl-VC-PAB-MMAU or MMAU-PAB-CV-maleimidoyl. In an embodiment, the antibody-drug conjugate comprises MMAU, maleimidocaproyl-VC-PAB-MMAU or MMAU-PAB-CV-maleimidoyl and an antibody. In an embodiment, the antibody-drug conjugate is a conjugate of MMAU, maleimidocaproyl-VC-PAB-MMAU or MMAU-PAB-CV-maleimidoyl and an antibody. In an embodiment, the conjugate comprises or is a conjugate of MMAU, maleimidocaproyl-VC-PAB-MMAU or MMAU-PAB-CV-maleimidoyl and trastuzumab. In an embodiment, the glycoside-to-antibody-ratio of the antibody-drug conjugate of MMAU, maleimidocaproyl-VC-PAB-MMAU or MMAU-PAB-CV-maleimidoyl and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of MMAU, maleimidocaproyl-VC-PAB-MMAU or MMAU-PAB-CV-maleimidoyl and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises beta-glucosyl-monomethylauristatin E (MMAX), maleimidocaproyl-VC-PAB-MMAX or MMAX-PAB-CV-maleimidoyl. In an embodiment, the molecule is MMAX, maleimidocaproyl-VC-PAB-MMAX or MMAX-PAB-CV-maleimidoyl. In an embodiment, the antibody-drug conjugate comprises MMAX, maleimidocaproyl-VC-PAB-MMAX or MMAX-PAB-CV-maleimidoyl and an antibody. In an embodiment, the antibody-drug conjugate is a conjugate of MMAX, maleimidocaproyl-VC-PAB-MMAX or MMAX-PAB-CV-maleimidoyl and an antibody. In an embodiment, the antibody-drug conjugate comprises or is a conjugate of MMAX, maleimidocaproyl-VC-PAB-MMAX or MMAX-PAB-CV-maleimidoyl and trastuzumab. In an embodiment, the glycoside-to-antibody-ratio of the antibody-drug conjugate of MMAX, maleimidocaproyl-VC-PAB-MMAX or MMAX-PAB-CV-maleimidoyl and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of MMAX, maleimidocaproyl-VC-PAB-MMAX or MMAX-PAB-CV-maleimidoyl and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises MMAG-PAB-CV-maleimidoyl. In an embodiment, the molecule is MMAG-PAB-CV-maleimidoyl. In an embodiment, the antibody-drug conjugate comprises MMAG-PAB-CV-maleimidoyl and an antibody. In an embodiment, the antibody-drug conjugate is a conjugate of MMAG-PAB-CV-maleimidoyl and an antibody. In an embodiment, the antibody-drug conjugate comprises or is a conjugate of MMAG-PAB-CV-maleimidoyl and trastuzumab, 2G12 or nimotuzumab. In an embodiment, the glycoside-to-antibody-ratio of the antibody-drug conjugate of MMAG-PAB-CV-maleimidoyl and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of MMAG-PAB-CV-maleimidoyl and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises 2-acetamido-2-deoxy-β-D-glucopyranosyl duocarmycin. In an embodiment, the molecule is 2-acetamido-2-deoxy-β-D-glucopyranosyl duocarmycin. In an embodiment, the antibody-drug conjugate comprises 2-acetamido-2-deoxy-β-D-glucopyranosyl duocarmycin and an antibody. In an embodiment, the antibody-drug conjugate is a conjugate of 2-acetamido-2-deoxy-β-D-glucopyranosyl duocarmycin and an antibody. In an embodiment, the glycoside-to-antibody-ratio of the antibody-drug conjugate of 2-acetamido-2-deoxy-β-D-glucopyranosyl duocarmycin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of 2-acetamido-2-deoxy-β-D-glucopyranosyl duocarmycin and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises Gal-duocarmycin or Gal-duocarmycin-PAB-CV-maleimidoyl. In an embodiment, the molecule is Gal-duocarmycin or Gal-duocarmycin-PAB-CV-maleimidoyl. In an embodiment, the antibody-drug conjugate comprises Gal-duocarmycin or Gal-duocarmycin-PAB-CV-maleimidoyl and an antibody. In an embodiment, the antibody-drug conjugate is a conjugate of Gal-duocarmycin or Gal-duocarmycin-PAB-CV-maleimidoyl and an antibody. In an embodiment, the antibody-drug conjugate is a conjugate of Gal-duocarmycin or Gal-duocarmycin-PAB-CV-maleimidoyl and trastuzumab. In an embodiment, the glycoside-to-antibody-ratio of the antibody-drug conjugate of Gal-duocarmycin or Gal-duocarmycin-PAB-CV-maleimidoyl and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of Gal-duocarmycin or Gal-duocarmycin-PAB-CV-maleimidoyl and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises glycosyl-maytansinoid, glycosyl-N-glucosylmaytansinoid, Gal-N-glucosylmaytansinoid or NeuAc-Gal-N-glucosylmaytansinoid. In an embodiment, the molecule is glycosyl-maytansinoid, glycosyl-N-glucosylmaytansinoid, Gal-N-glucosylmaytansinoid or NeuAc-Gal-N-glucosylmaytansinoid. In an embodiment, the antibody-drug conjugate comprises glycosyl-maytansinoid, glycosyl-N-glucosylmaytansinoid, Gal-N-glucosylmaytansinoid or NeuAc-Gal-N-glucosylmaytansinoid and an antibody. In an embodiment, the antibody-drug conjugate is a conjugate of glycosyl-maytansinoid, glycosyl-N-glucosylmaytansinoid, Gal-N-glucosylmaytansinoid or NeuAc-Gal-N-glucosylmaytansinoid and an antibody. In an embodiment, the glycoside-to-antibody-ratio of the antibody-drug conjugate of glycosyl-maytansinoid, glycosyl-N-glucosylmaytansinoid, Gal-N-glucosylmaytansinoid or NeuAc-Gal-N-glucosylmaytansinoid and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of glycosyl-maytansinoid, glycosyl-N-glucosylmaytansinoid, Gal-N-glucosylmaytansinoid or NeuAc-Gal-N-glucosylmaytansinoid and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises glycosyl-tubulysin, Gal-tubulysin or NeuAc-Gal-tubulysin. In an embodiment, the molecule is glycosyl-tubulysin, Gal-tubulysin or NeuAc-Gal-tubulysin. In an embodiment, the antibody-drug conjugate comprises glycosyl-tubulysin, Gal-tubulysin or NeuAc-Gal-tubulysin and an antibody. In an embodiment, the antibody-drug conjugate is a conjugate of glycosyl-tubulysin, Gal-tubulysin or NeuAc-Gal-tubulysin and an antibody. In an embodiment, the glycoside-to-antibody-ratio of the antibody-drug conjugate of glycosyl-tubulysin, Gal-tubulysin or NeuAc-Gal-tubulysin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of glycosyl-tubulysin, Gal-tubulysin or NeuAc-Gal-tubulysin and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises glycosyl-α-amanitin, Gal-α-amanitin or NeuAc-Gal-α-amanitin. In an embodiment, the molecule is glycosyl-α-amanitin, Gal-α-amanitin or NeuAc-Gal-α-amanitin. In an embodiment, the antibody-drug conjugate comprises glycosyl-α-amanitin, Gal-α-amanitin or NeuAc-Gal-α-amanitin and an antibody. In an embodiment, the antibody-drug conjugate is a conjugate of glycosyl-α-amanitin, Gal-α-amanitin or NeuAc-Gal-α-amanitin and an antibody. In an embodiment, the glycoside-to-antibody-ratio of the antibody-drug conjugate of 2-glycosyl-α-amanitin, Gal-α-amanitin or NeuAc-Gal-α-amanitin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of glycosyl-α-amanitin, Gal-α-amanitin or NeuAc-Gal-α-amanitin and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule comprises glycosyl-cryptophycin, Gal-cryptophycin or NeuAc-Gal-cryptophycin. In an embodiment, the molecule is glycosyl-cryptophycin, Gal-cryptophycin or NeuAc-Gal-cryptophycin. In an embodiment, the antibody-drug conjugate comprises glycosyl-cryptophycin, Gal-cryptophycin or NeuAc-Gal-cryptophycin and an antibody. In an embodiment, the antibody-drug conjugate is a conjugate of glycosyl-cryptophycin, Gal-cryptophycin or NeuAc-Gal-cryptophycin and an antibody. In an embodiment, the glycoside-to-antibody-ratio of the antibody-drug conjugate of glycosyl-cryptophycin, Gal-cryptophycin or NeuAc-Gal-cryptophycin and the antibody is 2, 3, 4, 5, 6, 7, 8, 9, 10, 11, 12, 13, 14, 15, 16, 17, 18, 19, or 20. In an embodiment, the glycoside-to-antibody-ratio of the antibody-drug conjugate of glycosyl-cryptophycin, Gal-cryptophycin or NeuAc-Gal-cryptophycin and the antibody is 2, 3, 4, 5, 6, 7, 8, 9, 10, 11, 12, 13, 14, 15, 16, 17, 18, 19, or 20, and the antibody is selected from the group consisting of an anti-EGFR1 antibody, cetuximab, imgatuzumab, matuzumab, nimotuzumab, necitumumab, panitumumab, zalutumumab, an epidermal growth factor receptor 2 (HER2/neu) antibody, margetuximab, pertuzumab, trastuzumab, ertumaxomab, 520C9XH22, an anti-CD22 antibody, bectumomab, moxetumomab, epratuzumab, inotuzumab, pinatuzumab, an anti-CD30 antibody, brentuximab, iratumumab, an anti-CD33 antibody, gemtuzumab, SGN-CD33A, lintuzumab, tositumomab, alemtuzumab, an anti-CD20 antibody, rituximab, epitumomab, ublituximab, obinutuzumab, ocaratuzumab, ocrelizumab, veltuzumab, ofatumumab, nofetumomab and ibritumomab or from the group consisting of an anti-EGFR1 antibody, an epidermal growth factor receptor 2 (HER2/neu) antibody, an anti-CD22 antibody, an anti-CD30 antibody, an anti-CD33 antibody, and an anti-CD20 antibody.

In an embodiment, the molecule is a molecule represented by formula 38

Formula 38

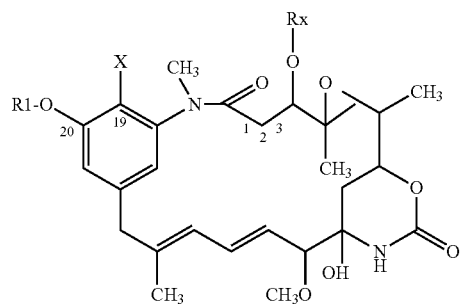

wherein X is Cl or H; R1 is H or saccharide bound via an O-glycosidic bond; and Rx is H, acyl group or L. L may be any linker group described in this specification.

In an embodiment, the antibody-drug conjugate is a conjugate represented by formula 38'

Formula 38'

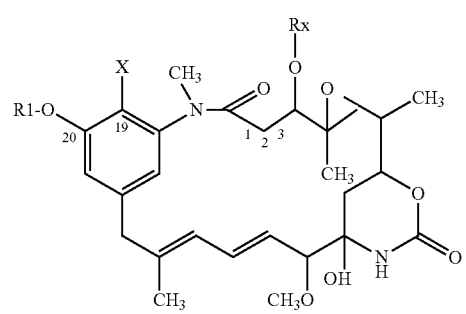

wherein X is Cl or H; R1 is saccharide bound via an O-glycosidic bond; and Rx is L-Ab. L may be absent or any linker group described in this specification; Ab may be any antibody described in this specification.

In an embodiment, the molecule is a molecule represented by formula 40

Formula 40

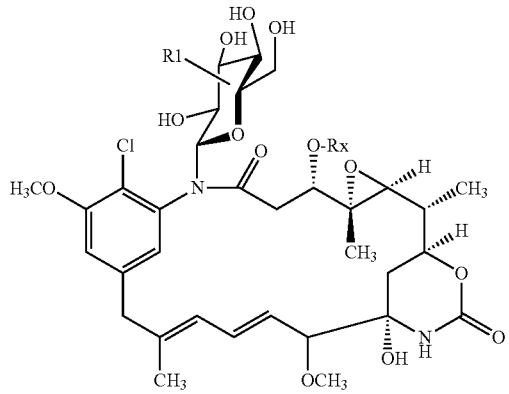

wherein R1 is a saccharide bound via an O-glycosidic bond to any one of the hydroxyl groups of the glycosyl moiety of the N-glucosylmaytansinoid; and Rx is H, acyl group or L. L may be any linker group described in this specification.

In an embodiment, the antibody-drug conjugate is a conjugate represented by formula 40'

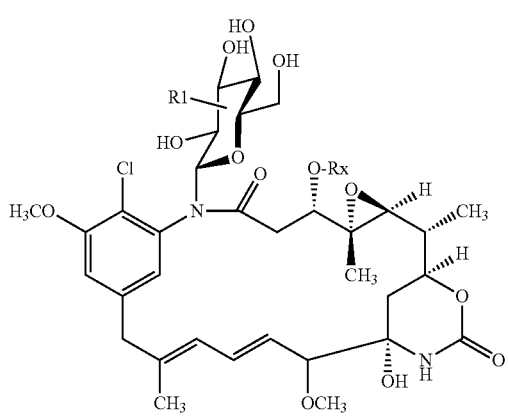

wherein R1 is a saccharide bound via an O-glycosidic bond to any one of the hydroxyl groups of the glycosyl moiety of the N-glucosylmaytansinoid; and Rx is L-Ab. L may be absent or any linker group described in this specification; Ab may be any antibody described in this specification.

In an embodiment, the molecule is a molecule represented by formula 41

Formula 41

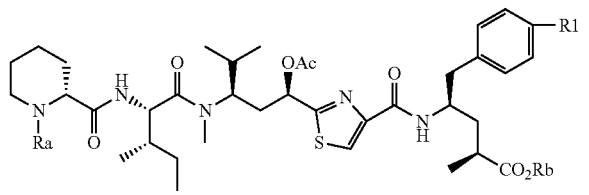

wherein R1 is a saccharide bound via an O-glycosidic bond; Ra is H, methyl, or L; Rb is H or L; and Ra Rb. L may be any linker group described in this specification.

In an embodiment, the antibody-drug conjugate is a conjugate represented by formula 41'

Formula 41'

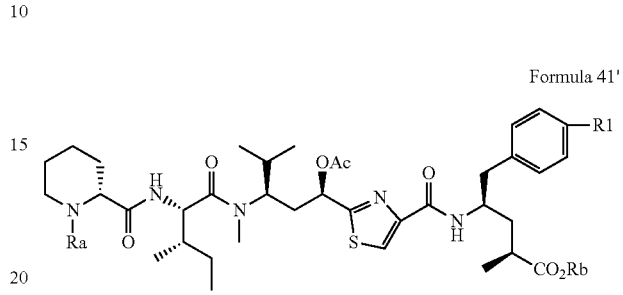

wherein R1 is a saccharide bound via an O-glycosidic bond; Ra is H, methyl, or L-Ab; Rb is H or L-Ab; and Ra Rb. L may be absent or any linker group described in this specification; Ab may be any antibody described in this specification In an embodiment, the molecule is a molecule represented by formula 42a Formula 42a

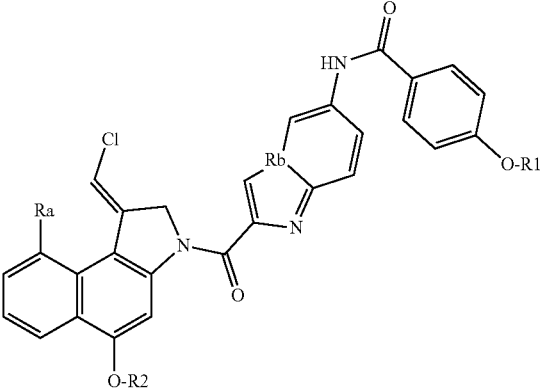

wherein R1 is H or a saccharide bound via an O-glycosidic bond; R2 is H or saccharide bound via an O-glycosidic bond or L; Ra is H or methyl; and Rb is CH or N. L may be any linker group described in this specification.

In an embodiment, the antibody-drug conjugate is a conjugate represented by formula 42a'

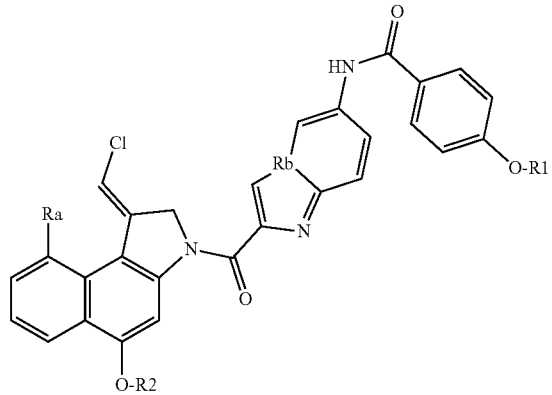

Formula 42a' wherein R1 is H or a saccharide bound via an O-glycosidic bond; R2 is L-Ab or a saccharide, the saccharide being bound to L-Ab and bound via an O-glycosidic bond to the duocarmycin; Ra is H or methyl; and Rb is CH or N. L may be absent or any linker group described in this specification; Ab may be any antibody described in this specification.

In an embodiment, the molecule is a molecule represented by formula 43

Formula 43 wherein Ra is H, saccharide bound via an O-glycosidic bond, or L; Rb is H, a saccharide bound via an O-glycosidic bond, or L; and Ra Rb. L may be any linker group described in this specification.

In an embodiment, the antibody-drug conjugate is a conjugate represented by formula 43'

Formula 43' wherein Ra is H, a saccharide bound via an O-glycosidic bond, or L-Ab; Rb is H, a saccharide bound via an O-glycosidic bond, or L-Ab; and Ra Rb. L may be absent or any linker group described in this specification; Ab may be any antibody described in this specification.

In an embodiment, the molecule is a molecule represented by formula 44

Formula 44 wherein R1 is H or a saccharide bound via an O-glycosidic bond; R is H, OH, amino, or L. L may be any linker group described in this specification.

In an embodiment, the antibody-drug conjugate is a conjugate represented by formula 44'

Formula 44' wherein R1 is H or a saccharide bound via an O-glycosidic bond; R is L-Ab. L may be absent or any linker group described in this specification; Ab may be any antibody described in this specification In an embodiment, the antibody-drug conjugate comprises or is a conjugate of O-β-D-galactopyranosylmonomethylauristatin E (MMAG) and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of O-β-D-galactopyranosylmonomethylauristatin E (MMAG) and trastuzumab, and the glycoside-to-antibody-ratio is 8 or 16.

In an embodiment, the antibody-drug conjugate comprises or is a conjugate of O-β-D-galactopyranosylmonomethylauristatin E (MMAG) and cetuximab, and the glycoside-to-antibody-ratio is 8 or 16.

In an embodiment, the antibody-drug conjugate comprises or is a conjugate of O-β-D-galactopyranosylmonomethylauristatin E (MMAG) and brentuximab, and the glycoside-to-antibody-ratio is 8 or 16.

In an embodiment, the antibody-drug conjugate comprises or is a conjugate of O-β-D-galactopyranosylmonomethylauristatin E (MMAG) and nimotuzumab, and the glycoside-to-antibody-ratio is 8 or 16.

In an embodiment, the antibody-drug conjugate comprises or is a conjugate of Val-Cit-PAB-MMAG and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of Val-Cit-PAB-MMAG and trastuzumab, and the glycoside-to-antibody-ratio is 8 or 16.

In an embodiment, the antibody-drug conjugate comprises or is a conjugate of Val-Cit-PAB-MMAG and cetuximab, and the glycoside-to-antibody-ratio is 8 or 16.

In an embodiment, the antibody-drug conjugate comprises or is a conjugate of Val-Cit-PAB-MMAG and brentuximab, and the glycoside-to-antibody-ratio is 8 or 16.

In an embodiment, the antibody-drug conjugate comprises or is a conjugate of Val-Cit-PAB-MMAG and nimotuzumab, and the glycoside-to-antibody-ratio is 8 or 16.

In an embodiment, the antibody-drug conjugate comprises or is a conjugate of O—(N-acetylneuraminyl-β-D-galactopyranosyl)-MMAE (MMAS) and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of O—(N-acetylneuraminyl-β-D-galactopyranosyl)-MMAE (MMAS) and trastuzumab, and the glycoside-to-antibody-ratio is 8 or 16.

In an embodiment, the antibody-drug conjugate comprises or is a conjugate of O—(N-acetylneuraminyl-β-D-galactopyranosyl)-MMAE (MMAS) and cetuximab, and the glycoside-to-antibody-ratio is 8 or 16.

In an embodiment, the antibody-drug conjugate comprises or is a conjugate of O—(N-acetylneuraminyl-β-D-galactopyranosyl)-MMAE (MMAS) and brentuximab, and the glycoside-to-antibody-ratio is 8 or 16.

In an embodiment, the antibody-drug conjugate comprises or is a conjugate of O—(N-acetylneuraminyl-β-D-galactopyranosyl)-MMAE (MMAS) and nimotuzumab, and the glycoside-to-antibody-ratio is 8 or 16.

In an embodiment, the antibody-drug conjugate comprises or is a conjugate of Val-Cit-PAB-MMAS and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of Val-Cit-PAB-MMAS and trastuzumab, and the glycoside-to-antibody-ratio is 8 or 16.

In an embodiment, the antibody-drug conjugate comprises or is a conjugate of Val-Cit-PAB-MMAS and cetuximab, and the glycoside-to-antibody-ratio is 8 or 16.

In an embodiment, the antibody-drug conjugate comprises or is a conjugate of Val-Cit-PAB-MMAS and brentuximab, and the glycoside-to-antibody-ratio is 8 or 16.

In an embodiment, the antibody-drug conjugate comprises or is a conjugate of Val-Cit-PAB-MMAS and nimotuzumab, and the glycoside-to-antibody-ratio is 8 or 16.

In an embodiment, the antibody-drug conjugate comprises or is a conjugate of duocarmycin β-D-galactopyranoside and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of duocarmycin β-D-galactopyranoside and trastuzumab, and the glycoside-to-antibody-ratio is 8 or 16. In an embodiment, the antibody-drug conjugate comprises or is a conjugate of duocarmycin β-D-galactopyranoside and cetuximab, and the glycoside-to-antibody-ratio is 8 or 16.

In an embodiment, the antibody-drug conjugate comprises or is a conjugate of duocarmycin β-D-galactopyranoside and brentuximab, and the glycoside-to-antibody-ratio is 8 or 16.

In an embodiment, the antibody-drug conjugate comprises or is a conjugate of duocarmycin β-D-galactopyranoside and nimotuzumab, and the glycoside-to-antibody-ratio is 8 or 16.

In an embodiment, the antibody-drug conjugate comprises or is a conjugate of duocarmycin sialylgalactoside and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of duocarmycin sialylgalactoside and trastuzumab, and the glycoside-to-antibody-ratio is 8 or 16.

In an embodiment, the antibody-drug conjugate comprises or is a conjugate of duocarmycin sialylgalactoside and cetuximab, and the glycoside-to-antibody-ratio is 8 or 16.

In an embodiment, the antibody-drug conjugate comprises or is a conjugate of duocarmycin sialylgalactoside and brentuximab, and the glycoside-to-antibody-ratio is 8 or 16.

In an embodiment, the antibody-drug conjugate comprises or is a conjugate of duocarmycin sialylgalactoside and nimotuzumab, and the glycoside-to-antibody-ratio is 8 or 16.

In an embodiment, the antibody-drug conjugate comprises or is a conjugate of Val-Cit-Gly-duocarmycin sialylgalactoside and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of Val-Cit-Gly-duocarmycin sialylgalactoside and trastuzumab, and the glycoside-to-antibody-ratio is 8 or 16.

In an embodiment, the antibody-drug conjugate comprises or is a conjugate of Val-Cit-Gly-duocarmycin sialylgalactoside and cetuximab, and the glycoside-to-antibody-ratio is 8 or 16.

In an embodiment, the antibody-drug conjugate comprises or is a conjugate of Val-Cit-Gly-duocarmycin sialylgalactoside and brentuximab, and the glycoside-to-antibody-ratio is 8 or 16.

In an embodiment, the antibody-drug conjugate comprises or is a conjugate of Val-Cit-Gly-duocarmycin sialylgalactoside and nimotuzumab, and the glycoside-to-antibody-ratio is 8 or 16.

In an embodiment, the antibody-drug conjugate comprises or is a conjugate of beta-D-Galactopyranosyl-(glycolic acid ester)-duocarmycin and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of beta-D-Galactopyranosyl-(glycolic acid ester)-duocarmycin and trastuzumab, and the glycoside-to-antibody-ratio is 8 or 16.

In an embodiment, the antibody-drug conjugate comprises or is a conjugate of beta-D-Galactopyranosyl-(glycolic acid ester)-duocarmycin and cetuximab, and the glycoside-to-antibody-ratio is 8 or 16.

In an embodiment, the antibody-drug conjugate comprises or is a conjugate of beta-D-Galactopyranosyl-(glycolic acid ester)-duocarmycin and brentuximab, and the glycoside-to-antibody-ratio is 8 or 16.

In an embodiment, the antibody-drug conjugate comprises or is a conjugate of beta-D-Galactopyranosyl-(glycolic acid ester)-duocarmycin and nimotuzumab, and the glycoside-to-antibody-ratio is 8 or 16.

In an embodiment, the antibody-drug conjugate comprises or is a conjugate of sialyl-beta-D-Galactopyranosyl-(glycolic acid ester)-duocarmycin and trastuzumab, cetuximab, brentuximab or nimotuzumab, and the glycoside-to-antibody-ratio is 5, 6, 7, 8, 9, 10, 11, 12, 13, 14, 15, 16, 17, 18, 19, or 20.

In an embodiment, the antibody-drug conjugate comprises or is a conjugate of sialyl-beta-D-Galactopyranosyl-(glycolic acid ester)-duocarmycin and trastuzumab, and the glycoside-to-antibody-ratio is 8 or 16.

In an embodiment, the antibody-drug conjugate comprises or is a conjugate of sialyl-beta-D-Galactopyranosyl-(glycolic acid ester)-duocarmycin and cetuximab, and the glycoside-to-antibody-ratio is 8 or 16.

In an embodiment, the antibody-drug conjugate comprises or is a conjugate of sialyl-beta-D-Galactopyranosyl-(glycolic acid ester)-duocarmycin and brentuximab, and the glycoside-to-antibody-ratio is 8 or 16.

In an embodiment, the antibody-drug conjugate comprises or is a conjugate of sialyl-beta-D-Galactopyranosyl-(glycolic acid ester)-duocarmycin and nimotuzumab, and the glycoside-to-antibody-ratio is 8 or 16.

In an embodiment, the antibody-drug conjugate comprises or is a conjugate selected from the group consisting of the following:

conjugate of O-β-D-galactopyranosylmonomethylauristatin E (MMAG) and antibody;
conjugate of Val-Cit-PAB-MMAG and antibody;
conjugate of N-(6-azido-6-deoxy-D-galactosyl)-MMAG and antibody;
a conjugate of O—(N-acetylneuraminyl-β-D-galactopyranosyl)-MMAE (MMAS) and antibody;
a conjugate of Val-Cit-PAB-MMAS and antibody;
a conjugate of N-(6-azido-6-deoxy-D-galactosyl)-MMAS and antibody;
a conjugate of MMAG and anti-EGFR antibody;
a conjugate of MMAS and anti-EGFR antibody;
a conjugate of β-D-4'-demethylepipodophyllotoxin β-D-4-galactopyranosylglucopyranoside (Galβ1,4Glc-PT) and antibody;
a conjugate of NeuAcα2,6Galβ1,4Glc-PT and antibody;
a conjugate of α2,6-N-acetyl-9-azidoneuraminyl-β-D-4-galactopyranos-ylglucopyranoside (9-azido-NeuAcα2,6Galβ1,4Glc-PT) and antibody;
a conjugate of 9-azido-NeuAcα2,6Galβ1,4Glc-PT and DBCO-modified antibody;
a conjugate of galactopyranosyl-DM1 and antibody;
a conjugate of α2,6-NeuAc-galactopyranosyl-DM1 and antibody;
a conjugate of 9-azido-sialyl derivative of galactopyranosyl-DM1 and antibody;
a conjugate of 9-azido-sialyl derivative of galactopyranosyl-DM1 and DBCO-modified antibody;
a conjugate of dexamethasone 21-O-beta-D-galactopyranoside (Gal-Dexa) and antibody;
a conjugate of NeuAcα2,6Gal-Dexa and antibody;
a conjugate of 9N3NeuAcα2,6Gal-Dexa and antibody;
a conjugate of 9N3NeuAcα2,6Gal-Dexa and DBCO-modified antibody;
a conjugate of β-1,4-galactosylated Xyl-taxol (Galβ1,4Xyl-Taxol) and antibody;
a conjugate of NeuAcα2,6Galβ1,4Xyl-Taxol and antibody;
a conjugate of 9-N3-NeuAcα2,6Galβ1,4Xyl-Taxol and antibody;
a conjugate of 9-N3-NeuAcα2,6Galβ1,4Xyl-Taxol and DBCO-modified antibody;
a conjugate of N-(6-azido-6-deoxy-D-galactosyl)-MMAF-IleVal(GlcNAcβ-)Ser and antibody;
a conjugate of N-(6-azido-6-deoxy-D-galactosyl)-MMAF-IleVal(GlcNAcβ-)Ser and DBCO-modified antibody;
a conjugate of ValCitPAB-MMAF-IleVal(GlcNAcβ)Ser and antibody;
a conjugate of dimeric duocarmycin β-D-galactopyranoside and antibody;
a conjugate of dimeric duocarmycin sialylgalactoside and antibody;
a conjugate of 9-azido-modified dimeric duocarmycin sialylgalactoside and antibody;
a conjugate of 9-azido-modified dimeric duocarmycin sialylgalactoside and DBCO-modified antibody;
a conjugate of duocarmycin β-D-galactopyranoside and antibody;
a conjugate of duocarmycin sialylgalactoside and antibody;
a conjugate of Val-Cit-Gly-duocarmycin sialylgalactoside and antibody;
a conjugate of Neu5Acα2,6Gal-duocarmycin and antibody;
a conjugate of Gal-Duocarmycin-PAB-CV-DBCO and antibody;
a conjugate of Neu5Acα2,6MMAG and antibody;
a conjugate of Neu5Acα2,3MMAG and antibody;
a conjugate of maleimidocaproyl-VC-PAB-MMAG and antibody;
a conjugate of beta-D-Galactopyranosyl-(glycolic acid ester)-duocarmycin and antibody;
a conjugate of sialyl-beta-D-Galactopyranosyl-(glycolic acid ester)-duocarmycin and antibody;
a conjugate of sialyl-beta-D-Galactopyranosyl-(glycolic acid ester)-duocarmycin and antibody;
a conjugate of O-β-D-galactopyranosylmonomethylauristatin E (MMAG) and trastuzumab, cetuximab, brentuximab or nimotuzumab;
a conjugate of Val-Cit-PAB-MMAG and trastuzumab, cetuximab, brentuximab or nimotuzumab;
a conjugate of O—(N-acetylneuraminyl-β-D-galactopyranosyl)-MMAE (MMAS) and trastuzumab, cetuximab, brentuximab or nimotuzumab;

a conjugate of Val-Cit-PAB-MMAS and trastuzumab, cetuximab, brentuximab or nimotuzumab;

a conjugate of duocarmycin β-D-galactopyranoside and trastuzumab, cetuximab, brentuximab or nimotuzumab;

a conjugate of duocarmycin sialylgalactoside and trastuzumab, cetuximab, brentuximab or nimotuzumab;

a conjugate of Val-Cit-Gly-duocarmycin sialylgalactoside and trastuzumab, cetuximab, brentuximab or nimotuzumab;

a conjugate of beta-D-Galactopyranosyl-(glycolic acid ester)-duocarmycin and trastuzumab, cetuximab, brentuximab or nimotuzumab;

a conjugate of sialyl-beta-D-Galactopyranosyl-(glycolic acid ester)-duocarmycin and trastuzumab, cetuximab, brentuximab or nimotuzumab; and a conjugate of beta-D-Galactopyranosyl-(glycolic acid ester)-MMAE and antibody;

a conjugate of glucuronyl-duocarmycin and antibody;

a conjugate of glucuronyl-duocarmycin and trastuzumab;

a conjugate of 2-amino-2-deoxy-β-D-glucopyranosyl duocarmycin and antibody;

a conjugate of 2-acylamido-2-deoxy-β-D-glucopyranosyl duocarmycin and antibody;

a conjugate of beta-glucuronyl-monomethylauristatin E (MMAU) and antibody;

a conjugate of maleimidocaproyl-VC-PAB-MMAU and antibody;

a conjugate of MMAU-PAB-CV-maleimidoyl and antibody;

a conjugate of MMAU-PAB-CV-maleimidoyl and trastuzumab;

a conjugate of beta-glucosyl-monomethylauristatin E (MMAX) and antibody;

a conjugate of maleimidocaproyl-VC-PAB-MMAX and antibody;

a conjugate of MMAX-PAB-CV-maleimidoyl and antibody;

a conjugate of MMAX-PAB-CV-maleimidoyl and trastuzumab;

a conjugate of MMAG-PAB-CV-maleimidoyl and antibody;

a conjugate of MMAG-PAB-CV-maleimidoyl and trastuzumab;

a conjugate of MMAG-PAB-CV-maleimidoyl and 2G12, nimotuzumab or trastuzumab;

a conjugate of 2-acetamido-2-deoxy-β-D-glucopyranosyl duocarmycin and antibody;

a conjugate of Gal-duocarmycin and antibody;

a conjugate of Gal-duocarmycin-PAB-CV-maleimidoyl and antibody;

a conjugate of Gal-duocarmycin-PAB-CV-maleimidoyl and trastuzumab;

a conjugate of glycosyl-maytansinoid and antibody;

a conjugate of glycosyl-N-glucosylmaytansinoid and antibody;

a conjugate of Gal-N-glucosylmaytansinoid and antibody;

a conjugate of NeuAc-Gal-N-glucosylmaytansinoid and antibody;

a conjugate of glycosyl-tubulysin and antibody;

a conjugate of Gal-tubulysin and antibody;

a conjugate of NeuAc-Gal-tubulysin and antibody;

a conjugate of glycosyl-α-amanitin and antibody;

a conjugate of Gal-α-amanitin and antibody;

a conjugate of NeuAc-Gal-α-amanitin and antibody;

a conjugate of glycosyl-cryptophycin and antibody;

a conjugate of Gal-cryptophycin and antibody; and a conjugate of NeuAc-Gal-cryptophycin and antibody.

In an embodiment, the glycoside-to-antibody-ratio is 2, 3, 4, 5, 6, 7, 8, 9, 10, 11, 12, 13, 14, 15, 16, 17, 18, 19, or 20.

In an embodiment, the molecule comprises or is a molecule selected from the group consisting of the following:

O-β-D-galactopyranosylmonomethylauristatin E (MMAG);

Val-Cit-PAB-MMAG;

N-(6-azido-6-deoxy-D-galactosyl)-MMAG;

O—(N-acetylneuraminyl-β-D-galactopyranosyl)-MMAE (MMAS);

Val-Cit-PAB-MMAS;

N-(6-azido-6-deoxy-D-galactosyl)-MMAS;

β-D-4'-demethylepipodophyllotoxin β-D-4-galactopyranosylglucopyranoside (Galβ1,4Glc-PT);

α2,6-N-acetylneuraminyl-β-D-4-galactopyranosylglucopyranoside (NeuAcα2,6Galβ1,4Glc-PT);

α2,6-N-acetyl-9-azidoneuraminyl-β-D-4-galactopyranosylglucopyranoside (9-azido-NeuAcα2,6Galβ1,4Glc-PT);

galactopyranosyl-DM1;

α2,6-NeuAc-galactopyranosyl-DM1;

9-azido-sialyl derivative of galactopyranosyl-DM1;

dexamethasone 21-O-beta-D-galactopyranoside (Gal-Dexa);

NeuAcα2,6Gal-Dexa;

9N3NeuAcα2,6Gal-Dexa;

β-1,4-galactosylated Xyl-taxol (Galβ1,4Xyl-Taxol);

NeuAcα2,6Galβ1,4Xyl-Taxol;

9-N3-NeuAcα2,6Galβ1,4Xyl-Taxol;

N-(6-azido-6-deoxy-D-galactosyl)-MMAF-IleVal (GlcNAcβ-Ser;

ValCitPAB-MMAF-IleVal(GlcNAcβ)Ser;

dimeric duocarmycin β-D-galactopyranoside;

dimeric duocarmycin sialylgalactoside;

duocarmycin β-D-galactopyranoside;

duocarmycin sialylgalactoside;

Val-Cit-Gly-duocarmycin sialylgalactoside;

Neu5Acα2,6Gal-Duocarmycin;

Gal-Duocarmycin-PAB-CV-DBCO;

Neu5Acα2,6MMAG;

Neu5Acα2,3MMAG;

maleimidocaproyl-VC-PAB-MMAG;

beta-D-Galactopyranosyl-(glycolic acid ester)-duocarmycin;

sialyl-beta-D-Galactopyranosyl-(glycolic acid ester)-duocarmycin;

beta-D-Galactopyranosyl-(glycolic acid ester)-MMAE;

2-amino-2-deoxy-β-D-glucopyranosyl duocarmycin;

2-acylamido-2-deoxy-β-D-glucopyranosyl duocarmycin;

beta-glucuronyl-monomethylauristatin E (MMAU);

beta-glucosyl-monomethylauristatin E (MMAX);

2-acetamido-2-deoxy-β-D-glucopyranosyl duocarmycin;

Gal-duocarmycin;

glycosyl-maytansinoid;

glycosyl-N-glucosylmaytansinoid;

Gal-N-glucosylmaytansinoid;

NeuAc-Gal-N-glucosylmaytansinoid;

glycosyl-tubulysin;

Gal-tubulysin;

NeuAc-Gal-tubulysin;

glycosyl-α-amanitin;

Gal-α-amanitin;

NeuAc-Gal-α-amanitin;

glycosyl-cryptophycin;

Gal-cryptophycin; and

NeuAc-Gal-cryptophycin.

An antibody-drug conjugate obtainable by the method according to one or more embodiments is also disclosed.

A pharmaceutical composition comprising the molecule according to one or more embodiments or the antibody-drug conjugate according to one or more embodiments is disclosed.

The pharmaceutical composition may further comprise a pharmaceutically acceptable carrier. Examples of suitable pharmaceutically acceptable carriers are well known in the art and may include e.g. phosphate buffered saline solutions, water, oil/water emulsions, wetting agents, and liposomes. Compositions comprising such carriers may be formulated by methods well known in the art. The pharmaceutical composition may further comprise other components such as vehicles, additives, preservatives, other pharmaceutical compositions administrated concurrently, and the like.

In an embodiment, the pharmaceutical composition comprises the antibody-drug conjugate, wherein n is at least 1, at least 1.1, at least 1.2, at least 1.3, at least 1.4, at least 1.5, at least 1.6, at least 1.7, at least 1.8, at least 1.9, at least 2, at least 2.1, at least 2.2, at least 2.3, at least 2.4, at least 2.5, at least 2.6, at least 2.7, at least 2.8, at least 2.9, at least 3, at least 3.1, at least 3.2, at least 3.3, at least 3.4, at least 3.5, at least 3.6, at least 3.7, at least 3.8, at least 3.9, at least 4, at least 4.1, at least 4.2, at least 4.3, at least 4.4, at least 4.5, at least 4.6, at least 4.7, at least 4.8, at least 4.9, at least 5, at least 5.1, at least 5.2, at least 5.3, at least 5.4, at least 5.5, at least 5.6, at least 5.7, at least 5.8, at least 5.9, at least 6, at least 6.1, at least 6.2, at least 6.3, at least 6.4, at least 6.5, at least 6.6, at least 6.7, at least 6.8, at least 6.9, at least 7, at least 7.1, at least 7.2, at least 7.3, at least 7.4, at least 7.5, at least 7.6, at least 7.7, at least 7.8, at least 7.9, at least 8, at least 8.1, at least 8.2, at least 8.3, at least 8.4, at least 8.5, at least 8.6, at least 8.7, at least 8.8, at least 8.9, at least 9, at least 9.1, at least 9.2, at least 9.3, at least 9.4, at least 9.5, at least 9.6, at least 9.7, at least 9.8, at least 9.9, at least 10, at least 11, at least 12, at least 13, at least 14, at least 15, at least 16, at least 17, at least 18, at least 19, or at least 20.

In an embodiment, the glycoside-to-antibody ratio of the pharmaceutical composition is in the range of 1 to about 100, or 1 to about 60, or 1 to about 20, or 1 to about 10; 2 to about 40, or 2 to about 20, or 2 to about 12, or 2 to about 10, or 2 to about 8, or 2 to about 6, or 2 to about 4; 3 to about 60, or 3 to about 40, or 3 to about 30, or 3 to about 20, or 3 to about 15, or 3 to about 10, or 3 to about 8, or 3 to about 6, or 3 to 4; 4 to about 60, or 4 to about 40, or 4 to about 20, or 4 to about 16, or 4 to about 12, or 4 to about 10, or 4 to about 8, or 4 to about 7, or 4 to about 6, or 4 to 5; over 3, over 4, over 5, over 6, over 7, over 8, over 9, over 10, over 11, over 12, over 13, over 14, over 15, or over 16; or the glycoside-to-antibody ratio is 1, 2, 3, 4, 5, 6, 7, 8, 9, 10, 12, 14, 15, 16, 18, 20, 21, 22, 24, 25, 26, 27, 28, 30, 32, 34, 35, 36, 38, 40, 42, 44, 45, 46, 48, 50, 52, 54, 55, 56, 58, 60, 62, 63, 64, 66, 68, 70, 72, 74, 76, 78, 80, 82, 84, 86, 88, 90, 92, 94, 96, 98, 100, or more than 100. The glycoside-to-antibody ratio may be determined from the pharmaceutical composition e.g. by MALDI-TOF MS or ESI-MS.

In an embodiment, n, drug-to-antibody ratio, and/or glycoside-to-antibody ratio of an antibody-drug conjugate may be determined using a MALDI-TOF MS.

In an embodiment, n, drug-to-antibody ratio, and/or glycoside-to-antibody ratio of an antibody-drug conjugate may be determined using an ESI-MS.

An exemplary method to determine n, drug-to-antibody ratio, and/or glycoside-to-antibody ratio for an antibody-drug conjugate (composition) is described in Example 23.

Exemplary methods to determine n, drug-to-antibody ratio, and/or glycoside-to-antibody ratio is described in Chen J, Yin S, Wu Y, Ouyang J. Development of a native nanoelectrospray mass spectrometry method for determination of the drug-to-antibody ratio of antibody-drug conjugates. Anal Chem. 2013 Feb. 5; 85(3):1699-1704. doi: 10.1021/ac302959p.

In an embodiment, the pharmaceutical composition comprises an effective amount of the antibody-drug conjugate according to one or more embodiments.

In an embodiment, the pharmaceutical composition comprises a therapeutically effective amount of the antibody-drug conjugate according to one or more embodiments.

The term "therapeutically effective amount" or "effective amount" of the antibody-drug conjugate should be understood as referring to the dosage regimen for modulating the growth of cancer cells and/or treating a patient's disease. The therapeutically effective amount can also be determined by reference to standard medical texts, such as the Physicians Desk Reference 2004. The patient may be male or female, and may be an infant, child or adult.

The term "treatment" or "treat" is used in the conventional sense and means attending to, caring for and nursing a patient with the aim of combating, reducing, attenuating or alleviating an illness or health abnormality and improving the living conditions impaired by this illness, such as, for example, with a cancer disease.

In an embodiment, the pharmaceutical composition comprises a composition for e.g. oral, parenteral, transdermal, intraluminal, intraarterial, intrathecal and/or intranasal administration or for direct injection into tissue. Administration of the pharmaceutical composition may be effected in different ways, e.g. by intravenous, intraperitoneal, subcutaneous, intramuscular, intratumoral, topical or intradermal administration.

An antibody-drug conjugate according to one or more embodiments or the pharmaceutical composition according to one or more embodiments for use as a medicament is disclosed.

An antibody-drug conjugate according to one or more embodiments or the pharmaceutical composition according to one or more embodiments for use in the treatment of cancer is disclosed.

In an embodiment, the cancer is selected from the group consisting of leukemia, lymphoma, breast cancer, prostate cancer, ovarian cancer, colorectal cancer, gastric cancer, squamous cancer, small-cell lung cancer, head-and-neck cancer, multidrug resistant cancer, glioma, melanoma and testicular cancer.

A method of treating and/or modulating the growth of and/or prophylaxis of tumor cells in humans or animals is disclosed, wherein the antibody-drug conjugate according to one or more embodiments or the pharmaceutical composition according to one or more embodiments is administered to a human or animal in an effective amount.

In an embodiment, the tumor cells are selected from the group consisting of leukemia cells, lymphoma cells, breast cancer cells, prostate cancer cells, ovarian cancer cells, colorectal cancer cells, gastric cancer cells, squamous cancer cells, small-cell lung cancer cells, head-and-neck cancer cells, multidrug resistant cancer cells, and testicular cancer cells.

A method of treating cancer in humans is disclosed, wherein the antibody-drug conjugate or the pharmaceutical composition according to one or more embodiments is administered to a human in an effective amount.

In an embodiment, the effective amount is a therapeutically effective amount.

In an embodiment, the antibody-drug conjugate or the pharmaceutical composition according to one or more embodiments is administered intravenously to a human in a therapeutically effective amount.

In an embodiment, the antibody-drug conjugate or the pharmaceutical composition according to one or more embodiments is administered intratumorally to a human in a therapeutically effective amount.

In an embodiment, the cancer is selected from the group consisting of head-and-neck cancer, leukemia, lymphoma, breast cancer, prostate cancer, ovarian cancer, colorectal cancer, gastric cancer, squamous cancer, small-cell lung cancer, multidrug resistant cancer and testicular cancer.

The embodiments of the invention described hereinbefore may be used in any combination with each other. Several of the embodiments may be combined together to form a further embodiment of the invention. A product or a method to which the invention is related may comprise at least one of the embodiments of the invention described hereinbefore.

The molecule and the antibody-drug conjugate according to one or more embodiments have a number of advantageous properties.

The presence of the saccharide renders the otherwise relatively poorly water-soluble auristatin or other toxic payload molecule moiety more soluble in aqueous and physiological solutions. The improved solubility also improves the retention of the antibody-drug conjugate in serum. It may also have high uptake in cells to which it is targeted and low uptake in cells and organs to which it is not targeted.

The antibody-drug conjugate according to one or more embodiments is less toxic in the absence or low activity of lysosomal and intracellular glycohydrolases. Since cancer cells typically display high activity of lysosomal and/or intracellular glycohydrolases, the auristatin moiety or other toxic payload moiety is preferentially released in cancer cells as compared to non-cancer cells.

The conjugate has low antigenicity.

The antibody-drug conjugate according to one or more embodiments also exhibits good pharmacokinetics. It has suitable retention in blood, high uptake in cells to which it is targeted and low uptake in cells and organs to which it is not targeted.

Auristatin and other toxic payload molecules are highly toxic drugs with a known track record in clinical applications.

The production process is relatively simple.

The antibody-drug conjugate according to one or more embodiments is sufficiently stable towards chemical or biochemical degradation during manufacturing or in physiological conditions, e.g. in blood, serum, plasma or tissues.

EXAMPLES

In the following, the present invention will be described in more detail. Reference will now be made in detail to the embodiments, examples of which are illustrated in the accompanying drawings. The description below discloses some embodiments in such detail that a person skilled in the art is able to utilize the invention based on the disclosure. Not all steps of the embodiments are discussed in detail, as many of the steps will be obvious for the person skilled in the art based on this specification.

Example 1. Synthesis of Galactosylated Monomethylauristatin E

Synthesis of O-β-D-galactopyranosyl-norephedrine

Norephedrine (Sigma; compound 1 in Scheme 1) is N-protected by addition of Boc-protection group using di-tert-butyl dicarbonate (Boc$_2$O) (V. Perron, S. Abbott, N. Moreau, D. Lee, C. Penney, B. Zacharie, *Synthesis*, 2009, 283-289; A. Sarkar, S. R. Roy, N. Parikh, A. K. Chakraborti, J. Org. Chem., 2011, 76, 7132-7140.). The N-Boc-norephedrine product (compound 2) is purified by preparative HPLC on Gemini 5 μm NX-AXIA-C18 reversed phase column (21.2×250 mm, 110 Å (Phenomenex)) eluted with ACN gradient in aqueous ammonium acetate.

To a solution containing N-Boc-norephedrine and pre-activated 4 Å molecular sieves in dry CH$_2$Cl$_2$:ACN is added 0.15 mol equiv TMSOTf at −20° C. The reaction mixture is stirred for minutes and 1.2 mol equiv. of 2,3,4,6-Tetra-O-benzoyl-D-galactopyranosyl trichloroacetimidate (Carbosynth) predissolved CH$_2$Cl$_2$ is added dropwise to the solution. The resulting mixture is stirred for 1-3 h at −20° C., brought to RT, diluted with CH$_2$Cl$_2$ and washed with sat. NaHCO$_3$-solution. The organic phase is then dried and the O-(β-2,3,4,6-Tetra-O-benzoyl-D-galactopyranosyl)-N-Boc-ephedrine is purified by preparative HPLC as above. The O-benzoyl groups are removed by dissolving the O-(β-2,3,4,6-Tetra-O-benzoyl-D-galactopyranosyl)-N-Boc-ephedrine in methanolic solution and adjusting the pH to about 9 with sodium methoxide. The debenzoylation reaction is allowed to run for several hours or overnight until complete as analyzed e.g. by MALDI-TOF mass spectrometry. The debenzoylated product (compound 3) is purified by preparative HPLC as above.

To obtain O-β-D-galactopyranosyl-norephedrine (compound 4), compound 3 is treated with trifluoroacetic acid solution to remove N-Boc protecting group.

Scheme 1. Synthesis of O-β-D-galactopyranosyl-norephedrine

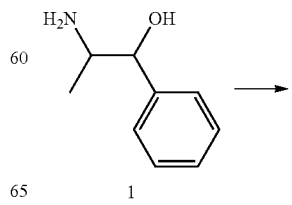

1

81

-continued

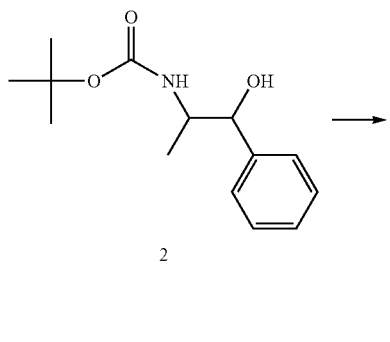

2

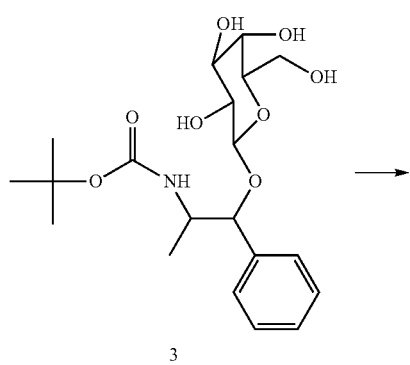

3

82

-continued

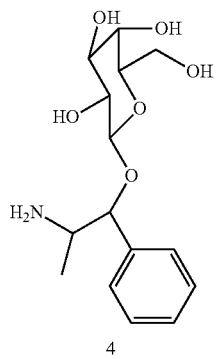

4

Synthesis of
O-β-D-galactopyranosyl-(N-Boc)-norephedrine

N-Boc-(N-Me)-Val-Val-Dil-Dap-OH (Concortis; compound 1 in Scheme 2) is dissolved in acetonitrile. 5× molar excess each of O-β-D-galactopyranosyl-norephedrine and DMT-MM are added, followed by 25 µl of diisopropylethylamine. The reaction mixtures is stirred overnight at room temperature. The product, N-Boc-O-β-D-galactopyranosyl-monomethylauristatin E (compound 2, Scheme 2) is isolated by reversed-phase chromatography as above.

To obtain O-β-D-galactopyranosylmonomethylauristatin E (MMAG; compound 3, Scheme 2), compound 2 is dissolved in TFA/DCM and incubated until acceptable level of deprotection is achieved as analyzed by MALDI-TOF MS. The MMAG product is purified by reversed-phase chromatography as above.

Scheme 2. Synthesis of O-β-D-galactopyranosylmonomethylauristatin E (MMAG)

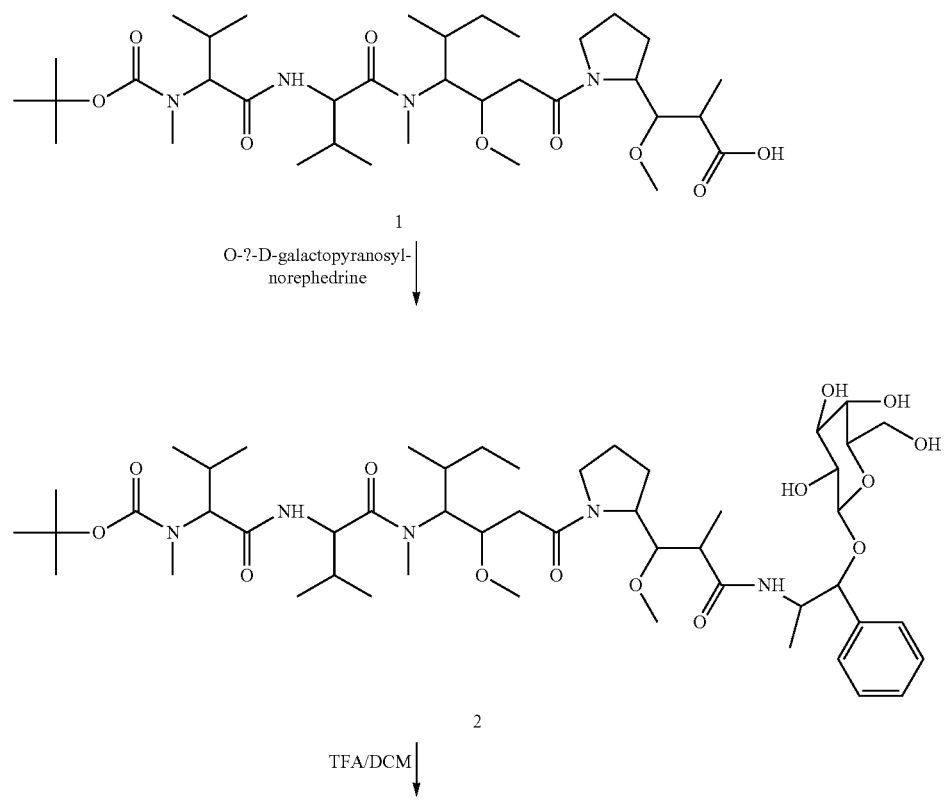

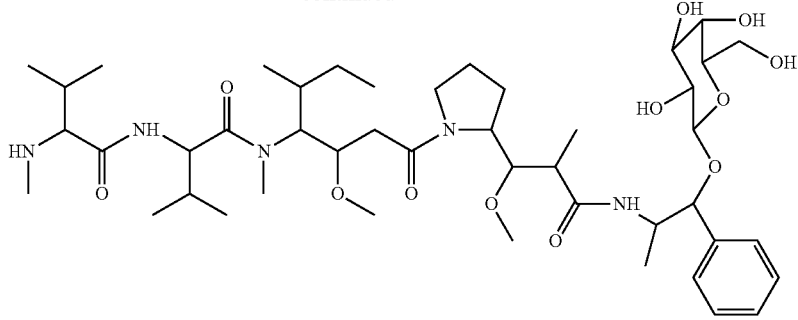

3

Example 2. O-β-D-galactosylation of monomethylauristatin E

Monomethylauristatin E (MMAE; Concortis; compound 1 in Scheme 3) is N-protected with Boc as described in Example 1. To a solution containing N-Boc-MMAE and pre-activated 4 Å molecular sieves in dry CH$_2$Cl$_2$:ACN is added 0.15 mol equiv TMSOTf at −20° C. The reaction mixture is stirred for 10 minutes and 1.2 mol equiv. of 2,3,4,6-Tetra-O-benzoyl-D-galactopyranosyl trichloroacetimidate (Carbosynth) predissolved CH$_2$Cl$_2$ is added dropwise to the solution. The resulting mixture is stirred for 1-3 h at −20° C., brought to RT, diluted with CH$_2$Cl$_2$ and washed with sat. NaHCO$_3$-solution. The organic phase is then dried and the O-(β-2,3,4,6-Tetra-O-benzoyl-D-galactopyranosyl)-N-Boc-MMAE is purified by preparative HPLC as above. The O-benzoyl groups are removed by dissolving the O-(β-2,3,4,6-Tetra-O-benzoyl-D-galactopyranosyl)-N-Boc-ephedrine in methanolic solution and adjusting the pH to about 9 with sodium methoxide. The debenzoylation reaction is allowed to run for several hours or overnight until complete as analyzed e.g. by MALDI-TOF mass spectrometry. The debenzoylated product is purified by preparative HPLC as above.

To obtain O-β-D-galactopyranosyl-MMAE (compound 2 in Scheme 3), O-(β-2,3,4,6-Tetra-O-benzoyl-D-galactopyranosyl)-N-Boc-MMAE is treated with trifluoroacetic acid solution to remove N-Boc protecting group. The deprotected product is isolated by preparative HPLC as above.

Scheme 3. Synthesis of O-β-D-galactopyranosyl-monomethylauristatin E (MMAG) by using MMAE.

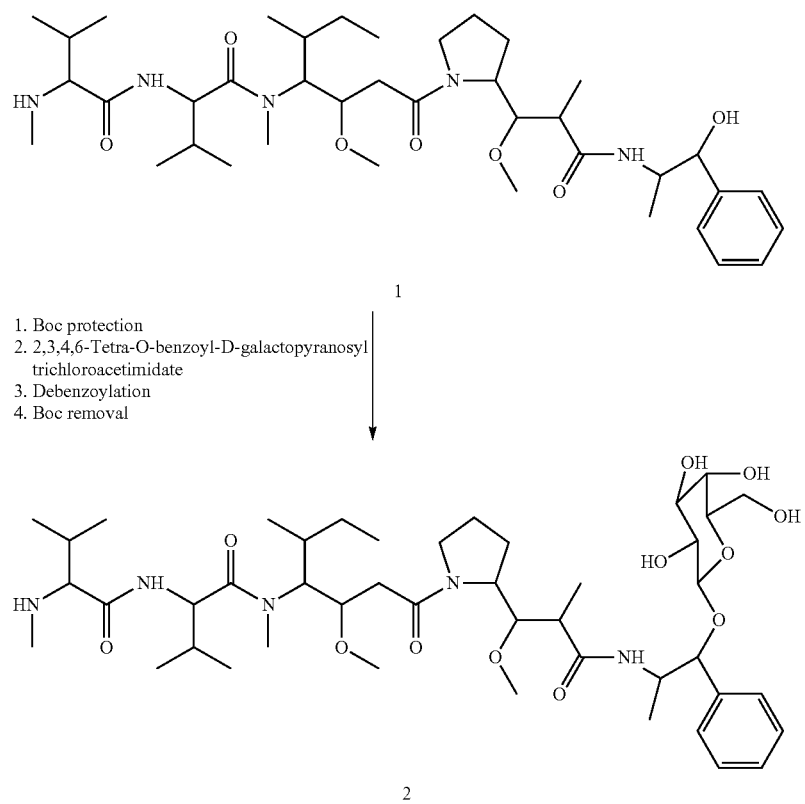

Example 3. Sialylation of Galactosylated MMAE

1 µmol of galactosylated MMAE, 20 µmol of CMP-Neu5Ac (Sigma) and 300 mU of *P. damsela* alpha-2,6-sialyltransferase (Sigma) are dissolved in 1 ml of 0.1 M Tris-HCl, pH 7.5. The reaction mixture is allowed to stir at +37° C. until acceptable level of sialylation is observed by MALDI-TOF MS analysis. The sialylated product, O-(α2,6-N-Acetylneuraminyl-β-D-galactopyranosyl)-MMAE, is isolated with preparative HPLC as above.

Example 4. Preparation of N-(6-azido-6-deoxy-D-galactosyl)-O-β-D-galactopyranosylmonomethylauristatin E 1 µmol of O-β-D-galactopyranosylmonomethyl-auristatin E (Example 1), 160 µmol of sodium cyanoborohydride and 95 µmol of 6-azido-6-deoxy-D-galactose (Carbosynth) are dissolved in 0.6 ml of DMSO containing 1% of diisopropylethylamine. The mixture is stirred at 60° C. for three days. The alkylated product (Scheme 4) is isolated with preparative HPLC as described in Example 1.

Scheme 4. Structure of N-(6-azido-6-deoxy-D-galactos-yl)-O–β-D-galactopyranosylmonomethylauristatin E

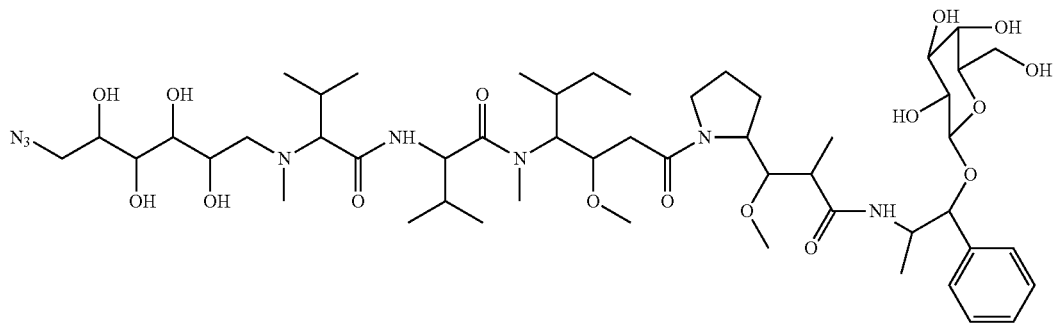

Example 5. Preparation of Val-Cit-PAB-MMAG

1 µmol of MMAG (Example 1) in DMF, 2 µmol of Fmoc-Val-Cit-PAB-pnp (Concortis), 2 µmol HOBt in DMF, and 40 µmol diisopropylethylamine are dissolved in 0.5 ml of DMF, and stirred for two days at room temperature. Fmoc is removed from the crude product by adding 150 µl of diethylamine and by stirring at room temperature overnight.

The product Val-Cit-PAB-MMAG (Scheme 5) is purified with preparative HPLC as described in Example 1.

Scheme 5. Structure of Val-Cit-PABC-(O-β-D-galacto-pyranosyl)monomethylauristatin E

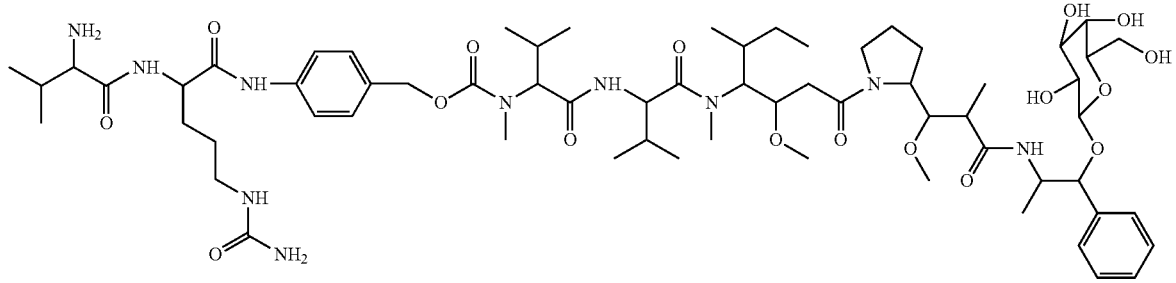

Example 6. Podophyllotoxin Derivatives and 9-azido-sialyl Derivative of beta-D-4'-demethylepipodophyllo-toxin glucopyranoside Glycosides can be incorporated into the hydroxyl group(s) of podophyllotoxin and epipodophyllotoxin and their analogues and derivatives. Such glycosides are available commercially, e.g. structure 3 in Scheme 6.

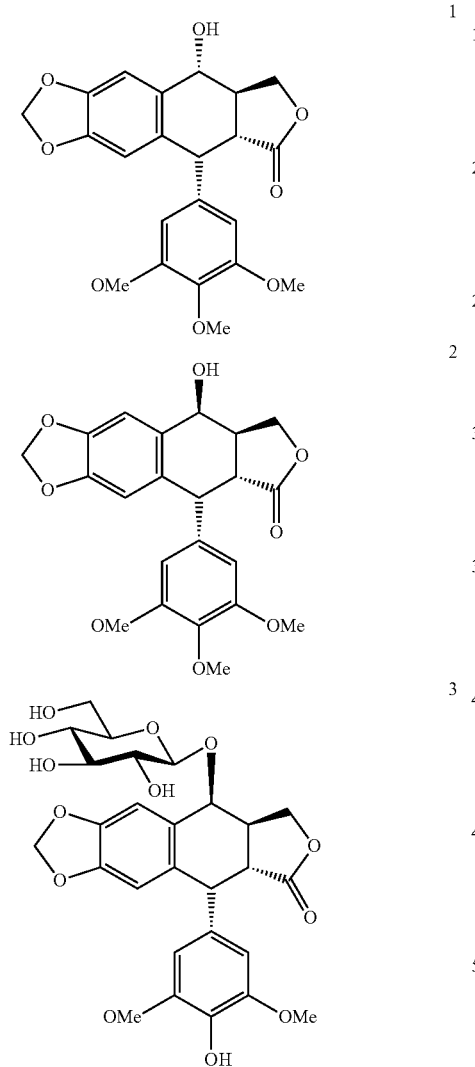

Scheme 6. Structures of podophyllotoxin (1), epipodophyllotoxin (2) and beta-D-4'-demethylepipodophyllo-toxin glucopyranoside (3).

Synthesis of 9-azido-sialyl derivative of beta-D-4'-demethylepipodophyllo-toxin glucopyranoside: 1 μmol of beta-D-4'-demethylepipodophyllo-toxin glucopyranoside (Glc-PT) (Toronto Research Chemicals) was beta-galactosylated in a reaction containing 10 μmol UDP-galactose, 0.5 U bovine milk beta-galactosyltransferase, 0.9 mg alpha-lactalbumin, 20 mM $MnCl_2$ and 50 mM MOPS, pH 7.2, in a total volume of 250 μl. After 120 h, the reaction mixture was applied to Bond-Elut C18 cartridge, washed with water and eluted with acetonitrile in water. MALDI-TOF MS analysis revealed the expected product (Galβ1,4Glc-PT) at m/z 747.26 [M+Na]$^+$, no Glc-PT was observed in the spectrum.

The Galβ1,4Glc-PT product was 9-azido-sialylated by incubation with 4 μmol CMP-9-$N_3$-sialic acid, 125 mU *P. damsela* alpha2,6-sialyltransferase (Sigma) and 0.1 M Tris-HCl, pH 7.5, in a total volume of 200 μl. After 24 h, MALDI-TOF MS analysis showed the expected 9-azido-sialylated product ($9N_3$NeuAcα2, 6Galβ1,4Glc-PT) (Scheme 7) at m/z 1063.3 [M+Na]$^+$. The product was isolated by HPLC using Gemini 5 μm NX-C18 reversed-phase column (4.6×250 mm (Phenomenex)) eluted with ACN gradient in aqueous ammonium acetate.

The corresponding NeuAcα2,6Galβ1,4Glc-PT derivative is prepared by incubation with 4 μmol CMP-sialic acid, 125 mU *P. damsela* alpha2,6-sialyltransferase (Sigma) and 0.1 M Tris-HCl, pH 7.5, in a total volume of 200 μl, and purified as described above.

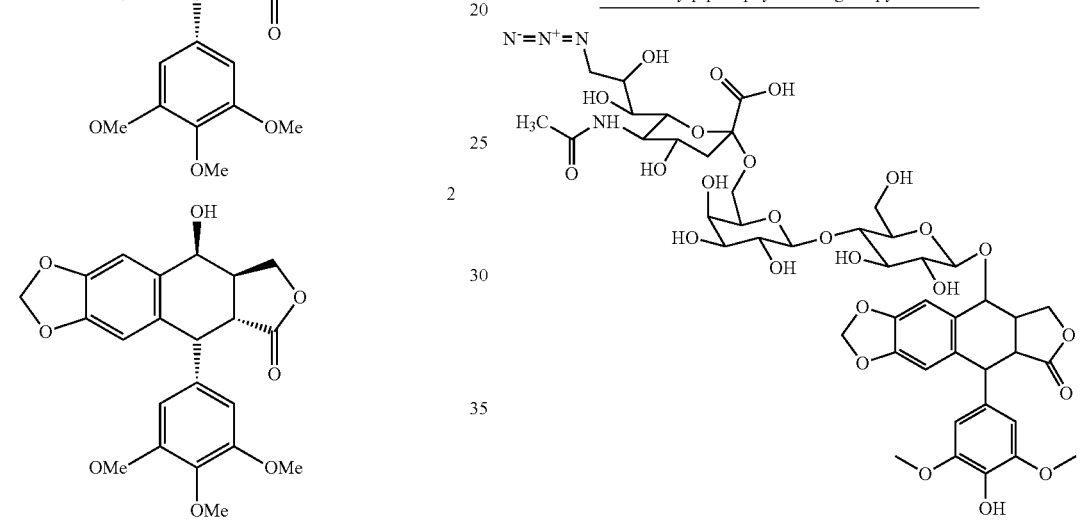

Scheme 7. 9-azido-sialyl derivative of beta-D-4'-demethylpipodophyllotoxin glucopyranoside

Example 7. Sialyl Derivative of galactopyranosyl-DM1

Protected Galactopyranoside (10).

To a solution containing 49 mg (0.25 mmol) 9 (Scheme 8) and pre-activated 4 Å MS in 4.0 ml dry $CH_2Cl_2$:ACN 3:1 was added 7.0 μl (0.15 equiv., 0.038 mmol) TMSOTf at −20° C. The reaction mixture was stirred for 10 minutes and 0.23 g (1.2 equiv., 0.3 mmol) 3 dissolved in 2.5 ml dry $CH_2Cl_2$ was added dropwise to the solution. The resulting mixture was stirred for 1.5 h, brought to rt, diluted with 20 ml $CH_2Cl_2$ and washed with 20 ml sat. $NaHCO_3$-solution. The organic phase was dried over $Na_2SO_4$, filtered and concentrated. The crude product was purified by column chromatography (hexane:EtOAc 2:1→1:1) to give 10 as a colorless oil (0.15 g, %). HRMS: calcd. for $C_{44}H_{39}O_{12}NNa$ [M+Na]$^+$ 796.236; found 796.252.

Deprotected Galactopyranoside (11).

0.15 g (0.19 mmol) 10 was dissolved in 5 ml MeOH:THF 3:1. The pH of the reaction mixture was adjusted to 8/9 with NaOMe and the mixture was then left to stir o/n until TLC indicated the reaction to be complete. The reaction mixture was neutralized with Ag 50w8 (H$^+$-form), filtered and concentrated to give the crude product. The crude product was purified by column chromatography (MeOH:$CH_2Cl_2$ 1:5) to give the intermediate (debenzoylated) product as a colorless oil (48 mg, 70%). HRMS: calcd. for $C_{16}H_{23}O_8NNa$ [M+Na]$^+$380.132; found 380.137. The intermediate product was dissolved in 3 ml dry MeOH and 16 mg Pd/C (10% Pd) was added. The reaction mixture was placed inside a hydrogenation vessel (with stirring) and the reactor was closed. The air was evacuated and the vessel was filled with hydrogen gas (40 psi). The reaction mixture was kept o/n, the filtered through celite and concentrated to give 11 as a colorless oil (19 mg, 65%). Selected NMR-data; $^1$H NMR (600 MHz, D$_2$O, 22° C.): δ 4.37 (d, 1H, J=7.9 Hz, H-1), 3.92 (m, 1H), 3.89 (ap d, 1H, J=3.2 Hz, H-4), 3.78-3.64 (m, 4H), 3.61 (dd, 1H, J=3.2, 9.9 Hz, H-3), 3.49 (dd, 1H, J=7.9, 9.9 Hz, H-2) and 2.86-2.77 (m, 2H) ppm.

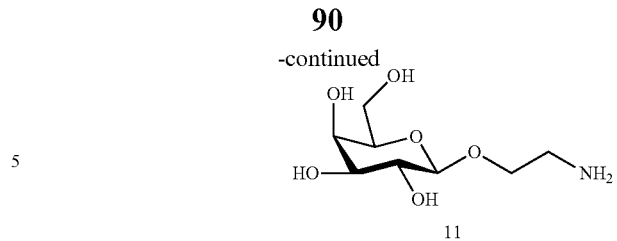

i) 1) TMSOTf, ACN, DCM, -20° C.; 2) 3, 77%; ii) 1) NaOMe, MeOH:THF 3:1, 70%; 2) Pd/C, H$_2$, MeOH, 65%.

Galactopyranosyl-DM1.

S-carboxymethylated DM-1 (CM-DM1) was prepared as described in WO2014/177771. To synthesize galactopyranosyl-DM1, 1 µmol CM-DM1 in DMF (20 µl), 3 µmol galactose-beta-aminoethyl glycoside (11), 19 µmol DMT-MM in MQ (60 µl) and 50 µl DMF were stirred at RT for overnight. The crude reaction mixture was analysed by MALDI-TOF mass spectra using 2,5-dihydroxybenzoic acid matrix, showing expected mass for galactopyranosyl-DM1 (m/z 1023 [M+Na]$^+$). Galactopyranosyl-DM1 was purified by HPLC with Gemini 5 µm NX-C18 reversed phase column (4.6×250 mm, 110 Å (Phenomenex)) eluted with ACN gradient in aqueous ammonium acetate.

The galactopyranosyl-DM1 is 9-azido-sialylated by incubation with CMP-9-N$_3$-sialic acid and *P. damsela* alpha2,6-sialyltransferase in 0.1 M Tris-HCl, pH 7.5. The 9-azido-sialylated product (Scheme 9) is purified by HPLC on Gemini 5 µm NX-C18 reversed phase column (4.6×250 mm, 110 Å (Phenomenex)) eluted with ACN gradient in aqueous ammonium acetate.

The corresponding sialyl derivative NeuAc-galactopyranosyl-DM1 is prepared by incubation with CMP-sialic acid and *P. damsela* alpha2,6-sialyltransferase in 0.1 M Tris-HCl, pH 7.5, and purified as described above.

Scheme 8.

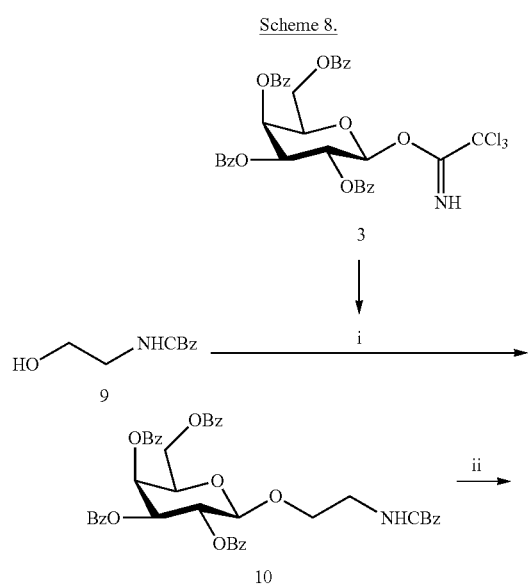

Scheme 9. 9-azido-sialyly derivative of galactopyranosyl-DM1

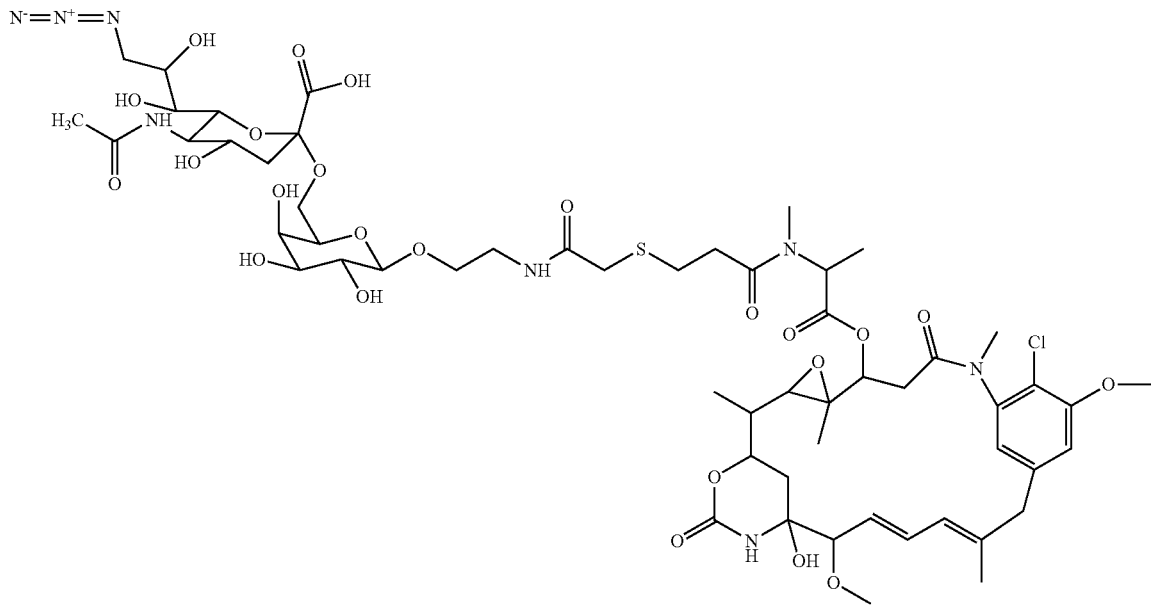

Example 8. Sialyl Derivatives of dexamethasone 21-O-beta-D-galactopyranoside 3 μmol of dexamethasone 21-O-beta-D-galactopyranoside (Gal-Dexa) (Carbosynth) was 9-azido-sialylated by incubation with 10 μmol CMP-9-$N_3$-sialic acid, 150 mU *P. damsela* alpha2,6-sialyltransferase (Sigma) and 0.1 M Tris-HCl, pH 7.5, in a total volume of 300 μl. After 24 h, MALDI-TOF MS analysis showed the expected 9-azido-sialylated product ($9N_3$NeuAcα2,6Gal-Dexa) at m/z 893.4 [M+Na]$^+$. The product was purified by HPLC on Gemini 5 μm NX-C18 reversed phase column (4.6×250 mm, 110 Å (Phenomenex)) eluted with ACN gradient in aqueous ammonium acetate.

The corresponding sialyl derivative is prepared by incubation of 3 μmol of dexamethasone 21-O-beta-D-galactopyranoside (Gal-Dexa) with 10 μmol CMP-sialic acid, 150 mU *P. damsela* alpha2,6-sialyltransferase (Sigma) and 0.1 M Tris-HCl, pH 7.5, in a total volume of 300 μl, and purified as above.

Scheme 10. 9-azido-sialyl derivative of dexamethasone 21-O-beta-D-galactopyranoside

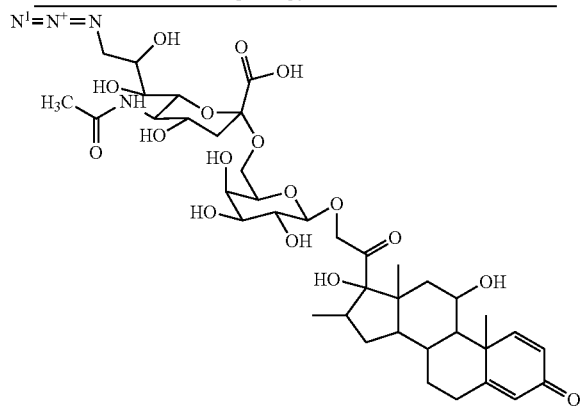

Example 9. β-1,4-Galactosylation of 10-deacetyl-xylosyltaxol 10-deacetyl-xylosyltaxol (Xyl-taxol) was subjected to galactosylation using bovine milk β-1,4-Galactosyltransferase (Sigma). 2 mM Xyl-taxol (Santa Cruz Biotechnology, 65,34% pure), 40 mM UDP-Gal, 2 mU/μl β-1,4-Galactosyltransferase, 0.22 mM α-lactalbumin and 20 mM $MnCl_2$ in 50 mM MOPS pH 7.2 were incubated in the presence of 5%, 10% or 20% DMSO o/we at +37° C. MALDI-TOF MS analysis of all three reaction mixtures after o/we reactions revealed major signal at m/z 1128 corresponding to β-1,4-galactosylated Xyl-taxol (Gal-Xyl-taxol). The reaction mixtures were purified with Bond Elut C18 cartridge (Varian). Reaction products retained in the cartridge were eluted with 60% aqueous acetonitrile. The Gal-Xyl-taxol product was isolated by HPLC using Gemini 5 μm NX-C18 reversed-phase column (4.6×250 mm (Phenomenex)) eluted with ACN gradient in aqueous ammonium acetate.

The Gal-Xyl-taxol is 9-azido-sialylated by incubation with CMP-9-$N_3$-sialic acid and *P. damsela* alpha2,6-sialyltransferase in 0.1 M Tris-HCl, pH 7.5. The 9-azido-sialylated product (Scheme 11) is purified by HPLC on Gemini 5 μm NX-C18 reversed phase column (4.6×250 mm, 110 Å (Phenomenex)) eluted with ACN gradient in aqueous ammonium acetate. The corresponding sialyl derivative is prepared similarly by using CMP-sialic acid instead of CMP-9-$N_3$-sialic acid in the reaction.

Scheme 11. Structure of 9-N3-NeuAcα2, 6Galβ1, 4Xyl-taxol

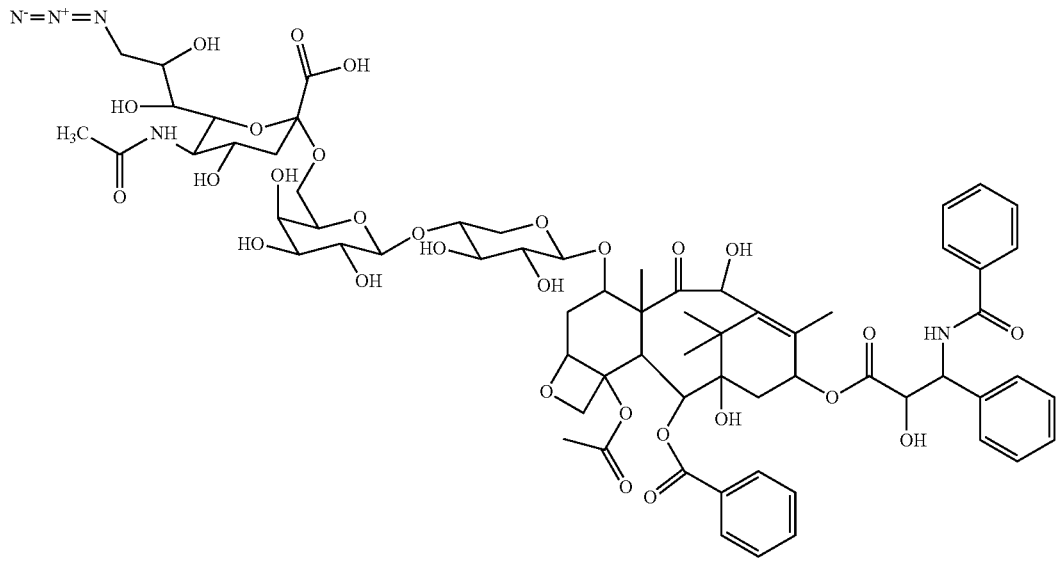

Example 10. Generation of Antibody-Drug Conjugates by Conjugation to Lysine or Cysteine Side Chains Antibody is reacted with dibenzocyclooctyl-NHS ester (NHS-DBCO; Jena Bioscience) as instructed by the supplier to form DBCO-antibody conjugated to lysine side chains. Depending on the molar ratio of NHS-DBCO and antibody, DBCO-to-antibody ratios selected from values from 1:1 to about 10:1, or 1.0-10.0 or greater, are achieved.

Alternatively, antibody is reacted with DBCO-maleimide (Jena Bioscience) as instructed by the supplier, after reduction of antibody disulfide bridges with a suitable reducing reagent, to form DBCO-antibody conjugated to cysteine side chains. Depending on the amount of free cysteine side chains per antibody and the molar ratio of NHS-DBCO and antibody, DBCO-to-antibody ratios selected from values between 2:1 to 8:1, or 2.0-8.0, are achieved. By controlling the reduction reaction to mild reduction, DBCO-to-antibody ratios from 2:1 to 4:1, or about 4:1, are achieved. By utilizing stronger reduction, DBCO-to-antibody ratios from 6:1 to 8:1, or about 8:1, are achieved.

The DBCO-antibody is purified by e.g. filtration. 9-azido-sialylated drug derivatives such as those prepared in the present Examples are conjugated to DBCO-antibody in copper-free click reaction in PBS with a 1.5 to 10-fold molar excess of drug versus DBCO units as described WO2014/177771. Antibody-drug conjugates are isolated with ultrafiltration.

Depending on the DBCO-to-antibody ratio, antibody-drug conjugates with drug-to-antibody ratio selected from values between 1:1 to about 10:1 or greater are achieved.

Example 11. Preparation of C-Terminally Modified monomethylauristatin F Derivatives N-(6-azido-6-deoxy-D-galactosyl)-MMAF (linker PCT), $NH_2$-Ile-Val-(GlcNAc($Ac_3$)-β-D-)Ser-OtBu (obtainable from custom synthesis), carboxylic acid activator EDC and hydroxybenzotriazole are dissolved in DMF and allowed to react to generate an amide bond between MMAF unit C-terminal —COOH unit and the glycosylated tripeptide. After removal of the C-terminal protecting group and deacetylation of the N-acetylglucosamine unit, the product N-(6-azido-6-deoxy-D-galactosyl)-MMAF-IleVal (GlcNAcβ-)Ser (Scheme 12) is isolated by HPLC on Gemini 5 μm NX-C18 reversed phase column (4.6×250 mm, 110 Å (Phenomenex)) eluted with ACN gradient in aqueous ammonium acetate.

Fmoc-ValCitPAB-MMAF (WO2014/177771), $NH_2$-Ile-Val-(GlcNAc-β-D-)Ser-OtBu (obtainable from custom synthesis and deacetylation of GlcNAc unit), carboxylic acid activator EDC and hydroxybenzotriazole are dissolved in DMF and allowed to react to generate an amide bond between MMAF unit C-terminal —COOH unit and the glycosylated tripeptide. After removal of the C-terminal protecting group by acid catalysis the product Fmoc-ValCit-PAB-MMAF-IleVal(GlcNAcβ)Ser (Scheme 12) is isolated by HPLC on Gemini 5 μm NX-C18 reversed phase column (4.6×250 mm, 110 Å (Phenomenex)) eluted with ACN gradient in aqueous ammonium acetate.

Antibody-drug conjugates of these MMAF derivatives may be prepared with methods described in WO2014/177771.

Scheme 12. Structure of (A) N-(6-azido-6-deoxy-D-galactosyl)-MMAF-IleVal (GlcNAcβ-) Ser and (B) Fmoc-ValCitPAB-MMAF-IleVal (GlcNAcβ) Ser

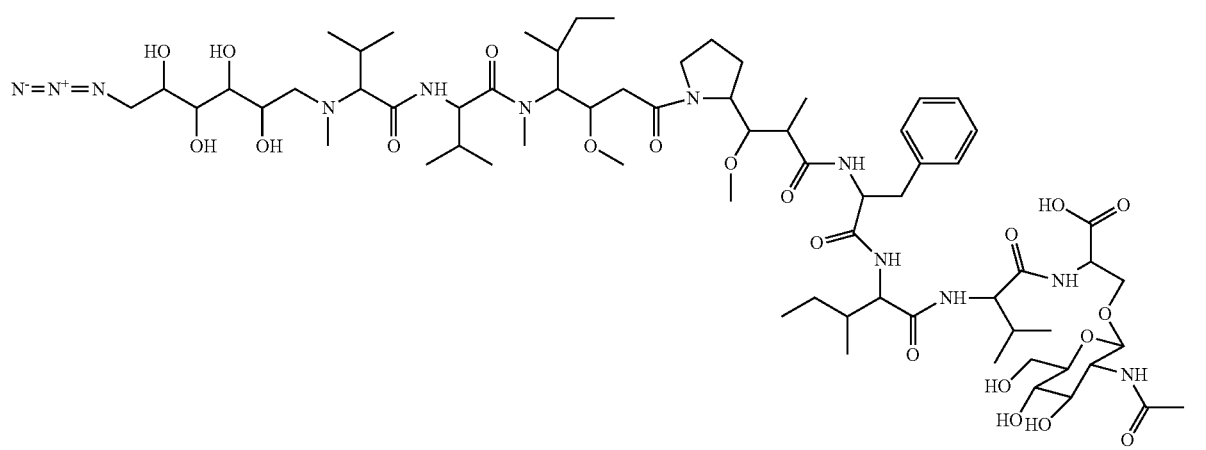

A

B

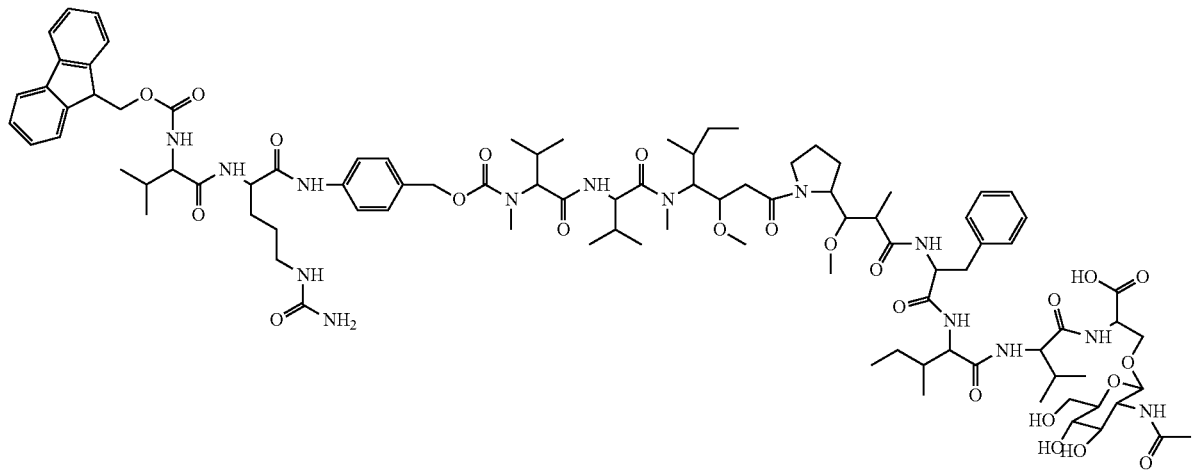

Example 12. Generation of Antibody-Drug Conjugates by Conjugation to Antibody Glycans To generate glycan-conjugated antibody-drug conjugates, azide groups are introduced to N-glycans of the antibody as described in WO2014/177771: N-glycans are galactosylated and 9-azido-sialylated by sequential incubation with 1) (1,4-galactosyltransferase (Sigma-Aldrich) and UDP-galactose and 2) α2,6-sialyltransferase (Roche) and CMP-9-azido-NeuAc (WO2014/177771). The azido-sialylated antibody thus obtained is incubated with an excess of DBCO-linker-drug in PBS, 2.5% DMSO. Reaction is allowed to proceed to completion at room temperature, after which unconjugated linker-drug is removed by repeated additions of PBS and centrifugations through Amicon Ultracel 30 k centrifugal filter. With mammalian cell-expressed antibody that contains only the conserved Fc domain N-glycans, drug-to-antibody ratio of 2.0 is achieved.

Alternatively, an antibody with additional N-linked glycans is utilized. Such antibodies can be obtained and trimmed into good acceptor structures for example as described in (WO2014/177771). With an antibody with one additional N-glycosylation site (for example cetuximab), drug-to-antibody ratios from about 4 to 6, or about 6.0, are achieved. With an antibody with two additional N-glycosylation sites, drug-to-antibody ratios from about 6 to 10, or about 8 to 10, are achieved. With an antibody with three additional N-glycosylation sites, drug-to-antibody ratios from about 10 to 14, or about 12 to 14, or about 14, are achieved.

Thus, depending on the glycan-to-antibody ratio, antibody-drug conjugates with drug-to-antibody ratio selected from values between 2:1 to about 14:1 or greater are achieved.

Example 13. Generation of Antibody-MMAG Conjugates

Fmoc-Val-Cit-PAB-monomethyl auristatin G (Fmoc-Val-Cit-PAB-MMAG, Fmoc-VC-PAB-MMAG) was synthesized from MMAG (Concortis, San Diego, USA) and Fmoc-Val-Cit-PAB-PNP (Concortis) by dissolving them in DMF and allowing to react to generate an amide bond between the N-terminal secondary amine of MMAG and the PAB self-immolative group. Fmoc was removed and the VC-PAB-MMAG product was isolated by HPLC on Gemini 5 μm NX-C18 reversed phase column (4.6×250 mm, 110 Å (Phenomenex)) eluted with ACN gradient in aqueous ammonium acetate. To obtain DBCO-VC-PAB-MMAG, 2 μmol VC-PAB-MMAG and 3× molar excess of DBCO-NHS ester (Jena Bioscience) in 295 μl DMF/5 μl diisopropylethylamine were stirred at RT overnight. The crude reaction mixture was analysed by MALDI-TOF mass spectra using 2,5-dihydroxybenzoic acid matrix, showing expected mass for DBCO-VC-PAB-MMAG (m/z 1594.9 [M+Na]$^+$) (Scheme 13).

To generate an Cetuximab-VC-PAB-MMAG antibody-drug conjugate (Scheme 14), azide groups were introduced to N-glycans of cetuximab (Merck KGaA) as described in WO2014/177771: N-glycans were galactosylated and 9-azido-sialylated by sequential incubation with 1) β1,4-galactosyltransferase (Sigma-Aldrich) and UDP-galactose and 2) α2,6-sialyltransferase (Roche) and CMP-9-azido-NeuAc (WO2014/177771). The azidosialylated antibody thus obtained was incubated with 20× molar excess of DBCO-VC-PAB-MMAG in PBS, 2.5% DMSO. Reaction was allowed to proceed 16 h at room temperature, after which unconjugated DBCO-VC-PAB-MMAG was removed by repeated additions of PBS and centrifugations through Amicon Ultracel 30 k centrifugal filter. A sample was taken to Fc-analysis, which revealed the expected major signal at m/z 27444 corresponding to Fc heavy chain fragment carrying DBCO-VC-PAB-MMAG group.

Scheme 13. Structure of DBCO-VC-PAB-MMAG.

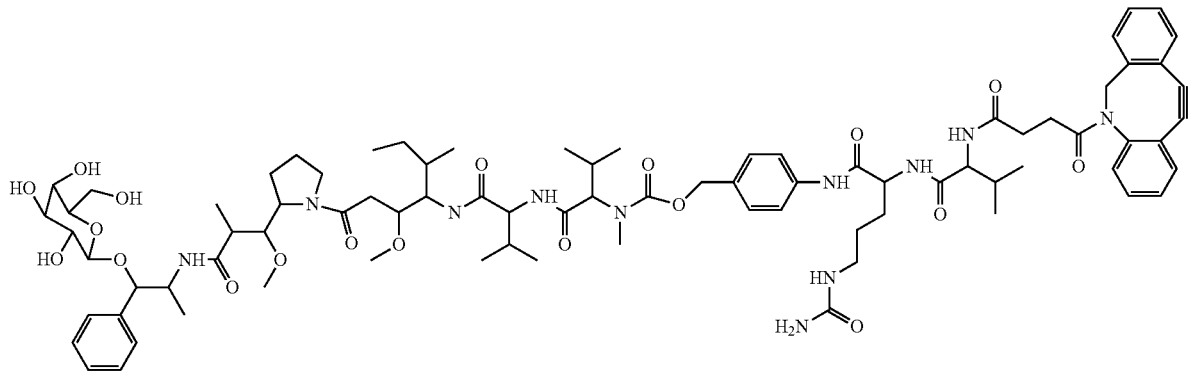

Scheme 14. Structure of Cetuximab-VC-PAB-MMAG antibody drug conjugate. For clarity, only sialic acid and galatose residues of the N-glycan are shown.

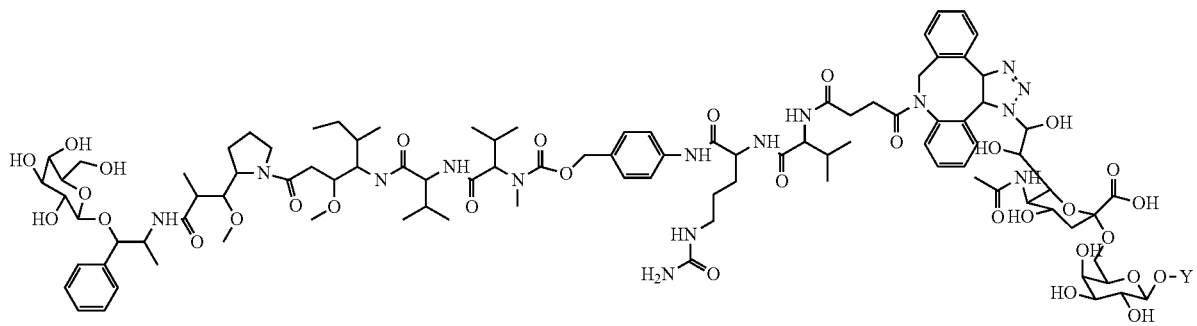

Example 14. Cytotoxicity of Glycoside-Drug and Antibody-Drug Conjugates

Cetuximab-VC-PAB-MMAG antibody-drug conjugate was prepared as described above but with drug-to-antibody ratio of 1:1. Its cytotoxicity against cancer cells was compared to cetuximab, MMAG and MMAE as free monomers. Human ovarian cancer cell line SKOV-3 (ATCC, Manassas, Va., USA) and head-and-neck squamous cell carcinoma cell line HSC-2 (Japanese Collection of Research Bioresources, Osaka, Japan) were grown according to the suppliers' recommendations. Log phase cultures were collected and cells were seeded onto 96-well plates and incubated for 24 h. Serial dilutions of test molecules were added to cells and cultures were incubated further for 96 h. Cell viability was evaluated using PrestoBlue cell viability reagent (Life Technologies, Carlsbad, Calif., USA) according to the manufacturer's instructions. Cells were incubated for 2 h, and dye reduction was measured by absorbance at 570 nm. The compounds were assayed 1-2 times in triplicate.

The results are expressed in Table 1 as IC50 values. MMAE was cytotoxic to the cells with an IC50 value of about 10 nM, whereas MMAG was not when applied to the culture medium in concentrations up to 100 nM. Also cetuximab as a naked antibody was not cytotoxic to the cells in these concentrations. However, the antibody-drug conjugate of MMAG (Cet-MMAG) showed increased cytotoxicity compared to MMAE. In conclusion, MMAG has high cytotoxicity as an antibody-drug conjugate against target cells, whereas it is relatively non-toxic to cells if not conjugated to antibody.

TABLE 1

Cytotoxicity to cancer cells of monomethylauristatin E (MMAE), O-β-D-galactopyranosylmonomethyl-auristatin E (MMAG), cetuximab (Cet) and cetuximab-VC-PAB-MMAG antibody-drug conjugate with drug-to-antibody ratio of 1:1 (Cet-MMAG).

| Compound | IC50 |
| --- | --- |
| MMAE | 10 nM |
| MMAG | n.d. (>100 nM) |
| Cet | n.d. (>100 nM) |
| Cet-MMAG | 1 nM |

IC50 values were determined as the concentration range wherein cancer cell viability falls to 50%.
n.d. indicates that IC50 was not reached in 100 nM concentration.

Example 15. Preparation of Duocarmycin Derivatives

Dimeric duocarmycin β-D-galactopyranoside (Scheme 15.A) is prepared for example as described in Tietze et al. (2010) Angew. Chem. Int. Ed. 49:7336-9. The dimeric β-D-galactopyranoside is then 9-azido-sialylated with *P. damsela* α2,6-sialyltransferase and about one equivalent of CMP-9-azido-NeuAc essentially as described above. After 16 h reaction, about ten equivalents of CMP-NeuAc is added and the reaction is allowed to proceed to completion for 16 h to obtain dimeric duocarmycin sialylgalactoside (Scheme 15.B). Antibody-drug conjugate of isolated dimeric duocarmycin sialylgalactoside and DBCO-modified antibody is prepared essentially as described above.

Duocarmycin A-ring β-D-galactopyranoside (Scheme 16.A) is prepared for example as described in Tietze et al. (2010) Angew. Chem. Int. Ed. 49:7336-9. B-ring is joined to the A-ring by amide bond formation and the duocarmycin β-D-galactopyranoside is then sialylated with *P. damsela* α2,6-sialyltransferase and CMP-NeuAc essentially as described above and isolated to obtain duocarmycin sialylgalactoside. Fmoc-Val-Cit-Gly N-terminally protected peptide is joined to the aromatic amine group by amide bond formation to obtain the Fmoc-Val-Cit-Gly-duocarmycin sialylgalactoside (Scheme 16.B) that is modified with azide or DBCO for antibody-drug conjugate generation essentially as described above.

Depending on the DBCO-to-antibody ratio, antibody-drug conjugates with drug-to-antibody ratio selected from values between 1:1 to about 10:1 or greater are achieved. Depending on the drug-to-antibody ratio, these antibody-drug conjugates have glycoside-to-antibody ratios between 2:1 to about 40:1 or greater.

Scheme 15. Structure of (A) dimeric duocarmycin β-D-galactopyranoside and (B) dimeric duocarmycin sialylgalactoside for antibody-drug conjugation

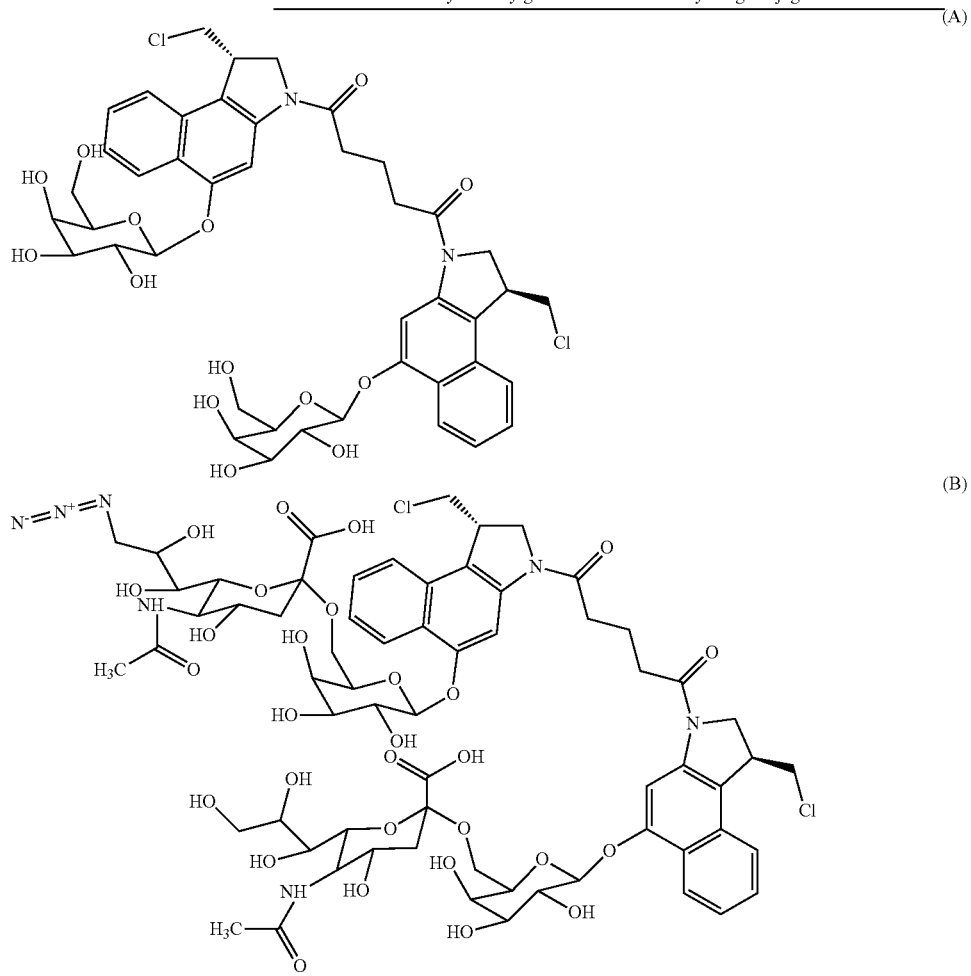

Scheme 16. Structure of (A) duocarmycin A-ring β-D-galactopyranoside and (B) Fmoc-Val-Cit-Gly-duocarmycin sialylgalactoside for antibody-drug conjugation

(B)

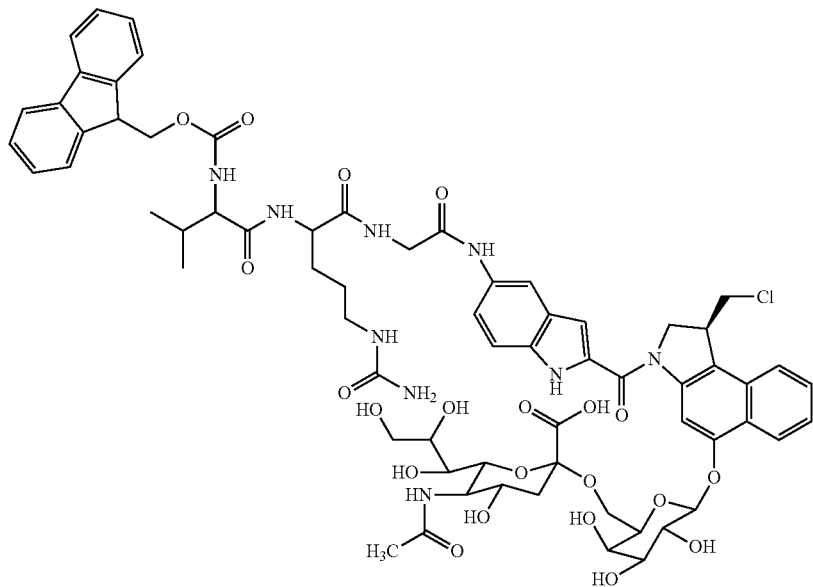

Example 16. Synthesis of Neu5Acα2,6Gal-Duocarmycin

The preparation of 2,3,4,6-tetra-O-Benzoyl-P-D-galactopyranosyl trichloroacetimidate (1) has been described previously in the literature (see for example: B. N. A. Mbadugha, F. M. Menger Org. Lett. 2003, 5, 4041) and synthetic routes similar to the ones utilized by Brimble et al. (M. A. Brimble, R. Kowalczyk, P. W. R. Harris, P. R. Dunbar, V. J. Muir Org. Biomol. Chem. 2008, 6, 112) were employed in the current synthesis. 5-Benzyloxy-3-(tert-butyloxycarbonyl)-1-(10-chloroethyl)-1,2-dihydro-3H-benz[e]indole (2) was purchased from Concortis Inc.

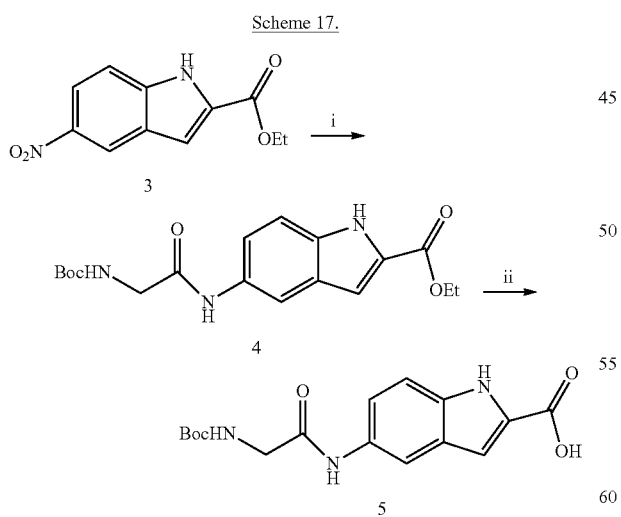

i) 1) Pd/C, H₂ (35 psi), EtoAc:MeOH; 2) Boc-Gly-OH, EDC, DMF;
ii) MeOH, NaOH.

Compound 4. 60 mg (0.27 mmol) Ethyl 5-nitroindole-2-carboxylate (3) was dissolved in 5 ml EtOAc:MeOH (5:1) and 15 mg Pd/C was added. The reaction vessel was placed inside a hydrogenation reactor and the hydrogen pressure was set to 35 psi. After 4 hours, the reaction mixture was diluted with EtoAc:MeOH (5:1), filtered through celite and concentrated. The crude product was utilized as such in the following step.

The crude product was dissolved in 6 ml DMF and 140 mg (3 equiv.) Boc-Gly-OH and 151 mg (3 equiv.) EDC were added. The resulting mixture was stirred o/n, diluted with EtOAc (20 ml) and washed with 15 ml NH₄Cl-solution and 15 ml brine. The organic phase was separated, dried with Na₂SO₄, filtered and concentrated to give the crude product. The crude product was purified by HPLC using Gemini 5 μm NX-AXIA-C18 reversed-phase column (21.2×250 mm (Phenomenex)) eluted with ACN gradient in aqueous ammonium acetate.

The crude product was utilized as such in the following step. HRMS: calcd. for $C_{18}H_{23}N_3O_5Na$ [M+Na]⁺384.153; found 384.342.

Compound 5. ~200 μmol (4) was dissolved in 1 ml MeOH and 1 ml 2 M NaOH is added. The resulting mixture was stirred 2×o/n and neutralized by 300 μl 6 M acetic acid. The crude product was purified by HPLC using Gemini 5 μm NX-AXIA-C18 reversed-phase column (21.2×250 mm (Phenomenex)) eluted with ACN gradient in aqueous ammonium acetate.

The crude product was utilized as such in the following step. HRMS: calcd. for $C_{16}H_{19}N_3O_5Na$ [M+Na]⁺356.122; found 356.177.

Scheme 18.

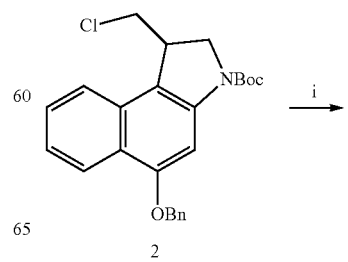

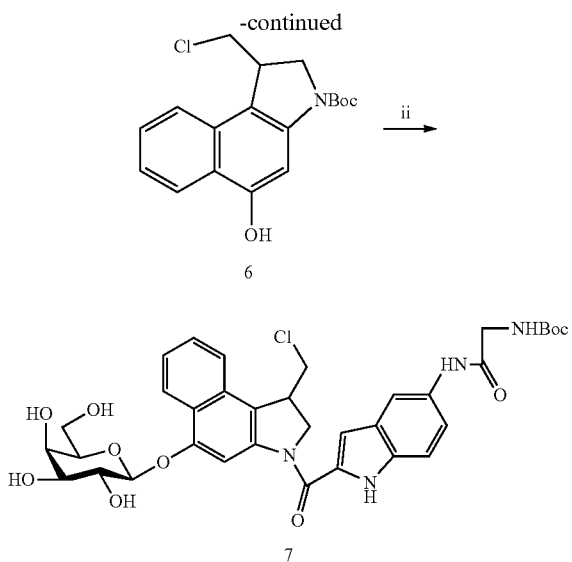

i) Pd/C, H$_2$ (35 psi), EtOAc: DCM: MeOH, 75%;
ii) 1) 1, BF$_3$•OEt$_2$, DCM, 0° C.; 2) BF$_3$•OEt$_2$, DCM; 3) 5, EDC, DMF;
4) NaOMe, MeOH (10% yield over 4 steps in one-pot).

concentrated and dried under vacuum. The crude product was dissolved in 4 ml dry DMF and 16 mg (0.8 equiv.) 5 and 20 mg (1.5 equiv.) EDC were added. The resulting mixture was stirred o/n at RT (in the dark). The reaction mixture was concentrated and the crude material dissolved in 5 ml MeOH. The pH was raised to 9 with NaOMe (5 M solution in MeOH) and the reaction mixture was stirred for 4 hours, neutralized with AcOH and concentrated to give the crude product. The crude product was purified by HPLC using Gemini 5 μm NX-AXIA-C18 reversed-phase column (21.2× 250 mm (Phenomenex)) eluted with ACN gradient in aqueous ammonium acetate.

HRMS: calcd. for C$_{35}$H$_{39}$ClN$_4$O$_{10}$Na [M+Na]$^+$ 733.225; found 733.424. α2,6-sialylation of compound 7 was carried out by incubating 320 nmol of compound 7 in a total volume of 80 μl 10% DMSO/0.1 M Tris-HCl, pH 7.5 containing 30 mM CMP-NeuAc and 92 mU *P. damsela* α2,6-sialyltransferase. The reaction mixture was incubated at +37 C for 64 h. MALDI-TOF mass spectrometric analysis of the reaction mixture revealed the presence of sialylated product (Neu5Acα2,6Gal-Duocarmycin; m/z 1024 [M+Na]$^+$, m/z 1046 [M-H+2Na]$^+$)(Scheme 19).

Scheme 19. Structure of Neu5Acα2, 6Gal-Duocarmycin

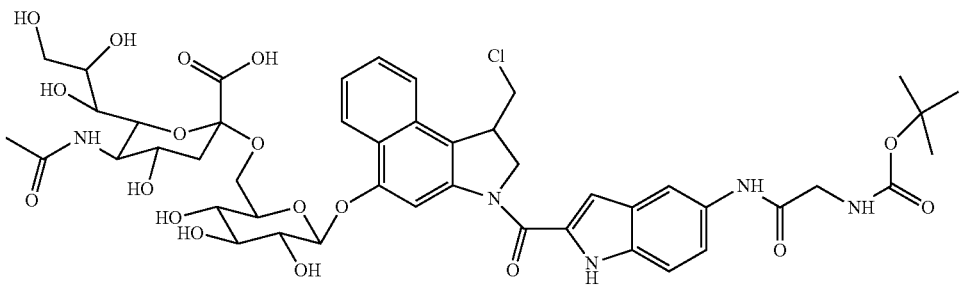

Compound 6. 32 mg (0.08 mmol) of 2 was dissolved in EtOAc and filtered through a pad of silica with Hexane: EtOAc 3:1 as eluent. The fractions containing product were collected and concentrated to give a white solid. The solid was dissolved in DCM:EtOAc:MeOH 4:2:1 and 13 mg Pd/C was added. The reaction vessel was placed inside a hydrogenation reactor and the pressure was set to 35 psi. The reaction mixture was stirred o/n, diluted with acetone, filtered through celite and concentrated. The crude product was purified by column chromatography to give 6 as a white solid (19 mg, 75%). HRMS: calcd. for C$_{18}$H$_{20}$ClNO$_3$ [M] 333.113; found 333.139. Selected NMR-data: $^1$H NMR (600 MHz, CDCl$_3$, 22° C.): δ 8.17 (d, 1H, J=8.3 Hz), 7.73 (br s, 1H), 7.64 (d, 1H, J=8.5 Hz), 7.50 (m, 1H), 7.34 (m, 1H), 4.30-3.30 (m, 5H), 1.60 (s, 9H) ppm.

Compound 7. 20 mg (0.06 mmol) of 6 was dissolved in 3.5 ml dry DCM (under argon) and the solution was added to a flask containing 65 mg (1.45 equiv.) of 1 (under argon). The resulting mixture was cooled on an ice bath and 4 μl (0.5 equiv.) BF$_3$.OEt$_2$ was added. The resulting mixture was stirred for 1.5 hours and 28 μl (3.5 equiv.) BF$_3$.OEt$_2$ was added. The reaction mixture was brought to RT and stirring was continued for 2.5 hours. The reaction mixture was Example 17. Synthesis of Gal-Duocarmycin-PAB-CV-DBCO Gal-Duocarmycin Boc was removed from Gal-Duocarmycin (300 nmol) by adding 300 μl 4 M HCl in dioxane. The reaction mixture was stirred at RT for 0.5 hours. MALDI-TOF mass analysis using 2,5-dihydroxybenzoic acid matrix showed the generation of expected deprotected product (m/z 633 [M+Na]$^+$). The crude product was dried in speedvac before the following step.

Gal-Duocarmycin-PAB-CV

~1 μmol Gal-Duocarmycin, 4.6 molar excess of Fmoc-Val-Cit-PAB-pnp, 0.4 μmol HOBt in DMF (4 μl), 2 μl DIPEA and 200 μl DMF were stirred at RT for 1.5 hours. The crude reaction mixture was analysed by MALDI-TOF mass spectra using 2,5-dihydroxybenzoic acid matrix, showing expected mass for Gal-Duocarmycin-PAB—VC-Fmoc (m/z 1260 [M+Na]$^+$).

Fmoc was removed by adding 100 μl of diethylamine and by stirring at room temperature for 1 hour. MALDI-TOF mass analysis using 2,5-dihydroxybenzoic acid matrix showed the generation of expected deprotected product (m/z 1038 [M+Na]).

Gal-Duocarmycin-PAB-CV-DBCO

~1 µmol Gal-Duocarmycin-PAB-CV, ~3 molar excess of DBCO-NHS ester in DMF (200 µl) and 6 µl DIPEA was stirred at RT o/n. The crude reaction mixture was analysed by MALDI-TOF mass spectra using 2,5-dihydroxybenzoic acid matrix, showing expected mass for Gal-Duocarmycin-PAB-CV-DBCO (m/z 1325 [M+Na]$^+$) (Scheme 20).

The crude product was purified by HPLC using Gemini 5 µm NX-AXIA-C18 reversed-phase column (21.2×250 mm (Phenomenex)) eluted with ACN gradient in aqueous ammonium bicarbonate.

Scheme 20. Structure of Gal-Duocarmycin-PAB-CV-DBCO

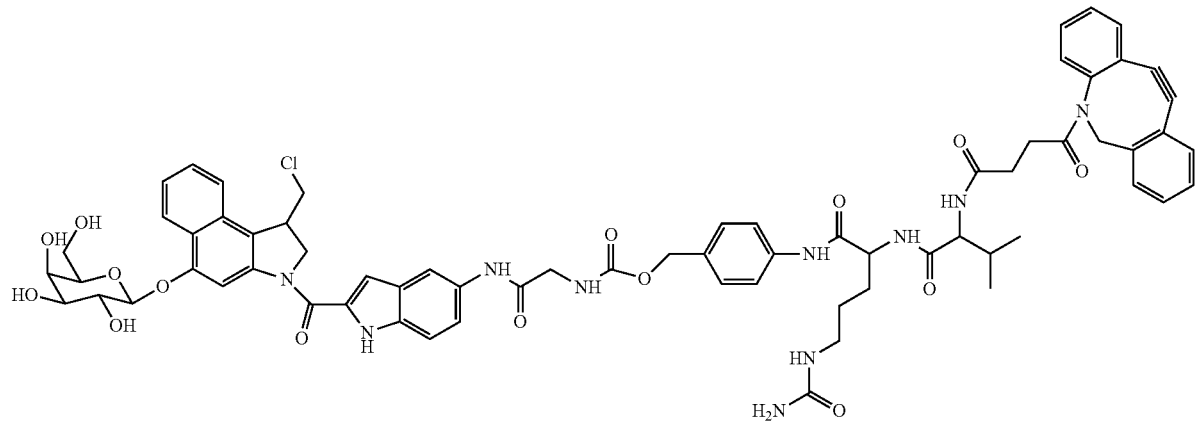

Example 18. Synthesis of Gal-Duocarmycin-PAB-CV-DBCO Antibody Drug Conjugate 200 µg azidosialylated antibody (an anti-EGFR or an anti-HER2), prepared as in WO 2014/17771 examples 21 and 45, was incubated with 19× molar excess of Gal-Duocarmycin-PAB-CV-DBCO in 5% mannitol, 0.1% Tween in PBS, 6.9% DMSO. Reaction was allowed to proceed 17 h at room temperature, after which unconjugated Gal-Duocarmycin-PAB-CV-DBCO was removed by repeated additions of 5% mannitol, 0.1% Tween in PBS and centrifugations through Amicon Ultracel 30 k centrifugal filter. 30 µg sample was taken to Fc-analysis. Fc-fragments were released by FabRICATOR enzyme (34 U) at 37° C. for 2 hours and purified with Poros R1 tips. Fc-fragments were eluted with 60% ACN, 0.1% TFA (5 µl). Fc-fragments were analysed by MALDI-TOF mass spectra using DHAP-matrix. The expected signal revealed at m/z 27176 (Anti-EGFR) and 27178 (Anti-HER) corresponding to Fc heavy chain fragment carrying Gal-Duocarmycin-PAB-CV-DBCO group. (FIG. 1)

Scheme 21. Structure of Gal-Duocarmycin-PAB-CV-DBCO antibody drug conjugate. For clarity, only sialic acid and galatose residues of the N-glycan are shown.

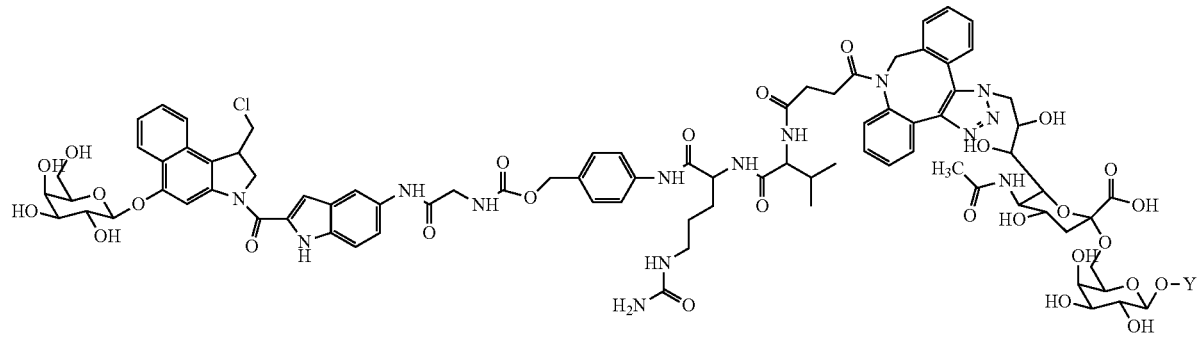

Example 19. Synthesis of Neu5Acα2,6MMAG

α2,6-sialylated MMAG prepared by incubating 8.7 mg of MMAG in a total volume 1500 µl of 5% DMSO/0.1 M Tris-HCl, pH 7.5 containing 30 mM CMP-NeuAc and 920 mU *P. damsela* α2,6-sialyltransferase. The reaction mixture was incubated at +37 C for 64 h. MALDI-TOF mass spectrometric analysis of the reaction mixture revealed the presence of sialylated product at m/z 1193.7, [M+Na]$^+$. The Neu5Acα2,6MMAG product (Scheme 22) was isolated by reversed-phase chromatography on HPLC using Gemini 5 µm NX-AXIA-C18 reversed-phase column (21.2×250 mm (Phenomenex)) eluted with ACN gradient in aqueous ammonium bicarbonate.

Scheme 22. Structure of Neu5Acα2, 6MMAG

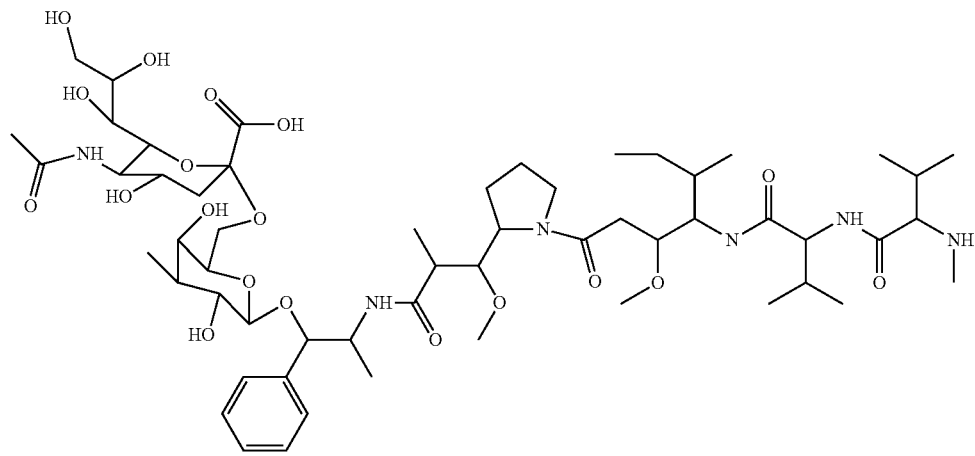

Example 20. Synthesis of Neu5Acα2,3MMAG

α2,3-sialylated MMAG was prepared as follows: MMAG was dissolved in 35 µl DMSO, and 14.3 mg of CMP-NeuAc was added in 300 µl 0.1 M Tris-HCl, pH 8.5. 50 µl of *P. multocida* α2,3-sialyltransferase suspension in 3.2 M ammonium sulphate (Prozomix) was exchanged to 0.1 M Tris-HCl, pH 8.5, by ultrafiltration on Amicon centrifugal filters (10K), and added to the reaction mixture. 0.1 M Tris-HCl, pH 8.5 was added to the reaction mixture to reach final volume of 750 µl. The reaction mixture was incubated at +37 C for 18 h. The Neu5Acα2,3MMAG product (Scheme 23) was isolated by reversed-phase chromatography on HPLC using Gemini 5 µm NX-AXIA-C18 reversed-phase column (21.2×250 mm (Phenomenex)) eluted with ACN gradient in aqueous ammonium bicarbonate. MALDI-TOF mass spectrometric analysis of the product fraction showed the expected mass (m/z 1193.6, [M+Na]+).

Scheme 23. Structure of Neu5Acα2, 3MMAG

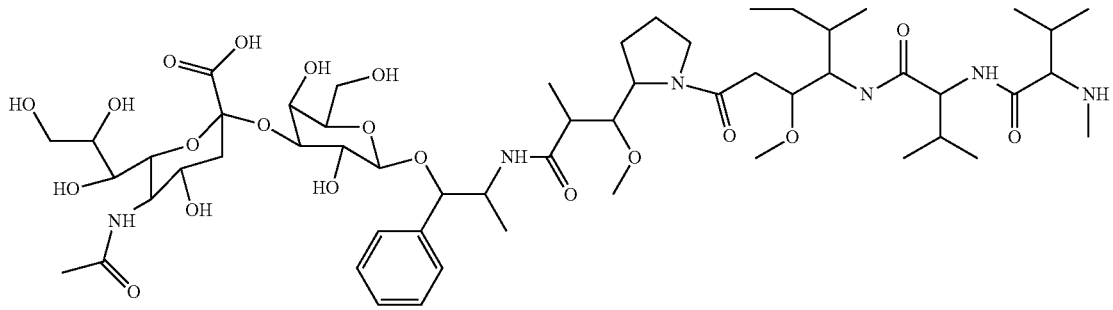

Example 21. Synthesis of maleimidocaproyl-VC-PAB-MMAG 4.1 mg (4.1 μmol) MMAG in DMF (40 μl), 2 molar excess of MC-Val-Cit-PAB-pnp (Concortis), 0.14 mg (1 μmol) HOBt in DMF (8 μl), 2 μl (11.4 μmol) diisopropylethylamine and 50 μl DMF were stirred o/n at room temperature. Maleimidocaproyl-Val-Cit-PAB-MMAG (Scheme 24) was purified by Äkta purifier (GE Healthcare) HPLC instrument with Gemini 5 μm NX-C18 reverse phase column (21.1×250 mm, 110 Å, AXIA (Phenomenex)) eluted with ACN gradient in aqueous ammonium acetate.

MALDI-TOF mass spectrometric analysis of the product fraction showed the expected mass (m/z 1501.2, [M+Na]$^+$).

Example 23. Synthesis of MMAE-PAB-CV-maleimidoyl- and MMAG-PAB-CV-maleimidoyl-Antibody Drug Conjugates Interchain disulphide bridges of trastuzumab (Herceptin®) were reduced with TCEP. 0.1 mM antibody was incubated with 1 mM TCEP and 1 mM DTPA in PBS for 1.5 h at +37° C. TCEP was removed by repeated additions of 1 mM DTPA, 5% mannitol, 0.1% Tween in PBS and centrifugations through Amicon Ultracel 30 K centrifugal filter.

Scheme 24. Structure of maleimidocaproyl-VC-PAB-MMAG

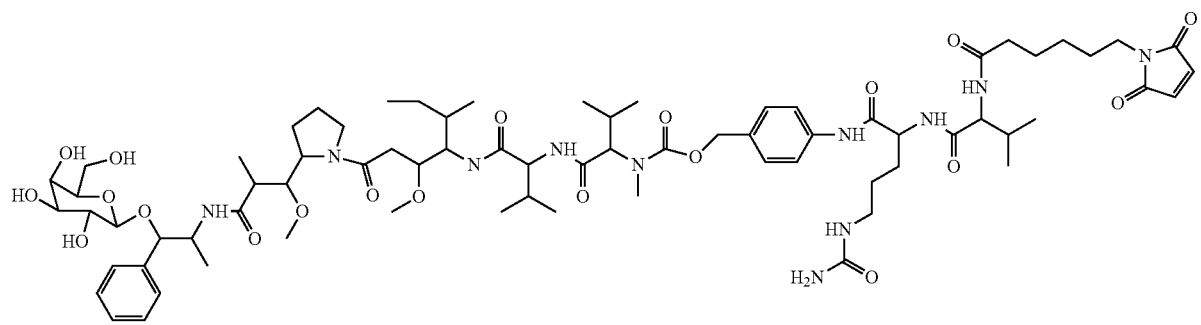

Example 22. Synthesis of maleimidocaproyl-VC-PAB-MMAE 3.3 mg (4 μmol) MMAE in DMF (40 μl), 2 molar excess of MC-Val-Cit-PAB-pnp, 0.14 mg (1 μmol) HOBt in DMF (8 μl), 2 μl (11.4 μmol) diisopropylethylamine and 50 μl DMF were stirred o/n at room temperature. Maleimidocaproyl Val-Cit-PAB-MMAE (Scheme 25) was purified by Äkta purifier (GE Healthcare) HPLC instrument with Gemini 5 μm NX-C18 reverse phase column (21.1×250 mm, 110 Å, AXIA (Phenomenex)) eluted with ACN gradient in aqueous ammonium acetate. MALDI-TOF mass spectrometric analysis of the product fraction showed the expected mass (m/z 1339.0, [M+Na]$^+$).

Antibody drug-conjugates (Scheme 26 and 27) were synthetized by incubating 0.1 mM antibody with 50× molar excess of MMAE-PAB-CV-maleimide or MMAG-PAB-CV-maleimide in the presence of 20% 1,2-propanediol, 0.8 mM DTPA, 4% mannitol, 0.08% Tween in PBS for 1 h at RT. Prior conjugation toxins were dissolved in DMSO to reach max 10% DMSO in final reaction vol. Extra toxin was removed by repeated additions of 5% mannitol, 0.1% Tween in PBS and centrifugations through Amicon Ultracel 30 K centrifugal filter. 30 μg sample was taken to Fc-analysis. Fc-fragments were released by FabRICATOR enzyme (34 U) at 37° C. for 2 hours and purified with Poros R1 tips. Fc-fragments were eluted with 60% ACN, 0.1% TFA (5 μl) and analysed with MALDI-TOF mass spectrometry.

Scheme 25. Structure of maleimidocaproyl-VC-PAB-MMAE.

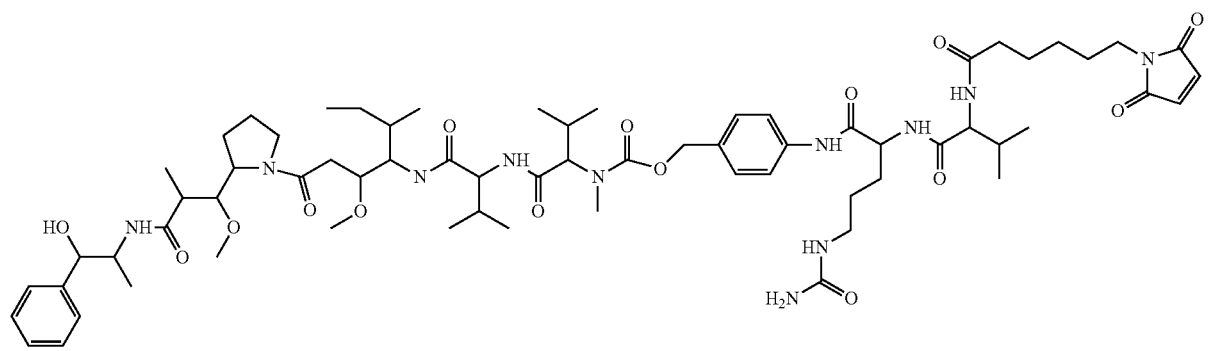

FIG. 2 shows the mass spectrum of MMAG-PAB-CV-maleimidoyl-antibody drug conjugate fragments. The light chains (LCs) were observed at m/z 24915 (LC+one MMAG) and m/z 26392

(LC+two MMAGs). Relative signal intensities of the two conjugates were 71% and 29%, respectively, and calculation of the weighed average yields an average of 1.29 MMAG for each LC. The heavy chain fragments (Fab-HCs) were observed at m/z 29809 (Fab-HC and three MMAGs), m/z 31282 (Fab-HC and four MMAGs), and m/z 32765 (Fab-HC and five MMAGs). Relative signal intensities of the three conjugates were 37%, 44% and 29%, respectively, and calculation of the weighed average yields an average of 4.32 MMAG for each Fab-HC. The heavy chain Fc fragments were observed at m/z 25229 and 25390 (GOF-Fc and G1F-Fc) and m/z 26708 and 26867 (GOF-Fc+one MMAG and G1F-Fc+one MMAG), and 76% of the Fc-HCs carried one MMAG. These masses corresponds to masses with clipped lysine. Thus the analysis demonstrated that all eight accessible cysteine residues had been reduced and modified (yielding an ADC with drug-to-antibody ratios up to 16, on average 12.7 and glycoside-to-antibody ratios up to 16, on average 12.7).

Thus, ADC molecules of MMAG-PAB-CV-maleimidoyl conjugated to trastuzumab having glycoside-to-antibody ratio of 8, 9, 10, 11, 12, 13, 14, 15 and 16 were formed.

Similarly, mass spectrometric analysis and calculation for the MMAE-PAB-CV-maleimidoyl-antibody drug conjugate fragments demonstrated that all eight accessible cysteine residues had been reduced and modified (yielding ADC with drug-to-antibody ratio up to 14, on average 9.6, but with glycoside-to-antibody ratio of 0).

Scheme 26. Structure of MMAG-PAB-CV-maleimidoyl-antibody drug conjugate.

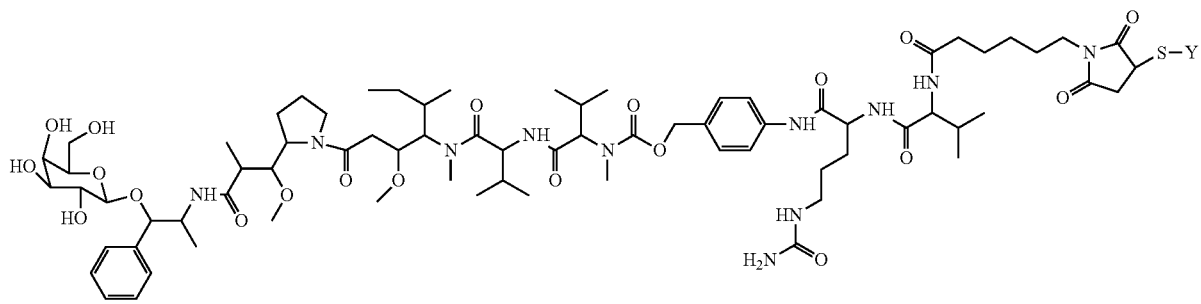

Scheme 27. Structure of MMAE-PAB-CV-maleimidoyl-antibody drug conjugate.

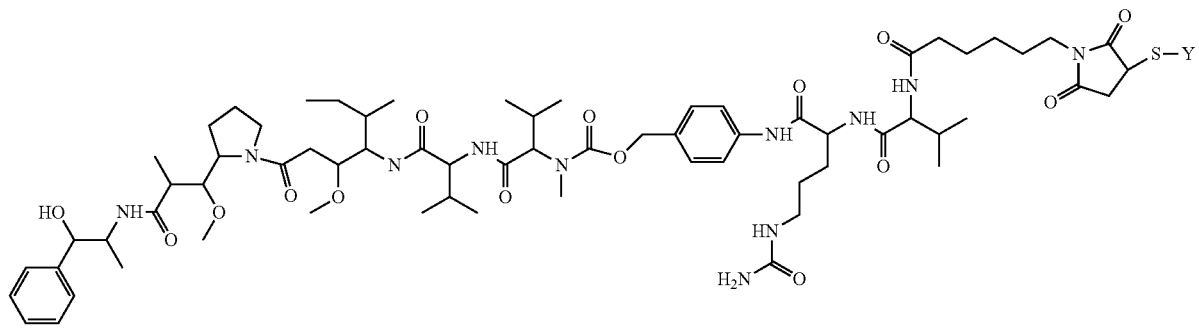

Example 25. In Vitro Assay with ADCs of Scheme 26 and Scheme 27

Cytotoxicity of antibody-drug conjugates was essentially performed as described in example 14 except culture of human ovarian cancer cell line SKOV-3 (ATCC, Manassas, Va., USA) was incubated with antibody-drug conjugates for 72 h. Table 2 shows the results.

TABLE 2

Viability of SKOV-3 ovarian cancer cells (ATCC) after treatment with Scheme 26 and Scheme 27 ADCs. Toxicologic profile of both Scheme 26 and Scheme 27 are identical. ADC 1 is MMAE-PAB-CV-maleimidoyl-Herceptin and ADC 2 is MMAG-PAB-CV-maleimidoyl-Herceptin.

|   | 3 pM | 10 pM | 30 pM | 100 pM | 300 pM | 1 nM | 3 nM | 10 nM | 30 nM | 100 nM |
|---|---|---|---|---|---|---|---|---|---|---|
| ADC 1 | 94.3 | 96.5 | 78.6 | 42.5 | 25.0 | 19.0 | 20.7 | 19.3 | 15.5 | 11.0 |
| ADC 2 | 101.0 | 92.7 | 70.1 | 32.4 | 20.4 | 20.7 | 20.4 | 18.6 | 14.9 | 8.5 |

Example 26. Synthesis of CBI-glycosyl-esters

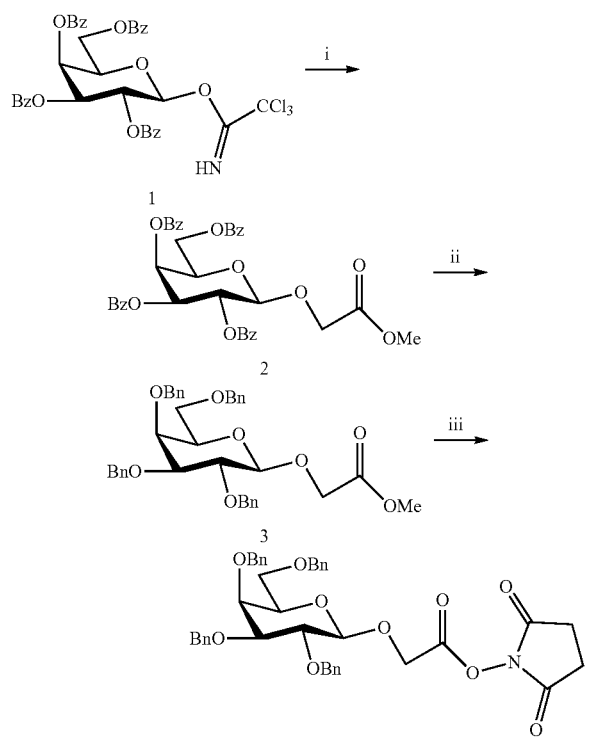

i) Methyl glycolate, TMSOTf, DCM;
ii) 1) NaOMe, MeOH; 2) NaH, BnBr, DMF;
iii) 1) NaOMe, MeOH:H$_2$O; 2) NHS, EDC, DMF.

Glycoside 2. Methyl glycolate is dissolved in dry DCM (under argon) and cooled to −20° C. 0.3 equiv. of TMSOTf is added and the resulting mixture is stirred for 10 min. 1.3 equiv. of 1 is dissolved in dry DCM and added dropwise to the reaction mixture. When the reaction is complete, as indicated by TLC, the reaction mixture is brought to RT, diluted with DCM and washed with satd. NaHCO$_3$-solution. The organic phase is separated, dried over Na$_2$SO$_4$, filtered and concentrated to give the crude product. The crude product is purified by column chromatography (for example, Hexane:EtOAc 5:1 as eluent) to give the target compound.

Glycoside 3. 2 is dissolved in MeOH and the pH is adjusted to 9/10 with NaOMe (5 M solution in MeOH). When the reaction is complete as determined by TLC, the reaction mixture is neutralized with DOWEX (H$^f$-form), filtered and concentrated. The crude product is purified by column chromatography (for example, DCM:MeOH 5:1) to give the intermediate product. This material is dissolved in dry DMF, cooled on an ice bath and 6 equiv. NaH is added. The resulting mixture is stirred for 15 minutes and 6 equiv. of BnBr is added. The reaction progress is monitored by TLC. Once the reaction is complete, the reaction is cooled on an ice bath and quenched with MeOH. The mixture is then diluted with EtOAc and washed with satd. NaHCO$_3$, H$_2$O and brine. The organic phase is separated, dried over Na$_2$SO$_4$, filtered and concentrated. The crude product is purified by column chromatography (for example, Hexane:EtOAc 6:1) to give 3.

Glycoside 4. 3 is dissolved in MeOH:H$_2$O and NaOMe is added. The reaction progress is monitored by TLC. Once the reaction is complete, the mixture is neutralized with DOWEX (H$^+$-form), filtered and concentrated. The product is purified by column chromatography. The intermediate product is dissolved in dry DMF and 1.5 equiv. of EDC and NHS is added. The resulting mixture is stirred o/n, diluted with EtOAc and washed with NH$_4$Cl and brine. The organic phase is separated, dried over Na$_2$SO$_4$, filtered and concentrated to give the crude product which is utilized as such in the following reaction sequence.

Scheme 29.

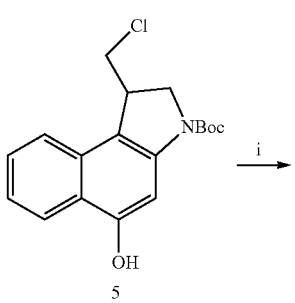

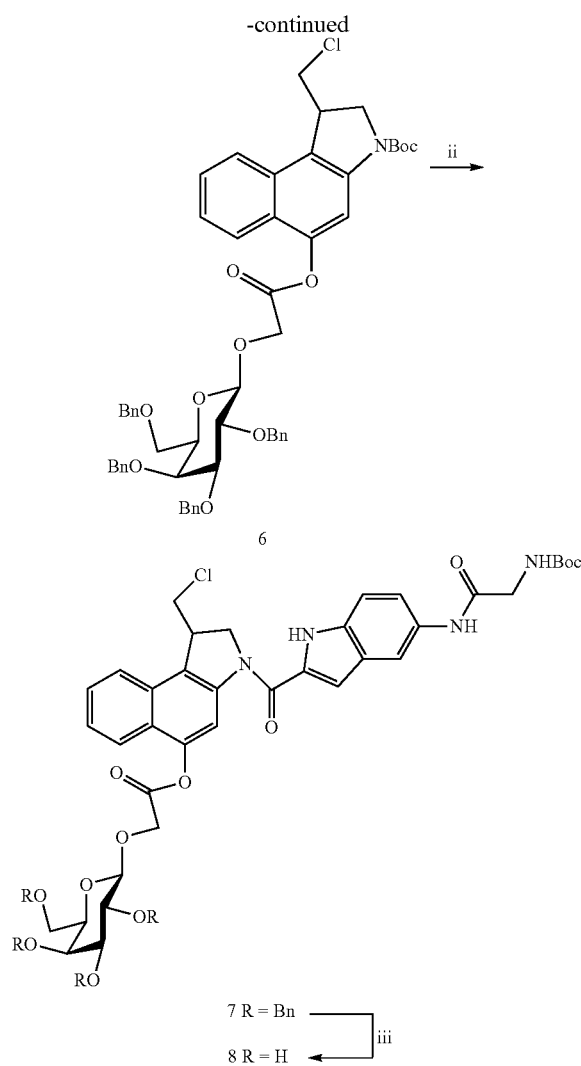

i) 4, pyridine (or Et₃N), DCM;
ii) 1) HCl (4M, in dioxane), DCM; 2) B-ring, EDC, DMF;
iii) Pd/C, H₂, EtOAc:MeOH.

CBI-glycoside 6. To a solution containing 4 (3 equiv.) and pyridine or Et$_3$N in dry DCM (at 0° C.) is added 5. The reaction progress is monitored by TLC. When the reaction is complete, the mixture is concentrated and purified by column chromatography or HPLC.

Duocarmycin-glycoside 7. 6 is dissolved and HCl (4 M in dioxane) is added to the solution. The reaction progress is monitored by TLC. Once the Boc-group is removed, the reaction mixture is concentrated and dried to give the intermediate product which is used as such in the following step.

The intermediate product is dissolved in dry DMF and 1.5 equiv. of the B-ring, and 1.5 equiv. of EDC is added. The resulting mixture is stirred o/n at RT, diluted with EtOAc and washed with H$_2$O and brine. The organic phase is dried over Na$_2$SO$_4$, filtered and concentrated. The crude product is purified by column chromatography or HPLC.

Duocarmycin-glycoside 8. Compound 7 is dissolved in EtOAc:MeOH 4:1 and Pd/C is added. The reaction vessel is placed inside a hydrogenation reactor and the hydrogen pressure is set to 35 psi. The reaction mixture is stirred o/n, diluted with EtOAc:MeOH (for example, 4:1), filtered through celite and concentrated. The crude product is purified by column chromatography or HPLC.

In similar fashion, other hydroxycarboxylic acids may be used to prepare analogs of glycoside 4 described above. These include e.g. 3-hydroxypropanoic acid, 4-hydroxybutanoic acid, 5-hydroxypentanoic acid, N-acetylserine, 2-hydroxybutanoic acid, N-acetylthreonine, lactic acid, malic acid, tartaric acid, and 3-hydroxyglutaric acid. The hydroxycarboxylic acid glycosides thus obtained may be esterified with compound 5 to obtain the corresponding CBI-glycoside esters.

Example 27. Stability Assays of Saccharide Conjugates

Stability of saccharide conjugate is evaluated by incubation at +37° C. for varying periods of time from about 1 hour to about 1 week in human or animal serum prepared by incubating blood in room temperature and centrifugation to remove the clot, or similarly incubating in human or animal plasma prepared by collection of fresh blood in heparinized tubes. The conjugate is isolated and analysed as described above to detect proportion of intact conjugate.

Example 28. Hydrolysis Assays of Saccharide Conjugates

Hydrolysis rate of saccharide conjugate is evaluated by incubation at +37° C. for varying periods of time from about 1 minute to about 1 day in presence of enzyme source at acidic pH, preferably at pH 4.5. The enzyme source is e.g. recombinant peptidase or glycohydrolase enzyme such as human lysosomal β-galactosidase or β-hexosaminidase available from R&D Systems, or a human or animal cell lysate as a source of all lysosomal enzymes, or human red blood cell membrane preparate as a source of lysosomal sialidase. The conjugate is isolated and analysed as described above to detect proportion of intact conjugate.

Example 29. Aggregation Assay of ADC

MMAE-PAB-CV-maleimidoyl-antibody drug conjugate (MMAE ADC) and MMAG-PAB-CV-maleimidoyl-antibody drug conjugate (MMAG ADC) were synthesized from trastuzumab (Herceptin®, Roche) as described in Example 23. The ADCs were shown to have high drug-to-antibody ratios (DAR8) by mass spectrometric analysis of liberated antibody fragments as described in Example 23: MMAE ADC had DAR=9.6, and MMAG ADC had DAR=12.7 and glycoside-to-antibody ratio of 12.7. The ADCs were formulated in 5% mannitol, 0.1% Tween in PBS (pH 7.4) and kept at +4° C.

Aggregation of the ADCs was induced with heat stress, wherein the ADCs and control antibody (Herceptin) were incubated at +40° C. for two days. After incubation, they were analyzed by size-exclusion HPLC on Superdex 200 10/300 column (GE Healthcare) in 200 mM potassium phosphate buffer, 250 mM potassium chloride. The eluate was followed by absorbance detection at 214 nm and 280 nm. Chromatograms in FIG. 3 show absorbance at 214 nm. As shown in the Figure, control antibody did not show any aggregation. The MMAE ADC was fully aggregated into high-molecular weight components whereas only 5% of the MMAG ADC (5.4% according to A214 nm detection) was aggregated, showing that the hydrophilic glycoside present in MMAG but not in MMAE was beneficial for aggregation resistance of the high-DAR ADC under heat stress.

Example 30. Synthesis of Gal-ester-Duocarmycin-PAB-CV-maleimidoyl-Antibody Drug Conjugates and sialylated NeuAc-Gal-Duocarmycin-PAB-CV-maleimidoyl-Antibody Drug Conjugates Gal-ester-Duocarmycin-PAB-CV-maleimide is prepared starting from duocarmycin-glycoside 8 of Scheme 29 (Boc-protected Gal-ester-Duocarmycin-$NH_2$) that is prepared as in Example 26. The Boc protecting group is removed and the maleimide conjugate is then prepared as described in Example 21, by reacting the Gal-ester-Duocarmycin-$NH_2$ with MC-Val-Cit-PAB-pNP. The Gal-ester-Duocarmycin-PAB-CV-maleimide thus obtained is purified by reversed-phase chromatography using Gemini 5 μm NX-C18 reversed-phase column (21.1×250 mm, 110 Å, AXIA (Phenomenex)) eluted with ACN gradient in aqueous ammonium acetate. Gal-ester-Duocarmycin-PAB-CV-maleimidoyl-ADC (Scheme 30) is prepared as described in Example 23: Interchain disulphide bridges of trastuzumab (Herceptin) are reduced with TCEP, and the free thiol antibody is purified by Amicon Ultracel K centrifugal filter. Antibody drug-conjugates are synthetized by incubating 0.1 mM antibody with 20-50× molar excess of Gal-ester-Duocarmycin-PAB-CV-maleimide in the presence of 20% 1,2-propanediol, 0.8 mM DTPA, 4% mannitol, 0.08% Tween in PBS for 1 h at RT. Prior conjugation toxins are dissolved in DMSO to reach max 10% DMSO in final reaction vol. Unconjugated toxin is removed by repeated additions of 5% mannitol, 0.1% Tween in PBS and centrifugations through Amicon Ultracel 30 K centrifugal filter. The drug-to-antibody ratio is measured by MALDI-TOF MS analysis as described in Example 23.

Neu5Acα2,6Gal-Duocarmycin is prepared as shown in Example 16. Boc is removed by incubating the compound in 4 M HCl in 1,4-dioxane, and the free amine compound NeuAc-Gal-Duocarmycin-$NH_2$ thus obtained in dried under reduced pressure. NeuAc-Gal-Duocarmycin-PAB-CV-maleimide is prepared as described in Example 21, by reacting NeuAc-Gal-Duocarmycin-$NH_2$ with MC-Val-Cit-PAB-pNP. The NeuAc-Gal-Duocarmycin-PAB-CV-maleimide thus obtained is purified by reversed-phase chromatography using Gemini 5 μm NX-C18 reversed-phase column (21.1×250 mm, 110 Å, AXIA (Phenomenex)) eluted with ACN gradient in aqueous ammonium acetate.

Alternatively, NeuAc-Gal-Duocarmycin-PAB-CV-maleimide may be produced by 2,6-sialylation of the Gal-Duocarmycin-PAB-CV-maleimide as follows: Gal-Duocarmycin (Example 16) is reacted with MC-Val-Cit-PAB-pNP as described in Example 21. The Gal-Duocarmycin-PAB-CV-maleimide thus obtained is purified by reversed-phase chromatography using Gemini 5 μm NX-C18 reversed-phase column (21.1×250 mm, 110 Å, AXIA (Phenomenex)) eluted with ACN gradient in aqueous ammonium acetate. The purified Gal-Duocarmycin-PAB-CV-maleimide is dissolved in DMSO and α2,6-sialylation is carried out by mixing the Gal-Duocarmycin-PAB-CV-maleimide solution with *P. damsela* α2,6-sialyltransferase and CMP-NeuAc in 0.1 M Tris-HCl, pH 7.5 as described in Example 16. The final concentration of DMSO in the sialylation reaction may vary between 5-50%, depending of the concentration and solubility of the duocarmycin acceptor compound in the reaction. The NeuAc-Gal-Duocarmycin-PAB-CV-maleimide thus obtained is purified by reversed-phase chromatography using Gemini 5 μm NX-C18 reversed-phase column (21.1×250 mm, 110 Å, AXIA (Phenomenex)) eluted with ACN gradient in aqueous ammonium acetate.

The NeuAc-Gal-Duocarmycin-PAB-CV-maleimidoyl-ADC is prepared as described in Example 23: Interchain disulphide bridges of trastuzumab (Herceptin) are reduced with TCEP, and the free thiol antibody is purified by Amicon Ultracel 30 K centrifugal filter. Antibody drug-conjugates are synthetized by incubating 0.1 mM antibody with 20-50× molar excess of NeuAc-Gal-Duocarmycin-PAB-CV-maleimide in the presence of 20% 1,2-propanediol, 0.8 mM DTPA, 4% mannitol, 0.08% Tween in PBS for h at RT. Prior conjugation toxins are dissolved in DMSO to reach max 10% DMSO in final reaction vol. Unconjugated toxin is removed by repeated additions of 5% mannitol, 0.1% Tween in PBS and centrifugations through Amicon Ultracel 30 K centrifugal filter. The drug-to-antibody ratio is measured by MALDI-TOF MS analysis as described in Example 23.

Alternatively, the NeuAc-Gal-Duocarmycin-PAB-CV-maleimidoyl-ADC may be produced by sialylation of Gal-Duocarmycin-PAB-CV-maleimidoyl-ADC: The Gal-Duocarmycin-PAB-CV-maleimide is prepared as described above, and the drug-maleimide is conjugates to the interchain disulphide bridges of trastuzumab (Herceptin) as described above. Unconjugated toxin is removed by Amicon Ultracel 30 K centrifugal filter as above. The drug-to-antibody ratio is measured by MALDI-TOF MS analysis as described in Example 23. The Gal-Duocarmycin-PAB-CV-maleimidoyl-ADC thus obtained is sialylated by incubating with *P. damsela* α2,6-sialyltransferase and CMP-NeuAc in 0.1 M Tris-HCl, pH 7.5 as described in Example 16. The NeuAc-Gal-Duocarmycin-PAB-CV-maleimidoyl-ADC is purified by affinity chromatography on Protein A or Protein G column according to manufacturer's instructions.

NeuAc-Gal-ester-Duocarmycin, NeuAc-Gal-ester-Duocarmycin-PAB-CV-maleimide and NeuAc-Gal-ester-Duocarmycin-PAB-CV-maleimidoyl-ADC are prepared similarly as above for NeuAc-Gal-Duocarmycin, NeuAc-Gal-ester-Duocarmycin-PAB-CV-maleimide and NeuAc-Gal-ester-Duocarmycin-PAB-CV-maleimidoyl-ADC, respectively, by substituting the molecule with corresponding molecule containing the ester linker.

Scheme 30. Structure of Gal-ester-Duocarmycin-PAB-CV-maleimide ADC.

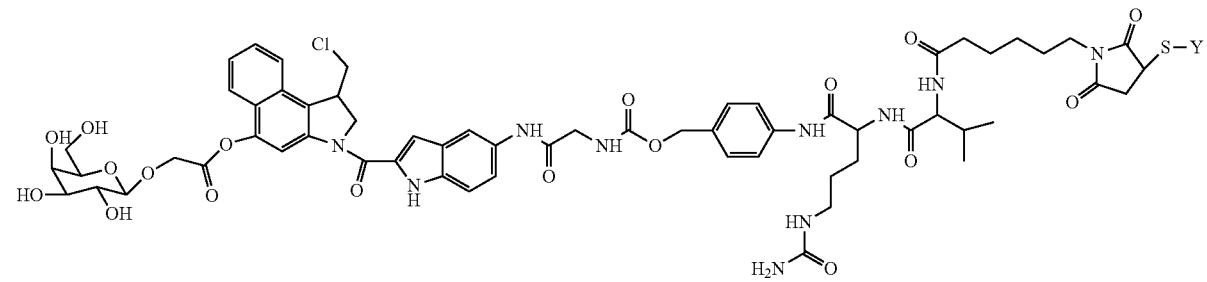

Example 31. Synthesis of Gal-Duocarmycin-PAB-CV-maleimide

Gal-Duocarmycin (Example 16) was reacted with MC-Val-Cit-PAB-pNP as described in Example 21. The Gal-Duocarmycin-PAB-CV-maleimide thus obtained (Scheme 31) was purified by reversed-phase chromatography using Gemini 5 µm NX-C18 reversed-phase column (21.1×250 mm, 110 Å, AXIA (Phenomenex)) eluted with ACN gradient in aqueous ammonium acetate.

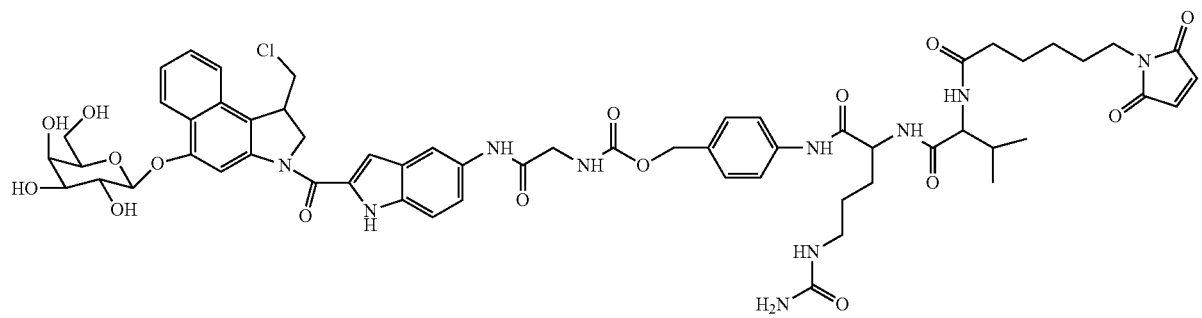

Scheme 31. Structure of Gal-Duocarmycin-PAB-CV-maleimide.

Example 32. Synthesis of Gal-Duocarmycin-PAB-CV-maleimidoyl-ADC

The Gal-Duocarmycin-PAB-CV-maleimidoyl-ADC (Scheme 32) was prepared as follows: Interchain disulphide bridges of trastuzumab (Herceptin) were reduced with TCEP, and the free thiol antibody was purified by Amicon Ultracel 30 K centrifugal filter. Antibody drug-conjugates were synthetized by incubating 0.1 mM antibody with 10× molar excess of Gal-Duocarmycin-PAB-CV-maleimide in the presence of 20% 1,2-propanediol, 0.8 mM DTPA, % mannitol, 0.08% Tween in PBS for 1 h at RT. Prior conjugation toxins were dissolved in DMSO to reach max 10% DMSO in final reaction vol. Unconjugated toxin was removed by repeated additions of 5% mannitol, 0.1% Tween in PBS and centrifugations through Amicon Ultracel 30 K centrifugal filter. The drug-to-antibody ratio was measured by MALDI-TOF MS analysis as described in Example 23, and the average DAR was found to be 6.

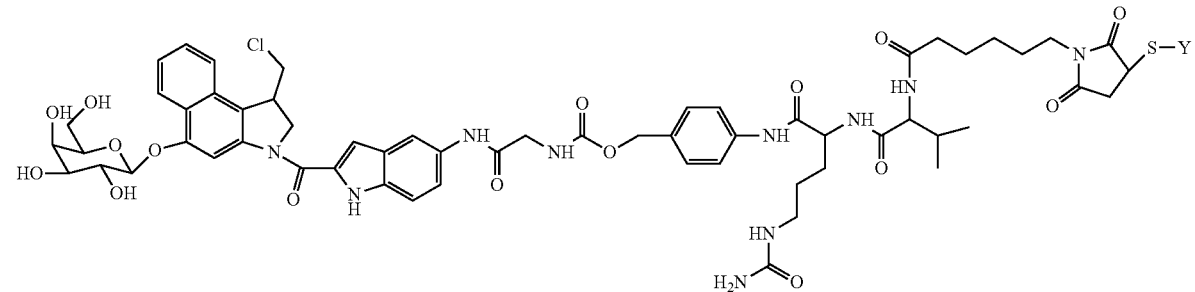

Scheme 32. Gal-Duocarmycin-PAB-CV-maleimide ADC

Example 33. Synthesis of Duocarmycin Glucuronide 2.9 mg (5.9 µmol) Duocarmycin MB (Concortis), 2.9 molar excess of 2,3,4-Tri-O-acetyl-a-D-glucuronide methyl ester trichloro-acetimidate and 700 µl dry CH$_2$Cl$_2$ were cooled on an ice bath. 2.5 µl (3.2 equiv.) BF$_3$.0Et$_2$ was added and the reaction mixture was stirred at RT for 0.5 hour. The reaction mixture was brought to RT and stirring was continued o/n. The resulting mixture was washed with 50% sat. NaHCO$_3$-solution and 50% sat. NaCl solution. The organic phase was dried with Na$_2$SO$_4$, filtered and concentrated. The 2,3,4-Tri-O-acetyl-beta-D-glucuronide methyl ester Duocarmycin was purified by HPLC with Gemini 5 µm NX-C18 reversed phase column (21.1×250 mm, 110 Å, AXIA (Phenomenex)) eluted with ACN gradient in aqueous ammonium acetate. MALDI-TOF mass spectrometric analysis of the product fraction showed the expected mass (m/z 730.3, [M+Na]$^+$). The product is subjected to alkaline hydrolysis as described in Example 16 to obtain the glucuronyl duocarmycin (Scheme 33)

Scheme 33. Structure of glucuronyl duocarmycin.

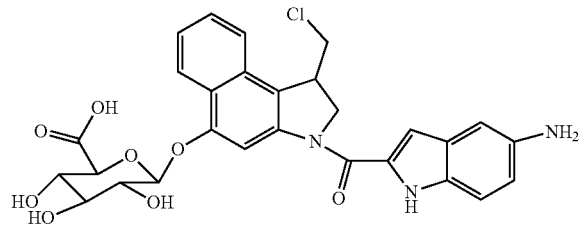

Example 34. Synthesis of 2-amino-2-deoxy-β-D-glucopyranosyl duocarmycin

Synthesis of 1-Hydroxy-3,4,6-Tri-O-acetyl-2-deoxy-2-phthalimido-b-D-glucopyranoside 0.85 ml ethylene diamine and 0.85 ml acetic acid were added to 80 ml tetrahydrofuran and the resulting mixture was stirred for 15 minutes. 4.94 g 1,3,4,6-Tetra-O-acetyl-2-deoxy-2-phthalimido-b-D-gluco-pyranoside was added and the suspension was stirred for 16 hours at RT. The reaction mixture was diluted with 100 ml dichloromethane and washed with 80 ml water, 80 ml 1 M HCl, 80 ml sat. NaHCO$_3$-solution and 80 ml brine. The organic phase was dried with Na$_2$SO$_4$, filtered and concentrated. MALDI-TOF mass analysis using 2,5-dihydroxybenzoic acid matrix showed the generation of expected deprotected product (m/z 458.3 [M+Na]$^+$). The product was dissolved in 20 ml dichloromethane and 40 ml EtOAc:hexane 1:5 was added. After 1.5 hours the precipitate was filtered off to be used in the following step.

Synthesis of 3,4,6-Tri-O-acetyl-2-deoxy-2-phthalimido-β-D-glucopyranosyl trichloroacetimidate 0.49 g 1-Hydroxy-3,4,6-Tri-O-acetyl-2-deoxy-2-phthalimido-b-D-glucopyranoside was dissolved in 5 ml dry dichloromethane and cooled on ice bath. 10 µl 1,8-Diazabicyclo[5,4,0]undec-7-ene and 1.35 ml trichloroacetonitrile was added and the resulting mixture was stirred at 0° C. for 1.5 hours. The reaction mixture was brought to RT, diluted with 20 ml dichloromethane and washed with 15 ml brine. The organic phase was dried with Na$_2$SO$_4$, filtered and concentrated. The crude product was purified by column chromatography (hexane:EtOAc 2:3+0.1% triethylamine) to give a colorless oil.

Synthesis of 3,4,6-Tri-O-acetyl-2-deoxy-2-phthalimido-β-D-glucopyranosyl duocarmycin 1.8 mg (3.7 µmol) Duocarmycin MB, 1.4 molar excess of 3,4,6-Tri-O-acetyl-2-deoxy-2-phthalimido-β-D-glucopyranosyl trichloroacetimidate donor and 500 µl dry CH$_2$Cl$_2$ were cooled on an ice bath. 1.0 µl (2.1 equiv.) BF$_3$.0Et$_2$ was added and the reaction mixture was stirred at RT for 0.5 hour. The reaction mixture was brought to RT and stirring was continued o/n.

The resulting mixture was washed with 50% sat. NaHCO$_3$-solution and 50% sat. NaCl solution. The organic phase was dried over Na$_2$SO$_4$, filtered and concentrated. TCA duocarmycin was purified by Äkta purifier (GE Healthcare) HPLC instrument with Gemini 5 µm NX-C18 reverse phase column (21.1×250 mm, 110 Å, AXIA (Phenomenex)) eluted with ACN gradient in aqueous ammonium acetate. MALDI-TOF mass spectrometric analysis of the product 3,4,6-Tri-O-acetyl-2-deoxy-2-phthalimido-β-D-glucopyranosyl duocarmycin showed the expected mass (m/z 831.4, [M+Na]$^+$). This product is subjected to reaction with di-tert-butyl-dicarbonate to obtain a N-Boc derivative, followed by treatment with ethylene diamine in n-butyl alcohol and ester hydrolysis as described in Example 16. These reactions yield the 2-amino-2-deoxy-β-D-glucopyranosyl duocarmycin shown in Scheme 34, which can be acylated by e.g. acetic anhydride to obtain 2-acetamido-2-deoxy-β-D-glucopyranosyl duocarmycin. Other carboxylic acid anhydrides or acyl halides may be used to obtain 2-acyl derivatives of glucosamine in analogous fashion.

Scheme 34. Structure of 2-amino-2-deoxy-B-D-glucopyranosyl duocarmycin.

Example 35. Synthesis of glucuronyl duocarmycin 4-(Boc-amino)benzoic acid amide 1.1 mg (1.5 µmol) Glucuronyl duocarmycin (Example 33) in DMF (84 µl), 3.3 molar excess of Boc-4-Abz-OH, 6.4 mg (33 µmol) EDAC in DMF (50 µl) and 3 µl (17 µmol) diisopropylethylamine were stirred for 3 hours, at room temperature. MALDI-TOF mass analysis using 2,5-dihydroxybenzoic acid matrix showed the generation of expected product (m/z 949.3 [M+Na]$^+$) (Scheme 35).

Lower DAR ADC is obtained by reducing trastuzumab with TCEP as in Example 23, followed by adding 10×molar excess of glucuronyl duocarmycin-PAB-CV-maleimide as in Scheme 35. Structure of glucuronyl duocarmycin 4-(Boc-amino)benzoic acid amide.

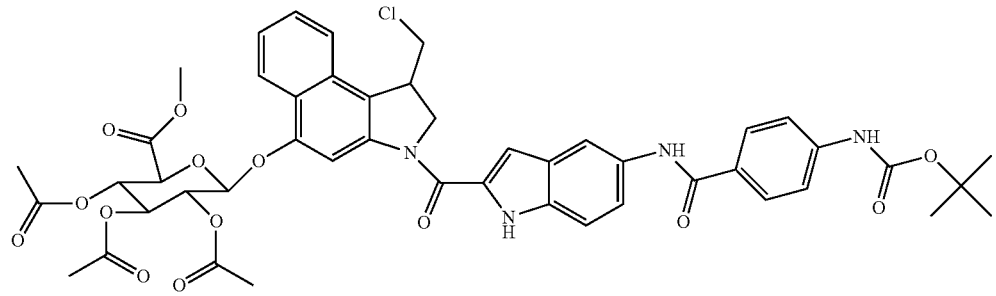

The glucuronyl duocarmycin 4-(Boc-amino)benzoic acid amide is deprotected by removing Boc and glucuronyl unit esters as described in Examples 16 and 17. The product is reacted with MC-Val-Cit-PAB-pNP as described in Example 21 and glucuronyl Duocarmycin-PAB-CV-maleimide thus obtained is purified by reversed-phase chromatography with ACN gradient in aqueous ammonium acetate.

The disulphide bridges of trastuzumab are reduced with TCEP as described in Example 23, and antibody drug-conjugates are synthetized by incubating 0.1 mM antibody with 50× molar excess of glucuronyl Duocarmycin-PAB-CV-maleimide in the presence of 20% 1,2-propanediol, 0.8 mM DTPA, 4% mannitol, 0.08% Tween in PBS for 1 h at RT. The glycoside-to-antibody ratio is analyzed by Fabricator cleavage and MALDI-TOF MS analysis as described in Example 18. The analysis shows that ADC molecules of glucuronyl duocarmycin-PAB-CV-maleimide conjugated to trastuzumab (Scheme 36) having glycoside-to-antibody ratio of 8, 9, 10, 11, 12, 13, 14, 15 and 16 are formed.

Example 39. The DAR is analyzed by Fabricator cleavage and MALDI-TOF MS analysis, and shows that ADC with drug-to-antibody ratios up to 8, or ADC molecules of glucuronyl duocarmycin-PAB-CV-maleimide conjugated to trastuzumab having glycoside-to-antibody ratio of 4, 5, 6, 7 or 8, are formed.

Example 36. Synthesis of maleimidocaproyl-VC-PAB-(beta-glucuronyl)-monomethylauristatin E 1.9 mg (2.2 µmol) beta-glucuronyl-monomethylauristatin E (MMAU) (Concortis) in DMF (200 µl), 1.9 molar excess of MC-Val-Cit-PAB-pnp, 2 µl 0.5 M (1 µmol) HOBt and 3 µl (17 µmol) diisopropylethylamine were stirred o/n at room temperature. Maleimidocaproyl Val-Cit-PAB-MMAU (Scheme 36) was purified by HPLC with Gemini 5 µm NX-C18 reverse phase column (21.1×250 mm, 110 Å, AXIA (Phenomenex)) eluted with ACN gradient in aqueous Scheme 36. Structure of glucuronyl Duocarmycin-PAB-CV-maleimide ADC

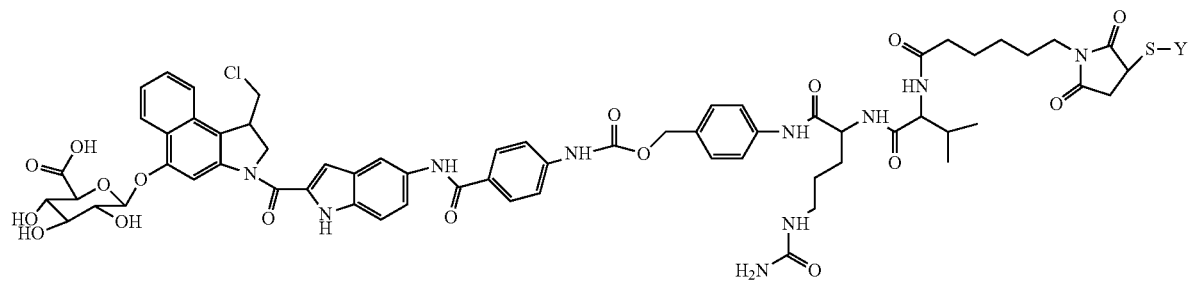

ammonium acetate. MALDI-TOF mass spectrometric analysis of the product fraction showed the expected mass (m/z 1514.0, [M+Na]⁺).

observed at m/z 30418 (Fab-HC+three MMAG). The heavy chain Fc fragments were observed at m/z 25227, 25393, 25555, 25716 and 25875 (GOF-Fc, G1F-Fc, G2F-Fc and Scheme 36. Structure of maleimidocaproyl-VC-PAB-MMAU.

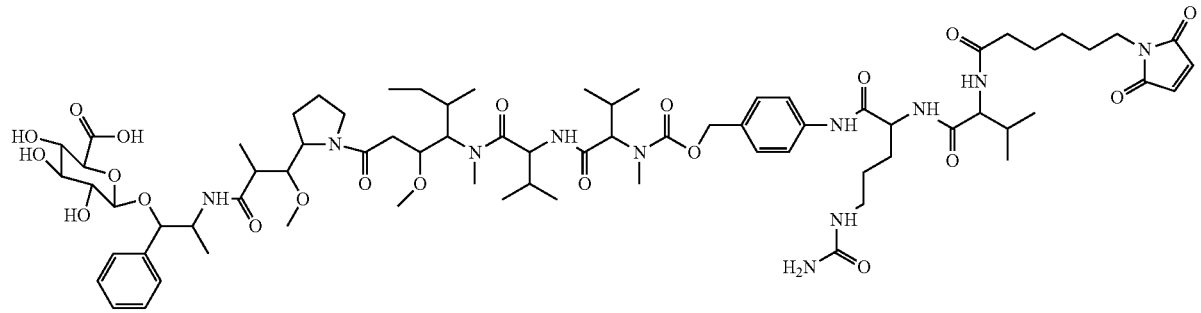

Example 37. Synthesis of maleimidocaproyl-VC-PAB-(beta-glucosyl)-monomethylauristatin E 2.0 mg (2.0 µmol) beta-glucosyl-monomethylauristatin E (Concortis) in DMF (200 µl), 2.2 molar excess of MC-Val-Cit-PAB-pnp, 2 µl 0.5 M (1 µmol) HOBt and 3 µl (17 µmol) diisopropylethylamine were stirred o/n at room temperature. Maleimidocaproyl-Val-Cit-PAB-(beta-glucosyl)-monomethylauristatin E (MMAX; Scheme 37) was purified by HPLC with Gemini 5 µm NX-C18 reversed phase column (21.1×250 mm, 110 Å, AXIA (Phenomenex)) eluted with ACN gradient in aqueous ammonium acetate. MALDI-TOF mass spectrometric analysis of the product fraction showed the expected mass (m/z 1501.3, [M+Na]⁺).

two Fc-fragments with either α-galactose-containing or hybrid-type N-glycans, respectively). These masses correspond to masses with clipped lysine.

Thus, the analysis demonstrated that all eight accessible cysteine residues had been reduced and modified yielding an ADC with drug-to-antibody ratio of 8, or ADC molecules of MMAG-PAB-CV-maleimidoyl conjugated to 2G12 having glycoside-to-antibody ratio of 8.

FIG. 5 shows the mass spectrum of MMAG-PAB-CV-maleimidoyl-nimotuzumab-antibody drug conjugate fragments. The light chains (LCs) were observed at m/z 24132 (LC) and 25623 (LC+one MMAG). The relative signal intensities of the two LC-fragments were 22% and 78% respectively, and calculation of the weighed average yielded Scheme 37. Structure of maleimidocaproyl-VC-PAB-(beta-glucosyl)-monomethylauristatin E (MMAX)

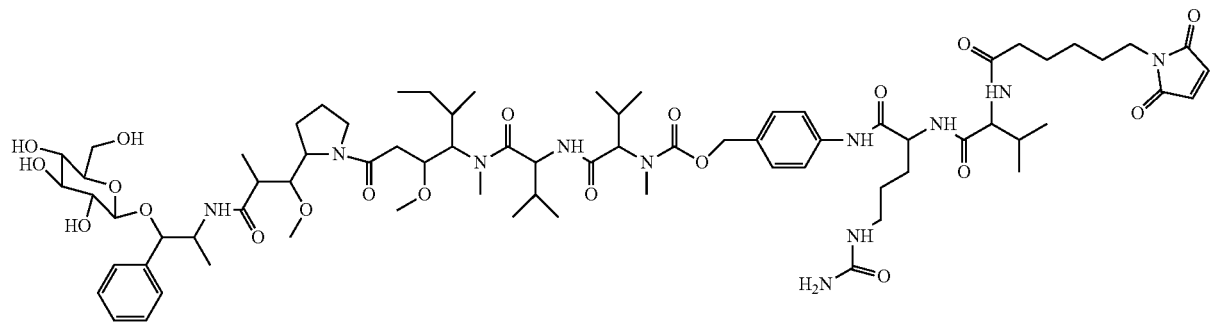

Example 38. Synthesis of MMAG-PAB-CV-maleimidoyl-Antibody Drug Conjugates

Interchain disuphide bridges of 2G12 (Anti-HIV-1 gp120, Polymun) and nimotuzumab (Biocon) were reduced with TCEP as described in Example 23. Antibody drug-conjugate was synthetized as described in Example 23 except 20×molar excess of Gal-Duocarmycin-PAB-CV-maleimide was used and Fc-analysis was performed on 30 µg sample.

FIG. 4 shows the mass spectrum of MMAG-PAB-CV-maleimidoyl-2G12-antibody drug conjugate fragments. The light chains (LCs) were observed at m/z 24796 (LC+one MMAG). An average of 1.0 MMAG for each LC was thus detected. The heavy chain fragments (Fab-HC) were an average of 0.78 MMAG for each LC. The heavy chain fragments (Fab-HC) were observed at m/z 28735 (Fab-HC+two MMAG) and 30220 (Fab-HC+three MMAG). The relative signal intensities of the two Fab HC-fragments were 22% and 78%. Calculation of the weighed average yielded an average of 2.78 MMAG for each Fab-HC. The heavy chain Fc fragments were observed at m/z 25222, 25393 (GOF-Fc and G1F-Fc, respectively). These masses correspond to masses with clipped lysine.

Thus, the analysis demonstrated that all eight accessible cysteine residues had been reduced and modified yielding an ADC with drug-to-antibody ratios up to 8 (on average 7.1) and glycoside-to-antibody ratios up to 8 (on average 7.1). Thus, ADC molecules of MMAG-PAB-CV-maleimidoyl conjugated to nimotuzumab having glycoside-to-antibody ratio of 4, 5, 6, 7, or 8 were formed.

Example 39. Synthesis of Gal-Duocarmycin-PAB-CV-maleimidoyl-Antibody Drug Conjugate Interchain disulphide bridges of trastuzumab were reduced with TCEP as in Example 23. Antibody drug-conjugate was synthetized as in Example 23 except that 10×molar excess of Gal-Duocarmycin-PAB-CV-maleimide was used. Fc-analysis was performed on 30 µg sample as in Example 23.

FIG. 6 shows the mass spectrum of Gal-Duocarmycin-PAB-CV-maleimidoyl-antibody drug conjugate fragments. The light chains (LCs) were observed at m/z 23430 (LC) and 24647 (LC+one Gal-Duocarmycin). The heavy chain fragments (Fab-HCs) were observed at m/z 27801 (Fab-HC+two Gal-Duocarmycin) and m/z 29002 (Fab-HC+three Gal-Duocarmycin). The heavy chain Fc fragments were observed at m/z 25229, 25392 and 25556 (GOF-Fc, G1F-Fc and G2F-Fc). These masses correspond to masses with clipped lysine. Thus, all eight accessible cysteine residues had been reduced and modified yielding an ADC with drug-to-antibody ratios up to 8, or ADC molecules of Gal-Duocarmycin-PAB-CV-maleimidoyl conjugated to trastuzumab having glycoside-to-antibody ratio of 4, 5, 6, 7 or 8, were formed.

Example 40. Synthesis of MMAU-PAB-CV-maleimidoyl-, MMAX-PAB-CV-maleimidoyl and MMAG-PAB-CV-maleimidoyl-Antibody Drug Conjugates Interchain disulphide bridges of trastuzumab were reduced with TCEP as in Example 23. Antibody drug-conjugates were synthetized as in Example 23 using MMAU-PAB-CV-maleimide, MMAX-PAB-CV-maleimide or MMAG-PAB-CV-maleimide and TCEP-reduced trastuzumab. Fc-analyses was performed on 30 µg sample as in Example 23.

FIG. 7 shows the mass spectrum of MMAU-PAB-CV-maleimidoyl-antibody drug conjugate fragments. The light chains (LCs) were observed at m/z 24926 (LC+MMAU). The heavy chain fragments (Fab-HCs) were observed at m/z 29854 (Fab-HC+3 MMAU). The heavy chain Fc fragments were observed at m/z 25227, 25389 and 25551 (GOF-Fc, G1F-Fc and G2F-Fc). These masses correspond to masses with clipped lysine. Some unidentified signals (m/z 24075, 27303, 28155 and 29005) were also detected (marked with *). The analysis demonstrated that all eight accessible cysteine residues had been reduced and modified yielding an ADC with drug-to-antibody ratio 8, or ADC molecules of MMAU-PAB-CV-maleimidoyl conjugated to trastuzumab having glycoside-to-antibody ratio of 8 were formed.

Figure 8:
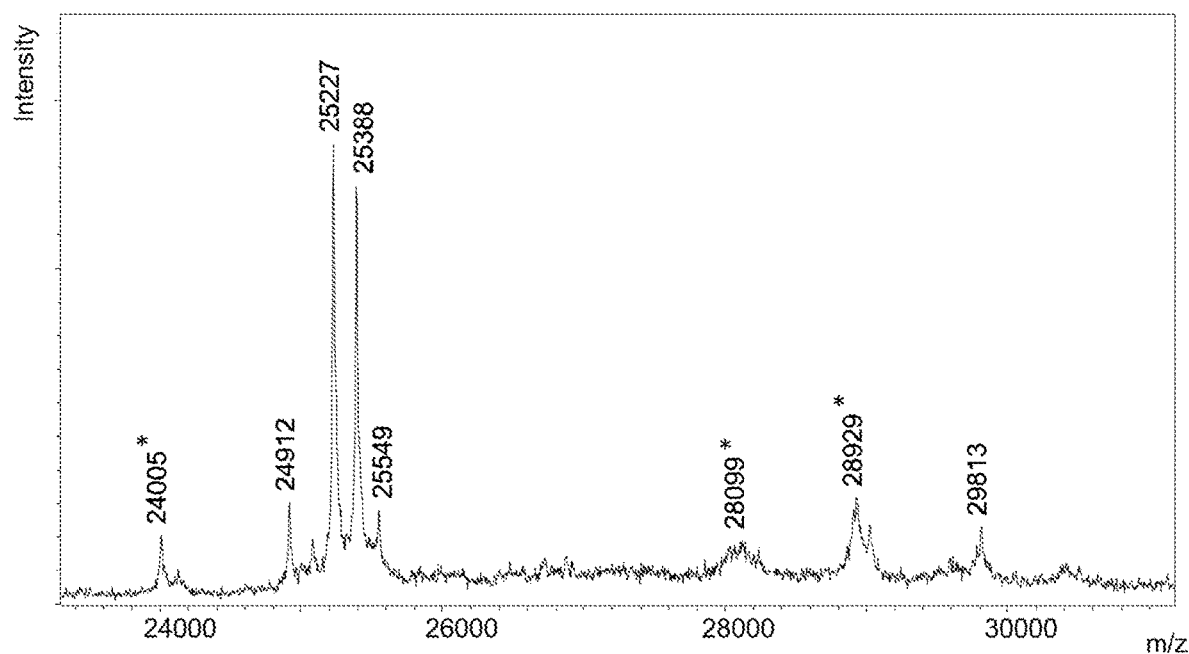

FIG. 8 shows the mass spectrum of MMAX-PAB-CV-maleimidoyl-antibody drug conjugate fragments. The light chains (LCs) were observed at m/z 24912 (LC+MMAX). The heavy chain fragments (Fab-HCs) were observed at m/z 29813 (Fab-HC+3 MMAX). The heavy chain Fc fragments were observed at m/z 25227, 25388 and 25549 (GOF-Fc, G1F-Fc and G2F-Fc). These masses correspond to masses with clipped lysine. Some unidentified signals (m/z 24005, 28099 and 28929) were also detected (marked with *). The analysis demonstrated that all eight accessible cysteine residues had been reduced and modified yielding an ADC with drug-to-antibody ratio 8, or ADC molecules of MMAX-PAB-CV-maleimidoyl conjugated to trastuzumab having glycoside-to-antibody ratio of 8 were formed.

In the mass spectrum of MMAG-PAB-CV-maleimidoyl-antibody drug conjugate fragments the light chains (LCs) were observed at m/z 23428 (LC) and 24911 (LC+MMAG). The heavy chain fragments (Fab-HCs) were observed at m/z 29804 (Fab-HC+3 MMAG) and 31280(Fab-HC+4 MMAG). The heavy chain Fc fragments were observed at m/z 25224, 25386 and 25544 (GOF-Fc, G1F-Fc and G2F-Fc). These masses correspond to masses with clipped lysine. Some unidentified signals (m/z 24136, 29016 and 30490) were also detected. Thus, accessible cysteine residues had been reduced and modified yielding an ADC with drug-to-antibody ratios up to 10, or ADC molecules of MMAG-PAB-CV-maleimidoyl conjugated to trastuzumab having glycoside-to-antibody ratio of 4, 5, 6, 7, 8, 9 or 10 were formed.

Example 41. In Vitro Assay with Trastuzumab ADCs

The in vitro assay was performed as in Example 14. Briefly, human ovarian cancer cell line SKOV-3 (ATCC, Manassas, Va., USA) was seeded onto 96-well plate and incubated overnight. Dilution series of antibody-drug conjugates were incubated with cells for 72 hours. Each ADC was tested in triplicate. Viability of the cells was determined with PrestoBlue cell viability reagent (Life Technologies, Carlsbad, Calif., USA) according to manufacturer's instructions. Reagent was incubated with cells for 2-2.5 h and absorbance was measured at 570 nm. The results are shown in Table 3.

TABLE 3

Viability of SKOV-3 ovarian cancer cells after treatment with trastuzumab ADCs. ADC 3 is MMAX-PAB-CV-maleimidoyl trastuzumab ADC, ADC 4 is MMAU-PAB-CV-maleimidoyl trastuzumab ADC, and ADC 5 is MMAG-PAB-CV-maleimidoyl trastuzumab ADC (from Example 39).

|      | 3 pM  | 10 pM | 30 pM | 100 pM | 300 pM | 1 nM | 3 nM | 10 nM | 30 nM | 100 nM |
|------|-------|-------|-------|--------|--------|------|------|-------|-------|--------|
| ADC3 | 103.1 | 113.1 | 109.5 | 99.2   | 77.1   | 56.8 | 43.4 | 42.5  | 37.7  | 37.9   |
| ADC4 | 105.3 | 101.6 | 92.1  | 68.7   | 32.8   | 24.4 | 19.9 | 23.2  | 22.6  | 21.6   |
| ADC5 | 102.9 | 100.6 | 81.7  | 55.0   | 28.4   | 26.4 | 24.7 | 25.3  | 21.2  | 29.7   |

Example 42. Glycosyl-maytansinoids and Conjugates 20-demethylmaytansinoids according to Scheme 38 are prepared as described in European patent application EP19790300469. The phenolic hydroxyl group at position 20 in demethylmaytansinoid (R1=H) is reacted with protected glycosyl donor in organic solvent as described above to form 20-glycosylmaytansinoid (R1=saccharide). The acyl group Rx in position 3 is derivatized with a linking group bearing a reactive group for example as described in U.S. Pat. No. 5,208,020, after which the protecting groups are removed. An antibody-drug conjugate of the glycosylmaytansinoid compound is prepared by conjugating the compound with a linker L to the antibody Ab for example as described in U.S. Pat. No. 6,441,163 (Scheme 39). One of skill in the art will understand that linking groups with other chemical groups (as described above) can also be used with the present invention, as can other maytansinoids.

Scheme 38. X is Cl or H; R1 is H or saccharide; Rx is H or acyl group.

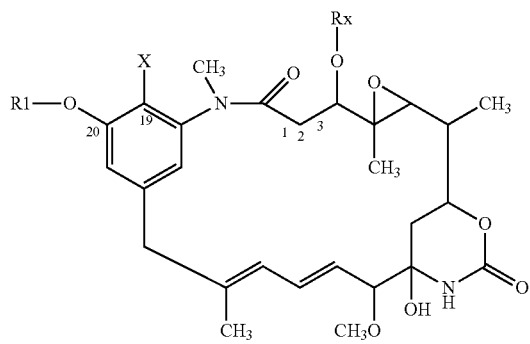

Scheme 39. L may be absent or any linker group described in this specification; Ab may be any antibody described in this specification.

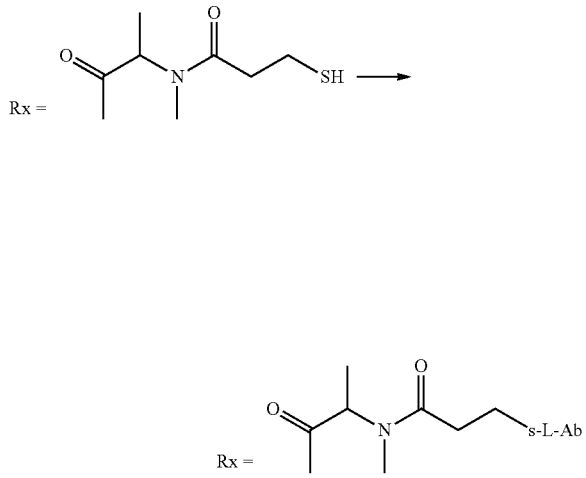

Alternatively, N-glucosylmaytansinoids according to Scheme 40 are prepared enzymatically as described in Zhao et al. 2008, Chemistry & Biology 15:863-74. The Rx group is according to Scheme 39. The glucosyl group is enzymatically β1,4-galactosylated and sialylated as described above. The compound is converted into an antibody-drug conjugate by conjugation to L-Ab as described above.

Scheme 40. Rx is as described in Scheme 39. L- is conjugated to antibody and n is the drug-to-antibody ratio. L may be absent or any linker group described in this specification.

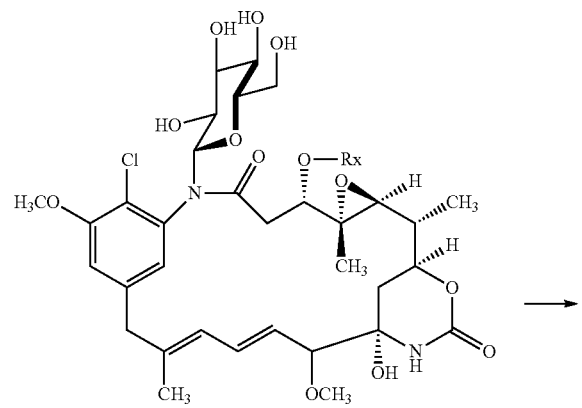

Example 43. Glycosyl-tubulysins and Conjugates

Tubulysin glycosides and antibody conjugates thereof according to Scheme 41 are prepared. A procedure is essentially according to Cohen et al. 2014 (Cancer Res 74:5700-10) without labeling with radioactive isotopes, and wherein the tubulysin is glycosylated with a glycosyl donor as described in the preceding examples before coupling to the linker and antibody. Drug-to-antibody ratio and glycoside-to-antibody ratio of at least four, between 4-8, about 8, at least 8, between 8-16, about 12, about 16, or at least 16, are achieved by adding the desired amount of activated linker-drug to antibody.

Scheme 41. R1 is OH or O-saccharide; Ra is H, methyl, or L-Ab; Rb is H or L-Ab; and Ra ≠ Rb. L may be absent or any linker group described in this specification; Ab may be any antibody described in this specification.

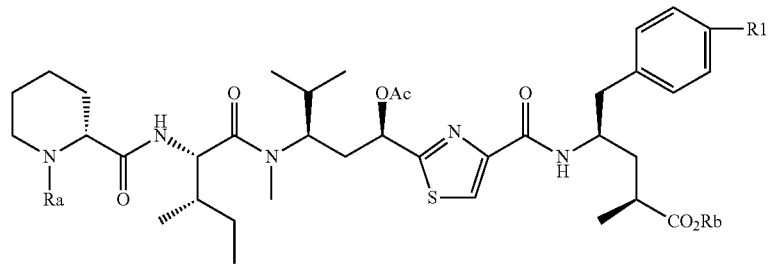

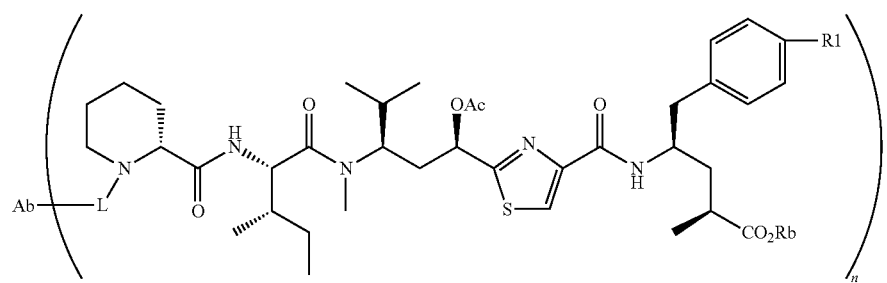

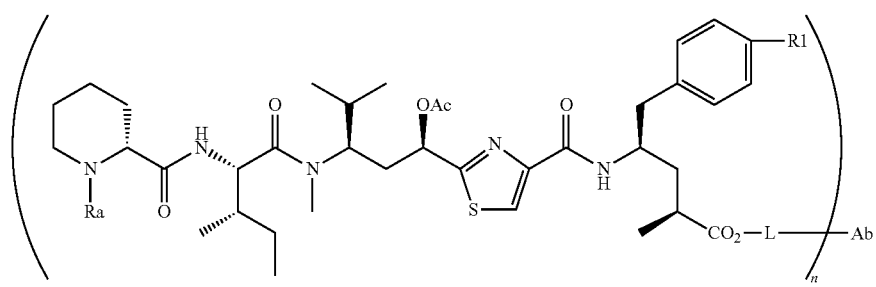

Example 44. Glycosyl-duocarmycins and Conjugates

Duocarmycin analogues are prepared as in van der Lee et al. 2015, Mol. Cancer Ther. 14:692-703, and glycosylated with a glycosyl donor to the phenolic hydroxyl group as described above (Scheme 42a, Ra=methyl, Rb=N, and R1 is saccharide). Antibody-drug conjugates are prepared with hydrophilic valine-citrulline linker as described in van der Lee et al. 2015 (Scheme 42b) with drug-to-antibody ratio and glycoside-to-antibody ratio of at least four, between 4-8, about 8, at least 8, between 8-16, about 12, about 16, or at least 16, by adding the desired amount of activated linker-drug to antibody (Scheme 42b).

Scheme 42a. R1 is H or saccharide; R2 is H or saccharide or L-Ab; Ra is H or methyl; and Rb is CH or N. L may be absent or any linker group described in this specification; Ab may be any antibody described in this specification.
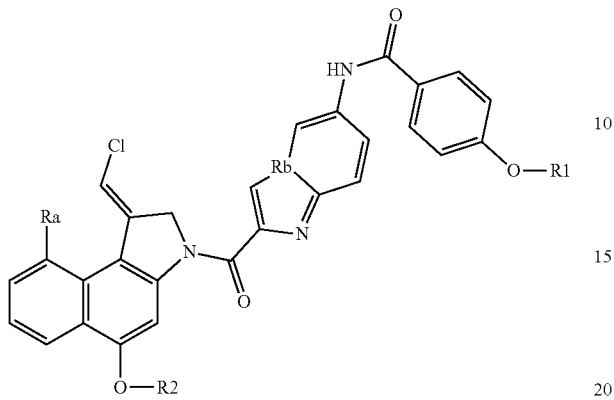
Scheme 42b. R1 is H or saccharide. L may be absent or any linker group described in this specification; Ab may be any antibody described in this specification.
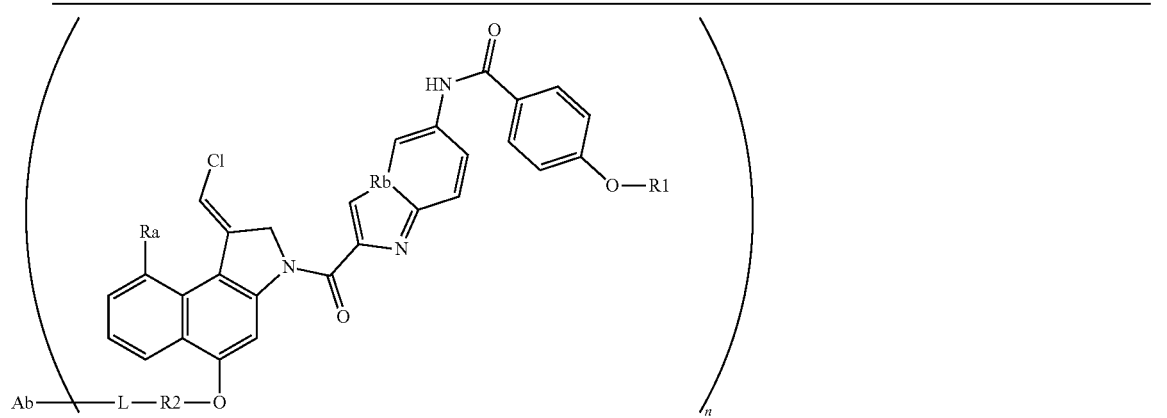
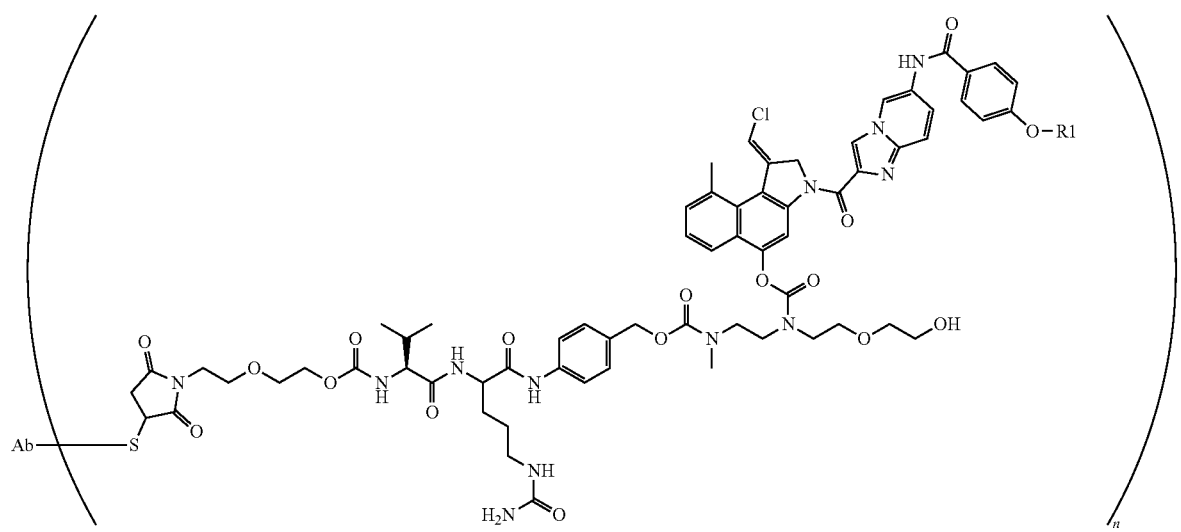

Example 45. Glycosyl-α-amanitins and Conjugates

Glycosyl-α-amanitins and antibody-drug conjugates according to Scheme 43 are prepared. For modification of the position Ra with L-Ab and position Rb with the glycoside, a procedure essentially according to Moldenhauer et al. 2012 (J. Natl. Cancer Inst. 104:622-34), α-amanitin (Sigma) is allowed to react with glutaric anhydride (Sigma-Aldrich) in pyridine at room temperature in the dark for 24 hours and washed with diethylether, and the glutarate ester becomes the Ra substituent. The Rb position is then O-glycosylated with a glycosyl donor as in the preceding Examples. The carboxylic acid of the glutarate is then activated as an NHS ester and linked to an antibody to form an antibody-drug conjugate as described in Moldenhauer et al. 2012. ADCs with drug-to-antibody ratio and glycoside-to-antibody ratio of at least four, between 4-8, about 8, at least 8, between 8-16, about 12, about 16, or at least 16, are prepared by adding the desired amount of activated linker-drug to antibody (Scheme 43).

Scheme 43. Ra is H, saccharide, or L-Ab; Rb is H, saccharide, or L-Ab; and Ra ≠ Rb. L may be absent or any linker group described in this specification; Ab may be any antibody described in this specification.

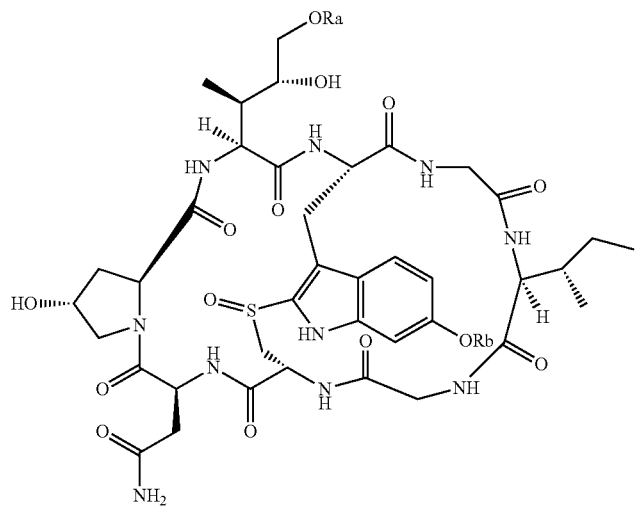

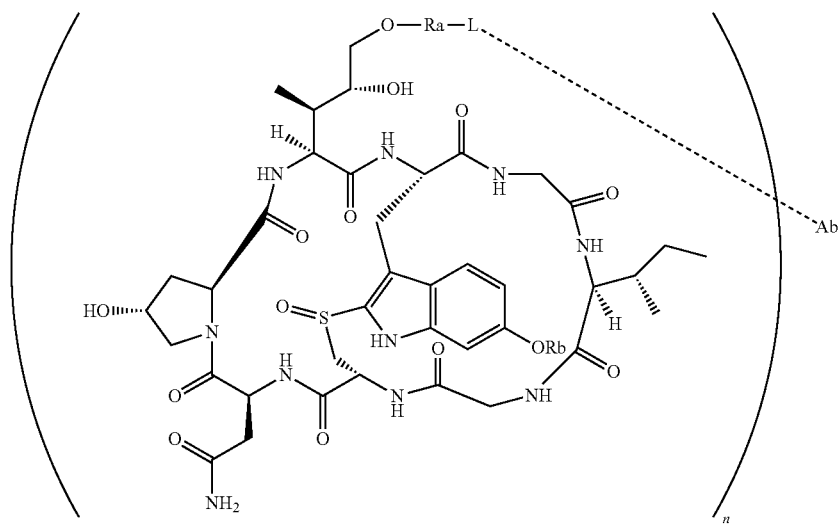

Example 46. Glycosyl-cryptophycins and Conjugates

Glycosyl-cryptophycins and antibody-drug conjugates according to Scheme 44 are prepared essentially according to Eissler et al. 2009 (Chem. Eur. J. 15:11273-87), wherein the unit B (Scheme 1, Eissler et al. 2009) is based on dimethyl-O-glycosyltyrosine and the glycosyl unit is protected. After the ring closure, the protective groups are removed to obtain glycosyl-cryptophycin and antibody-drug conjugates are produced to obtain conjugates with drug-to-antibody ratio and glycoside-to-antibody ratio of at least four, between 4-8, about 8, at least 8, between 8-16, about 12, about 16, or at least 16, by adding the desired amount of activated linker-drug to antibody (Scheme 44).

Scheme 44. R1 is H or saccharide; R is H, OH, amino, or L-Ab. L may be absent or any linker group described in this specification; Ab may be any antibody described in this specification.

It is obvious to a person skilled in the art that with the advancement of technology, the basic idea of the invention may be implemented in various ways. The invention and its embodiments are thus not limited to the examples described above, instead they may vary within the scope of the claims.

The invention claimed is:

1. An antibody-drug conjugate comprising a toxic payload of Formula VII:

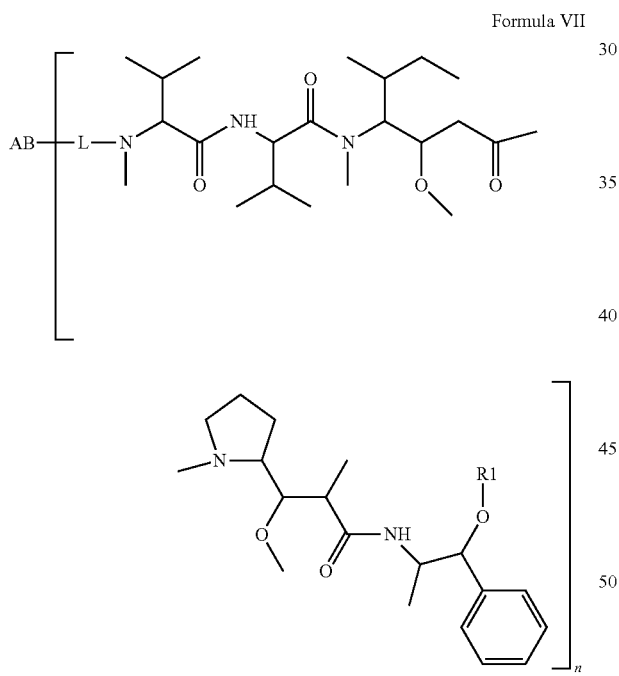

Formula VII wherein:

AB is an antibody or a fragment thereof;

L is absent or a linker group;

wherein:

a) R1 is a saccharide bound via an O-glycosidic bond to the toxic payload molecule; or, b) R1 is L"-R1', wherein R1' is a saccharide bound via an O-glycosidic bond to L", and L" is bound via an ester bond to a hydroxyl group of the toxic payload molecule, and L" has a structure according to Formula XII:

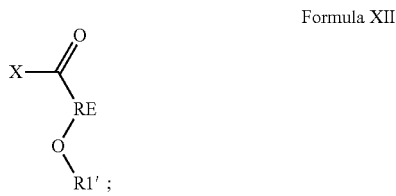

Formula XII and wherein:

X is the bond to the toxic payload molecule; R1' is the saccharide bound via the O-glycosidic bond;

RE is selected from the group consisting of —$CH_2$—, —$CH_2CH_2$—, —$CH_2CH_2CH_2$—, —$CH_2CH_2CH_2CH_2$—, $C_1$-$C_4$ alkyl, heteroalkyl, branched alkyl, branched heteroalkyl, cyclic alkyl, or cyclic heteroalkyl, and substituted $C_1$-$C_4$ alkyl, heteroalkyl, branched alkyl, branched heteroalkyl, cyclic alkyl, and cyclic heteroalkyl; and, n is at least 1.

2. The antibody-drug conjugate according to claim 1 wherein R1 or R1' is a monosaccharide selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid, and the monosaccharide is bound to the toxic payload molecule via the 0-glycosidic bond.

3. The antibody-drug conjugate according to the claim 2, wherein the monosaccharide further comprises a modification, wherein the modification is sulfate, phosphate, carboxyl, amino, or O-acetyl modification of the monosaccharide.

4. The antibody-drug conjugate according to claim 1, wherein the monosaccharide comprises a β-D-galactose or a neuraminic acid, or the monosaccharide is a β-D-galactose or a neuraminic acid.

5. The antibody-drug conjugate according to claim 1, wherein the R1 or R1' is a disaccharide.

6. The antibody-drug conjugate according to claim 5, wherein the disaccharide comprises a neutral monosaccharide and a charged monosaccharide.

7. The antibody-drug conjugate according to the claim 6, wherein the charged monosaccharide is neuraminic acid, D-glucuronic acid, L-iduronic acid, or a monosaccharide modified with sulfate, phosphate, carboxyl or amino group.

8. The antibody-drug conjugate according to claim 5, wherein the disaccharide comprises neuraminic acid α2,3- or α2,6-linked to β-D-galactose, or the saccharide is a disaccharide, wherein neuraminic acid is α2,3- or α2,6-linked to β-D-galactose.

9. The antibody-drug conjugate according to claim 1, wherein the saccharide is an oligosaccharide and the oligosaccharide is bound to the toxic payload molecule via the O-glycosidic bond, or the oligosaccharide is bound via an O-glycosidic bond to L", L" is bound via an ester bond to a hydroxyl group of the toxic payload molecule and has a structure according to formula XII.

10. The antibody-drug conjugate according to claim 1, wherein the O-glycosidic bond is hydrolysable by a lysosomal or an intracellular glycohydrolase.

11. The antibody-drug conjugate according to claim 10, wherein the saccharide comprises at least two monosaccharides selected from the group consisting of β-D-galactose, N-acetyl-β-D-galactosamine, N-acetyl-α-D-galactosamine, N-acetyl-β-D-glucosamine, β-D-glucuronic acid, α-L-iduronic acid, α-D-galactose, α-D-glucose, β-D-glucose, α-D-mannose, β-D-mannose, α-L-fucose, β-D-xylose, neuraminic acid.

12. The antibody-drug conjugate according to claim 11, wherein the saccharide further comprises a modification, wherein the modification is sulfate, phosphate, carboxyl, amino, or O-acetyl modification of a monosaccharide.

13. The antibody-drug conjugate according to claim 1, wherein the antibody is selected from the group consisting of bevacizumab, tositumomab, etanercept, trastuzumab, adalimumab, alemtuzumab, gemtuzumab ozogamicin, efalizumab, rituximab, infliximab, abciximab, basiliximab, palivizumab, omalizumab, daclizumab, cetuximab, panitumumab, epratuzumab, 2G12, lintuzumab, nimotuzumab and ibritumomab tiuxetan.

14. The antibody-drug conjugate according to claim 1, wherein n is in the range of 1 to about 20.

15. The antibody-drug conjugate according to claim 1, wherein the linker group comprises a linker group represented by formula VIII

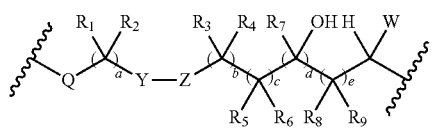

Formula VIII wherein

Y is an oxygen, sulphur, amine, amide, peptide or absent, wherein the peptide is an $E_1$-P-$E_2$ unit in which $E_1$ and $E_2$ are independently C=O, O or $NR_p$, wherein $R_p$ is H, $C_1$-$C_6$ alkyl or substituted $C_1$-$C_6$ alkyl, P is a peptide unit from 2 to 5 amino acids in length, and $E_1$ and $E_2$ can independently be linked to the peptide through the terminal nitrogen, terminal carbon or through a side chain of one of the amino acids of the peptide;

Z is a saccharide or absent;

$R_1$, $R_2$, $R_3$, $R_4$, $R_5$, $R_6$, $R_7$, $R_8$ and $R_9$ are each independently H, OH, amine, $C_2$-$C_6$ acylamide, carboxyl, substituted carboxyl, $C_1$-$C_6$ alkyl or substituted $C_1$-$C_6$ alkyl;

W is H, $CH_2OH$, $CH_3$, carboxyl, substituted carboxyl, $C_1$-$C_6$ alkyl or substituted $C_1$-$C_6$ alkyl;

a is an integer from 0 to 6;

b is 0 or 1;

c and e are each independently an integer from 0 to 7;

d is an integer in the range of 1 to 7; and

Q is E'-F'-E, wherein F' is an amine, amide, disulfide, thioether, thioester, hydrazone, Schiff base, oxime, olefin metathesis reaction product, triazole or phosphine group, or other group generated by the reaction of the functional group F-E and the functional group F', wherein F is a functional group that can react with an amine, thiol, azide, alkene, alkyne, aldehyde, ketone, carboxylic acid or hydroxylamine, and F' is an amine, thiol, azide, alkene, alkyne, aldehyde, ketone, carboxylic acid or hydroxylamine; and E is absent or a polyethyleneoxy unit of formula $(CH_2CH_2O)_p$, wherein p is an integer from 2 to about 20; and E and E' are each independently absent or a polyethyleneoxy unit of formula $(CH_2CH_2O)_p$, wherein p is an integer from 2 to about 20.

16. The antibody-drug conjugate according to claim 1, wherein the linker group comprises a peptide and optionally a self-immolative group.

17. The antibody-drug conjugate according to claim 16, wherein the peptide is a peptide cleavable by a lysosomal peptidase, optionally selected from the group consisting of L-Gly-L-Gly, L-Val-L-Cit, L-Phe-L-Leu, L-Leu-L-Ala-L-Leu, L-Leu-L-Ala-L-Ala and L-Ala-L-Leu-L-Ala-L-Leu.

18. The antibody-drug conjugate according to claim 16, wherein the self-immolative group is a para-aminobenzoyl group (PAB).

19. The antibody-drug conjugate according to claim 1, wherein the antibody-drug conjugate comprises or is a conjugate selected from the group consisting of the following:
- a conjugate of O-β-D-galactopyranosylmonomethylauristatin E (MMAG) and antibody;
- a conjugate of Val-Cit-PAB-MMAG and antibody;
- a conjugate of N-(6-azido-6-deoxy-D-galactosyl)-MMAG and antibody;
- a conjugate of O-(N-acetylneuraminyl-β-D-galactopyranosyl)-MMAE (MMAS) and antibody;
- a conjugate of Val-Cit-PAB-MMAS and antibody;
- a conjugate of N-(6-azido-6-deoxy-D-galactosyl)-MMAS and antibody;
- a conjugate of MMAG and anti-EGFR antibody;
- a conjugate of MMAS and anti-EGFR antibody;
- a conjugate of Neu5Acα2,6MMAG and antibody;
- a conjugate of Neu5Acα2,3MMAG and antibody;
- a conjugate of maleimidocaproyl-VC-PAB-MMAG and antibody;
- a conjugate of O-β-D-galactopyranosylmonomethylauristatin E (MMAG) and trastuzumab, cetuximab, brentuximab or nimotuzumab;
- a conjugate of Val-Cit-PAB-MMAG and trastuzumab, cetuximab, brentuximab or nimotuzumab;
- a conjugate of O-(N-acetylneuraminyl-β-D-galactopyranosyl)-MMAE (MMAS) and trastuzumab, cetuximab, brentuximab or nimotuzumab;
- a conjugate of Val-Cit-PAB-MMAS and trastuzumab, cetuximab, brentuximab or nimotuzumab;
- a conjugate of beta-glucuronyl-monomethylauristatin E (MMAU) and antibody;
- a conjugate of maleimidocaproyl-VC-PAB-MMAU and antibody;
- a conjugate of MMAU-PAB-CV-maleimidoyl and antibody;
- a conjugate of beta-glucosyl-monomethylauristatin E (MMAX) and antibody;
- a conjugate of maleimidocaproyl-VC-PAB-MMAX and antibody;
- a conjugate of MMAX-PAB-CV-maleimidoyl and antibody; and,
- a conjugate of MMAG-PAB-CV-maleimidoyl and antibody.

20. The antibody-drug conjugate according to claim 1, wherein the glycoside-to-antibody ratio is in the range of 1 to about 100.

21. A pharmaceutical composition comprising the antibody-drug conjugate according to claim 1.

22. A pharmaceutical composition comprising the antibody-drug conjugate according to claim 1, wherein n is at least 1.

23. A method of treating and/or modulating the growth of tumor cells in humans or animals, wherein the antibody-drug conjugate according to claim 1 or a pharmaceutical composition according to claim 21 is administered to a human or animal in an effective amount.

24. The method according to claim 23, wherein the tumor cells are selected from the group consisting of leukemia cells, lymphoma cells, breast cancer cells, prostate cancer cells, ovarian cancer cells, colorectal cancer cells, gastric cancer cells, squamous cancer cells, small-cell lung cancer cells, head-and-neck cancer cells, multidrug resistant cancer cells, and testicular cancer cells.

25. The pharmaceutical composition of claim 21 further comprising at least one pharmaceutically acceptable excipient.

26. The pharmaceutical composition of claim 21 suitable for oral, parenteral, transdermal, intraluminal, intraarterial, intrathecal, or intranasal administration, and/or for direct injection into tissue.

27. A method for treating cancer comprising administering an antibody-drug conjugate of claim 1 to a patient in need thereof.

28. The method of claim 27 wherein the cancer is selected from the group consisting of leukemia, lymphoma, breast cancer, prostate cancer, ovarian cancer, colorectal cancer, gastric cancer, squamous cancer, small-cell lung cancer, head-and-neck cancer, multidrug resistant cancer, and testicular cancer.

29. The method of claim 27 wherein administration is administered by a route selected from the group consisting of intravenous, intraperitoneal, subcutaneous, intramuscular, intratumoral, topical, and intradermal.

30. An antibody-drug conjugate comprising a toxic payload of Formula VII:

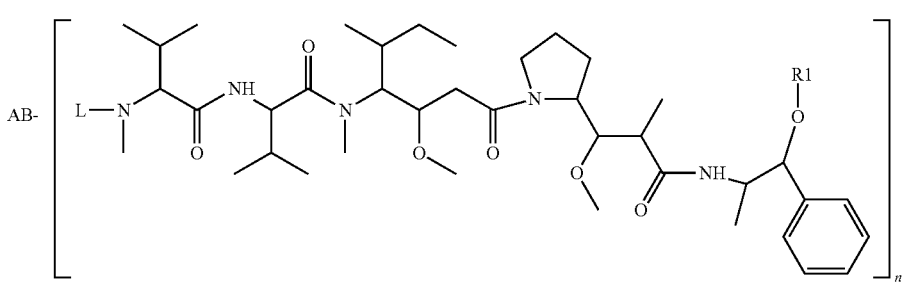

Formula VII wherein:

AB is an antibody or a fragment thereof;

L is absent or a linker group; and,

R1 is a saccharide bound via an O-glycosidic bond to the toxic payload molecule.

31. A pharmaceutical composition comprising the antibody-drug conjugate according to claim 30.

32. A method for treating cancer comprising administering an antibody-drug conjugate of claim 30 to a patient in need thereof.

33. A method for treating cancer comprising administering a pharmaceutical composition of claim 31 to a patient in need thereof.

* * * * *

UNITED STATES PATENT AND TRADEMARK OFFICE
CERTIFICATE OF CORRECTION

PATENT NO. : 10,973,920 B2
APPLICATION NO. : 15/320917
DATED : April 13, 2021
INVENTOR(S) : Jari Helin et al.

It is certified that error appears in the above-identified patent and that said Letters Patent is hereby corrected as shown below:

In the Claims

Claim 2, Column 142, Line 61, "0-glycosidic bond" should read -- O-glycosidic bond --

Claim 9, Column 143, Line 28, "bond to L", L" is bound" should read -- bond to L", and L" is bound --

Claim 9, Column 143, Line 29, "has a structure according to formula XII" should read -- has the structure according to formula XII --

Claim 11, Column 143, Line 45, "neuraminic acid" should read -- and neuraminic acid --

Claim 19, Column 145, Line 17, "Neu5Acα2,6MMAG" should read -- Neu5Acα2,6-MMAG --

Claim 19, Column 145, Line 18, "Neu5Acα2,3MMAG" should read -- Neu5Acα2,3-MMAG --

Claim 30, Column 146, should read

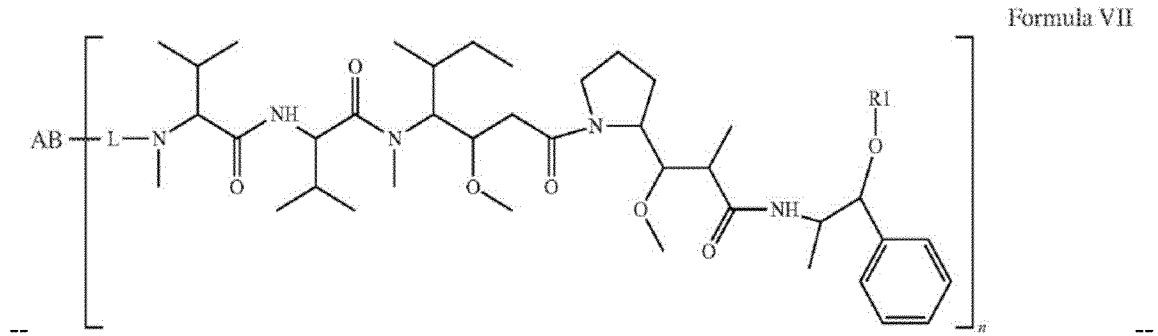

Signed and Sealed this
Fifteenth Day of August, 2023

Katherine Kelly Vidal
*Director of the United States Patent and Trademark Office*